United States Patent
Combette et al.

(10) Patent No.: US 11,331,364 B2
(45) Date of Patent: May 17, 2022

(54) USE FOR JNK INHIBITOR MOLECULES FOR TREATMENT OF VARIOUS DISEASES

(71) Applicant: Xigen Inflammation Ltd., Limassol (CY)

(72) Inventors: Jean-Marc Combette, Saint Cergues (FR); Catherine Deloche, Geneva (CH)

(73) Assignee: XIGEN INFLAMMATION LTD., Limassol (CY)

( * ) Notice: Subject to any disclaimer, the term of this patent is extended or adjusted under 35 U.S.C. 154(b) by 0 days.

(21) Appl. No.: 16/430,697

(22) Filed: Jun. 4, 2019

(65) Prior Publication Data

US 2020/0093883 A1 Mar. 26, 2020

Related U.S. Application Data

(63) Continuation of application No. 15/321,904, filed as application No. PCT/EP2015/001293 on Jun. 26, 2015, now abandoned.

(30) Foreign Application Priority Data

Jun. 26, 2014 (WO) ................ PCT/EP2014/001737
Oct. 8, 2014 (WO) ................ PCT/EP2014/002723

(51) Int. Cl.
| A61K 38/00 | (2006.01) |
| A61K 9/00 | (2006.01) |
| A61K 38/10 | (2006.01) |
| C07K 7/06 | (2006.01) |
| C07K 14/47 | (2006.01) |

(52) U.S. Cl.
CPC .......... *A61K 38/005* (2013.01); *A61K 9/0019* (2013.01); *A61K 9/0034* (2013.01); *A61K 9/0048* (2013.01); *A61K 9/0063* (2013.01); *A61K 38/10* (2013.01); *C07K 7/06* (2013.01); *C07K 14/4703* (2013.01); *A61K 38/00* (2013.01); *C07K 2319/10* (2013.01); *Y02A 50/30* (2018.01)

(58) Field of Classification Search
CPC ........ C07K 7/06; A61K 38/005; A61K 38/00; A61K 38/10
See application file for complete search history.

(56) References Cited

U.S. PATENT DOCUMENTS

| 4,631,211 A | 12/1986 | Houghten |
| 4,698,327 A | 10/1987 | Nagarajan et al. |
| 4,732,890 A | 3/1988 | Bonelli et al. |
| 5,169,933 A | 12/1992 | Anderson et al. |
| 5,595,756 A | 1/1997 | Bally et al. |
| 5,597,895 A | 1/1997 | Gaynor et al. |
| 5,670,617 A | 9/1997 | Frankel et al. |
| 5,672,479 A | 9/1997 | Johnson et al. |
| 5,674,980 A | 10/1997 | Frankel et al. |
| 5,686,264 A | 11/1997 | Gaynor et al. |
| 5,747,641 A | 5/1998 | Frankel et al. |
| 5,756,684 A | 5/1998 | Johnson et al. |
| 5,804,604 A | 9/1998 | Frankel et al. |
| 5,840,313 A | 11/1998 | Vahlne et al. |
| 5,880,261 A | 3/1999 | Waeber et al. |
| 5,989,814 A | 11/1999 | Frankel et al. |
| 5,994,108 A | 11/1999 | Gaynor et al. |
| 5,994,109 A | 11/1999 | Woo et al. |
| 6,043,083 A | 3/2000 | Davis et al. |
| 6,117,632 A | 9/2000 | O'Mahony |
| 6,265,386 B1 | 7/2001 | Campbell |
| 6,284,456 B1 | 9/2001 | Jones et al. |
| 6,300,317 B1 | 10/2001 | Szoka, Jr. et al. |
| 6,316,003 B1 | 11/2001 | Frankel et al. |
| 6,348,185 B1 | 2/2002 | Piwnica-Worms |
| 6,420,031 B1 | 7/2002 | Parthasarathy et al. |
| 6,448,283 B1 | 9/2002 | Ylikoski et al. |
| 6,495,663 B1 | 12/2002 | Rothbard et al. |
| 6,586,403 B1 | 7/2003 | Mathison et al. |
| 6,610,820 B1 | 8/2003 | Bonny |
| 6,620,914 B1 | 9/2003 | Waeber et al. |
| 6,630,351 B1 | 10/2003 | Monahan et al. |
| 6,653,443 B2 | 11/2003 | Zhang et al. |
| 6,673,908 B1 | 1/2004 | Stanton, Jr. |
| 6,740,524 B1 | 5/2004 | Akuta et al. |
| 6,780,970 B2 | 8/2004 | Bonny |
| 6,881,825 B1 | 4/2005 | Robbins et al. |
| 6,960,648 B2 | 11/2005 | Bonny |
| 7,033,597 B2 | 4/2006 | Bonny |
| 7,034,109 B2 | 4/2006 | Bonny |
| 7,148,215 B2 | 12/2006 | Ratcliffe et al. |

(Continued)

FOREIGN PATENT DOCUMENTS

| CA | 2738951 A1 | 7/2010 |
| CN | 101263157 A | 9/2008 |

(Continued)

OTHER PUBLICATIONS

Hsieh et al. "Treatment of interstitial cystitis in women", Taiwanese Journal of Obstetrics and Gynecology, 2012, 526-532 (Year: 2012).*
Lazzeri et al. Intravesical infusion of resiniferatoxin by a temporary in situ drug delivery system to treat interstitial cystitis: a pilot study. Eur Urol., 2004, pp. 98-102 (Year: 2004).*
National Institute of Diabetes and Digestive and Kidney Diseases (NIDDK), "Interstitial Cystitis (Painful Bladder Syndrome)", https://www.niddk.nih.gov/health-information/urologic-diseases/interstitial-cystitis-painful-bladder-syndrome; retrieved Dec. 19, 2020 (Year: 2020).*
Cervigni, M, "Bladder Pain Syndrome", Glob. libr. women's med. 2014 (Year: 2014).*
Aoyagi et al., "Intravesical Non-Alkalinized Lidocaine Instillation for Interstitial Cystitis/Bladder Pain Syndrome Patients",Open Journal of Urology, 2012, 2, 223-226 (Year: 2012).*

(Continued)

*Primary Examiner* — Lianko G Garyu
(74) *Attorney, Agent, or Firm* — Harness Dickey & Pierce P.L.C.

(57) ABSTRACT

The present invention relates to the use of novel JNK inhibitor molecules and their use in a method of treatment of the human or animal body by therapy.

17 Claims, 63 Drawing Sheets

Specification includes a Sequence Listing.

(56) References Cited

U.S. PATENT DOCUMENTS

| | | |
|---|---|---|
| 7,166,692 B2 | 1/2007 | Karas |
| 7,538,091 B2 | 5/2009 | Bonny |
| 7,635,681 B2 | 12/2009 | Bonny |
| 7,803,749 B2 | 9/2010 | Bonny |
| 7,943,574 B2 | 5/2011 | Bonny |
| 8,063,012 B2 | 11/2011 | Watt et al. |
| 8,080,517 B2 | 12/2011 | Bonny |
| 8,183,339 B1 | 5/2012 | Bonny |
| 8,236,924 B2 | 8/2012 | Bonny |
| 8,278,413 B2 | 10/2012 | Bonny |
| 8,569,447 B2 | 10/2013 | Bonny |
| 8,748,395 B2 | 6/2014 | Bonny |
| 8,981,052 B2 | 3/2015 | Bonny |
| 9,006,185 B2 | 4/2015 | Bonny |
| 9,150,618 B2 | 10/2015 | Combette et al. |
| 9,180,159 B2 | 11/2015 | Bonny |
| 9,290,538 B2 | 3/2016 | Bonny |
| 9,610,330 B2 | 4/2017 | Bonny |
| 9,624,267 B2 | 4/2017 | Bonny |
| 10,596,223 B2 * | 3/2020 | Combette ............... A61P 11/00 |
| 2002/0042423 A1 | 4/2002 | Richert et al. |
| 2002/0090696 A1 | 7/2002 | Miller et al. |
| 2002/0103229 A1 | 8/2002 | Bhagwat et al. |
| 2003/0100549 A1 | 5/2003 | Salituro et al. |
| 2003/0104622 A1 | 6/2003 | Robbins et al. |
| 2003/0108539 A1 | 6/2003 | Bonny |
| 2003/0124113 A1 | 7/2003 | Hillman et al. |
| 2003/0148395 A1 | 8/2003 | Liu |
| 2003/0220480 A1 | 11/2003 | Bonny |
| 2004/0058875 A1 | 3/2004 | Gamache |
| 2004/0082509 A1 | 4/2004 | Bonny |
| 2004/0265879 A1 | 12/2004 | Iversen et al. |
| 2005/0019366 A1 | 1/2005 | Zeldis |
| 2005/0043241 A1 | 2/2005 | Bonny |
| 2005/0059597 A1 | 3/2005 | Tymianski |
| 2005/0106695 A1 | 5/2005 | Bonny |
| 2006/0094753 A1 | 5/2006 | Pang et al. |
| 2006/0166881 A1 | 7/2006 | Hotchkiss et al. |
| 2006/0178310 A1 | 8/2006 | Bonny |
| 2006/0223807 A1 | 10/2006 | Davis et al. |
| 2006/0258706 A1 | 11/2006 | Saindane et al. |
| 2006/0270646 A1 | 11/2006 | Graczyk et al. |
| 2007/0003531 A1 | 1/2007 | Mukherji et al. |
| 2007/0015779 A1 | 1/2007 | Griffin et al. |
| 2007/0060514 A1 | 3/2007 | Bonny |
| 2008/0008749 A1 | 1/2008 | Pearlman et al. |
| 2008/0051410 A1 | 2/2008 | Watterson et al. |
| 2008/0274956 A1 | 11/2008 | Bonny et al. |
| 2009/0281036 A1 | 11/2009 | Meyer |
| 2009/0305968 A1 | 12/2009 | Bonny |
| 2009/0306579 A1 | 12/2009 | Jaffe et al. |
| 2010/0098635 A1 | 4/2010 | Lamping |
| 2010/0216716 A1 | 8/2010 | Bonny |
| 2010/0256041 A1 | 10/2010 | Bonny et al. |
| 2010/0331335 A1 | 12/2010 | Sham et al. |
| 2011/0052566 A1 | 3/2011 | Rosenblum et al. |
| 2011/0183888 A1 | 7/2011 | Bonny |
| 2012/0058137 A1 | 3/2012 | Bonny |
| 2012/0071483 A1 | 3/2012 | Cohen et al. |
| 2012/0101046 A1 | 4/2012 | Hirai et al. |
| 2012/0142584 A1 | 6/2012 | Bonny |
| 2012/0148590 A1 | 6/2012 | Bonny |
| 2012/0258982 A1 | 10/2012 | Cheung et al. |
| 2012/0328609 A1 | 12/2012 | Lewcock et al. |
| 2014/0057834 A1 | 2/2014 | Bonny |
| 2014/0309400 A1 | 10/2014 | Combette et al. |
| 2015/0133393 A1 | 5/2015 | Combette et al. |
| 2016/0089413 A1 | 3/2016 | Combette et al. |
| 2016/0115200 A1 | 4/2016 | Combette et al. |
| 2016/0199444 A1 | 7/2016 | Combette et al. |
| 2016/0264630 A1 | 9/2016 | Bonny |
| 2017/0056466 A1 | 3/2017 | Combette et al. |
| 2017/0128516 A1 | 5/2017 | Combette et al. |
| 2017/0137481 A1 | 5/2017 | Combette et al. |
| 2017/0290877 A1 | 10/2017 | Combette et al. |
| 2017/0320917 A1 | 11/2017 | Bonny |
| 2018/0170983 A1 | 6/2018 | Combette et al. |
| 2019/0060392 A1 | 2/2019 | Combette et al. |

FOREIGN PATENT DOCUMENTS

| | | |
|---|---|---|
| CN | 1738901 B | 5/2010 |
| EP | 84691 A1 | 8/1983 |
| EP | 0375040 A2 | 6/1990 |
| EP | 679716 A1 | 11/1995 |
| EP | 897002 A2 | 2/1999 |
| EP | 1364949 A1 | 11/2003 |
| EP | 1676574 A2 | 7/2006 |
| EP | 2627346 A1 | 8/2013 |
| FR | 2767323 A1 | 2/1999 |
| JP | 1958-146538 | 9/1983 |
| JP | 2002-221294 A | 8/2002 |
| JP | 2002534479 A | 10/2002 |
| JP | 2003511071 A | 3/2003 |
| JP | 2003-531871 A | 10/2003 |
| JP | 2004-66595 A | 3/2004 |
| JP | 2004-516811 A | 6/2004 |
| JP | 2005512259 A | 4/2005 |
| JP | 2005-525096 A | 8/2005 |
| JP | 2006-501165 A | 1/2006 |
| JP | 2006-502719 A | 1/2006 |
| JP | 2006-512143 A | 4/2006 |
| JP | 2006516546 A | 7/2006 |
| JP | 2007-503617 A | 2/2007 |
| JP | 2008-519785 A | 6/2008 |
| JP | 2011-524861 A | 9/2011 |
| JP | 2012-513427 | 6/2012 |
| JP | 5485265 B2 | 5/2014 |
| JP | 2014/206564 A | 10/2014 |
| JP | 2015502372 A | 1/2015 |
| JP | 5711666 B2 | 5/2015 |
| JP | 2015/197193 A | 11/2015 |
| JP | 5824085 B2 | 11/2015 |
| WO | 1992018138 A1 | 10/1992 |
| WO | 1993018759 A1 | 9/1993 |
| WO | 1994004562 A1 | 3/1994 |
| WO | 1994004686 A1 | 3/1994 |
| WO | 1994005311 A1 | 3/1994 |
| WO | 1994023751 A1 | 10/1994 |
| WO | 1995034295 A1 | 12/1995 |
| WO | 1996034093 A1 | 10/1996 |
| WO | 1997005265 A1 | 2/1997 |
| WO | 1997010836 A1 | 3/1997 |
| WO | 1998011907 A1 | 3/1998 |
| WO | 1998023781 A1 | 6/1998 |
| WO | 1998044106 A1 | 10/1998 |
| WO | 1998047913 A2 | 10/1998 |
| WO | 1998049188 A1 | 11/1998 |
| WO | 1998051325 A2 | 11/1998 |
| WO | 1998051825 A1 | 11/1998 |
| WO | 1998052614 A2 | 11/1998 |
| WO | 1999007728 A2 | 2/1999 |
| WO | 9920624 A1 | 4/1999 |
| WO | 1999016787 A1 | 4/1999 |
| WO | 1999049879 A1 | 10/1999 |
| WO | 1999050282 A2 | 10/1999 |
| WO | 1999058561 A1 | 11/1999 |
| WO | 1999067284 A2 | 12/1999 |
| WO | 2000012587 A2 | 3/2000 |
| WO | 2000041719 A1 | 7/2000 |
| WO | 2001010888 A1 | 2/2001 |
| WO | 2001013957 A2 | 3/2001 |
| WO | 2001015511 A2 | 3/2001 |
| WO | 2001027268 A2 | 4/2001 |
| WO | 2001/043774 A1 | 6/2001 |
| WO | 2001039784 A1 | 6/2001 |
| WO | 2001082975 A2 | 11/2001 |
| WO | 2001/098324 A1 | 12/2001 |
| WO | 2002031109 A2 | 4/2002 |
| WO | 2002032437 A1 | 4/2002 |
| WO | 2002061105 A2 | 8/2002 |
| WO | 2002062396 A2 | 8/2002 |
| WO | 2002065986 A2 | 8/2002 |
| WO | 2002069930 A1 | 9/2002 |

(56) References Cited

FOREIGN PATENT DOCUMENTS

| | | |
|---|---|---|
| WO | 2002081504 A2 | 10/2002 |
| WO | 2003/008553 A2 | 1/2003 |
| WO | 2003057725 A2 | 7/2003 |
| WO | 2003075917 A1 | 9/2003 |
| WO | 2002081505 A3 | 10/2003 |
| WO | 2003/106491 A2 | 12/2003 |
| WO | 2003103698 A1 | 12/2003 |
| WO | 2004026406 A1 | 4/2004 |
| WO | 2004035793 A1 | 4/2004 |
| WO | 2004037196 A2 | 5/2004 |
| WO | 2004060318 A2 | 7/2004 |
| WO | 2004054501 A3 | 8/2004 |
| WO | 2004070052 A3 | 10/2004 |
| WO | 2003103718 A3 | 11/2004 |
| WO | 2004092339 A3 | 5/2005 |
| WO | 2005097116 A1 | 10/2005 |
| WO | 2006/001582 A1 | 1/2006 |
| WO | 2004022580 A3 | 2/2006 |
| WO | 2006021458 A2 | 3/2006 |
| WO | 2006050930 A2 | 5/2006 |
| WO | 2004045535 A3 | 7/2006 |
| WO | 2007031098 A1 | 3/2007 |
| WO | 2007031280 A2 | 3/2007 |
| WO | 2005084158 A3 | 7/2007 |
| WO | 2008028860 A1 | 3/2008 |
| WO | 2008094208 A2 | 8/2008 |
| WO | 2008095943 A1 | 8/2008 |
| WO | 2009137602 A1 | 11/2009 |
| WO | 2009/144038 A1 | 12/2009 |
| WO | 2009143864 A1 | 12/2009 |
| WO | 2009143865 A1 | 12/2009 |
| WO | 2009144037 A1 | 12/2009 |
| WO | 2010065850 A2 | 6/2010 |
| WO | 2010072405 A1 | 7/2010 |
| WO | 2010072406 A1 | 7/2010 |
| WO | 2010091310 A1 | 8/2010 |
| WO | 2010113753 A1 | 10/2010 |
| WO | 2011/082328 A1 | 7/2011 |
| WO | 2011160653 A1 | 12/2011 |
| WO | 2011160827 A2 | 12/2011 |
| WO | 2012048721 A1 | 4/2012 |
| WO | 2012048893 A1 | 4/2012 |
| WO | 2013091670 A1 | 6/2013 |
| WO | 2013091896 A1 | 6/2013 |
| WO | WO-2013091896 A1 * | 6/2013 ................ A61P 1/04 |
| WO | 2014206426 A1 | 12/2014 |
| WO | 2014206564 A1 | 12/2014 |
| WO | 2015197193 A3 | 2/2016 |

OTHER PUBLICATIONS

Aarts et al., "Treatment of Ischemic Brain Damage by Perturbing NMDA Receptor PSD-95 Protein Interactions," Science, 298(5594):846-850 (2002).

Abaza et al. "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," Journal of Protein Chemistry, 11(5):433-444 (1992).

Adle-Biassette et al., "Neuronal apoptosis does not correlate with dementia in HIV infection but is related to microglial activation and axonal damage," Neuropathology and Applied Neurobiology, 25(2):123-133 (1999).

Adler et al., "Regulation of JNK signaling by GSTp," The EMBO Journal, 18(5):1321-1334 (1999).

Ahmed et al., Basal Cancer Cell Survival Involves JNK2 Suppression of a Novel JNK1 /c-Jun /Bcl-3 Apoptotic Network. PLoS One Oct. 6, 2009;4(10):e7305.

Aisen et al., "A randomized controlled trial of prednisone in Alzheimer's disease," Neurology, 54(3): 588-593 (2000).

Aldrian-Herrada et al., "A peptide nucleic acid {PNA) is more rapidly internalized in cultured neurons when coupled to a retro-inverso delivery peptide. The antisense activity depresses the target mRNA and protein in magnocellular oxytocin neurons," Nucleic Acids Research, 26(21):4910-4916 (1998).

Asanuma et al., "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett. 359(1-2):57-60 (2004) (abstract only).

Assi et al., "The specific JNK inhibitor SP600125 targets tumour necrosis factor-alpha production and epithelial cell apoptosis in acute murine colitis" Immunology, 118(1):112-121 (2006).

Ausubel, Using Synthetic Oligonucleotides as Probes. Current Protocols in Molecular Biology 1988; suppl.: pp. 6.4.01-6.4.10.

Barichello et al., "Dexamethasone treatment reverses cognitive impairment but increases brain oxidative stress in rats submitted to pneumococcal meningitis," Oxidative Medicine and Cellular Longevity, 347(20):1-7 (2011).

Barr et al., "Identification of the Critical Features of a Small Peptide Inhibitor of JNK Activity," Science, 282(5389):642-643 (1998).

Berendsen, "A glimpse of the Holy Grail?" Science 282(5389):642-643 (1998).

Bessalle et al., "All-D-magainin: chirality, antimicrobial activity and proteolytic Resistance," FEBS Letters, 274(1-2):151-155 (1990).

Bloch et al., "Increased ERK and JNK activation and decreased ERK/JNK ratio are associated with long-term organ damage in patients with systemic lupus erythematosus," Rheumatology 53(6): 1034-1042 (2014).

Bogoyevitch et al, Taking the cell by stealth or storm? Protein transduction domains (PTDs) as versatile vectors for delivery. DNA Cell Biol. Dec. 2002;21(12):879-894.

Bonny et al., "A JIP-1-related Nuclear Protein Present in Insulin-secreting Cells" The Journal of Biological Chemistry, 273(4):1843-1846 (1998).

Bonny et al., "Cell-Permeable Peptide Inhibitors of JNK Novel Blockers of Beta-Cell Death. Diabetes," 50(1):77-82 (2001).

Bonny et al., "Pancreatic-Specific Expression of the Glucose Transporter Type 2 Gene: Identification of cis-Elements and Islet-Specific trans-Acting Factors," Molecular Endocrinology, 9(10):1413-1426 (1995).

Bonny et al., "Targeting the JNK Pathway as a Therapeutic Protective Strategy for Nervous System Diseases," Reviews in the Neurosciences, 16(1): 57-67 (2005).

Borsello et al., "A peptide inhibitor of c-Jun N-terminai kinase protects against excitotoxicity and cerebral ischemia" Nature Medicine 9(9):1180-1186 (2003).

Borsello et al., "Use of cell-permeable peptides to prevent neuronal degeneration" TRENDS in Molecular Medicine, 10(5):239-244 (2004).

Bost et al., The Jun Kinase 2 Isoform Is Preferentially Required for Epidermal Growth Factor-Induced Transformation of Human A549 Lung Carcinoma Cells. Mol Cell Biol. Mar. 1999;19(3):1938-1949.

Bowie, Deciphering the Message in Protein Sequences: Tolerance to Amino Acid Substitutions. Science Mar. 1, 19906;247(4948):1306-1310.

Bradley et al., "Limits of Cooperativity in a Structurally Modular Protein: Response of the Notch Ankyrin Domain to Analogous Alanine Substitutions in Each Repeat" J. Mol. Biol., 324(2): 373-386 (2002).

Brady et al., "Drug Design. Reflections on a peptide," Nature, 368(6473):692-693 (1994).

Branden et al., A peptide nucleic acid -nuclear localization signal fusion that mediates nuclear transport of DNA. Nat Biotechnol Aug. 1999; 17(8):784-787.

Branden et al., Introduction to Protein Structure, Garland Publishing Inc., New York, p. 2471(1999).

Branden et al., Introduction to Protein Structure, Second Edition, Garland Publishing, Inc., USA, p. 382 (1999).

Briand et al., A retro-inverso peptide corresponding to the GH loop of foot-and-mouth disease virus elicits high levels of long-lasting protective neutralizing antibodies. Proc Natl Acad Sci U S A. Nov. 11, 1997,94(23):12545-12450.

Brugidou et al., The Retro-Inverso Form of a Homeobox- Derived Short Peptide is Rapidly Internalised by Cultured Neurones: A New

(56) References Cited

OTHER PUBLICATIONS

Basis for an Efficient Intracellular Delivery System. Biochem Biophys Res Commun Sep. 14, 1995; 214(2): 685-693.
Budur et al., "A pharmacogenetics supported clinical trial to delay onset of mild cognitive impairment due to Alzheimer's disease using low dose pioglitazone: the tomorrow study," Neuropsychopharmacology, 39(1): S342 (2014).
Cardozo et al., Cell-permeable peptides induce dose-and length-dependent cytotoxic effects. Biochimica et Biophysica Acta 2007; 1768(9): 2222-2234.
Cerbone et al., "AS601245, an anti-inflammatory JNK inhibitor, and clofibrate have a synergistic effect in inducing cell responses and in affecting the gene expression profile in CaCo-2 colon cancer cells," PPAR Research, vol. 2012: 269751, 1-16 (2012).
Chaloin et al., Design of Carrier Peptide-Oligonucleotide Conjugates with Rapid Membrane Translocation and Nuclear Localization Properties. Biochem Biophys Res Commun Feb. 13, 1998; 243(2):601-608.
Chang et al., JNK1 Is Required for Maintenance of Neuronal Microtubules and Controls Phosphorylation of Microtubule-Associated Proteins. Dev Cell. Apr. 2003;4(4):521-533.
Chemical Abstracts Accession No. 2004:27781 & CAS Registry File CN 647864-97-9 copyright 2014:2pp.
Chemical Abstracts Database, Accession No. 133:204452 CA, (Sep. 29, 2000), 3 pages; XP002554007.
Chen et al., "The Role of o-Jun N-terminal Kinase (JNK) in Apoptosis induced by Ultraviolet C and gamma Radiation," J. of Bio. Chem., 271(50):31929-31936 (1996).
Chie et al., Identification of the Site of Inhibition of Oncogenic ras-p21-induced Signal Transduction by a Peptide from a ras Effector Domain. Journal of Protein Chemistry Nov. 1999; 18(8): 881-884.
Chorev and Goodman, A Dozen Years of Retro-Inverso Peptidomimetics. Acc. Chem. Res. 1993; 26(5): 266-273.
Chorev and Goodman, Recent developments in retro peptides and proteins—an ongoing topochemical exploration. Trends Biotechnol Oct. 1995: 13(10):438-445.
Creighton, Protein-Protein Interactions. Encyclopedia of Molecular Biology vol. 1, 1999:2027-2033.
Cui et al., JNK pathway: diseases and therapeutic potential. Acta Pharmacol Sin. May 2007;28(5):601-608.
Dang and Lee, Nuclear and Nucleolar Targeting Sequences of c-erb-A, c-myb, N-myc, p53, HSP70, and HIV tat Proteins. The Journal of Biological Chemistry Oct. 25, 1989; 264(30): 18019-18023.
Database UniProt, Retrieved from EBI, Database Accession No. Q9WVI9, Abstract (Feb. 28, 2003).
De Paiva et al., Essential Role for c-Jun N-Terminal Kinase 2 in Corneal Epithelial Response to Desiccating Stress. Arch Ophthalmol. Dec. 2009;127(12):1625-1631.
Derossi et al., Cell Internalization of the Third Helix of the Antennapedia Homeodomain Is Receptor-independent. The Journal of Biological Chemistry Jul. 26, 1996; 271(30): 18188-18193.
Designing Custom Peptides. Sigma Genosys website, <http://www.sigmagenosys.com/peptide_design.asp>, Dec. 16, 2004, 2 pages.
Dickens et al., A Cytoplasmic Inhibitor of the JNK Signal Transduction Pathway. Science Aug. 1, 1997;277(5326):693-696.
Ohelke et al., Van Regenmortel et al., Saito et al., Peptide Science-Present and Future, Edited by Y. Shimonishi, Kluwer Academic Publishers, Dordrecht, The Netherlands, pp. 782-787 and 805-807 (1999).
Okitsu et al., Protein Transduction Domains Enable isolated islets to Efficiently internalize the Target Protein. Transplantation Proceedings Feb. 2003; 35(1): 479.
Pan et al., Small peptide inhibitor of JNKs protects against MPTP-induced nigral dopaminergic injury via inhibiting the JNK-signaling pathway. Laboratory Investigation Feb. 2010; 90(2): 156-167.
Parenteau et al., Free uptake of cell-penetrating peptides by fission yeast. FEBS Letters, Aug. 29, 2005;579(21):4873-4878.
Parkinson's Disease: Challenges, Progress, and Promise., National Institute of Neurological Disorders and Stroke, NIH Publication No. 05-5595, <http://www.ninds.nih.gov/disorders/parkinsons_disease/parkinsons_research_pr.htm>, Dec. 2004.
Patel et al., Getting into the Brain: Approaches to Enhance Brain Drug Delivery. CNS Drugs. 2009;23(1):35-58.
Penco et al., Identification of an import signal for, and the nuclear localization of, human lactoferrin. Biotechnol. Appl. Biochem, Dec. 2001; 34 (Pt 3): 151-159.
Pennington, "Solid-Phase Synthesis of Peptides Containing the CH2NH Reduced Bond Surrogate," Methods in Molecular Biology Chapter 12, Peptide Synthesis Protocols, Pennington/Dunn (Eds.), Humana Press Inc., Tolowa, NJ, USA, 35:241-247 (1994).
Pinilla et al., Chap 5: The Versatility of Nonsupport-Bound Combinatorial Libraries. Combinatorial Peptide and Nonpeptide Libraries: A Handbook, ed. By G. Jung, VCH: 139-171 (1997).
Pirvola et al., Rescue of Hearing, Auditory Hair Cells, and Neurons by CEP-1347/KT7515, an Inhibitor of c-Jun N-Terminal Kinase Activation. The Journal of Neuroscience Jan. 1, 2000; 20 (1): 43-50.
Polyakov et al., Novel Tat-peptide chelates for direct transduction of technetium-99m and rhenium into human cells for imaging and radiotherapy. Bioconjug Chem. Nov.-Dec. 2000;11(6):762-771.
Prantner et al., Synthesis and Characterization of a Gd-DOTA-D-Permeation Peptide for Magnetic Resonance Relaxation Enhancement of Intracellular Targets. Molecular Imaging Oct. 2003; 2(4):333-341.
Qin and Qin, TAT Protein Transduction Domains: New Promise for Protein Therapy. Chin J Biochem Molec Biol. 2007;23(7):519-524-Incl Engl transl abstract only.
Ramanathan et al., Targeting the Sodium-Dependent Multivitamin Transporter (SMVT) for improving the Oral Absorption Properties of a Retro-Inverso Tat Nonapeptide. Pharmaceutical Research, Jul. 2001;18(7):950-956.
Ribeiro MM et al., Heme oxygenase-1 fused to a TAT peptide transduces and protects pancreatic beta-cells. Biochem Biophys Res Commun Jun. 13, 2003; 305(4):876-881.
Rickels et al., "Phage display selection of ligand residues important for Src homology 3 domain binding specificity," Proc Natl Acad Sci USA., 92(24):10909-10913 (1995).
Robinson et al., Properties and structure-activity studies of cyclic beta-hairpin peptidomimetics based on the cationic antimicrobial peptide protegrin I. Bioorg Med Chem Mar. 15, 2005; 13(6): 2055-2064.
Roduit, Raphael and Schorderet, Daniel F.—MAP Kinase Pathways in UV-Induced Apoptosis of Retinal Pigment—Epithelium ARPE19 Cells—Apoptosis—2008—vol. 13, No. 3, pp. 343-353—DOI 10.1007/s10495-008-0179-8—Springer Science +Business Media, LLC—USA.
Rojas et al., Controlling Epidermal Growth Factor (EGF)-stimulated Ras Activation in Intact Cells by a Cell-permeable Peptide Mimicking Phosphorylated EGF Receptor. J Biol Chem Nov. 1, 1996; 271(44): 27456-27461.
Roy et al., Role of the JNK signal transduction pathway in inflammatory bowel disease. World Journal of Gastroenterology Jan. 14, 2008; 14(2): 200-202.
Ruben et al., Structural and Functional Characterization of Human Immunodeficiency Virus tat Protein. Journal of Virology Jan. 1989; 63(1): 1-8.
Rudikoff et al., Single amino acid substitution altering antigen-binding specificity. Proc Natl Acad. Sci. USA Mar. 1982; 79(6):1979-1983.
Rudinger, Characteristics of the amino acids as components of a peptide hormone sequence. Peptide Hormones Jun. 1976, University Park Press, Baltimore, pp. 1-7.
Saar et al., Cell-penetrating peptides: A comparative membrane toxicity study. Anal Biochem. Oct. 1, 2005;345(1):55-65.
Sabapathy, Role of the JNK Pathway in Human Diseases. Prog Mol Biol Transi Sci. 2012;106:145-169.
Saito and Paterson, Contribution of Peptide Backbone Atoms to Binding of an Antigenic Peptide to Class I Major Histocompatibility Complex Molecule. Molecular Immunology Nov.-Dec. 1997; 34(16-17):1133-1145.

(56) References Cited

OTHER PUBLICATIONS

Sakane T. et al., "Current Concepts: Behcet's disease," The New England Journal of Medicine, 341(17):1284-1291 (1999).
Salh, c-Jun N-terminal kinases as potential therapeutic targets. Expert Opin Ther Targets. Oct. 2007;11(10):1339-1353.
Schimmer AD et al., The BH3 domain of BAD fused to the Antennapedia peptide induces apoptosis via its alpha helical structure and independent of Bd-2. Cell Death Differ Jul. 2001; 8(7): 725-733.
Schinzel and Drueckes, The phosphate recognition site of *Escherichia coli* maltodextrin phosphorylase. FEBS Lett Jul. 29, 1991; 286(1-2): 125-128.
Schwarze et al., In Vivo Protein Transduction: Delivery of a Biologically Active Protein into the Mouse. Science Sep. 3, 1999; 285(5433): 1569-1572.
Sebestyen et al., DNA vector chemistry: The covalent attachment of signal peptides to plasmid DNA. Nature Biotechnology Jan. 1998; 16(1):80-85.
Seki et al., A Liver Full of JNK: Signaling in Regulation of Ceil Function and Disease Pathogenesis, and Clinical Approaches. Gastroenterology. Aug. 2012;143(2):307-320.
Shimazawa et al., "Inhibitor of double stranded RNA-dependent protein kinase protects against cell damage induced by ER stress," Neurosci Lett., 409(3):192-195 (2006).
Smilek et al., A single amino acid change in a myelin basic protein peptide confers the capacity to prevent rather than induce experimental autoimmune encephalomyelitis. Proc. Natl. Acad. Sci. USA Nov. 1, 1991; 88(21):9633-9637.
Soejima et al., "Activation of MKK4 (SEK1), JNK, and C-Jun in Labial Salivary Infiltrating T Cells in Patients With Sjogren's Syndrome," Rheumatology International, 27(4): 329-333 (2006).
Spatola et al., "Chapter 11. Cyclic Peptide Libraries: Recent Developments," in Combinatorial Peptide and Nonpeptide Libraries: A Handbook (ed G. Jung), Wiley-VCH Verlag GmbH, Weinheim, Germany, pp. 327-347 (1997).
Stedman's Online Medical Dictionary Definition of "inflammation", 28th edition, Obtained from www.pdrel.com, last viewed on Dec. 18, 2010, 2 pages.
Stevens et al., Efficient Generation of Major Histocompatibility Complex Class 1-Peptide Complexes Using Synthetic Peptide Libraries. The Journal of Biological Chemistry Jan. 30, 1998; 273(5): 2874-2884.
Stevens et al., Peptide length preferences for rat and mouse MHC class I molecules using random peptide libraries. Eur. J. Immunol. 1998;28(4): 1272-1279.
Sumara et al., "Jnking" atherosclerosis. Cell Mol Life Sci. Nov. 2005;62(21):2487-2494.
Tachibana et al., JNK1 is required to preserve cardiac function in the early response to pressure overload. Biochem Biophys Res Common. May 19, 2006;343(4):1060-1066.
Tan et al., Selective Inhibition of ErbB2-Overexpressing Breast Cancer In vivo by a Novel TAT-Based ErbB2-Targeting Signal Transducers and Activators of Transcription 3-Blocking Peptide. Cancer Res Apr. 1, 2006,66(7):3764-3772.
Torchilin, Fluorescence microscopy to follow the targeting of liposomes and micelles to cells and their intracellular fate. Advanced Drug Delivery Reviews Jan. 2, 2005;57(1): 95-109.
Torgerson et al.—Regulation of NF-kappa B, AP-1, NFAT, and STATI Nuclear Import in T Lymphocytes by Noninvasive Delivery of Peptide Carrying the Nuclear Localization Sequence of NF-kappa B p50—Journal of Immunology—1998—pp. 6084-6092—vol. 161—The American Association of Immunologists—USA.
Touchard et al.—A Peptide Inhibitor of c-Jun N-Terminal Kinase for the Treatment of Endotoxin-Induced Uveitis—Immunology and Microbiology—Investigative Ophthalmology & Visual Science—Sep. 2010—pp. 4683-4693—vol. 51—No. 9—Association for Research in Vision and Ophthalmology—USA.
Van Regenmortel and MULLER, D-peptides as Immunogens and diagnostic reagents. Current Opinion in Biotechnoloy Aug. 1998; 9(4):377-382.

Vives et al.—Structure-Activity Relationship Study of the Plasma Membrane Translocating Potential of a Short Peptide from HIV-1 Tat Protein—Letters in Peptide Science—1997—pp. 429-436—vol. 4—Kluwer Academic Publishers—The Netherlands.
Vives et al., A Truncated HIV-1 Tat Protein Basic Domain Rapidly Translocates through the Plasma Membrane and Accumulates in the Cell Nucleus. The Journal of Biological Chemistry Jun. 20, 1997; 272(25):16010-16017.
Vocero-Akbani et al., Killing HIV-infected cells by transduction with an HIV protease-activated caspase-3 protein. Nature Medicine Jan. 1999; 5(1): 29-33.
Hollos, P., et al.," JNK Regulation of Depression and Anxieity," Brain Plasticity, 3:145-155 (2017/2018).
Fung, A. T., et al., "Multifocal Choroiditis Without Panuveits," Clinical Characteristics and Progression, Retina, 34:98-107.
Essex, R. W., et al., "Idiopathic Multifocal Choroiditis: A Comment on Present and Past Nomenclature," Retina, The Journal of Retinal And Vitreous Disease, 33(1):1-4 (2013).
Adhikary, G., et al.," C-Jun NH2 terminal kinase (JNK) is an essential mediator of Toll-like receptor 2-induced corneal inflammation," Journal of Leukoeyte Biology, 83:991-997 (2008).
Office Action dated Mar. 11, 2020 in U.S. Appl. No. 15/934,735.
Kelekar and Thompson, Bcl-2-family proteins: the role of the BH3 domain in apoptosis. Trends Cell Biol. Aug. 1998;8(8):324-330.
Kennedy and Davis, Role of JNK in Tumor Development. Cell Cycle May-Jun. 2003; 2(3); 199-201.
Kida et al., Design and synthesis of a Tat-related gene transporter: A tool for carrying the adenovirus vector into cells. Bioorganic & Medicinal Chemistry Letters Feb. 2006; 16(3): 743-745.
Kieber-Emmons et al., Therapeutic peptides and peptidomimetics. Current Opinion in Biotechnology Aug. 1997; 8(4):435-441.
Killick et al, Ciusterin regulates ß-amyloid toxicity via Dickkopf-I-driven induction of the wnt-PCP-JNK pathway. Mol Psychiatry. Jan. 2014;19(1):88-98.
Kisselev, Polypeptide Release Factors in Prokaryotes and Eukaryotes: Same Function, Different Structure. Structure Jan. 2002 ; 10(1):8-9.
Kuan et al., A critical role of neural-specific JNK3 for ischemic apoptosis. Proc Natl Acad Sci USA., Dec. 9, 2003;100(25):15184-15189.
Kugler et al., MAP kineaseathways involved in glioblastoma response to erucylphosphocholine, Int J Oncol. Dec. 2004;25(6):1721-1727.
Lebleu, Delivering information-rich drugs-prospects and challenges. Trends Biotechnol. Apr. 1996;14(4):109-10.
Lee et al., c-Jun N-terminal Kinase (JNK) Mediates Feedback Inhibition of the Insulin Signaling Cascade. The Journal of Biological Chemistry Jan. 31, 2003;278(5): 2896-2902.
Lewis et al., Lymphoma Cell Uptake of Radiometal- and Fluorescent-Labelled Bd-2 Antisense Pna Conjugates is Mediated by a Retro-Inverso Delivery Peptide. J. Label Compd. Radiopharm.2003; 46(S1): S13.
Li, Specificity and versatility of SH3 and other proline-recognition domains: structural basis and implications for cellular signal transduction. Biochem. J. Sep. 15. 2005; 390(Pt 3): 641-653.
Lim et al., Penetration enhancement in mouse skin and lipolysis in adipocytes by TAT-GKH, a new cosmetic ingredient, journal of Cosmetic Science Sep.-Oct. 2003; 54(5): 483-491.
Lin et al., Inhibition of Nuclear Translocation of Transcription Factor NF-kappa B by a Synthetic Peptide Containing a Cell Membrane-permeable Motif and Nuclear Localization Sequence. The Journal of Biological Chemistry Jun. 16, 1995; 270(24): 14255-14258.
Lloyd-Williams et al., Chapter 5: formation of Disulfide Bridges. Chemical Approaches to the Synthesis of Peptides and Proteins. Library of Congress Cataloging-in-Publication Data c. 1997, CRC Press LLC: 209-236.
Lloyd-Williams et al., Chapter 6: Peptide Libraries. Chemical Approaches to the Synthesis of Peptides and Proteins. Library of Congress Cataloging-in-Publication Data c. 1997, CRC Press LLC: 237, 264-267.
Manheimer, PH0878; 1g kappa chain V region. NCB I Sequence Viewer v2., GenBank May 30, 1997.

(56) References Cited

OTHER PUBLICATIONS

Mann and Frankel, Endocytosis and targeting of exogenous HIV-1 Tat Protein. The EMBO Journal, Jul. 1991; 10(7): 1733-1739.
Manning et al., "Targeting JNK for therapeutic benefit: from junk to gold?" Nature Reviews Drug Discovery, 2: 554-565 (2003).
Marino et al., Inhibition of experimental autoimmune encephalomyelitis in SJL mice by oral administration of retro-inverso derivative of encephalitogenic epitope P87-99. Eur. J. Immunol. Aug. 1999; 29(8):2560-2566.
Marks et al., Protein Targeting by Tyrosine- and Di-leucine-based Signals: Evidence for Distinct Saturable Components, J Cell Biol. Oct. 1996; 135(2): 341-354.
Mayer, SH3 domains: complexity in moderation. Journal of Cell Science Apr. 2001; 114(Pt 7): 1253-1263.
Mazur and Perrino, Identification and Expression of the TREXI and TREX2 cDNA Sequences Encoding Mammalian 3'->5' Exonucleases. The Journal of Biological Chemistry Jul. 9, 1999; 274(28):19655-19660.
Melikov and Chernomordik, Arginine-rich cell penetrating peptides: from endosomaluptake to nuclear delivery. Cellular and Molecular Life Sciences Dec. 2005; 62(23):2739-2749.
Melino et al., "The effect of the JNK Inhibitor, JIP peptide, on human T lymphocyte proliferation and cytokine production," 181(10): 7300-7306 (2008).
Messer, "MBC 3320 Posterior Pituitary Hormones," Vasopressin and Oxytocin. http://www.neurosci.pharm.utoledo.edu /MBC3320 /vasopressin.htm, Apr. 2000 3:1-5.
Mi et al., Characterization of a Class of Cationic Peptides Able to Facilitate Efficient Protein Transduction in Vitro and in Vivo. Molecular Therapy Oct. 2000; 2(4):339-347.
Milano et al., A peptide inhibitor of c-Jun NH2-terminal kinase reduces myocardial ischemia-reperfusion injury and infarct size in vivo. Am J Physiol Heart Circ Physiol Apr. 2007; 292(4): H 1828-H 1835.
Mitsuyama et al., Pro-inflammatory signaling by Jun-N-terminal kinase in inflammatory bowel disease. Int J Mol Med. Mar. 2006;17(3):449-455.
Mooi et al., Regulation and structure of an *Escherichia coli* gene coding for an outer membrane protein involved in export of K88ab fimbrial subunits. Nucleic Acids Research Mar. 25, 1986; 14(6): 2443-2457.
Moon et al., Bd-2 overexpression attenuates SP600125- induced apoptosis in human leukemia U937 cells. Cancer Letters Jun. 18, 2008; 264(2): 316-325.
Mooser et al.—Genomic Organization, Fine-Mapping, and Expression of the Human Islet—Brain 1 (IB1) /C-Jun-Amino-Terminal Kinase Interacting Protein-1 (JIP-1) Gene—Genomics—Jan. 15, 1999—pp. 202-208—vol. 55—Academic Press—USA.
Moschos et al., Lung Delivery Studies Using siRNA Conjugated to TAT(48-60) and Penetratin Reveal Peptide Induced Reduction in Gene Expression and Induction of Innate Immunity. Bioconjug Chem. Sep.-Oct. 2007;18 (5):1450-1459.
Moulin et al. "Islet-brain (IB)/JNK-interacting proteins (JIPs): future targets for the treatment of neurodegenerative diseases?" Current Neurovascular Research, 1(2):111-127 (2004).
Nagahara et al., Transduction of full-length TAT fusion proteins into mammalian cells: TAT-p27Kipl induces cell migration. Nature Medicine Dec. 1998; 4(12): 1449-1452.
Nakamura et al., "Expression of mitogen activated protein kinases in labial salivary glands of patients with Sjogren's syndrome," Annals of the Rheumatic Diseases, 58(6):382-385 (1999).
NCBI Sequence Viewer—Accession No. AAD20443—Reports—Islet—Brain 1 (*Homo sapiens*)—Two References—Mooser et al.—Mar. 17, 1999—2 pages—USA.
NCBI Sequence Viewer—Accession No. AAD22543—Reports—Islet—Brain 1 (Rattus Norvegicus)—Three References—Bonny et al.—Mar. 1, 2006—2 pages—USA.
NCBI Sequence Viewer—Accession No. AF074091—Reports—*Homo sapiens* Islet-Brain 1 mRNA—Complete Cds.—Two References—Mooser et al.—Mar. 17, 1999—2 pages—USA.
NCBI Sequence Viewer—Accession No. AF108959—Reports—Rattus Norvegicus Islet.—Brain 1 (IB1) mRNA—Complete Cds.—Three References—Bonny et al.—Mar. 1, 2006—2 pages—USA.
NCBI Sequence Viewer—Accession No. AF218778—Reports—*Homo sapiens* Islet-Brain 2 mRNA—Complete Cds—Three References—Kristensen et al.—Mar. 2, 2006—2 pages—USA.
NCBI Sequence Viewer—Accession No. PH0878—Reports—Ig Kappa Chain V Region (Anti-DNA, SNA)—Human (Fragment) One Reference—Manheimer-Lory et al.—May 30, 1997—1 page—USA.
Negri et al., Design of a Novel Peptide inhibitor of the JNK Signaling Pathway. Diabetes Abstract Book, 61st Scientific Sessions, Pennsylvania Convention Center, Philadelphia, PA 2001; 50 Supplement (2): A294 (1217-P).
Neundorf et al., Detailed Analysis Concerning the Biodistribution and Metabolism of Human Calcitonin-Derived Cell-Penetrating Peptides. Bioconjugate Chem. Aug. 2008; 19(8): 1596-1603.
Ngo et al., Computational Complexity, Protein Structure Prediction, and the Levinthal Paradox. The Protein Folding Problem and Tertiary Structure Prediction c. Birchuser Boston 1994; 433, 491-495.
Noguchi et al., Cell Permeable Peptide of JNK Inhibitor Prevents Islet Apoptosis Immediately After Isolation and Improves Islet Graft Function. Am J Transplant. Aug. 2005;5(8):1848-1855.
Noguchi et al., Effect of JNK Inhibitor During islet Isolation and i ransplantation. Transplant Proc. Mar. 2008;40(2):379-381.
Noguchi et al., Regulation of c-Myc through Phosphorylation at Ser-62 and Ser-71 by c-Jun N-Terminal Kinase. J Biol Chem Nov. 12, 1999; 274(46): 32580-32587.
Nori and Kopecek, intracellular targeting of polymer-bound drugs for cancer chemotherapy. Advanced Drug Delivery Reviews Feb. 28, 2005;57(4):609-636.
Nori et al., Tat-Conjugated Synthetic Macromolecules Facilitate Cytoplasmic Drug Delivery To Human Ovarian Carcinoma Cells. Bioconjugate Chem. Jan.-Feb. 2003; 14(1): 44-50.
133:204452, Interaction of native RNAs with Tat peptides. Chemical Abstracs Database Sep. 2000 29:1-3.
Agrawal, Vishal and Kishan, KV. Radha—Promiscuous Binding Nature of SH3 Domains to their Target Proteins—Protein and Peptide Letters—2002—pp. 185-193—vol. 9—No. 3—Bentham Science Publishers Ltd.—USA.
Auerbach et al., "Angiogenesis assays: Problems and pitfalls," Cancer and Metastasis Reviews, 19: 167-172 (2000).
Barr et al., Identification of the Critical Features of a Small Peptide Inhibitor of JNK Activity. The Journal of Biochemical Chemistry Mar. 29, 2002; 277(13):10987-10997.
Branden and Tooze, Prediction, Engineering and Design of Protein Structures, Introduction to Protein Structure, 1991:247.
Chung et al., "Endogenous Nerve Growth Factor Regulates Collagen Expression and Bladder Hypertrophy Through AKT and MARK Pathways During Cystitis," Journal of Biological Chemistry, 285: 4206-4212 (2010).
Conti et al., "Atherosclerosis: a chronic inflammatory disease mediated by mast cells", Central European Journal of Immunology, 2015, pp. 380-386 (Year: 2015).
International Search Report and Written Opinion dated Jun. 2, 2010 issued in PCT/EP2009/009228.
International Search Report and Written Opinion dated Apr. 27, 2010 issued in PCT/EP2009/009229.
Database WPI, 2010, Thomson Scientific, Table 1, 1-4_ XP002643212.
Donath et al.,Type 2 diabetes as an inflammatory disease, Nature Reviews—Immunology, 2011, pp. 98-107 (Year: 2011).
Duby et al. (Contributors)—Using Synthetic Oligonucleotides as Probes—Current Protocols in Molecular Biology—Supplement 2—Apr. 1988—pp. 6.4.1-6.4.10—John Wiley & Sons—Document No. XP 002044485—USA.
Dugan et al., "Role of c-Jun N- terminal Kinase (JNK) activation in micturition reflexes in cyclophosphamide (CYP)-induced cystitis in female rats", Society for Neuroscience Abstract Viewer and itinerary Planner,2011,41st Ann. Meeting of the Society-for-Neuroscience Washington, DC, USA. Nov. 12-16 (Year: 2011).

(56) References Cited

OTHER PUBLICATIONS

Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.
Fujita et al.—Prophylactic or Therapeutic Agent for Retinal Diseases and Method for Preventing or Treating Retinal Diseases, Each Comprising JNK (C-JUN N-Terminal Kinase)-Inhibiting Peptide, and Use of the Peptide—International Application No. PCT/JP2010/55208—Santen Pharmaceutical Co., Lid.—Database WPI—Thompson Scientific—pp. 1-4—XP-002643212—USA.
Guichard et al., "Mimicry of an immunodominant Epitope of Foot and Mouth Disease Virus with Retro-inverson Isomers: A New Approach in the Design of Peptide Based Vaccines," Peptides (Ramage et al. ed) 447-448 (1996).
Guichard et al., Partially Modified Retro -inverson Psudopeptides as Non-natural Ligands for the Human Class I Histocompatibility Molecule, HLA-A2, Peptides (Ramage et al. ed) 449-450 (1996).
Guichard et al., Chapters 165 and 166; Gur'Yanov et al., Chapter 167: In R. Ramage and R. Epton (eds.), Peptides 1996 : Proceedings of the Twenty-Fourth European Peptide Symposium (Sep. 813, 1996, Edinburgh, Scotland), European Peptide Society, Mayflower Scientific Ltd., United Kingdom), pp. 447-451 (1998).
Hillier et al., *Homo sapiens* cDNA clone. EMBL Sequence Database, 1995 R85141.
Horvath et al., "Somatostatin Octa- and Heptapeptides, Structural and Biological Characteristics," Peptides (Ramage el al, ed) 483-484 (1996).
Horvath et al., Chapter 183; Hruby et al., Chapter 184; In R. Ramage and R. Epton (eds,), Peptides 1996 : Proceedings of the Twenty-Fourth European Peptide Symposium (Sep. 8-13, 1996, Edinburgh, Scotland), European Peptide Society, Mayflower Scientific Ltd., United Kingdom), pp. 483-486 (1996).
Hruby et al., "Design of Potent and Specific Melanotropin Agonists and Antagonists: Investigating Ligands for New Receptors," Peptides (Ramage et al, ed) 485 -486 (1996).
Jain, R., "Barriers to Drug Delivery in Solid Tumors," Scientific American, 58-65 (1994).
Janin, "Protein-Protein Interactions" Encyclopedia of Molecular Biology (Creighton, ed.) 2027-2033 (1999).
Juszczak et al., "Animal models of overactive bladder: Cyclophosphamide (CYP)-induced cystitis in rats", N46, EAU 3rd North Eastern European Meeting (NEEM)/ European Urology Supplements 8 (2009) 583-584 (Year: 2009).
Kishan, KV. Radha and Agrawal, Vishal—SH3-like Fold Proteins are Structurally Conserved and Functionally Divergent—Current Protein and Peptide Science—1995—pp. 143-150—vol. 6—Bentham Science Publishers Ltd.—USA.
Multifocal choroiditis, "National Center of Advancing Translational Science," https : / /rarediseases.info.nih.gov/diseases /9824 /multifocal-choroiditis; 5 pages (2017).
Murdoch et al., "Chronic inflammation and asthma," Mutation Research, 2010, pp. 24-39 (Year: 2010).
NCBI Sequence Viewer—Accession No. AAF32323—Reports—Islet-Brain 2 (*Homo sapiens*)—Two References—Negri et al.—Feb. 9, 2000—2 pages—USA.
Neidle, S. ed., "Cancer Drug Design and Discovery," Elsevier/ Acaderic Press, 427-431 (2008).
Oehlke et al., Rapid Translocation of Amphipathic a-Helical and (3-Sheet-Forming Peptides through Plasma Membranes of Endothelian Cells, Peptide Science—Present and Future (Shimonishi eds.), Kluwer Academic Publisher, United Kingdom, pp. 782-783 (1999).
Pennington, Michael W. and Dunn, Ben M. {Editors)—Chapter 11—Design of Novel Synthetic Peptides including Cyclic Conformationally and Topgraphically Constrained Analogs—Hruby, Victor and Bonner, G. Gregg—Methods in Molecular Biology—vol. 35—Peptide Synthesis Protocols—1994—pp. 201-239—Humana Press Inc.—USA.
Q9WVI9, JIPI_Mouse Standard; PRT; 707 AA. Database UniProt 2003.
Ramage and Epton, Peptides 1996: Proceedings of the Twenty-Fourth European Peptide Symposium. The European Peptide Society c. 1998: 447-451, 483-487.
Rovina et al., "Inflammation and Immune Response in COPD: Where Do We Stand?," Mediators of Inflammation, 2013, pp. 1-9 Year: 2013).
Saito et al., "Contribution of peptide backbone atoms to binding of antigenic peptide to class I major histocompatibility complex molecule," Peptide Science—Present and Future (Shimonishi, ed.) 805-807 (1999).
Sclip A et al. c-Jun N-terminai kinase has a key role in Alzheimer disease synaptic dysfunction in vivo. Cell Death and Disease, 5, e1019. Published online Jan. 23, 2014. (Year: 2014).
Sclip A et al. c-Jun N-terminal kinase regulates soluble Abeta oligomers and cognitive impairment in AD mouse model. J. Biol. Chem. 286(51), 43871-43880. (Year: 2011).
Selective Dimerisation of Cysteines to form Heterodimers. NJE Feb. 3, 1997.
Sharma N et al. SP600125, a competitive inhibitor of JNK attenuates streptozotocin induced neurocognitive deficit and oxidative stress in rats. Pharmacology, Biochemistry and Behavior, 96, 386-394. (Year: 2010).
Shimonishi, Peptide Science—Present and Future: Proceedings of the 1st International Peptide Symposium. C. 1999 Kluwer Academic Publishers: 782-787, 805-807.
Sporn et al., "Chemoprevention of cancer," Carcinogenesis, 21: 525-530 (2000).
TgCRND8 Research Model, Alzforum, www.alzforum.org /research-models /tgcrnd8, retrieved Nov. 25, 2018. (Year: 2018).
Theoretical p1 /Mw average of the amino acid sequence DQSRPVOPFLNLTTPRKPRPPRRRQRRKKRG; http: //web.expasy.org /cgi- bin /compute_pi /pi_tool; obtained Sep. 20, 2017; p. 1 (2017).
Thoren et al.—The Antennapedia Peptide Penetratin Translocates across Lipid Bilayers—The First Direct Observation—FEBS Letters—2000—pp. 265-268—No. 482—Federation of European Biochemical Societies—Elsevier Science B.V.—Europe.
Todd et al., "GeneticProtection from the Inflammatory Disease Type 1 Diabetes in Humans and Animal Models ", Immunity, pp . 387-395 (Year: 2001).
Tournier et al.—Mitogen-Activated Protein Kinase Kinase 7 is an Activator of the c-Jun NH2-Terminal Kinase—Cell Biology—Proceedings of the National Academy of Science—Jul. 1997—pp. 7337-7342—vol. 94—National Academy of Science—USA.
Tsuyoshi et al., Behcet's disease. NE J Med. 1999:1284-1291.
Van Regenmortel et al., "Peptide analogues as vaccines and immunomodulators," Peptide Science—Present and Future (Shimonishi, ed) 784-787 (1999).
Wyszko et al., "Interaction of Native RNAs with Tat Peptides," RNA Biochemistry and Biotechnology, NATO Science Series, 70:277-290 (1999); Chemical Abstracts Database Accession Na 133:204452.
XG-102 C-Terminal acid, Compound Summary for CID 72941992, PubChem, pubchem.ncbi.nlm.nih.gov/compound /72941992#section =Top. retrieved Nov. 24, 2018. (Year: 2018).
Office Action dated Feb. 1, 2016 issued in U.S. Appl. No. 14/367,706, 24 pages.
Office Action dated Apr. 8, 2019 issued in U.S. Appl. No. 15/934,735, 8 pages.
Office Action dated Mar. 21, 2014 issued in U.S. Appl. No. 13/141,314, 21 pages.
Office Action dated Jul. 31, 2014 issued in U.S. Appl. No. 13/141,314, 17 pages.
Office Action dated Aug. 27, 2015 issued in U.S. Appl. No. 13/141,314, 9 pages.
Office Action dated Mar. 23, 2017 issued in U.S. Appl. No. 14/891,067, 14 pages.
Office Action dated Nov. 20, 2017 issued in U.S. Appl. No. 14/891,067, 12 pages.
Office Action dated Jun. 14, 2018 issued in U.S. Appl. No. 14/891,067, 15 pages.
Office Action dated Mar. 22, 2019 issued in U.S. Appl. No. 14/891,067, 17 pages.

(56) References Cited

OTHER PUBLICATIONS

Office Action dated Sep. 27, 2019 issued in U.S. Appl. No. 14/891,067, 10 pages.
Office Action dated Aug. 16, 2018 issued in U.S. Appl. No. 15/321,893, 8 pages.
Office Action dated Dec. 4, 2017 issued in U.S. Appl. No. 15/321,904, 14 pages.
Office Action dated Nov. 29, 2018 issued in U.S. Appl. No. 15/737,480, 16 pages.
Office Action dated Jan. 30, 2019 issued in U.S. Appl. No. 15/628,771, 17 pages.
Office Action dated Aug. 24, 2017 issued in U.S. Appl. No. 15/516,943, 14 pages.
Office Action dated Jun. 15, 2018 issued in U.S. Appl. No. 15/516,943, 9 pages.
Office Action dated Jan. 10, 2019 issued in U.S. Appl. No. 15/516,943, 10 pages.
Office Action dated Aug. 8, 2019 issued in U.S. Appl. No. 15/516,943, 11 pages.
Office Action dated Dec. 11, 2013 issued in U.S. Appl. No. 14/035,450, 9 pages.
Office Action dated Sep. 24, 2014 issued in U.S. Appl. No. 14/035,450, 7 pages.
Office Action dated Apr. 27, 2015 issued in U.S. Appl. No. 14/035,450, 10 pages.
Office Action dated Aug. 31, 2015 issued in U.S. Appl. No. 14/035,450, 10 pages.
Office Action dated May 2, 2016 issued in U.S. Appl. No. 14/035,450, 10 pages.
Office Action dated Oct. 23, 2017 in U.S. Appl. No. 15/217,326, 21 pages.
Office Action dated May 13, 2018 in U.S. Appl. No. 15/217,326, 16 pages.
Office Action dated Feb. 7, 2019 in U.S. Appl. No. 15/217,326, 14 pages.
Office Action dated Jan. 26, 2017 in U.S. Appl. No. 14/849,374, 19 pages.
Office Action dated Sep. 26, 2017 in U.S. Appl. No. 14/849,374, 16 pages.
Office Action dated Mar. 29, 2017 in U.S. Appl. No. 15/045,058, 43 pages.
Office Action dated Jul. 22, 2015 in U.S. Appl. No. 14/144,938, 12 pages.
Office Action dated Dec. 28, 2010 in U.S. Appl. No. 12/066,657, 27 pages.
Office Action dated Jun. 28, 2010 in U.S. Appl. No. 12/066,657, 9 pages.
Office Action dated Jul. 19, 2012 in U.S. Appl. No. 12/066,657, 13 pages.
Office Action dated Jul. 8, 2011 in U.S. Appl. No. 12/101,911, 14 pages.
Office Action dated Aug. 29, 2006 in U.S. Appl. No. 10/457,614, 21 pages.
Office Action dated Oct. 12, 2007 in U.S. Appl. No. 10/457,614, 17 pages.
www.healthline.com—"What is Cystitis?", obtained Sep. 21, 2019; pp. 1-14 (Year: 2019).
Bennett, Bryden L., et al., "SP600125, an anthrapyrazolone inhibitor of Jun N-terminal kinase," PNAS, 98(24):13681-13686, Nov. 20, 2001.
Office Action dated Oct. 31, 2019 issued in U.S. Appl. No. 15/934,735, 9 pages.
NIH, "Panuveitis", https://rarediseases.info.nih.gov/diseases/8577/panuveitis; 2016, pp. 1-7 (2016).
Garg, "Successful Management of Uveitis in a Patient with Unilateral Multifocal Choroiditis", Insert to Retina Today, pp. 1-8 (2019).
Voet and Voet, Abnormal Hemoglobins. Biochemistry Second Edition c. 1995; section 9.3:235-241.
Wadia et al., Delivery of Novel AntiCancer Peptides by Protein Transduction Domains. American Pharmaceutical Review, 7(3): 65-69 (2004).
Waldmeier et al., Recent clinical failures in Parkinson's disease with apoptosis inhibitors underline the need for a paradigm shift in drug discovery for neurodegenerative diseases. Biochemical Pharmacology Nov. 15, 2006; 72(10):1197-1206.
Walsh et al., Erythrocyte survival is promoted by plasma and suppressed by a Bak-derived BH3 peptide that interacts with membrane-associated Bcl-X(L). Blood May 1, 2002; 99(9): 3439-3448.
Wang et al., "JNK inhibition as a potential strategy in treating Parkinson's disease," Drug News Perspect., 17(10):646-654 (2004).
Wang et al., A Single Amino Acid Determines Lysophopholipid Specificity of the S1 P1 (EDG1) and LPA1 (EDG2) Phospholipid Growth Factor Receptors. J Biol Chem. Dec. 28, 2001;276(52):49213-49220.
Wells, Additivity of Mutational Effects in Proteins. Biochemistry Sep. 18, 1990;29(37):8509-8517.
Wender et al., The design, synthesis, and evaluation of molecules that enable or enhance cellular uptake: Peptoid molecular transporters. Proc Natl Acad Sci USA Nov. 21, 2000; 97(24):13003-13008.
Weston et al., "The JNK signal transduction pathway," Curr. Opin. Cell Biol., 19(2):142-149, (2007).
Westwick et al., Activation of Jun Kinase Is an Early Event in Hepatic Regeneration. J Clin invest. Feb. 1995;95(2):803-810.
Whitmarsh and Davis, Transcription factor AP-1 regulation by mitogen-activated protein kinase signal transduction pathways. Journal of Molecular Medicine Oct. 1996; 74(10):589-607.
Whitmarsh et al., A Mammalian Scaffold Complex That Selectively Mediates MAP Kinase Activation. Science Sep. 11, 1998; 281(5383):1671-1674.
Wilson, Preventing Nerve Cell Death in ALS. Internet http://www.als.ca /_news /57.aspx?print =1& Dec. 5, 2001: 1-2.
Wishart et al., A Single Mutation Converts a Novel Phosphotyrosine Binding Domain into a Dual-specificity Phosphatase. J Biol Chem Nov. 10, 1995;270(45):26782-26785.
Witkowski et al., Conversion of a Beta-Ketoacyl Synthase to a Malonyl Decarboxylase by Replacement of the Active-Site Cysteine with Glutamine. Biochemistry Sep. 7, 1999; 38(36): 11643-11650.
Yamamoto et al., Molecular Design of Bioconjugated Cell Adhesion Peptide with a Water-Soluble Polymeric Modifier for Enhancement of Antimetastatic Effect. Current Drug Targets Apr. 2002; 3(2):123-130.
Yang et al., Differential targeting of MAP kinases to the ETS-domain transcription factor Elk-1. The EMBO Journal Mar. 16, 1998; 17(6): 1740-1749.
Yasuda et al., The JIP Group of Mitogen-Activated Protein Kinase Scaffold Proteins. Molecular and Cellular Biology, Oct. 1999; 19(10): 7245-7254.
Zhang et al., Preparation of functionally active cell-permeable peptides by single-step ligation of two peptide modules. Proc. Natl. Acad. Sci. USA Aug. 4, 1998; 95(16): 9184-9189.
Zoukhri et al., c-Jun NH2-terminal kinase mediates interleukin-1 beta-induced inhibition of lacrimal gland secretion. J Neurochem Jan. 2006;96: 126-135.
Database WPI, Thompson Scientific, Accession No. 2010-M79716, 3 pages (2010).
U.S. Appl. No. 14/891,067, filed Nov. 13, 2016.
U.S. Appl. No. 15/217,326, filed Jul. 22, 2016.
U.S. Appl. No. 15/516,943, filed Apr. 5, 2017.
U.S. Appl. No. 15/934,735, filed Mar. 23, 2018.
U.S. Appl. No. 16/222,387, filed Dec. 17, 2018.
U.S. Appl. No. 16/525,234, filed Jul. 29, 2019.
Extended European Search Report from European Application No. 20000027.1 dated Jul. 28, 2020.
Dickens et al., Database—Uniprot—Retrieved from EBI—Database Accession No. Q9W19—Abstracts—32-28-2003—Document No. XP-002366175—USA.
Dietz and Bahr, Delivery of bioactive molecules into the cell: the Trojan horse approach. Mol. Cell, Neurosci. Oct. 2004;27(2):85-131.

(56) References Cited

OTHER PUBLICATIONS

Dominguez-Bendala et al., TAT-Mediated Neurogenin 3 Protein Transduction Stimulates Pancreatic Endocrine Differentiation In Vitro. Diabetes Mar. 2005; 54(3): 720-726.
Du et al., JNK inhibition reduces apoptosis and neovascularization in a murine model of age-related macular degeneration, Proc Natl Acad Sci USA. Feb. 5, 2013;110(6):2377-2382.
Dugan et al., "Role of c-Jun N-terminal Kinase (JNK) activation in micturition reflexes in cyclophosphamide (CYP)-induced cystitis in female rats," Journal of Molecular Neuroscience, 54(3):360-369 (2014).
Elliott and Ohare, Intercellular Trafficking and Protein Delivery by a Herpesvirus Structural Protein. Cell Jan. 24, 1997; 88(2): 223-233.
EMBL Sequence Database—R85141, Hillier et al., *Homo sapiens*,The WashU-Merck EST Project, p. 1, XP-002076858, USA (Aug. 17, 1995).
Fawell et al., Tat-mediated delivery of heterologous proteins into cells. Proc. Natl. Acad. Sci. USA Jan. 18, 1994; 91(2):664-668.
Ferrandi et al., Inhibition of C-Jun N-terminal kinase decreases cardiomyocyte apoptosis and infarct size after myocardial ischemia and repertusion in anaesthetized rats. Br J Pharmacol. Jul. 2004;142(6):953-960.
Fornoni et al., The L-isoform but not D-isoforms of a JNK inhibitory peptide protects pancreatic Beta-cells. Biochem Biophys Res Commun Mar. 2, 2007;354(1):227-233.
Frankel and Pabo, Cellular Uptake of the Tat Protein from Human Immunodeficiency Virus. Cell Dec. 23, 1988; 55(6): 1189-1193.
Frankel et al., Activity of synthetic peptides from the Tat protein of human immunodeficiency virus type 1. Proc. Natl. Acad. Sci. USA Oct. 1989; 86(19):7397-7401.
Futaki et al., Arginine-rich Peptides: An Abundant Source of Membrane-Permeable Peptides Having Potential as Carriers for Intracellular Protein Delivery. The Journal of Biological Chemistry Feb. 23, 2001; 276(8): 5836-5840.
Gammon et al., Quantitative Analysis of Permeation Peptide Complexes Labeled with Technetium-99m: Chiral and Sequence-Specific Effects on Net Cell Uptake., Bioconjugate Chem. Mar.-Apr. 2003; 14(2): 368-376.
GenBank Database Accession No. AAD20443. islet-brain 1 [*Homo sapiens*], GenBank Mar. 17, 1999: 1-2.
GenBank Database Accession No. AAD22543. islet-brain 1 (Rattus norvegicus]. GenBank Mar. 1, 2006: 1-2.
GenBank Database Accession No. AF074091. *Homo sapiens* islet-brain 1 mRNA, complete cds. GenBank Mar. 17, 1999: 1-2.
GenBank Database Accession No. AF108959. Rattus norvegicus islet-brain 1 (IBI) mRNA, complete cds. GenBank Mar. 1, 2006: 1-3.
GenBank Database Accession No. AF218778. *Homo sapiens* islet-brain 2 mRNA, complete cds. GenBank Mar. 2, 2006: 1-2.
Giorello et al., Inhibition of Cancer Cell Growth and c-Myc Transcriptional Activityby a c-Myc Helix 1-Type Peptide Fused to an Internalization Sequence. Cancer Research Aug. 15, 1998: 58(16): 3654-3659.
Gotthardt et al., Interactions of the Low Density Lipoprotein Receptor Gene Family with Cytosolic Adaptor and Scaffold Proteins Suggest Diverse Biological Functions in Cellular Communication and Signal Transduction. The Journal of Bioiogical Chemistry Aug. 18, 2000; 275(33):25616-25624.
Guichard et al., Antigenic mimicry of natural L-peptides with retro-inverso-peptidomimetics. Proc. Natl. Acad. Sci. USA Oct. 11, 1994; 91(21): 9765-9769.
Guichard et al., Partially Modified Retro-Inverso Pseudopeptides as Non-natural Ligands for the Human Class I Histocompatibility Molecule HLA-A2. Journal of Medicinal Chemistry May 10, 1996; 39(10): 2030-2039.
Guichard et al.; Horvath et al.; Hruby et al., Peptides 1996: Proceedings of the twenty-fourth European Peptide Symposium, Sep. 8-13, 1996, Edinburgh, Scotland; Ramage /Epton (Eds.), The European Peptide Society, Mayflower Scientific Ltd., Kingswinford, pp. 447-450 and 483-486 (1996).

Gunaseelan et al., Synthesis of Poly( ethylene glycol)-Based Saquinavir Prodrug Conjugates and Assessment of Release and Anti-HIV-1 Bioactivity Using a Novel Protease Inhibition Assay, Bioconjugate Chem. Nov.-Dec. 2004; 15(6): 1322-1333.
Gura, Systems for identifying New Drugs Are Often Faulty. Science Nov. 7, 1997; 278(5340):1041-1042.
Hanyu et al., "Pioglitazone improved cognition in a pilot study on patients with Alzheimer's disease and mild cognitive impairmenl with diabetes mellitus," Journal of the American Geriatrics Society, 57(1):177-179 (2009).
Hauber et al., Mutational Analysis of the Conserved Basic Domain of Human Immunodeficiency Virus tat Protein. Journal of Virology Mar. 1989: 63(3): 1181-1187.
Hawiger, Noninvasive intracellular delivery of functional peptides and proteins. Current Opinion in Chemical Biology Feb. 1999; 3(1):89-94.
Hayashi et al., Development of oligoarginine-drug conjugates linked to new peptidic self-cleavable spacers toward effective intestinal absorption. Bioorganic & Medicinal Chemistry Letters Sep. 15, 2007; 17(18): 5129-5132.
Heemskerk et al., From chemical to drug: neurodegeneration drug screening and the ethics of clinical trials. Nat Neurosci Nov. 2002; 5 Suppl:1027-1029.
Herve et al., On The Immunogenic Properties of Retro-Inverso Peptides. Total Retro-Inversion of T-Cell Epitopes Causes a Loss Of Binding To Mhc II Molecules. Molecular Immunology Feb. 1997; 34(2): 157-163.
Hirt et al., D-JNKI1, a Cell-Penetrating c-Jun-N-Terminal Kinase Inhibitor, Protects Against Cell Death in Severe Cerebral Ischemia, Stroke. Jul. 2004;35(7):1738-1743.
Ho et al., Synthetic Protein Transduction Domains: Enhanced Transduction Potential in Vitro and in Vivo. Cancer Research Jan. 15, 2001; 61(2): 474-477.
Holinger et al., Bak BH3 Peptides Antagonize Bc1-xL Function and Induce Apoptosis through Cytochrome cindependent Activation of Caspases. The Journal of Biological Chemistry, May 7, 1999; 274(19): 13298-13304.
Holzberg et al., Disruption of the C-JUN-JNK Complex by a Cell-permeable Peptide Containing the c-JUN delta Domain Induces Apoptosis and Affects a Distinct Set of Interleukin-1-induced Inflammatory Genes. The Journal of Biological Chemistry Oct. 10, 2003; 278(41): 40213-40223.
Hommes et al., Inhibition of Stress-Activated MAP Kinases Induces Clinical Improvement in Moderate to Severe Crohn's Disease. Gastroenterology. Jan. 2002;122(1):7-14.
Houghten, General method for the rapid solid -phase synthesis of large numbers of peptides: Specificity of antigen-antibody interaction at the level of individual amino acids. Proc. Natl. Acad. Sci. USA Aug. 1985; 82(15): 5131-5135.
Hruby and Bonner, Chapter 11: Design of Novel Synthetic Peptides Including Cyclic Conformationally and Topgraphically Constrained Analogs. Peptide Synthesis Protocols, 1994 Humana Press Inc. :201-239.
Hunot et al., JNK-mediated induction of cyclooxygenase 2 is required for neurodegeneration in a mouse model of Parkinson's disease. Proc Natl Acad Sci USA. Jan. 13, 2004;101(2):665-670.
Huq et al., Specific recognition of HIV-1 TAR RNA by a D-Tat peptide. Nature Structural Biology Nov. 1997; 4(11):881-882.
Inhibit. Dictionary.com The American Heritage® Stedman's Medical Dictionary Copyright c. 2002, 2001, 1995 by Houghton Mifflin Company. Published by Houghton Mifflin Company.Oct. 10, 2007.
InVivoGen, Inc. SP600125 MAP Kinase Inhibitor-Autophagy Inhibitor-JNK inhibitor. Downloaded Jun. 9, 2014:2pp.
Iyer et al., RDP58, a rationally designed peptide, inhibits multiple forms of pathogenic inflammation through the inhibition of p38MAPK and JNK. Biopolymers Jan. 2013;71(3):298.
Jackson et al., Heat shock induces the release of fibroblast growth factor 1 from NIH 3T3 cells. Proc. Natl. Acad. Sci. USA Nov. 1992; 89(22): 10691-10695.
Jaeschke et al., Disruption of the Jnk2 (Mapk9) gene reduces destructive insulitis and diabetes in a mouse model of type I diabetes. Proc Natl Acad Sci USA. May 10, 2005;102(19):6931-6935.

(56) References Cited

OTHER PUBLICATIONS

Jameson et al., A rationally designed CD4 analogue inhibits experimental allergic encephalomyelitis. Nature Apr. 21, 1994; 368(6473): 744-746.

Johnson and Nakamura, The c-jun kinase/stress-activated pathway: Regulation, function and role in human disease. Biochimica et Biophysica Acta 2007; 1773(8):1341-1348.

Josephson et al., High-Efficiency Intracellular Magnetic Labeling with Novel Superparamagnetic-Tat Peptide Conjugates. Bioconjug Chem. Mar.-Apr. 1999;10(2):186-191.

Kaneto et al., Possible novel therapy for diabetes with cell-permeable JNK-inhibitory peptide, Nat Med. Oct. 2004; 10(10):1128-1132.

* cited by examiner

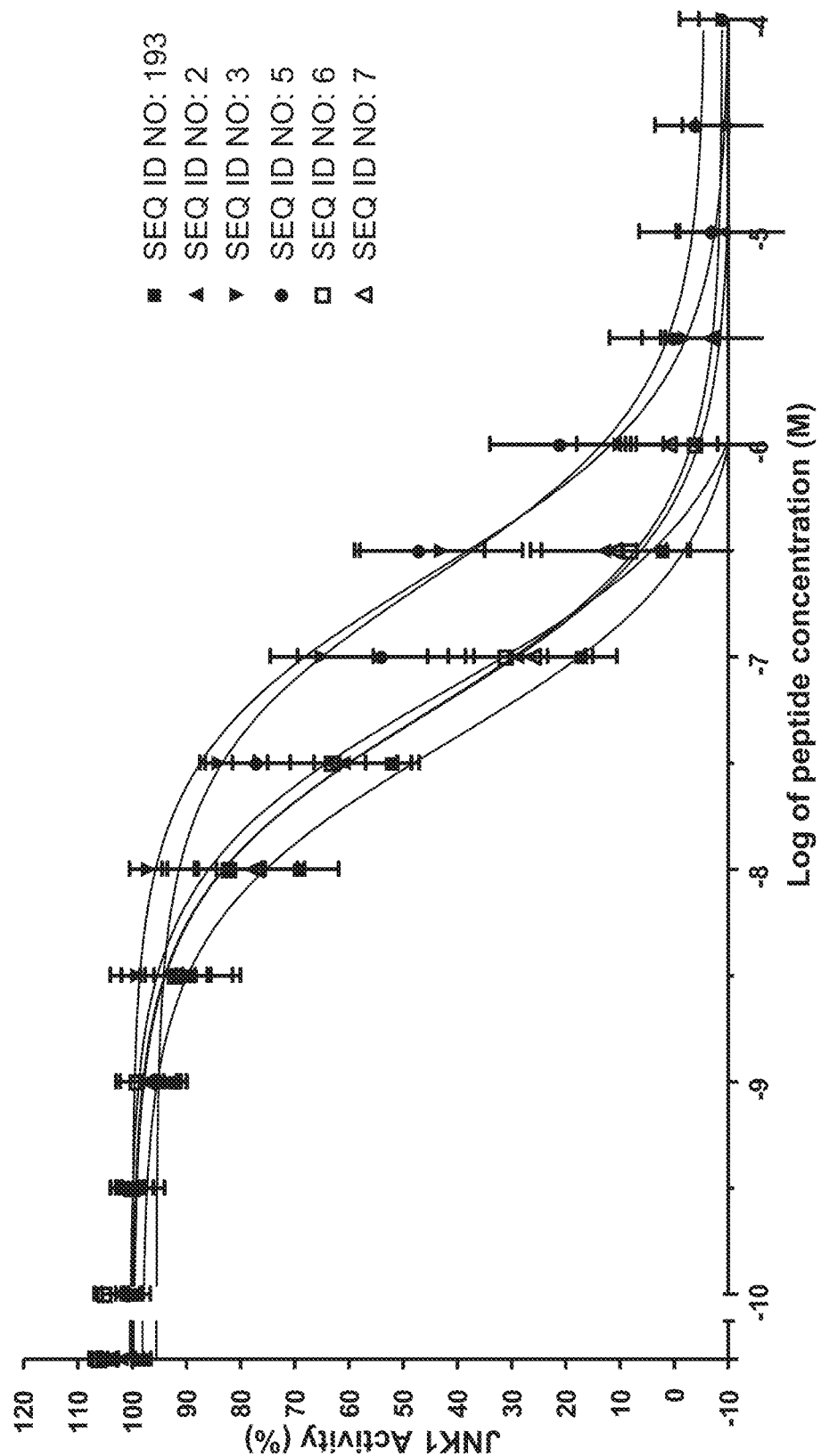

| SEQ ID NO: | Sequence | | | hJNK1 | | | hJNK2 | | | hJNK3 | | |
|---|---|---|---|---|---|---|---|---|---|---|---|---|
| | | | | IC50 | SEM | n | IC50 | SEM | n | IC50 | SEM | n |
| 193 | NH2 | R P K R P T T L N L F | CONH2 | 39,52 | 0,57 | 2 | 183,85 | 50,45 | 2 | 67,68 | 13,92 | 2 |
| 2 | NH2 | r P K R P T T L N L F | CONH2 | 65,55 | 26,03 | 3 | 423,53 | 241,45 | 3 | 103,32 | 36,53 | 3 |
| 3 | NH2 | R P K R P T T L N L F | CONH2 | 311,63 | 99,86 | 4 | 1213,53 | 437,87 | 4 | 359,47 | 161,02 | 4 |
| 5 | NH2 | R P K R P T T L n L F | CONH2 | 347,55 | 174,17 | 4 | 1501,88 | 701,33 | 4 | 387,15 | 179,51 | 4 |
| 6 | NH2 | R P K R P T T L r L F | CONH2 | 90,50 | 29,63 | 4 | 358,75 | 105,28 | 4 | 119,50 | 39,82 | 4 |
| 7 | NH2 | R P K R P T T L N l F | CONH2 | 69,53 | 21,75 | 4 | 278,18 | 51,43 | 4 | 88,97 | 26,72 | 4 |

Fig. 2

| SEQ ID NO: | | Sequence | | hJNK1 | | | hJNK2 | | | hJNK3 | | |
|---|---|---|---|---|---|---|---|---|---|---|---|---|
| | | | | iC50 | SEM | n | iC50 | SEM | n | iC50 | SEM | n |
| 196 | NH2 | G R K K R R Q R R R P P P R P K R P T T L N L F P Q V P R S Q D | CONH2 | 42,20 | 8,17 | 8 | 8,43 | 2,01 | 6 | 5,22 | 0,71 | 6 |
| 197 | CONH2 | G r k k r r q r r r p p p r p k r p t t l n l f p q v p r s q d | NH2 | 24358,50 | 10019,91 | 8 | 801,77 | 114,66 | 11 | 1294,24 | 255,51 | 11 |
| 194 | NH2 | G R K K R R Q R R R P P P R P K R P T T L N L F P Q V P R S Q D | CONH2 | 13,99 | 0,06 | 2 | 12,70 | 0,48 | 2 | 2,59 | 0,06 | 2 |
| 195 | NH2 | G R K K R R Q R R R P P P R P K R P T T L N L F P Q V P R S Q D | CONH2 | 10,77 | 1,83 | 2 | 11,26 | 0,56 | 2 | 4,92 | 0,27 | 2 |
| 172 | NH2 | r K K R r Q R R r R P k R P a T L N L f | CONH2 | 722,49 | 124,58 | 7 | 54,66 | 13,04 | 7 | 102,32 | 47,81 | 7 |
| 200 | NH2 | r K K R r Q R R r R P k A A a A A N A f | CONH2 | NA | NA | 6 | 3324,00 | 2469,99 | 6 | 3820,81 | 3190,08 | 6 |
| 46 | NH2 | r K K r r Q R R r r | CONH2 | NA | NA | 3 | 5340,33 | 1803,08 | 3 | 6130,86 | 5323,73 | 3 |
| 173 | NH2 | r K K R r Q R R r R P k R P T T L r L f | CONH2 | 88,36 | 4,02 | 2 | 30,03 | 0,16 | 2 | 16,76 | 2,03 | 2 |
| 174 | NH2 | r K K R r Q R R r R P t R P T T L N L f | CONH2 | 333,73 | 36,46 | 3 | 120,13 | 4,53 | 3 | 63,12 | 6,04 | 3 |
| 175 | NH2 | r K K R r Q R R r R P t R P T T L N L f | CONH2 | 185,30 | 18,10 | 3 | 82,30 | 9,26 | 3 | 60,60 | 6,01 | 3 |
| 176 | NH2 | r K K R r Q R R r R P k R P T T L N L w | CONH2 | 131,17 | 12,28 | 3 | 40,33 | 4,60 | 3 | 22,38 | 1,60 | 3 |
| 177 | NH2 | r K K R r Q R R r R P k R P T D L N L f | CONH2 | 355,10 | 34,02 | 3 | 87,20 | 7,12 | 3 | 45,38 | 6,70 | 3 |
| 178 | NH2 | r K K R r Q R R r R P t R P T T L r L w | CONH2 | 329,33 | 12,26 | 3 | 105,60 | 42,64 | 3 | 30,41 | 5,81 | 3 |
| 179 | NH2 | r K K R r Q R R r R P t R P T T L r L f | CONH2 | 249,47 | 22,35 | 3 | 122,11 | 20,73 | 3 | 45,66 | 3,79 | 3 |
| 180 | NH2 | r K K R r Q R R r R P t R P T D L r L w | CONH2 | 265,20 | 34,65 | 3 | 117,65 | 10,58 | 3 | 46,99 | 8,21 | 3 |
| 181 | NH2 | r K K R r Q R R r R P t R P T D L r L w | CONH2 | 293,70 | 9,79 | 2 | 160,22 | 40,13 | 2 | 47,56 | 5,77 | 2 |
| 182 | NH2 | r K K R r Q R R r R P t R P a T L N L f | CONH2 | 1677,50 | 34,50 | 2 | 166,40 | 20,80 | 2 | 59,36 | 2,35 | 2 |
| 183 | NH2 | r K K R r Q R R r R P t R P a T L N L f | CONH2 | 2688,00 | 494,00 | 2 | 427,30 | 25,00 | 2 | 199,20 | 3,90 | 2 |
| 184 | NH2 | r K K R r Q R R r R P - K R P a T L N L f | CONH2 | 2426,00 | 129,00 | 2 | 205,95 | 8,25 | 2 | 129,45 | 9,65 | 2 |
| 185 | NH2 | r K K R r Q R R r R P k R P s T L N L f | CONH2 | 765,65 | 78,15 | 2 | 72,09 | 2,85 | 2 | 35,52 | 6,34 | 2 |
| 186 | NH2 | r K K R r Q R R r R P k R P q T L N L f | CONH2 | 1021,30 | 100,70 | 2 | 52,59 | 2,73 | 2 | 44,24 | 4,80 | 2 |
| 187 | NH2 | r K K R r Q R R r R P k R P k T L N L f | CONH2 | 594,45 | 40,45 | 2 | 37,88 | 5,47 | 2 | 25,41 | 6,95 | 2 |
| 188 | NH2 | r K K R r Q R R r G K R R K A L K L f | CONH2 | 1421,00 | 98,00 | 2 | 98,14 | 27,26 | 2 | 36,12 | 2,46 | 2 |
| 189 | NH2 | r K K R r Q R R r G K R R K A L r L f | CONH2 | 22270,00 | 5090,00 | 2 | 175,60 | 1,30 | 2 | 127,72 | 31,88 | 2 |
| 190 | NH2 | r K K R r Q R R r R K A L r L f | CONH2 | 8969,50 | 2070,50 | 2 | 148,20 | 9,70 | 2 | 159,35 | 13,45 | 2 |

Fig. 4

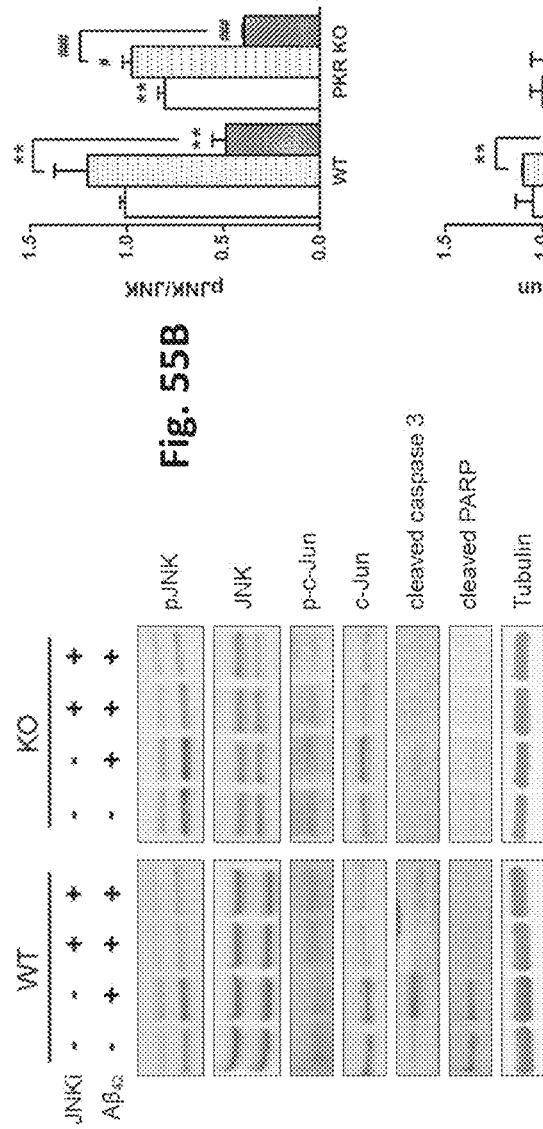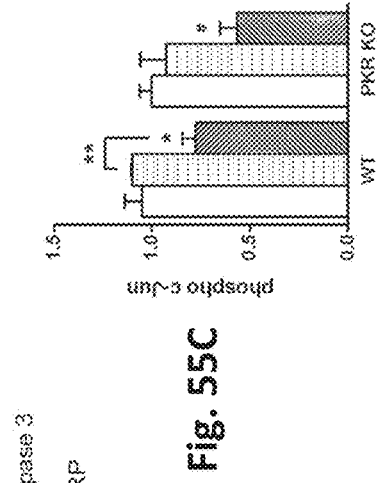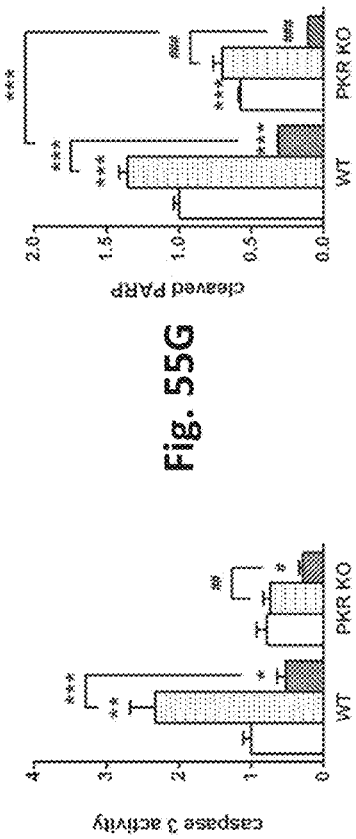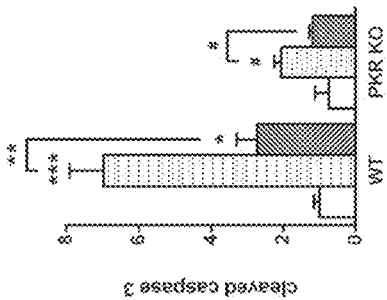

USE FOR JNK INHIBITOR MOLECULES FOR TREATMENT OF VARIOUS DISEASES

FIELD

The present invention relates to the field of enzyme inhibition, in particular to (poly-)peptide inhibitors of c-Jun amino terminal kinase (JNK). In particular, the present invention relates to using these JNK inhibitors in the treatment of various diseases.

BACKGROUND

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors and receptor tyrosine kinases. In mammalian cells, JNK has been implicated in biological processes such as oncogenic transformation and mediating adaptive responses to environmental stress. JNK has also been associated with modulating immune responses, including maturation and differentiation of immune cells, as well as effecting programmed cell death in cells identified for destruction by the immune system. This unique property makes JNK signaling a promising target for developing pharmacological intervention. Among several neurological disorders, JNK signaling is particularly implicated in ischemic stroke and Parkinson's disease, but also in other diseases as mentioned further below. Furthermore, the mitogen-activated protein kinase (MAPK) p38alpha was shown to negatively regulate the cell proliferation by antagonizing the JNK-c-Jun-pathway. The mitogen-activated protein kinase (MAPK) p38alpha therefore appears to be active in suppression of normal and cancer cell proliferation and, as a further, demonstrates the involvement of JNK in cancer diseases (see e.g. Hui et al., Nature Genetics, Vol 39, No. 6, June 2007). It was also shown, that c-Jun N-terminal Kinase (JNK) is involved in neuropathic pain produced by spinal nerve ligation (SNL), wherein SNL induced a slow and persistent activation of JNK, in particular JNK1, whereas p38 mitogen-activated protein kinase activation was found in spinal microglia after SNL, which had fallen to near basal level by 21 days (Zhuang et al., The Journal of Neuroscience, Mar. 29, 2006, 26(13):3551-3560)). In 2007 (Biochemica et Biophysica Acta, pp. 1341-1348), Johnson et al. discussed in a review the c-Jun kinase/stress-activated pathway, the involvement of JNK signalling in diseases such as the involvement in excitotoxicity of hippocampal neurons, liver ischemia, reperfusion, neurodegenerative diseases, hearing loss, deafness, neural tube birth defects, cancer, chronic inflammatory diseases, obesity, diabetes, in particular insulin-resistant diabetes, and proposed that it is likely that selective JNK inhibitors are needed for treatment of various diseases with a high degree of specificity and lack of toxicity.

Inhibition or interruption of the JNK signalling pathway is thus a promising approach in combating disorders strongly related to JNK signalling. However, there are only a few inhibitors of the JNK signaling pathway known so far.

Inhibitors of the JNK signaling pathway as already known in the prior art include e.g. upstream kinase inhibitors (for example, CEP-1347), small chemical inhibitors of JNK (SP600125 and AS601245), which directly affect kinase activity e.g. by competing with the ATP-binding site of the protein kinase, and peptide inhibitors of the interaction between JNK and its substrates (see e.g. Kuan et al., Current Drug Targets—CNS & Neurological Disorders, February 2005, vol. 4, no. 1, pp. 63-67; WO 2007/031280; all incorporated herewith by reference). WO 2007/031280 discloses small cell permeable fusion peptides, comprising a so-called TAT transporter sequence derived from the basic trafficking sequence of the HIV-TAT protein and an amino acid inhibitory sequence of IB1.

WO 2007/031280 discloses in particular two specific sequences, L-TAT-IB1 (GRKKRRQRRRPPRPKRPT-TLNLFPQVPRSQD, herein SEQ ID NO: 196) and D-TAT-IB1 (dqsrpvqpflnlttprkprpprrrqrrkkrg; herein SEQ ID NO: 197), the latter being the retro-inverso sequence of L-TAT-IB1. Due to the HIV TAT derived transporter sequence, these fusion peptides are more efficiently transported into the target cells, where they remain effective until proteolytic degradation.

Since ATP independent peptide inhibitors of JNK are usually more specific inhibitors, they are frequently the first choice if it comes to inhibiting JNK. However, even the peptide inhibitors disclosed in WO 2007/031280 are not optimal for all purposes. For example, compound L-TAT-IB1 (herein SEQ ID NO: 196) which consists of L amino acids only, is quickly proteolytically degraded. In order to overcome this problem the inventors of WO 2007/031280 also suggested D-TAT-IB1 (herein SEQ ID NO: 197), which comprises D amino acids. To be more precise, D-TAT-IB1 exhibits the retro-inverso sequence of L-TAT-IB1. Incorporation of D-amino acids is made difficult by the fact that the change in stereochemistry may lead to a loss of function. The retro-inverso approach may be employed to reduce said risk because the use of i) only D-amino acids ii) but in the inverse peptide sequence may more likely yield an acceptable conformational analogue to the original peptide than incorporating one or more D-amino acids into the original sequence. In the case of WO 2007/031280 this approach resulted nevertheless in a significant decrease in inhibitory capacity in comparison to L-TAT-IB1 (see FIG. 4). Additionally, the retro-inverso peptide is extremely stable towards proteolytic digestion with the consequence that controlled digestions, for example in time sensitive experiments, are hardly possible.

JNK inhibitors have been discussed, proposed and successfully tested in the art as treatment for a variety of disease states. Already in 1997, Dickens et al. described the c-Jun amino terminal kinase inhibitor JIP-1 and proposed JIP-1 as candidate compounds for therapeutic strategies for the treatment of for example chronic myeloid leukaemia, in particular, in the context of Bcr-Abl caused transformation of pre-B-cells (Science; 1997; 277(5326):693-696).

In 2001, Bonny and co-workers published that cell-permeable peptide inhibitors of JNK confirm long term protection to pancreatic β-cells from IL-1β-induced apoptosis and may, thus, preserve β-cells in the autoimmune destruction in the course of diabetes (Diabetes, 50, 2001, p. 77-82).

Bonny et al. (Reviews in Neurosciences, 2005, p. 57-67) discussed also the inhibitory action of the JNK inhibitor D-JNKI-1 and other JNK inhibitors in the context of excitotoxicity, neuronal cell death, hypoxia, ischemia, traumatic brain damage, epilepsy, neurodegenerative diseases, apoptosis of neurons and inner ear sensory auditory cells etc.

In WO 98/49188 JIP-1 derived inhibitors of JNK signalling are proposed for the treatment of neurodegenerative diseases, such as Parkinson's disease or Alzheimer's disease; stroke and associated memory loss, autoimmune diseases such as arthritis; other conditions characterized by inflammation; malignancies, such as leukemias, e.g. chronic myelogenous leukemia (CML); oxidative damage to organs such as the liver and kidney; heart diseases; and transplant rejections.

Borsello et al. (Nat Med, 2003, (9), p. 1180-1186) published that a peptide inhibitor of c-Jun-N-terminal kinase protects against excitotoxicity and cerebral ischemia.

Assi et al. have published that another specific JNK-inhibitor, SP600125, targets tumor necrosis factor-α production and epithelial cell apoptosis in acute murine colitis. The authors concluded that inhibition of JNK is of value in human inflammatory bowel disease treatment (Immunology; 2006, 118(1):112-121).

In Kennedy et al. (Cell Cycle, 2003, 2(3), p. 199-201), the role of JNK signalling in tumor development is discussed in more detail.

Lee Yong Hee et al. (J Biol Chem 2003, 278(5), P. 2896-2902) showed that c-Jun N-terminal kinase (JNK) mediates feedback inhibition of the insulin signalling cascade and have proposed that inhibition of JNK signalling is a good therapeutic approach to reduce insulin resistance in diabetic patients.

Milano et al. (Am J Physiol Heart Circ Physiol 2007; 192(4): H1828-H1835) discovered that a peptide inhibitor of c-Jun $NH_2$-terminal kinase reduces myocardial ischemia-reperfusion injury and infarct size in vivo. The authors of said study used a peptide inhibitor, D-JNKI-I, a two domain peptide containing a 20 amino acid sequence of the minimal JNK-binding domain of islet-brain-1/JNK-interacting protein-1, linked to a 10 amino acid TAT sequence of the human immuno deficiency virus TAT protein that mediates intracellular translocation. The authors have concluded that a reduction in JNK activity and phosphorylation due to the presence of said inhibitor is important in the preservation of cardiac function in rats in the phase of ischemia and apoptosis.

A further group has published that small peptide inhibitors of JNKs protect against MPTP-induced nigral dopaminergic injury via inhibiting the JNK-signalling pathway (Pan et al., Laboratory investigation, 2010, 90, 156-167). The authors concluded that a peptide comprising residues 153-163 of murine JIP-1 fused to TAT peptide offers neuroprotection against MPTP injury via inhibiting the JNK-signalling pathway and provides a therapeutic approach for Parkinson's disease.

For hearing damage, Pirvola et al. (The Journal of Neuroscience, 2000, 20(1); 43-50) described the rescue of hearing, auditory hair cells and neurons by CEP-1347/KT7515, an inhibitor of c-Jun-N-terminal kinase activation. The authors suggested in general that therapeutic intervention in the JNK signalling cascade may offer opportunities to treat inner ear injuries. Treatment of hearing loss by means of administering JNK-inhibitory peptides is also disclosed for example in WO 03/103698.

For retinal diseases and age-related macula degeneration in particular, Roduit et al. (Apoptosis, 2008, 13(3), p. 343-353) have likewise suggested to use JNK-inhibition as therapeutic approach. Similar considerations relying on JNK-inhibition are disclosed for example in WO 2010/113753 for the treatment of age-related macular degeneration, diabetic macular edema, diabetic retinopathy, central exudative chorioretinopathy, angioid streaks, retinal pigment epithelium detachment, multifocal choroiditis, neovascular maculopathy, retinopathy of prematurity, retinitis pigmentosa, Leber's disease, retinal artery occlusion, retinal vein occlusion, central serous chorioretinopathy, retinal macroaneurysm, retinal detachment, proliferative vitreoretinopathy, Stargardt's disease, choroidal sclerosis, chorioderemia, vitelliform macular dystrophy, Oguchi's disease, fundus albipunctatus, retinitis *punctata albescens*, and gyrate atrophy of choroid and retina.

Zoukhri et al. (Journal of Neurochemistry, 2006, 96, 96, 126-135) identified that c-Jun $NH_2$-terminal kineae mediates interleukin-1β-induced inhibition of lacrimal gland secretion. They concluded that JNK plays a pivotal role in IL-1 β-mediated inhibition of lacrimal gland secretion and subsequent dry eye.

For uveitis, Touchard et al. (Invest Ophthalmol Vis Sci, 2010, 51(9); 4683-4693) have suggested to use D-JNKI 1 as effective treatment.

For IBD (inflammatory bowel disease) Roy et al. (World J Gastroenterol 2008, 14(2), 200-202) have highlighted the role of the JNK signal transduction pathway therein and have proposed to use peptidic JNK inhibitors for the treatment of said disease state.

Beckham et al (J Virol. 2007 July; 81(13):6984-6992) showed that the JNK inhibitor D-JNKI-1 is effective in protecting mice from viral encephalitis, and suggest thus JNK inhibition as promising and novel treatment strategy for viral encephalitis.

Palin et al. (Psychopharmacology (Berl). 2008 May; 197(4):629-635) used the same JNK inhibitor, D-JNKI-1, and found that pre-treatment with D-JNKI-1 (10 ng/mouse), but not D-TAT, significantly inhibited all three indices of sickness induced by central TNFalpha and suggested that JNK inhibition as means for treating major depressive disorders that develop on a background of cytokine-induced sickness behaviour.

In WO 2010/151638 treatment of the neurodegenerative disease spinal muscular atrophy by way of JNK inhibition was proposed.

The above introductory section highlights on the basis of selected publications the usefulness of JNK inhibitors in the treatment of various diseases. Thus, there is a constant need in the art for JNK inhibitors for use in the treatment of human (and animal) diseases.

SUMMARY

Thus, the problem to be solved by the present invention was to provide further (peptide) inhibitors of JNK for the treatment of specific diseases.

The object of the present invention is solved by the inventor by means of the subject-matter set out below and in the appended claims.

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 1A-1C: Show illustration of the inhibitory efficacy of several JNK inhibitors according to the present invention, which was investigated by in vitro AlphaScreen assay (Amplified Luminescence Proximity Homogeneous-Screen Assay).

FIG. 1A: Inhibition of JNK1 by SEQ ID NOs: 193, 2, 3, 5, 6, and 7.

FIG. 1B: Inhibition of JNK2 by SEQ ID NOs: 193, 2, 3, 5, 6, and 7.

FIG. 1C: Inhibition of JNK3 by SEQ ID NOs: 193, 2, 3, 5, 6, and 7.

FIG. 2: Table illustrating the inhibitory efficacy of several JNK inhibitors (SEQ ID NOs: 193, 2, 3, 5, 6, and 7) according to the present invention. Given are the IC50 values in the nM range, the respective standard error of the mean and the number of experiments performed (n).

FIG. 3A: Inhibition of JNK1 by SEQ ID NOs: 194, 195, 172, 200, 46, 173, 174, 175, 176, 177, 178, 179, 180, 181 and 197.

FIG. 3B: Inhibition of JNK2 by SEQ ID NOs: 194, 195, 172, 200, 46, 173, 174, 175, 176, 177, 178, 179, 180, 181 and 197.

FIG. 3C: Inhibition of JNK3 by SEQ ID NOs: 194, 195, 172, 200, 46, 173, 174, 175, 176, 177, 178, 179, 180, 181 and 197.

FIG. 3D: Inhibition of JNK1 by SEQ ID NOs: 194, 195, 172, 200, 46, 182, 183, 184, 185, 186, 187, 188, 189, 190 and 197.

FIG. 3E: Inhibition of JNK2 by SEQ ID NOs: 194, 195, 172, 200, 46, 182, 183, 184, 185, 186, 187, 188, 189, 190 and 197.

FIG. 3F: Inhibition of JNK3 by SEQ ID NOs: 194, 195, 172, 200, 46, 182, 183, 184, 185, 186, 187, 188, 189, 190 and 197.

FIG. 4: Table illustrating the inhibitory efficacy of several JNK inhibitors according to the present invention, which are fusion proteins of a JNK inhibitory (poly-)peptide sequence and a transporter sequence. Given are the IC50 values in the nM range, the respective standard error of the mean (SEM) and the number of experiments performed (n).

FIG. 7A: TNF release (THP1pma 6 h 3 ng/ml LPS); FIG. 7B: TNF-α release (THP1pma 6 h long/ml LPS); FIG. 7C: IL 6 release (THP1pma 6 h long/ml LPS); FIG. 7D: MCP1 release (THP1pma 6 h 3 ng/ml LPS).

(FIG. 54A) Immunoblot analysis of primary mouse cortical neuron cultures exposed to 2 μM or 25 μM of Aβ1-42 (Aβ$_{42}$) during 5 hours. Neurons were pre-treated with or without 5 μM or 10 μM of the specific inhibitor, XG-104. (FIG. 54B) Corresponding histogram showing no modification of JNK activity with 2 μM of Aβ$_{42}$. Pre-treatment with 5 μM and 10 μM of XG-104 decreased JNK activity by respectively 29.2% and 60%. 25 μM Aβ$_{42}$ treatment of the neurons increased JNK activity by 14%. Pre-treatment with 5 μM and 10 μM XG-104 decreased JNK activity by, 17.5% and 59.6%, respectively. In both Aβ$_{42}$ cell stress conditions, 10 μM XG-104 concentration was more effective to decrease JNK activity. (FIG. 54C) Neuronal apoptosis is measured by the level of cleaved PARP protein, which increases during apoptosis. Both Aβ$_{42}$ stress conditions did not significantly exacerbate spontaneous apoptosis. Pre-treatment with 5 μM and 10 μM XG-104 decreased PARP cleavage by 46.8% and 80.2%, respectively, with 2 μM Aβ$_{42}$ and decreased by 69% and 80.6%, respectively, with 25 μM Aβ$_{42}$.

FIG. 55A-FIG. 55G show for Example 26 the decrease of neuronal apoptosis after PKR down-regulation and/or JNK inhibition with XG-104, referred to as "JNKi" (in FIG. 55). (FIG. 55A) Immunoblot results of the levels of JNK and c-Jun activation, caspase 3 and PARP cleaved activated fragments in primary neuronal cultures of WT and PKR$^{-/-}$ mice, treated by 2 μM of Aβ42 after or not pre-inhibition of JNK with 10 μM JNKi compound. (FIG. 55B-FIG. 55D) Corresponding histograms of JNK activity (FIG. 55B), phospho c-Jun (FIG. 55C), and total c-Jun (FIG. 55D). (FIG. 55E and FIG. 55G) Apoptosis is measured by the level of cleaved caspase 3 (FIG. 55E), caspase 3 activity measured in the cell culture supernatant (FIG. 55F) and cleaved PARP (FIG. 55G). Data are means±SEM (n≥3 per condition). *P<0.05, P<0.01, and *P<0.001.

DETAILED DESCRIPTION

JNK Inhibitors

Figure 1B:
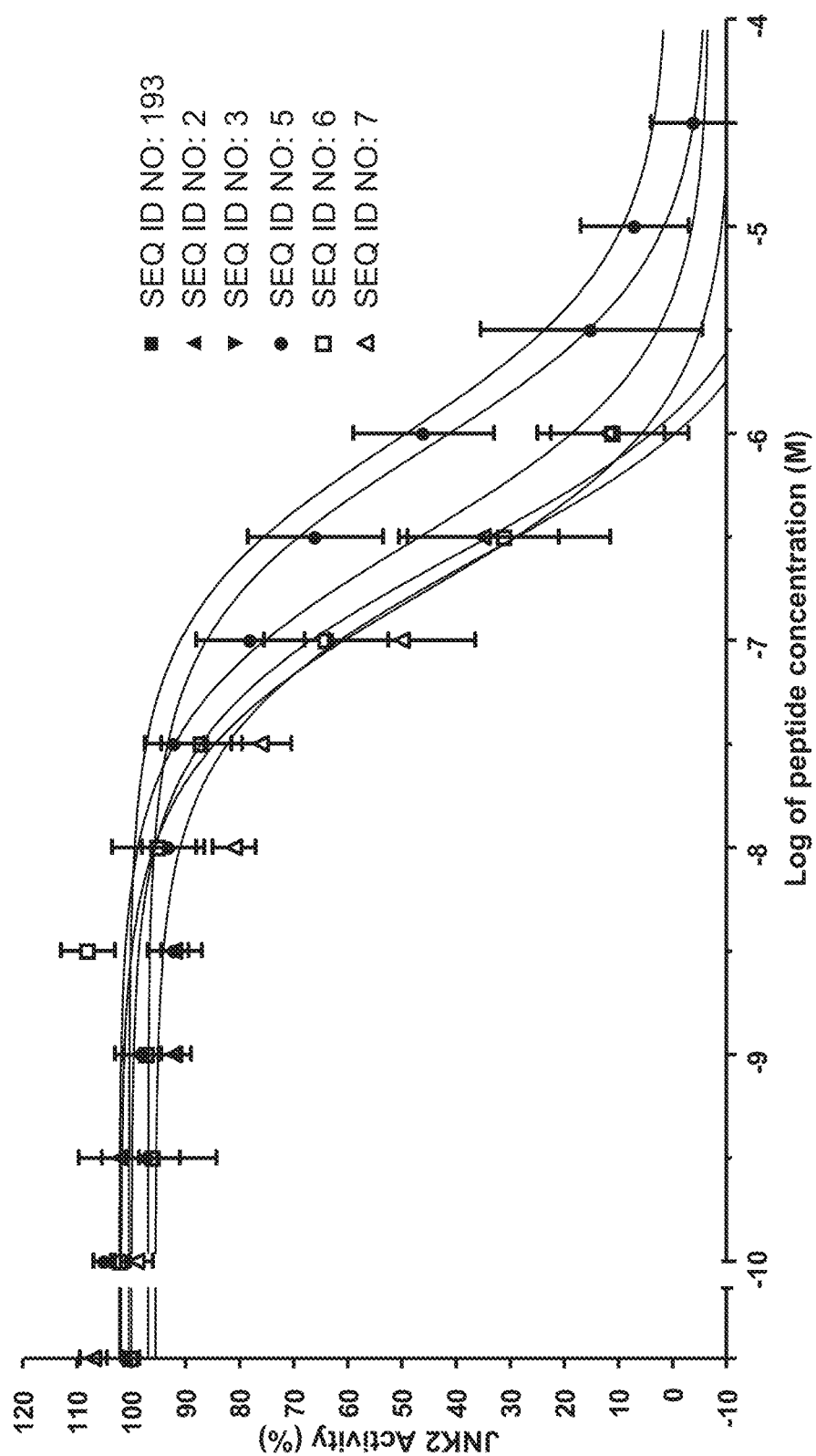
Figure 1C:
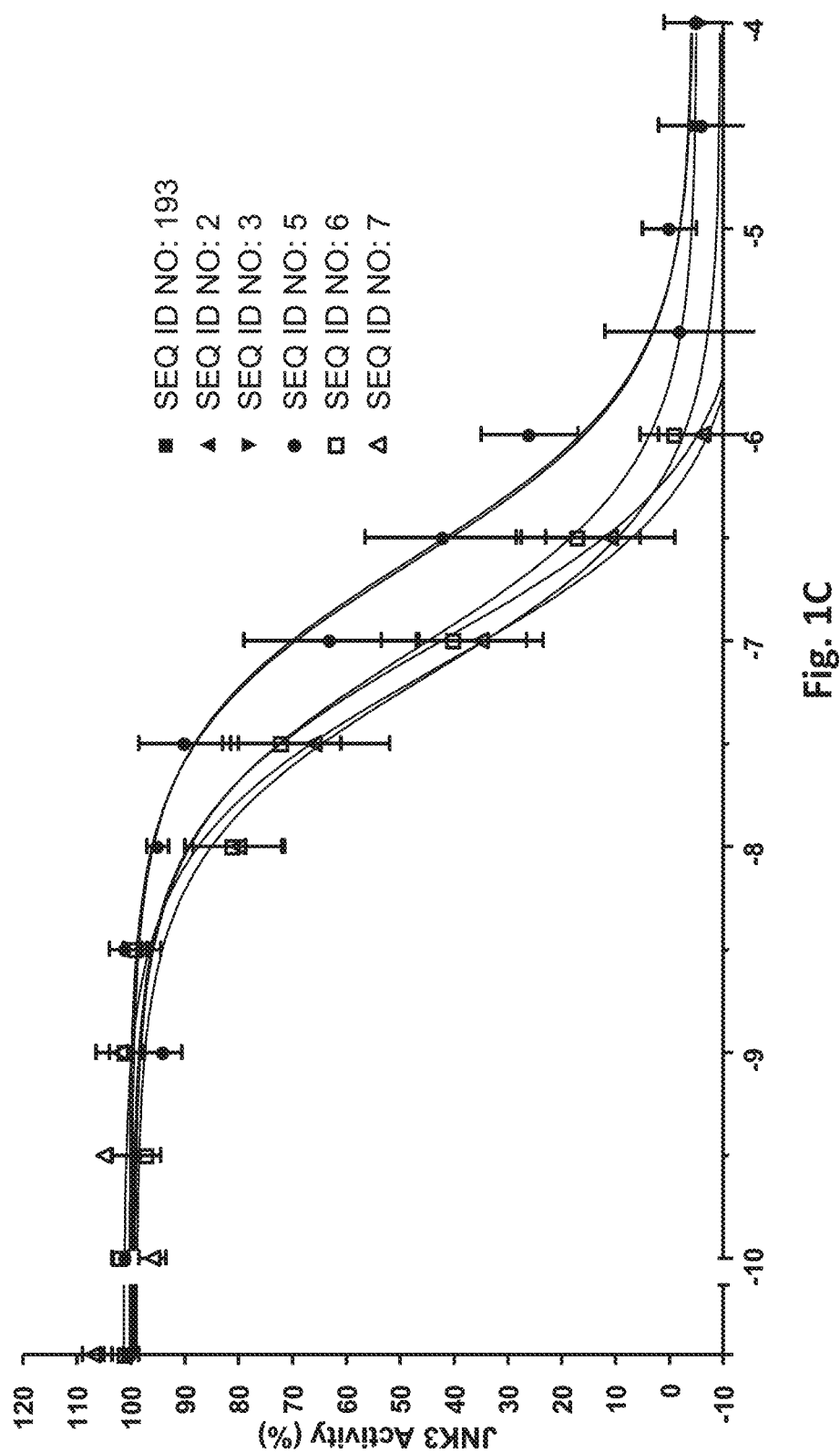
Figure 3A:
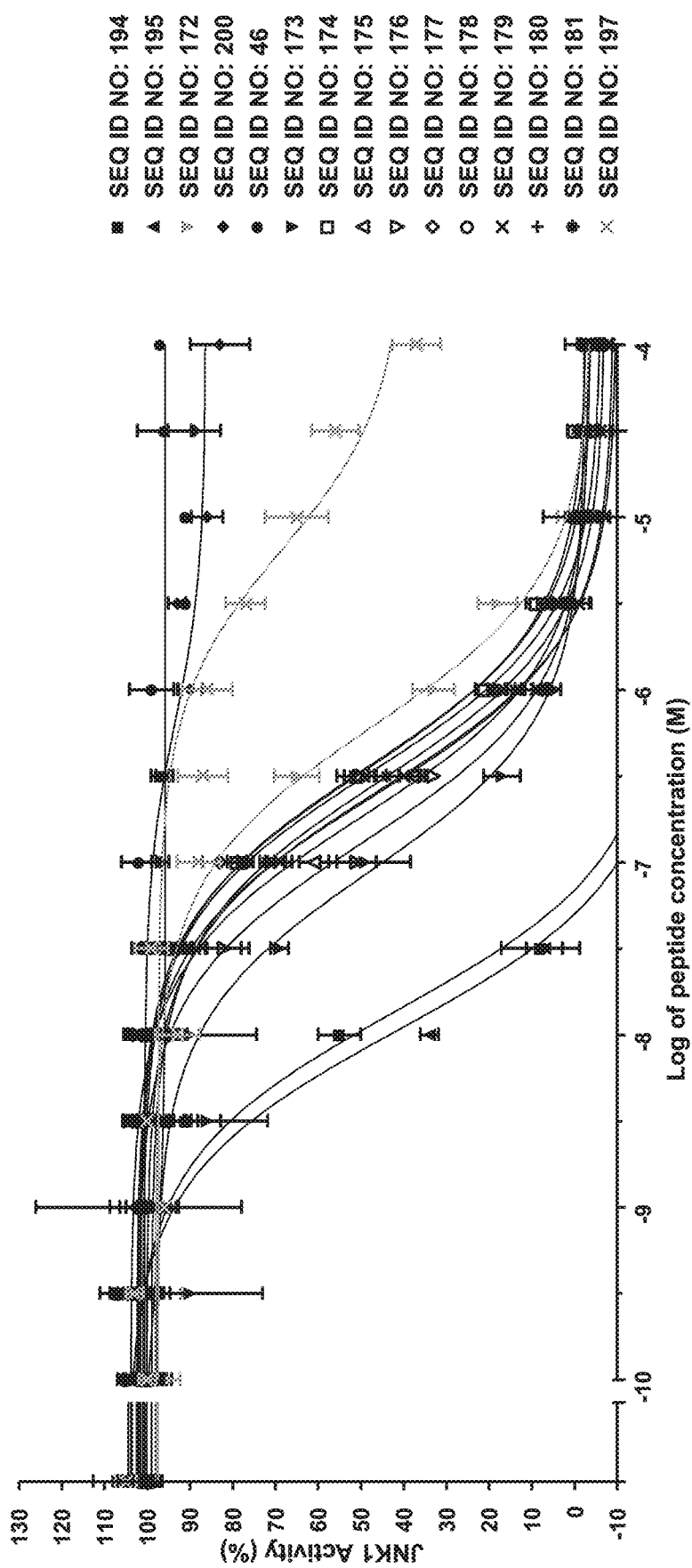
FIG. 3A-3F: Show illustration of the inhibitory efficacy of several JNK inhibitors according to the present invention, which are fusion proteins of a JNK inhibitory (poly-)peptide sequence and a transporter sequence. The inhibitory efficacy was determined by means of in vitro AlphaScreen assay (Amplified Luminescence Proximity Homogeneous-Screen Assay).
Figure 3B:
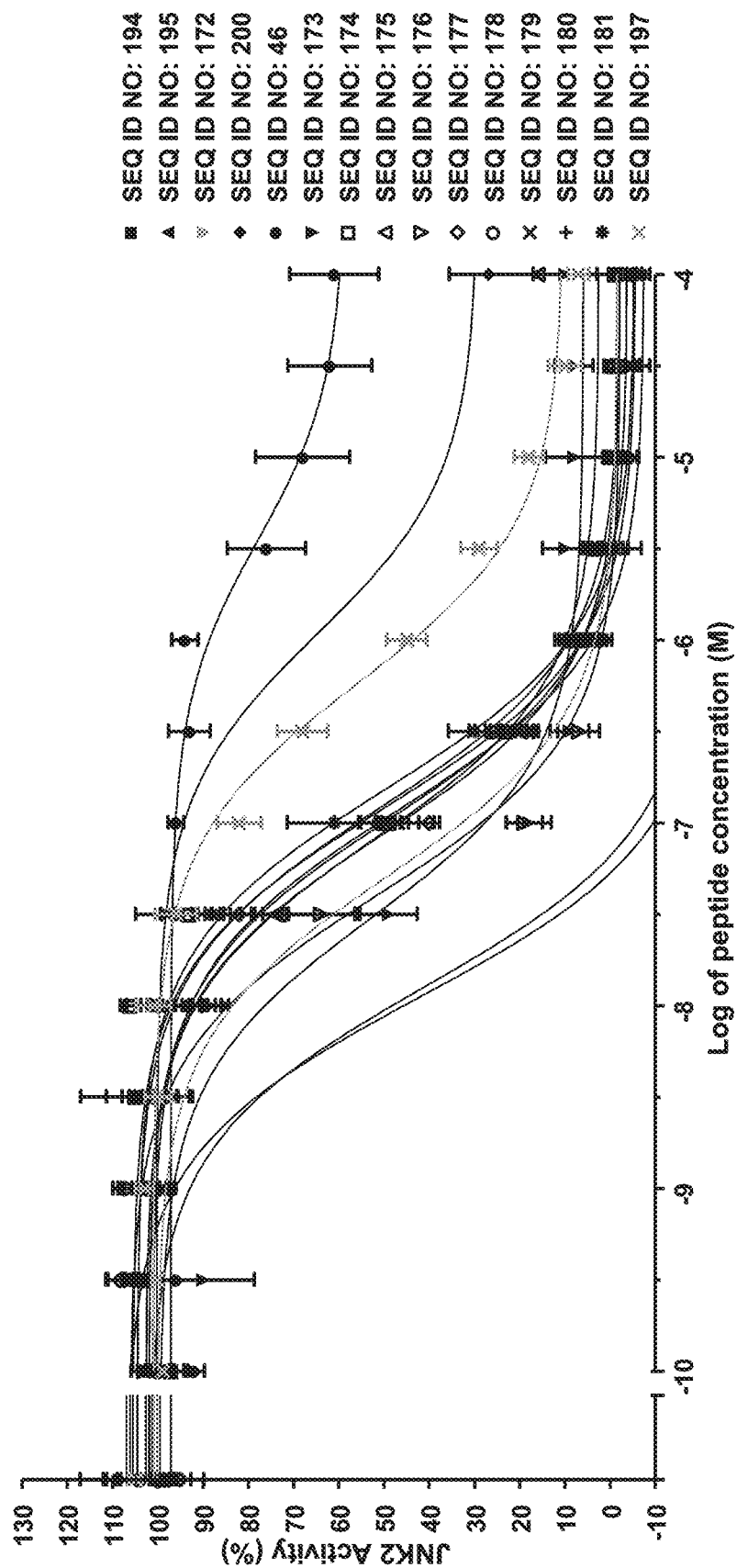
Figure 3C:
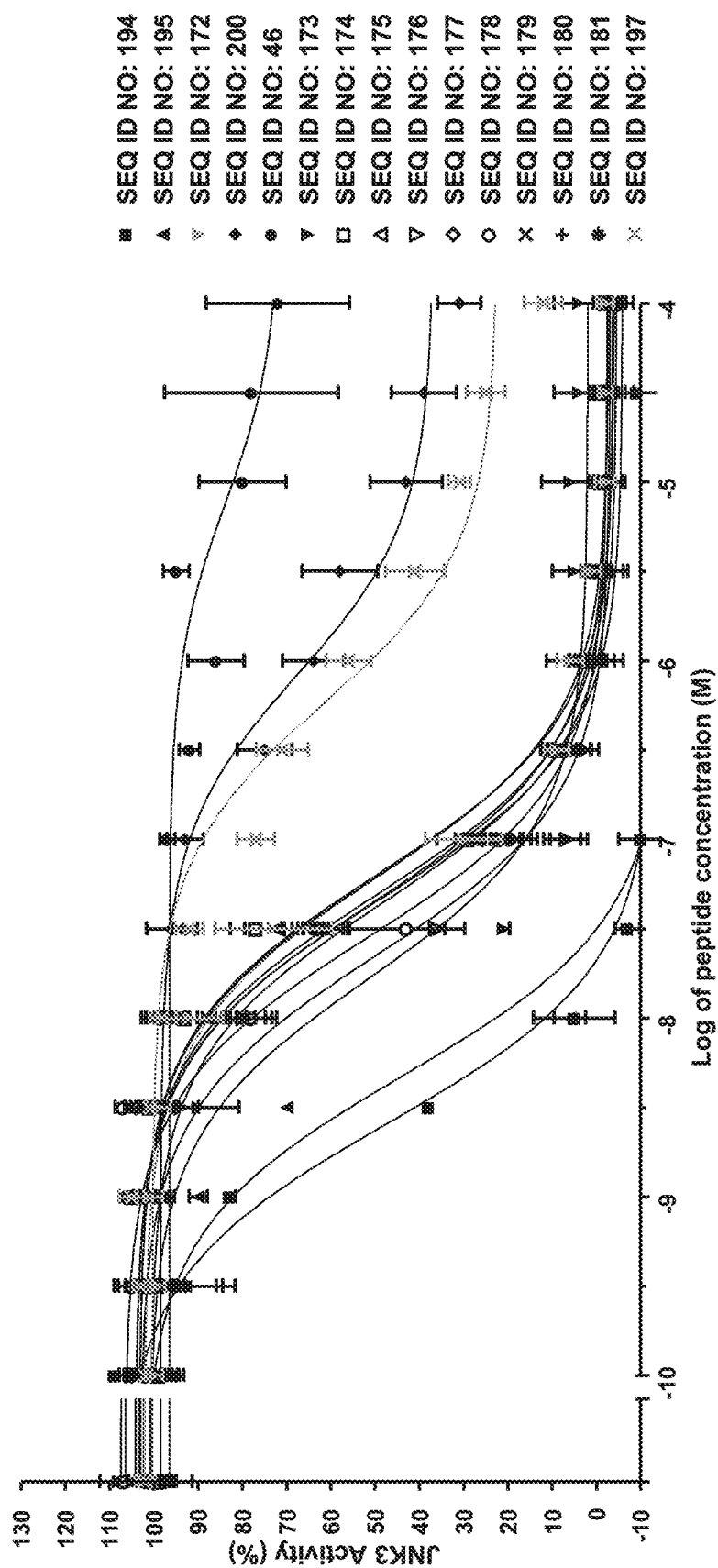
Figure 3D:
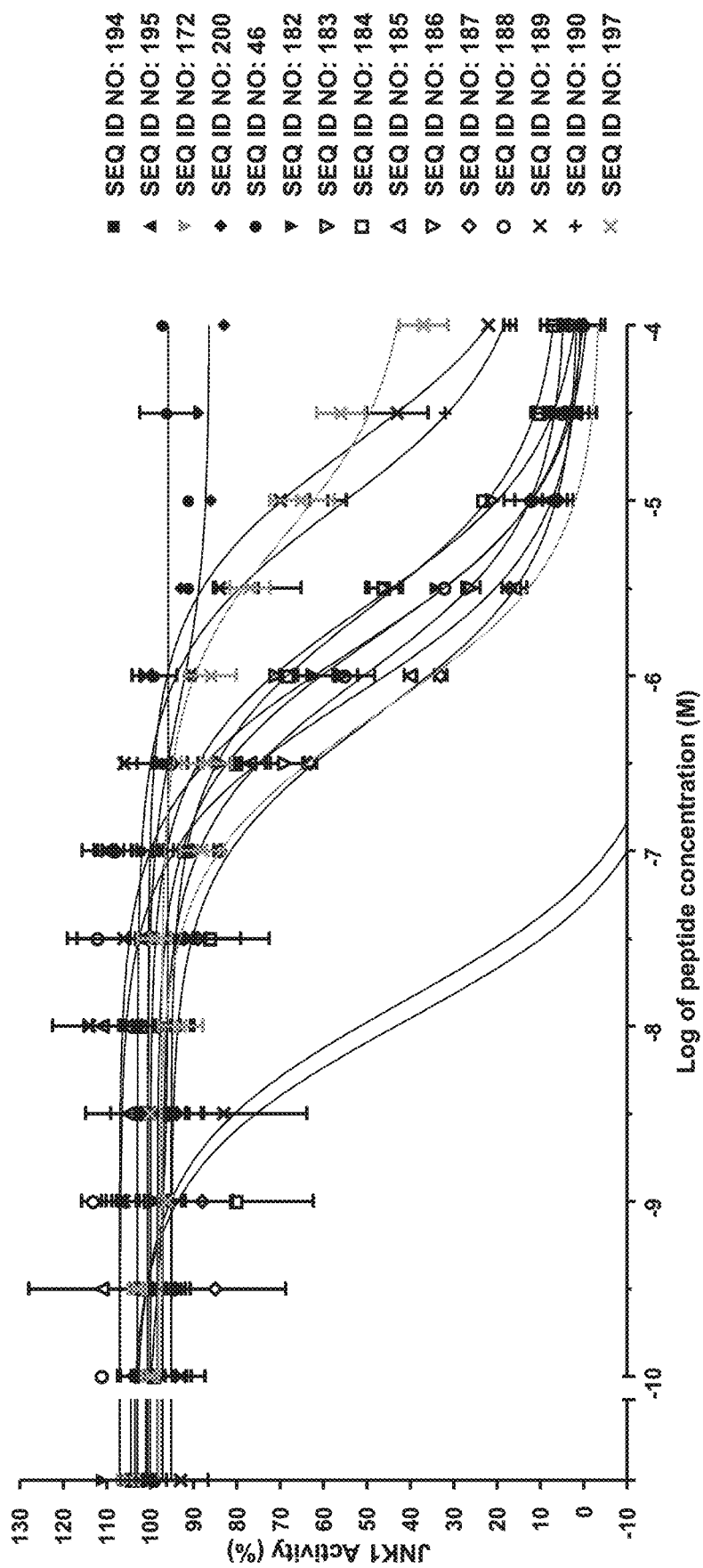
Figure 3E:
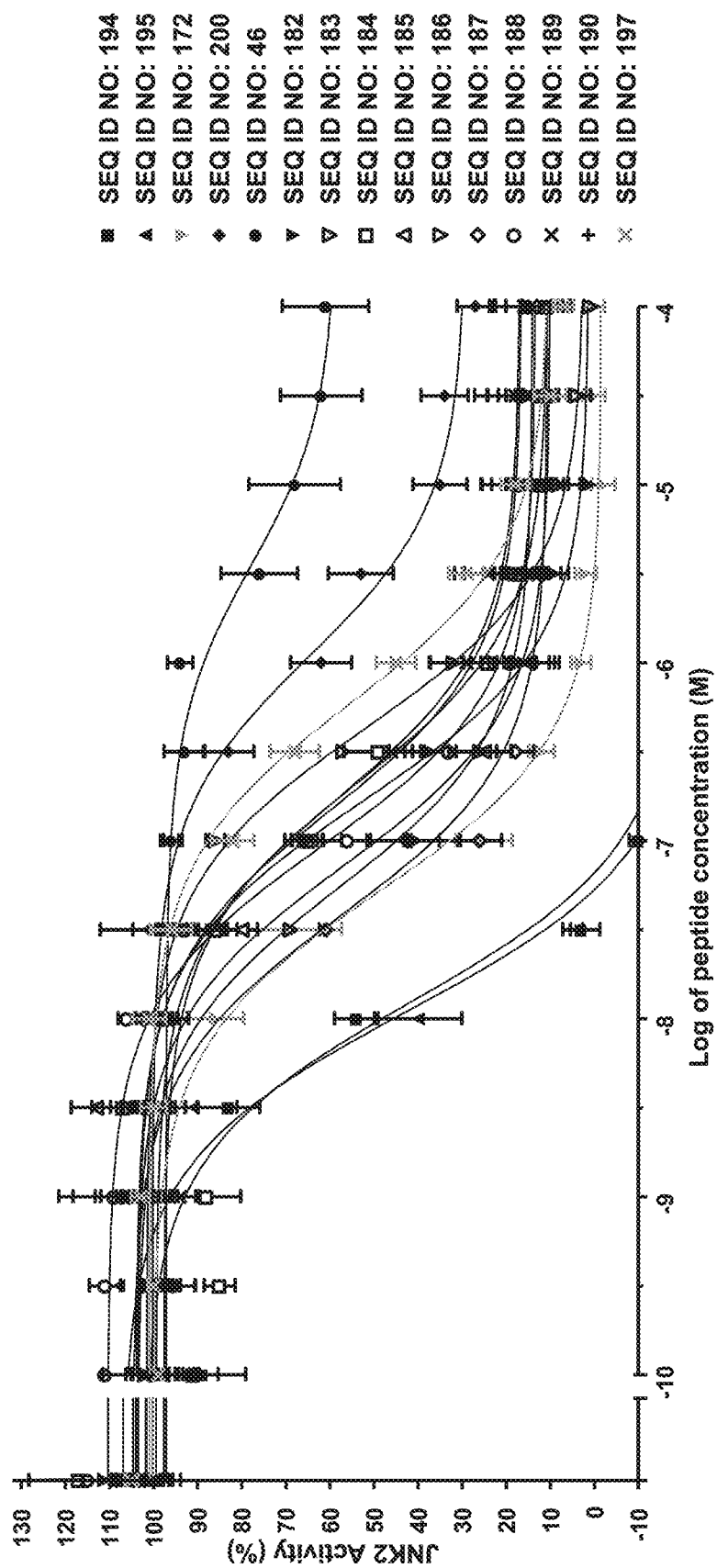
Figure 3F:
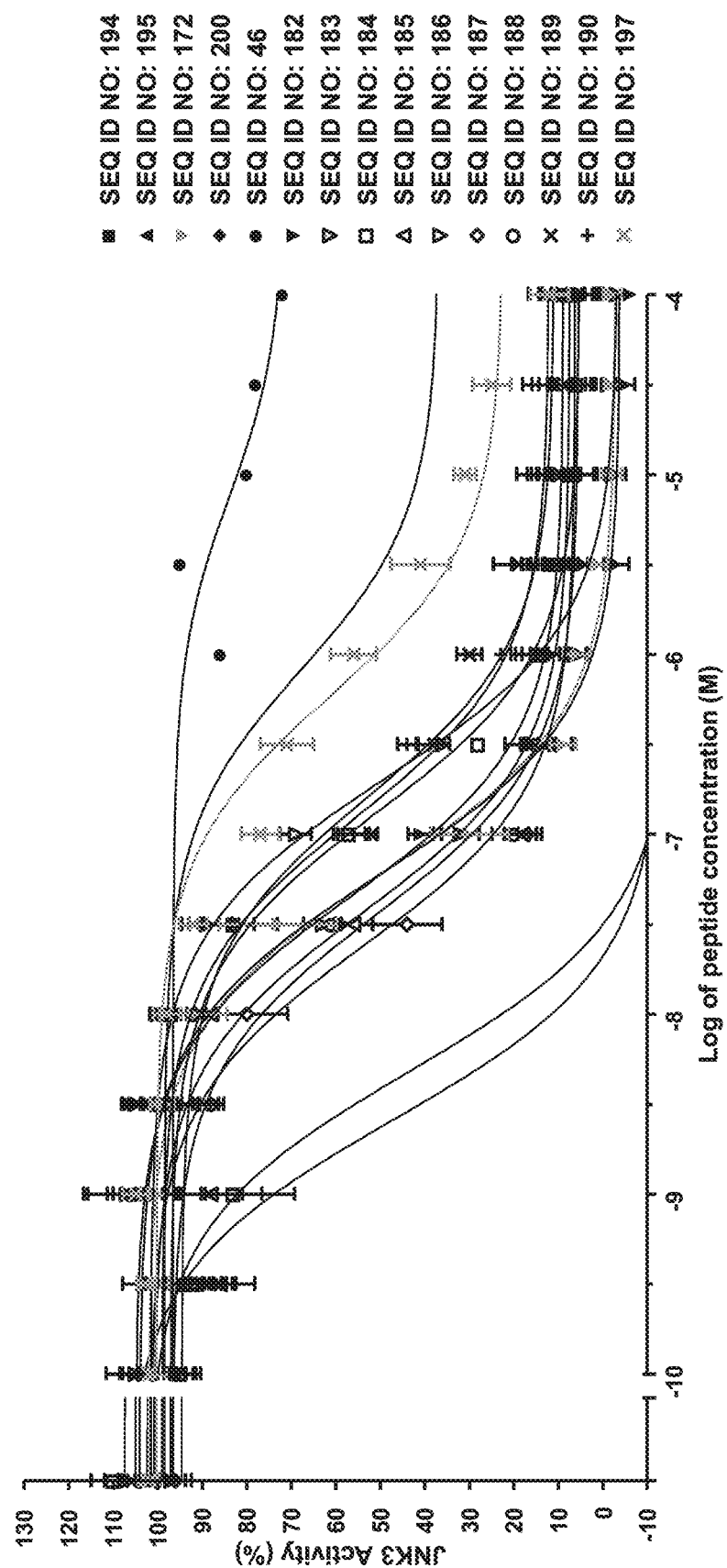
Figure 5A:
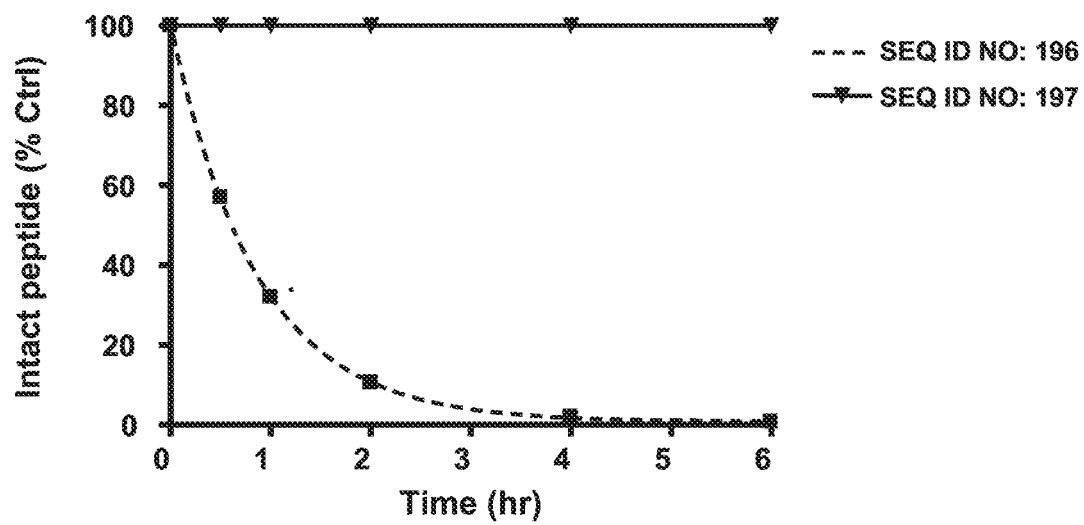
FIG. 5A-5B: Stability of JNK inhibitors with SEQ ID NOs: 172, 196 and 197 in 50% human serum. The JNK inhibitor with SEQ ID NO: 196 was totally degraded into amino acids residues within 6 hours (FIG. 5A). The JNK inhibitor with SEQ ID NO: 172 was completely degraded only after 14 days (FIG. 5B). The JNK inhibitor with SEQ ID NO: 197 was stable at least up to 30 days (FIG. 5B).
Figure 5B:
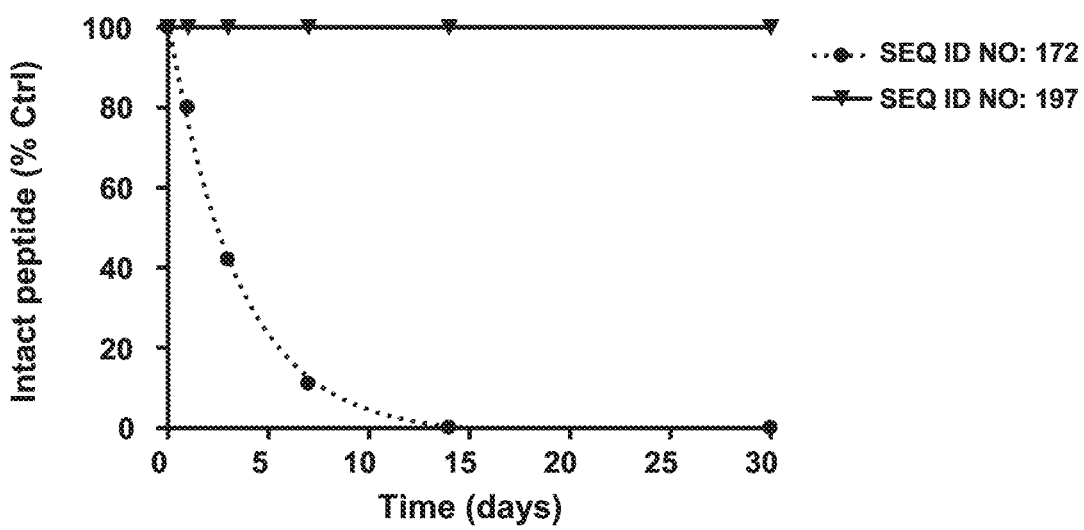

In a first aspect the present invention relates to a JNK inhibitor, which comprises an inhibitory (poly-)peptide sequence according to the following general formula:

(SEQ ID NO: 1)
$X_1-X_2-X_3-R-X_4-X_5-X_6-L-X_7-L-X_8$, wherein X1 is an amino acid selected from amino acids R, P, Q and r, wherein X2 is an amino acid selected from amino acids R, P, G and r, wherein X3 is an amino acid selected from amino acids K, R, k and r, wherein X4 is an amino acid selected from amino acids P and K, wherein X5 is an amino acid selected from amino acids T, a, s, q, k or is absent, wherein X6 is an amino acid selected from amino acids T, D and A, wherein X7 is an amino acid selected from amino acids N, n, r and K; and wherein X8 is an amino acid selected from F, f and w, with the proviso that at least one, at least two, at least three, at least four, at least five or six of the amino acids selected from the group consisting of X1, X2, X3, X5, X7 and X8 is/are a D-amino acid(s), preferably with the proviso that at least one, at least two, at least three or four of the amino acids selected from the group consisting of X3, X5, X7 and X8 is/are a D-amino acid(s), for use in a method for treatment of the human or animal body by therapy, in particular for the treatment of the diseases/disorders disclosed herein.

The inhibitory (poly-)peptide sequence of the JNK inhibitor according to the present invention comprises L-amino acids and in most embodiments D-amino acids. Unless specified otherwise, L-amino acid residues are indicated herein in capital letters, while D amino acid residues are indicated in small letters. Glycine may be indicated in capital or small letters (since there is no D- or L-glycine). The amino acid sequences disclosed herein are always given from N- to C-terminus (left to right) unless specified otherwise. The given amino acid sequence may be modified or unmodified at the C- and/or N-terminus, e.g. acetylation at the C-terminus and/or amidation or modification with cysteamide at the N-terminus. Such conceivable, but optional modifications at the C- and/or N-terminus of the amino acid sequences disclosed herein are—for sake of clarity—not specifically indicated.

The JNK inhibitors of the present invention are (poly-)peptide inhibitors of the c-Jun N-terminal kinase (JNK). Said inhibitors inhibit the kinase activity of c-Jun N-terminal kinase (JNK), i.e. prevent or reduce the extent of phosphorylation of JNK substrates, such as c-Jun, ATF2 and/or Elk-1 by e.g. blocking the JNK activity. A person skilled in the art will understand that the term "inhibitor", as used herein, does not comprise compounds which irreversibly destroy the c-Jun N-terminal kinase (JNK) molecule and/or kinase activity. Accordingly, the JNK inhibitory activity of the inhibitors of the present invention typically refers to compounds which bind in a competitive or non-competitive manner to JNK. Furthermore, the term "inhibiting JNK activity" as used herein, refers to the inhibition of the kinase activity of c-Jun N-terminal kinase (JNK).

Furthermore, as used herein, a JNK inhibitor comprises at least one functional unit of a polymer of amino acids, i.e. a (poly-)peptide sequence. Moreover, this at least one functional polymer of amino acids provides for inhibition of JNK activity. The amino acid monomers of said inhibitory (poly-)peptide sequence are usually linked to each other via peptide bonds, but (chemical) modifications of said peptide bond(s) or of side chain residues may be tolerable, provided the inhibitory activity (inhibition of JNK activity) is not totally lost, i.e. the resulting chemical entity still qualifies as JNK inhibitor as functionally defined herein. The term "(poly-)peptide" shall not be construed as limiting the length of the (poly-)peptide unit. Preferably, the inhibitory (poly-)peptide sequence of the JNK inhibitors of the present invention is less than 500, 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, or less than 12 amino acids long. Preferably, the inhibitory (poly-)peptide sequence does not have less than 10 amino acid residues, more preferably not less than 11 amino acid residues.

Furthermore, a "JNK inhibitor" of the present invention inhibits JNK activity, e.g. exhibits with regard to the inhibition of human JNK mediated phosphorylation of a c-Jun substrate (SEQ ID NO: 198) an IC 50 value of:
a) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK1,
b) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK2, and/or
c) less than 3000 nM, more preferably less than 2000 nM, even more preferably less than 1000 nM, even more preferably less than 500 nM, even more preferably less than 250 nM, even more preferably less than 200 nM, even more preferably less than 150 nM, most preferably less than 100 nM with regard to inhibition of human JNK3.

For some applications, it is preferred that the inhibitor inhibits human JNK2 and/or human JNK3 according to the above definition, but not JNK1 according to the above definition.

Whether JNK activity is inhibited or not, may easily be assessed by a person skilled in the art. There are several methods known in the art. One example is a radioactive kinase assay or a non-radioactive kinase assay (e.g. Alpha screen test; see for example Guenat et al. J Biomol Screen, 2006; 11: pages 1015-1026).

A JNK inhibitor according to the present invention may thus for example comprise an inhibitory (poly-)peptide sequence according to any of SEQ ID NOs: 2 to 27 (see table 1).

TABLE 1

Examples for inhibitory (poly-)peptide sequences of JNK-inhibitors according to the present invention

| Amino acid sequence | SEQ ID NO: |
|---|---|
| rPKRPTTLNLF | 2 |
| RPkRPTTLNLF | 3 |
| RPKRPaTLNLF | 4 |
| RPKRPTTLnLF | 5 |
| RPKRPTTLrLF | 6 |
| RPKRPTTLNLf | 7 |
| RPkRPaTLNLf | 8 |
| RPkRPTTLNLf | 9 |
| RPkRPTTLrLf | 10 |
| RRrRPTTLNLf | 11 |
| QRrRPTTLNLf | 12 |
| RPkRPTTLNLw | 13 |
| RPkRPTDLNLf | 14 |
| RRrRPTTLrLw | 15 |
| QRrRPTTLrLw | 16 |
| RRrRPTDLrLw | 17 |
| QRrRPTDLrLw | 18 |
| RRrRPaTLNLf | 19 |
| QRrRPaTLNLf | 20 |
| RrKRPaTLNLf | 21 |
| RPkRPsTLNLf | 22 |
| RPkRPqTLNLf | 23 |
| RPkRPkTLNLf | 24 |
| rGKRKALKLf | 25 |
| rGKRKALrLf | 26 |
| RRrRKALrLf | 27 |

The JNK inhibitor according to the present invention may also be a JNK inhibitor (variant) which comprises an inhibitory (poly-)peptide sequence sharing at least 50%, more preferably at least 55%, more preferably at least 60%, more preferably at least 65%, more preferably at least 70%, more preferably at least 75%, more preferably at least 80%, more preferably at least 85%, most preferably at least 90%, more preferably at least 95% sequence identity with a sequence selected from SEQ ID NOs: 1-27, in particular with SEQ ID NO: 8,
preferably with the proviso that with regard to the respective sequence selected from SEQ ID NOs: 1-27, such inhibitory (poly-)peptide sequence sharing sequence identity
a) maintains the L-arginine (R) residue on position 4,
b) maintains the two L-leucine (L) residues at position 8 and 10 (positions 7 and 9 with regard to SEQ ID NOs: 25-27),
c) exhibits one, two, three, four, five or six D-amino acid(s) at the respective positions corresponding to the amino acids selected from the group consisting of X1, X2, X3, X5, X7 and X8 of SEQ ID NO: 1 and respective positions in SEQ ID NOs: 2-27, more preferably exhibits one, two, three or four D-amino acid(s) at the positions corresponding to the amino acids selected from the group consisting of X3, X5, X7 and X8 of SEQ ID NO: 1 and respective positions in SEQ ID NOs: 2-27, and d) still inhibits JNK activity (i.e. is a JNK inhibitor as defined herein).

Certainly, variants disclosed herein (in particular JNK inhibitor variants comprising an inhibitory (poly-)peptide sequence sharing—within the above definition—a certain degree of sequence identity with a sequence selected from SEQ ID NOs: 1-27), share preferably less than 100% sequence identity with the respective reference sequence.

In view of said definition and for sake of clarity the residues which may preferably not be altered variants of JNK inhibitors comprising SEQ ID NOs: 1-27 (see a) and b) in the above definition) are underlined in table 1.

The non-identical amino acids are preferably the result of conservative amino acid substitutions.

Conservative amino acid substitutions, as used herein, may include amino acid residues within a group which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, Ile) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art. The isomer form should preferably be maintained, e.g. K is preferably substituted for R or H, while k is preferably substituted for r and h.

Further possible substitutions within the above definition for JNK inhibitor variants are for example:

a) one, two or more of X1, X2, X3, X4, X5, X6, X7 and/or X8 of SEQ ID NO: 1 or the corresponding positions within the respective sequence selected from SEQ ID NOs: 2-27 are substituted for A or a, b) X1 or X8 of SEQ ID NO: 1 or the corresponding position within the respective sequence selected from SEQ ID NOs: 2-27 is deleted;

c) X5 of SEQ ID NO: 1 or the corresponding position within the respective sequence selected from SEQ ID NOs: 2-27 is E, Y, L, V, F or K;

d) X5 of SEQ ID NO: 1 or the corresponding position within the respective sequence selected from SEQ ID NOs: 2-27 is E, L, V, F or K; or e) one, two or three of X1, X2, X3 of SEQ ID NO: 1 or the corresponding positions within the respective sequence selected from SEQ ID NOs: 2-27 are neutral amino acids.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. For purposes of determining sequence identity, the substitution of an L-amino acid for a D-amino acid (and vice versa) is considered to yield a non-identical residue, even if it is merely the D- (or L-isomer) of the very same amino acid.

Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448.). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences.

Certainly, the JNK inhibitor according to the present invention may comprise—in addition to the inhibitory (poly-)peptide sequence mentioned above—additional sequences or sequence elements, domains, labels (e.g. fluorescent or radioactive labels), epitopes etc., as long as the ability to inhibit JNK activity as defined herein is not lost. For example, the JNK inhibitor according to the present invention may also comprise a transporter sequence. A "transporter sequence" as used herein, is a (poly-)peptide sequence providing for translocation of the molecule it is attached to across biological membranes. Accordingly, a JNK inhibitor according to the present invention comprising a transporter sequence is preferably capable of translocating (e.g. the conjugated cargo compound) across biological membranes. Thus, such JNK inhibitors of the present invention may more readily enter into a cell, a cellular subcompartment and/or into the nucleus of a cell.

Said transporter sequence may be joined for example (e.g. directly) N-terminally or (e.g. directly) C-terminally to the inhibitory (poly-)peptide sequence of the JNK inhibitor, preferably by a covalent linkage. The transporter sequence and the inhibitory (poly-)peptide sequence may also be spaced apart, e.g. may be separated by intermediate or linker sequences. It is also contemplated that the transporter sequence may be positioned entirely elsewhere in the JNK inhibitor molecule than the inhibitory (poly-)peptide sequence, in particular if the JNK inhibitor is a more complex molecule (e.g. comprising several domains, is a multimeric conjugate etc.). It is also contemplated that the transporter sequence and the inhibitory (poly-)peptide sequence may overlap. However, the JNK inhibitory activity of the JNK inhibitory portion needs to be maintained. Examples for such overlapping instances are given further below.

Transporter sequences for use with the JNK inhibitor of the present invention may be selected from, without being limited thereto, transporter sequences derived from HIV TAT (HIV), e.g. native proteins such as e.g. the TAT protein (e.g. as described in U.S. Pat. Nos. 5,804,604 and 5,674,980, each of these references being incorporated herein by reference), HSV VP22 (*Herpes simplex*) (described in e.g. WO 97/05265; Elliott and O'Hare, Cell 88: 223-233 (1997)), non-viral proteins (Jackson et al, Proc. Natl. Acad. Sci. USA 89: 10691-10695 (1992)), transporter sequences derived from Antennapedia, particularly from *Drosophila antennapedia* (e.g. the antennapedia carrier sequence thereof), FGF, lactoferrin, etc. or derived from basic peptides, e.g. peptides having a length of at least 5 or at least 10 or at least 15 amino acids, e.g. 5 to 15 amino acids, preferably 10 to 12 amino acids, Such transporter sequences preferably comprise at least 50%, more preferably at least 80%, more preferably 85% or even 90% basic amino acids, such as e.g. arginine, lysine and/or histidine, or may be selected from e.g. arginine rich peptide sequences, such as RRRRRRRRR ($R_9$; SEQ ID NO: 152), RRRRRRRR ($R_8$; SEQ ID NO: 153), RRRRRRR ($R_7$; SEQ ID NO: 154), RRRRRR ($R_6$, SEQ ID NO: 155), RRRRR ($R_5$, SEQ ID NO: 156) etc., from VP22, from PTD-4 proteins or peptides, from RGD-$K_{16}$, from PEPT1/2 or PEPT1/2 proteins or peptides, from SynB3 or SynB3 proteins or peptides, from PC inhibitors, from P21 derived proteins or peptides, or from JNKI proteins or peptides.

Examples of transporter sequences for use in the JNK inhibitor of the present invention are in particular, without being limited thereto, basic transporter sequences derived from the HIV-1 TAT protein. Preferably, the basic transporter sequence of the HIV-1 TAT protein may include sequences from the human immunodeficiency virus HIV-1 TAT protein, e.g. as described in, e.g., U.S. Pat. Nos. 5,804,604 and 5,674,980, each incorporated herein by reference. In this context, the full-length HIV-1 TAT protein has 86 amino acid residues encoded by two exons of the HIV TAT gene. TAT amino acids 1-72 are encoded by exon 1, whereas amino acids 73-86 are encoded by exon 2. The full-length TAT protein is characterized by a basic region which contains two lysines and six arginines (amino acids 49-57) and a cysteine-rich region which contains seven cysteine residues (amino acids 22-37). The basic region (i.e., amino acids 49-57) was thought to be important for nuclear localization. Ruben, S. et al., J. Virol. 63: 1-8 (1989); Hauber, J. et al., J. Virol. 63 1181-1187 (1989). The cysteine-rich region mediates the formation of metal-linked dimers in vitro (Frankel, A. D. et al, Science 240: 70-73 (1988); Frankel, A. D. et al., Proc. Natl. Acad. Sci USA 85: 6297-6300 (1988)) and is essential for its activity as a transactivator (Garcia, J. A. et al., EMBO J. 7: 3143 (1988); Sadaie, M. R. et al., J. Virol. 63:1 (1989)). As in other regulatory proteins, the N-terminal region may be involved in protection against intracellular proteases (Bachmair, A. et al., Cell 56: 1019-1032 (1989)). Preferred TAT transporter sequences for use in the JNK inhibitor of the present invention are preferably characterized by the presence of the TAT basic region amino acid sequence (amino acids 49-57 of naturally-occurring TAT protein); the absence of the TAT cysteine-rich region amino acid sequence (amino acids 22-36 of naturally-occurring TAT protein) and the absence of the TAT exon 2-encoded carboxy-terminal domain (amino acids 73-86 of naturally-occurring TAT protein). More preferably, the transporter sequence in the JNK inhibitor of the present invention may be selected from an amino acid sequence containing TAT residues 48-57 or 49 to 57 or variants thereof.

Preferably, the transporter sequence in a given JNK inhibitor of the present invention also exhibits D-amino acids, for example in order to improve stability towards proteases. Particularly preferred are transporter sequences which exhibit a specific order of alternating D- and L-amino acids. Such order of alternating D- and L-amino acids (the motif) may follow—without being limited thereto—the pattern of any one of SEQ ID NOs: 28-30:

$$d_l LLL_x d_m LLL_y d_n;$$ (SEQ ID NO: 28)

$$dLLLd(LLLd)_a;$$ (SEQ ID NO: 29)
and/or $$dLLLdLLLd;$$ (SEQ ID NO: 30)

wherein: d is a D-amino acid;
L is a L-amino acid;
a is 0-3, preferably 0-2, more preferably 0, 1, 2 or 3, even more preferably 0, 1, or 2 and most preferably 1;
l, m and n are independently from each other 1 or 2, preferably 1;
x and y are independently from each other 0, 1 or 2, preferably 1.

Said order of D- and L-amino acids (motif) becomes relevant when the transporter sequence is synthesized, i.e. while the amino acid sequence (i.e. the type of side chain residues) remains unaltered, the respective isomers alternate. For example, a known transporter sequence derived from HIV TAT is RKKRRQRRR (SEQ ID NO: 43). Applying the D-/L amino acid order of SEQ ID NO: 30 thereto would yield rKKRrQRRr (SEQ ID NO: 46).

In a particular embodiment the transporter sequence of the JNK inhibitor of the present invention may comprise at least one sequence according to rXXXrXXXr (SEQ ID NO: 31), wherein:
r represents an D-enantiomeric arginine;
X is any L-amino acid (including glycine);
and wherein each X may be selected individually and independently of any other X within SEQ ID NO: 31. Preferably at least 4 out of said 6× L-amino acids within SEQ ID NO: 31 are K or R. In another embodiment the JNK inhibitor according to the present invention comprises the transporter sequence $rX_1X_2X_3rX_4X_5X_6r$ (SEQ ID NO: 32), wherein $X_1$ is K, $X_2$ is K, $X_3$ is R and $X_4$, $X_5$, and $X_6$ are any L-amino acid (including glycine) selected independently from each other. Similarly, the transporter sequence of the JNK inhibitor according to the present invention may comprise the sequence rX₁X₂X₃rX₄X₅X₆r (SEQ ID NO: 33), wherein X₄ is Q, X₅ is R, X₆ is R and X₁, X₂, and X₃ are any L-amino acid (including glycine) selected independently from each other. The inventive JNK inhibitor may also comprise the sequence rX₁X₂X₃rX₄X₅X₆r (SEQ ID NO: 34), wherein one, two, three, four, five or six X amino acid residues are chosen from the group consisting of: X₁ is K, X₂ is K, X₃ is R, X₄ is Q, X₅ is R, X₆ is R, while the remaining X amino acid residues not selected from above group may be any L-amino acid (including glycine) and are selected independently from each other. X₁ is then preferably Y and/or X₄ is preferably K or R.

Examples of transporter sequences for use in the inventive JNK inhibitor molecule may be selected, without being limited thereto, from sequences as given in table 2 below, (SEQ ID NOs: 31-170) or from any fragment or variant or chemically modified derivative thereof (preferably it retains the function of translocating across a biological membrane).

TABLE 2

Examples for transporter (poly-)peptide sequences for use in the JNK-inhibitors according to the present invention

| SEQUENCE/PEPTIDE NAME | SEQ ID NO | | AA SEQUENCE |
|---|---|---|---|
| r3 (generic) | 31 | 9 | rXXXrXXXr |
| r3 (generic; right half) | 32 | 9 | rKKRrX₄X₅X₆r |
| r3 (generic; left half) | 33 | 9 | rX₁X₂X₃rQRRr |
| r3 (generic; individual) | 34 | 9 | rX₁X₂X₃rX₄X₅X₆r |
| TAT (1-86) | 35 | 86 | MEPVDPRLEP WKHPGSQPKT ACTNCYCKKC CFHCQVCFIT KALGISYGRK KRRQRRRPPQ GSQTHQVSLS KQPTSQSRGD PTGPKE |
| TAT (37-72) | 36 | 36 | CFITKALGIS YGRKKRRQRR RPPQGSQTHQ VSLSKQ |
| TAT (37-58) | 37 | 22 | CFITKALGIS YGRKKRRQRR RP |
| TAT (38-58)GGC | 38 | 24 | FITKALGISY GRKKRRQRRR PGGC |
| TAT CGG(47-58) | 39 | 15 | CGGYGRKKRR QRRRP |
| TAT (47-58)GGC | 40 | 15 | YGRKKRRQRR RPGGC |
| TAT (1-72) Mut | 40 | 15 | MEPVDPRLEP WKHPGSQPKT AFITKALGIS YGRKKRRQRR |
| Cys/Ala 72 | 41 | 56 | RPPQGSQTHQ VSLSKQ |
| L-TAT (s1a) | 42 | 10 | GRKKRRQRRR (NH₂-GRKKRRQRRR-COOH) |
| L-TAT (s1b) | 43 | 9 | RKKRRQRRR (NH₂-GRKKRRQRRR-COOH) |
| L-TAT (s1c) | 44 | 11 | YDRKKRRQRRR |
| D-TAT | 45 | 9 | rrrqrrkkr |
| r3-L-TAT | 46 | 9 | rKKRrQRRr |
| r3-L-TATi | 47 | 9 | rRRQrRKKr |
| βA-r₃-L-TAT | 48 | 9 | βA-rKKRrQRRr (βA: beta alanine) |
| βA-r₃-L-TATi | 49 | 9 | βA-rRRQrRKKr (βA: beta alanine) |
| FITC-βA-r₃-L-TAT | 50 | 9 | FITC-βA-rKKRrQRRr (βA: beta alanine) |
| FITC-βA-r₃-L-TATi | 51 | 9 | FITC-βA-rRRQrRKKr (βA: beta alanine) |
| TAT(s2-1) | 52 | 9 | rAKRrQRRr |
| TAT(s2-2) | 53 | 9 | rKARrQRRr |
| TAT(s2-3) | 54 | 9 | rKKArQRRr |
| TAT(s2-4) | 55 | 9 | rKKRrARRr |
| TAT(s2-5) | 56 | 9 | rKKRrQARr |
| TAT(s2-6) | 57 | 9 | rKKRrQRAr |
| TAT(s2-7) | 58 | 9 | rDKRrQRRr |

TABLE 2-continued

Examples for transporter (poly-)peptide sequences for use in the JNK-inhibitors according to the present invention

| SEQUENCE/PEPTIDE NAME | SEQ ID NO | | AA SEQUENCE |
|---|---|---|---|
| TAT(s2-8) | 59 | 9 | rKDrQRRr |
| TAT(s2-9) | 60 | 9 | rKKDrQRRr |
| TAT(s2-10) | 61 | 9 | rKKRrDRRr |
| TAT(s2-11) | 62 | 9 | rKKRrQDRr |
| TAT(s2-12) | 63 | 9 | rKKRrQRDr |
| TAT(s2-13) | 64 | 9 | rEKRrQRRr |
| TAT(s2-14) | 65 | 9 | rKERrQRRr |
| TAT(s2-15) | 66 | 9 | rKKErQRRr |
| TAT(s2-16) | 67 | 9 | rKKRrERRr |
| TAT(s2-17) | 68 | 9 | rKKRrQERr |
| TAT(s2-18) | 69 | 9 | rKKRrQREr |
| TAT(s2-19) | 70 | 9 | rFKRrQRRr |
| TAT(s2-20) | 71 | 9 | rKFRrQRRr |
| TAT(s2-21) | 72 | 9 | rKKFrQRRr |
| TAT(s2-22) | 73 | 9 | rKKRrFRRr |
| TAT(s2-23) | 74 | 9 | rKKRrQFRr |
| TAT(s2-24) | 75 | 9 | rKKRrQRFr |
| TAT(s2-25) | 76 | 9 | rRKRrQRRr |
| TAT(s2-26) | 77 | 9 | rKRRrQRRr |
| TAT(s2-27) | 78 | 9 | rKKKrQRRr |
| TAT(s2-28) | 79 | 9 | rKKRrRRRr |
| TAT(s2-29) | 80 | 9 | rKKRrQKRr |
| TAT(s2-30) | 81 | 9 | rKKRrQRKr |
| TAT(s2-31) | 82 | 9 | rHKRrQRRr |
| TAT(s2-32) | 83 | 9 | rKHRrQRRr |
| TAT(s2-33) | 84 | 9 | rKKHrQRRr |
| TAT(s2-34) | 85 | 9 | rKKRrHRRr |
| TAT(s2-35) | 86 | 9 | rKKRrQHRr |
| TAT(s2-36) | 87 | 9 | rKKRrQRHr |
| TAT(s2-37) | 88 | 9 | rIKRrQRRr |
| TAT(s2-38) | 89 | 9 | rKIRrQRRr |
| TAT(s2-39) | 90 | 9 | rKKIrQRRr |
| TAT(s2-40) | 91 | 9 | rKKRrIRRr |
| TAT(s2-41) | 92 | 9 | rKKRrQIRr |
| TAT(s2-42) | 93 | 9 | rKKRrQRIr |
| TAT(s2-43) | 94 | 9 | rLKRrQRRr |
| TAT(s2-44) | 95 | 9 | rKLRrQRRr |

TABLE 2 -continued

Examples for transporter (poly-)peptide sequences for use in the JNK-inhibitors according to the present invention

| SEQUENCE/PEPTIDE NAME | SEQ ID NO | | AA SEQUENCE |
|---|---|---|---|
| TAT(s2-45) | 96 | 9 | rKKLrQRRr |
| TAT(s2-46) | 97 | 9 | rKKRrLRRr |
| TAT(s2-47) | 98 | 9 | rKKRrQLRr |
| TAT(s2-48) | 99 | 9 | rKKRrQRLr |
| TAT(s2-49) | 100 | 9 | rMKRrQRRr |
| TAT(s2-50) | 101 | 9 | rKMRrQRRr |
| TAT(s2-51) | 102 | 9 | rKKMrQRRr |
| TAT(s2-52) | 103 | 9 | rKKRrMRRr |
| TAT(s2-53) | 104 | 9 | rKKRrQMRr |
| TAT(s2-54) | 105 | 9 | rKKRrQRMr |
| TAT(s2-55) | 106 | 9 | rNKRrQRRr |
| TAT(s2-56) | 107 | 9 | rKNRrQRRr |
| TAT(s2-57) | 108 | 9 | rKKNrQRRr |
| TAT(s2-58) | 109 | 9 | rKKRrNRRr |
| TAT(s2-59) | 110 | 9 | rKKRrQNRr |
| TAT(s2-60) | 111 | 9 | rKKRrQRNr |
| TAT(s2-61) | 112 | 9 | rQKRrQRRr |
| TAT(s2-62) | 113 | 9 | rKQRrQRRr |
| TAT(s2-63) | 114 | 9 | rKKQrQRRr |
| TAT(s2-64) | 115 | 9 | rKKRrKRRr |
| TAT(s2-65) | 116 | 9 | rKKRrQQRr |
| TAT(s2-66) | 117 | 9 | rKKRrQRQr |
| TAT(s2-67) | 118 | 9 | rSKRrQRRr |
| TAT(s2-68) | 119 | 9 | rKSRrQRRr |
| TAT(s2-69) | 120 | 9 | rKKSrQRRr |
| TAT(s2-70) | 121 | 9 | rKKRrSRRr |
| TAT(s2-71) | 122 | 9 | rKKRrQSRr |
| TAT(s2-72) | 123 | 9 | rKKRrQRSr |
| TAT(s2-73) | 124 | 9 | rTKRrQRRr |
| TAT(s2-74) | 125 | 9 | rKTRrQRRr |
| TAT(s2-75) | 126 | 9 | rKKTrQRRr |
| TAT(s2-76) | 127 | 9 | rKKRrTRRr |
| TAT(s2-77) | 128 | 9 | rKKRrQTRr |
| TAT(s2-78) | 129 | 9 | rKKRrQRTr |
| TAT(s2-79) | 130 | 9 | rVKRrQRRr |
| TAT(s2-80) | 131 | 9 | rKVRrQRRr |
| TAT(s2-81) | 132 | 9 | rKKVrQRRr |

TABLE 2 -continued

Examples for transporter (poly-)peptide sequences for use in the JNK-inhibitors according to the present invention

| SEQUENCE/PEPTIDE NAME | SEQ ID NO | | AA SEQUENCE |
|---|---|---|---|
| TAT(s2-82) | 133 | 9 | rKKRrVRRr |
| TAT(82-83) | 134 | 9 | rKKRrQVRr |
| TAT(s2-84) | 135 | 9 | rKKRrQRVr |
| TAT(s2-85) | 136 | 9 | rWKRrQRRr |
| TAT(s2-86) | 137 | 9 | rKWRrQRRr |
| TAT(s2-87) | 138 | 9 | rKKWrQRRr |
| TAT(s2-88) | 139 | 9 | rKKRrWRRr |
| TAT(s2-89) | 140 | 9 | rKKRrQWRr |
| TAT(s2-90) | 141 | 9 | rKKRrQRWr |
| TAT(s2-91) | 142 | 9 | rYKRrQRRr |
| TAT(s2-92) | 143 | 9 | rKYRrQRRr |
| TAT(s2-93) | 144 | 9 | rKKYrQRRr |
| TAT(s2-94) | 145 | 9 | rKKRrYRRr |
| TAT(s2-95) | 146 | 9 | rKKRrQYRr |
| TAT(s2-96) | 147 | 9 | rKKRrQRYr |
| TAT(s2-97) | 148 | 8 | rKKRrQRr |
| TAT(s2-98) | 149 | 9 | rKKRrQRrK |
| TAT(s2-99) | 150 | 9 | rKKRrQRrR |
| r3R6 | 151 | 9 | rRRRrRRRr |
| L-R9 | 152 | 9 | RRRRRRRRR |
| L-R8 | 153 | 8 | RRRRRRRR |
| L-R7 | 154 | 7 | RRRRRRR |
| L-R6 | 155 | 6 | RRRRRR |
| L-R5 | 156 | 5 | RRRRR |
| r9 | 157 | 9 | rrrrrrrrr |
| r6R4 (D/L) | 158 | 9 | rRrRrRrRr |
| r6R4 (DD/LL) | 159 | 9 | rrRRrrRRr |
| PTD-4 | 160 | 11 | YARAAARQARA |
| PTD-4 (variant 1) | 161 | 11 | WARAAARQARA |
| PTD-4 (variant 2) | 162 | 11 | WARAQRAAARA |
| L-Pi Penetratin | 163 | 16 | RQVKVWFQNRRMKWKK |
| D-Pi Penetratin | 164 | 16 | KKWKMRRNQFWVKVQR |
| JNKI, bestfit | 165 | 17 | WKRAAARKARAMSLNLF |
| JNKI, bestfit (variant 1) | 166 | 17 | WKRAAARAARAMSLNLF |
| MDCK transcytose sequence | 167 | 9 | RYRGDLGRR |
| YKGL | 168 | 4 | YKGL |

TABLE 2 -continued

Examples for transporter (poly-)peptide sequences for use in the JNK-inhibitors according to the present invention

| SEQUENCE/PEPTIDE NAME | SEQ ID NO | AA | SEQUENCE |
|---|---|---|---|
| P1 | 169 | 4 | RRTK |
| P66 | 170 | 4 | RRPK |

As mentioned above, transporter sequences may also be selected from fragments or variants of the above sequences of table 2 (with the proviso that such fragment or variant retain preferably the function to provide for translocation across biological membranes). In this specific context, variants and/or fragments of those transporter sequences preferably comprise a peptide sequence sharing at least 10%, at least 20%, at least 30%, at least 40%, at least 50%, at least 60%, at least 70%, at least 80% or at least 85%, preferably at least 90%, more preferably at least 95% and most preferably at least 99% sequence identity over the whole length of the sequence with such a transporter sequence as defined in Table 2. In this specific context, a "fragment" of a transporter sequence as defined in Table 2, is preferably to be understood as a truncated sequence thereof, i.e. an amino acid sequence, which is N-terminally, C-terminally and/or intrasequentially truncated compared to the amino acid sequence of the original sequence.

Furthermore, a "variant" of a transporter sequence or its fragment as defined above, is preferably to be understood as a sequence wherein the amino acid sequence of the variant differs from the original transporter sequence or a fragment thereof as defined herein in one or more mutation(s), such as one or more substituted, (or, if necessary, inserted and/or deleted) amino acid(s). Preferably, variants of such a transporter sequence as defined above have the same biological function or specific activity compared to the respective original sequence, i.e. provide for transport, e.g. into cells or the nucleus. In this context, a variant of such a transporter sequence as defined above may for example comprise about 1 to 50, 1 to 20, more preferably 1 to 10 and most preferably 1 to 5, 4, 3, 2 or 1 amino acid alterations. Variants of such a transporter sequence as defined above may preferably comprise conservative amino acid substitutions. The concept of conservative amino acid substitutions is known in the art and has already been set out above for the JNK inhibitory (poly-)peptide sequence and applies here accordingly.

The length of a transporter sequence incorporated in the JNK inhibitor of the present invention may vary. It is contemplated that in some embodiments the transporter sequence of the JNK inhibitor according to the present invention is less than 150, less than 140, less than 130, less than 120, less than 110, less than 100, less than 90, less than 80, less than 70, less than 60, less than 50, less than 40, less than 30, less than 20, and/or less than 10 amino acids in length.

Whether a specific transporter sequence is still functional in the context of the JNK inhibitor according to the present invention may readily be determined by a person skilled in the art. For instance, the JNK inhibitor comprising a transporter domain may be fused to a label, e.g. a fluorescent protein such as GFP, a radioactive label, an enzyme, a fluorophore, an epitope etc. which can be readily detected in a cell. Then, the JNK inhibitor comprising the transporter sequence and the label is transfected into a cell or added to a culture supernatant and permeation of cell membranes can be monitored by using biophysical and biochemical standard methods (for example flow cytometry, (immuno)fluorescence microscopy etc.).

Specific examples of JNK inhibitors according to the present invention comprising a transporter sequence are given in table 3:

TABLE 3

Examples for JNK inhibitors comprising an inhibitory (poly-)peptide sequence and a transporter sequence

| Amino acid sequence | AA | SEQ ID NO: |
|---|---|---|
| rKKRrQRRrRPkRPTTLNLf | 20 | 171 |
| rKKRrQRRrRPkRPaTLNLf | 20 | 172 |
| rKKRrQRRrRPkRPTTLrLf | 20 | 173 |
| rKKRrQRRrRPTTLNLf | 17 | 174 |
| rKKRrQRrRPTTLNLf | 16 | 175 |
| rKKRrQRRrRPkRPTTLNLw | 20 | 176 |
| rKKRrQRRrRPkRPTDLNLf | 20 | 177 |
| rKKRrQRRrRPTTLrLw | 17 | 178 |
| rKKRrQRrRPTTLrLw | 16 | 179 |
| rKKRrQRRrRPTDLrLw | 17 | 180 |
| rKKRrQRrRPTDLrLw | 16 | 181 |
| rKKRrQRRrRPaTLNLf | 17 | 182 |
| rKKRrQRrRPaTLNLf | 16 | 183 |
| rKKRrQRrKRPaTLNLf | 17 | 184 |
| rKKRrQRRrRPkRPsTLNLf | 20 | 185 |
| rKKRrQRRrRPkRPqTLNLf | 20 | 186 |
| rKKRrQRRrRPkRPkTLNLf | 20 | 187 |
| rKKRrQRRrGKRKALKLf | 18 | 188 |
| rKKRrQRRrGKRKALrLf | 18 | 189 |
| rKKRrQRRrRKALrLf | 16 | 190 |

As mentioned above, in a particular embodiment of the present invention the transporter sequence and the inhibitory (poly-)peptide sequence may overlap. In other words, the N-terminus of the transporter sequence may overlap with the C-terminus of the inhibitory (poly-)peptide sequence or the C-terminus of the transporter sequence may overlap with the N-terminus of the inhibitory (poly-)peptide sequence. The latter embodiment is particularly preferred. Preferably, the transporter sequence overlaps by one, two or three amino acid residues with the inhibitory (poly-)peptide sequence. In such scenario, a given transporter sequence may overlap with SEQ ID NO:1 or the respective variants thereof at position 1 (X1), position 1 and 2 (X1, X2), positions 1, 2 and 3 (X1, X2, X3).

SEQ ID NOs: 174, 175, 178, 179, 180, 181, 182, 183, 184, 188, 189 and 190 are examples for JNK inhibitors according to the present invention, wherein transporter sequence and the inhibitory (poly-)peptide sequence overlap, e.g.

rKKRrQRRrRPTTLNLf (SEQ ID NO: 174)

is an overlap of SEQ ID NO: 46 (underlined) and SEQ ID NO: 11 (italics).

The JNK inhibitor according to the present invention may also be selected from JNK inhibitors, which are a variant of any one of the JNK inhibitors according to SEQ ID NOs: 171-190. Preferably, such variant shares at least 50%, more preferably at least 55%, more preferably at least 60%, more preferably at least 65%, more preferably at least 70%, more preferably at least 75%, more preferably at least 80%, more preferably at least 85%, more preferably at least 90%, most preferably at least 95% sequence identity with the sequence of SEQ ID NOs: 171-190, in particular with SEQ ID NO: 172, with the proviso that with respect to the inhibitory (poly-)peptide sequence within said sequences of SEQ ID NOs: 171-190 (see for reference inhibitory (poly-)peptide sequence of SEQ ID NO: 1 and specific examples of SEQ ID NOs: 2-27)) such sequence sharing sequence identity a) maintains the L-arginine (R) residue on position 4 within the inhibitory (poly-)peptide sequence,
b) maintains the two L-leucine (L) residues at position 8 and 10 (positions 7 and 9 with regard to SEQ ID NOs: 25-27) within the inhibitory (poly-)peptide sequence,
c) exhibits at least one, at least two, at least three, at least four, at least five or six D-amino acid(s) at the respective positions corresponding to the amino acids selected from the group consisting of X1, X2, X3, X5, X7 and or X8 of SEQ ID NO: 1 and respective positions in SEQ ID NOs: 2-27, more preferably exhibits at least one, at least two, at least three or four D-amino acid(s) at the positions corresponding to the amino acids selected from the group consisting of X3, X5, X7 and X8 of SEQ ID NO: 1 and respective positions in SEQ ID NOs: 2-27, and
d) inhibits JNK activity (i.e. is a JNK inhibitor as defined herein).

In view of said definition and for sake of clarity the residues which may preferably not be altered in variants of JNK inhibitors comprising SEQ ID NOs: 171-190 (see a) and b) in the above definition) are underlined in table 3.

The non-identical amino acids in the variants of JNK inhibitors comprising SEQ ID NOs: 171-190 are preferably the result of conservative amino acid substitutions (see above). Certainly, the further possible substitutions mentioned above are also contemplated for variants of JNK inhibitors comprising SEQ ID NOs: 171-190. Likewise, the present invention certainly also contemplates variants of any one of the JNK inhibitors according to SEQ ID NOs: 171-190, which deviate from the original sequence not or not exclusively in the inhibitory (poly-)peptide sequence, but exhibits variant residues in the transporter sequence. For variants and fragments of transporter sequences, the respective disclosure herein is pertinent.

As mentioned previously, the transporter sequence and the JNK inhibitory (poly-)peptide sequence of the JNK inhibitors according to the present invention need not necessarily be directly linked to each other. They may also be linked by e.g. an intermediate or linking (poly-)peptide sequences. Preferred intermediate or linking sequences separating the inhibitory (poly-)peptide sequences and other (functional) sequences such as transporter sequences consist of short peptide sequences of less than 10 amino acids in length, like a hexamer, a pentamer, a tetramer, a tripeptide or a dipeptide or a single amino acid residue. Particularly preferred intermediate sequence are one, two or more copies of di-proline, di-glycine, di-arginine and/or di-lysine, all either in L-amino acid form only, or in D-amino acid form only, or with mixed D- and L-amino acids. Alternatively, other known peptide spacer or linker sequences may be employed as well.

A particularly preferred JNK inhibitor according to the present invention comprises SEQ ID NO: 8 (or a sequence sharing sequence identity with SEQ ID NO: 8 with the scope and limitations defined further above) and a transporter sequence. The transporter sequence is preferably selected from any one of SEQ ID Nos: 31-170 or variants thereof as defined herein, even more preferably from any one of SEQ ID NOs: 31-34 and 46-151. A particularly preferred embodiment of a JNK inhibitor according to the present invention is a JNK inhibitor comprising SEQ ID NO: 8 and SEQ ID NO: 46 (or sequences sharing respective sequence identity thereto within the scope and limitations defined above). A preferred example is a JNK inhibitor comprising the sequence of SEQ ID NO: 172 or respective variants thereof varying in the transporter sequence and/or the inhibitory (poly-)peptide sequence as defined herein.

In a further aspect, the present invention relates to a JNK inhibitor comprising
a) an inhibitory (poly-)peptide comprising a sequence from the group of sequences consisting of RPTTLNLF (SEQ ID NO: 191), KRPTTLNLF (SEQ ID NO: 192), RRPTTLNLF and/or RPKRPTTLNLF (SEQ ID NO: 193), and
b) a transporter sequence, preferably a transporter sequence selected from the transporter sequences disclosed in table 2 or variants/fragments thereof, even more preferably selected from SEQ ID NOs: 31-34 and 46-151 or respective variants or fragments thereof.

The transporter sequence and the inhibitory (poly-)peptide sequence may overlap. Preferred transporter sequences for said embodiment of the invention are particularly the transporter sequence of SEQ ID NO: 46, preferably (covalently) linked (e.g. directly) to the N-terminus of the inhibitory (poly-)peptide sequence.

A JNK inhibitor of the present invention may also be a JNK inhibitor comprising or consisting of the sequence GRKKRRQRRRPPKRPTTLNLFPQVPRSQD (SEQ ID NO: 194), or the sequence GRKKRRQRRRPT-TLNLFPQVPRSQD (SEQ ID NO: 195).

In a further aspect, the present invention relates to a (poly-)peptide comprising a transporter sequence selected from the group of sequences consisting of rKKRrQRr (SEQ ID NO: 148), rKKRrQRrK (SEQ ID NO: 149), and/or rKKRrQRrR (SEQ ID NO: 150).

As used herein, "comprising" a sequence or a given SEQ ID NO as disclosed herein usually implies that (at least) one copy of said sequence is present, e.g. in the JNK inhibitor molecule. For example, one inhibitory (poly-)peptide sequence will usually suffice to achieve sufficient inhibition of JNK activity. However, it is contemplated according to the invention to use two or more copies of the respective sequence (e.g. two or more copies of an inhibitory (poly-) peptide sequence of different or same type and/or two or more copies of a transporter sequence of different or the same type) may also employed for the inventive (poly) peptide, as long as the overall ability of the resulting molecule to inhibit JNK activity is not abolished (i.e. the respective molecule is still a JNK inhibitor as defined herein).

The inventive JNK inhibitors may be obtained or produced by methods well-known in the art, e.g. by chemical synthesis via solid-phase peptide synthesis using Fmoc (9-fluorenylmethyloxycarbonyl) strategy, i.e. by successive rounds of Fmoc deprotection and Fmoc-amino acid coupling cycles. A commercial service offering such peptide synthesis is provided by many companies, for example the company PolyPeptide (StraBbourg, France).

The JNK inhibitors for use according to the present invention may optionally be further modified, in particular at the amino acid residues of the inhibitory (poly-peptide) sequence. Possible modifications may for example be selected from one or more of items (i) to (xiii) of the group consisting of:
 (i) radioactive labels, i.e. radioactive phosphorylation or a radioactive label with sulphur, hydrogen, carbon, nitrogen, etc.;
 (ii) colored dyes (e.g. digoxygenin, etc.);
 (iii) fluorescent groups (e.g. fluorescein, etc.);
 (iv) chemiluminescent groups;
 (v) groups for immobilization on a solid phase (e.g. His-tag, biotin, strep-tag, flag-tag, antibodies, epitopes, etc.);
 (vi) pegylation,
 (vii) glycosylation,
 (viii) hesylation,
 (ix) protease cleavage sites (e.g. for controlled release of the JNK inhibitor)
 (x) peptide backbone modifications (e.g. ($\Psi CH_2$—NH) bonds)
 (xi) protection of amino acid side chain residues,
 (xii) protection of N- and/or C-terminus (e.g. N-terminal amidation or C-terminal acetylation)
 (xiii) a combination of elements of two or more of the elements mentioned under (i) to (xii).

Particularly preferred are modifications selected from (i) to (xi) and combinations of elements of two or more of the elements mentioned under (i) to (xi). In this context, the present invention relates in a further aspect to a JNK inhibitor as disclosed herein modified with modifications selected from (i) to (xi) or modified with a combination of two or more of the elements mentioned under (i) to (xi), and a pharmaceutical composition (see below) comprising such modified JNK inhibitor.

Pharmaceutical Compositions

The JNK inhibitors as defined according to the invention can be formulated in a pharmaceutical composition, which may be applied in the prevention or treatment of any of the diseases as defined herein. Typically, such a pharmaceutical composition used according to the present invention includes as an active component a JNK inhibitor as defined herein, in particular a JNK inhibitor comprising or consisting of an inhibitory (poly-)peptide sequence according to SEQ ID NO: 1, as defined herein. Preferably, the active compound is a JNK inhibitor comprising or consisting of an inhibitory (poly-)peptide sequence according to any one of SEQ ID NOs: 2-27, optionally in (covalent) conjugation (via or without a linker sequence) with any suitable transporter sequence; if a transporter sequence is attached, any of the sequences according to any one of SEQ ID NOs: 171-190, or a variant thereof as defined herein, preferably a sequence according to SEQ ID NOs: 172, or a variant thereof as defined herein, may be selected.

The inventors of the present invention additionally found that the JNK-inhibitors as defined herein, in particular if fused to a transporter sequence; exhibit a particularly pronounced uptake rate into cells involved in the diseases of the present invention. Therefore, the amount of a JNK-inhibitor inhibitor in the pharmaceutical composition to be administered to a subject, may—without being limited thereto—be employed on the basis of a low dose within that composition. Thus, the dose to be administered may be much lower than for peptide drugs known in the art, such as DTS-108 (Florence Meyer-Losic et al., Clin Cancer Res., 2008, 2145-53). Thereby, for example a reduction of potential side reactions and a reduction in costs is achieved by the inventive (poly)peptides.

Preferably, the dose (per kg body weight), e.g. to be administered on a daily basis to the subject, is in the range of up to about 10 mmol/kg, preferably up to about 1 mmol/kg, more preferably up to about 100 µmol/kg, even more preferably up to about 10 µmol/kg, even more preferably up to about 1 µmol/kg, even more preferably up to about 100 nmol/kg, most preferably up to about 50 nmol/kg.

Thus, the dose range may preferably be from about 0.01 pmol/kg to about 1 mmol/kg, from about 0.1 pmol/kg to about 0.1 mmol/kg, from about 1.0 pmol/kg to about 0.01 mmol/kg, from about 10 pmol/kg to about 1 pmol/kg, from about 50 pmol/kg to about 500 nmol/kg, from about 100 pmol/kg to about 300 nmol/kg, from about 200 pmol/kg to about 100 nmol/kg, from about 300 pmol/kg to about 50 nmol/kg, from about 500 pmol/kg to about 30 nmol/kg, from about 250 pmol/kg to about 5 nmol/kg, from about 750 pmol/kg to about 10 nmol/kg, from about 1 nmol/kg to about 50 nmol/kg, or a combination of any two of said values.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980. Accordingly, a "safe and effective amount" for components of the pharmaceutical compositions as used according to the present invention means an amount of each or all of these components, that is sufficient to significantly induce a positive modification of diseases or disorders strongly related to JNK signalling as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of such a component will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

The pharmaceutical composition as used according to the present invention may furthermore comprise, in addition to one or more of the JNK inhibitors, a (compatible) pharmaceutically acceptable carrier, excipient, buffer, stabilizer or other materials well known to those skilled in the art.

In this context, the expression "(compatible) pharmaceutically acceptable carrier" preferably includes the liquid or non-liquid basis of the composition. The term "compatible" means that the constituents of the pharmaceutical composition as used herein are capable of being mixed with the pharmaceutically active component as defined above and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated.

If the pharmaceutical composition as used herein is provided in liquid form, the pharmaceutically acceptable carrier will typically comprise one or more (compatible) pharmaceutically acceptable liquid carriers. The composition may comprise as (compatible) pharmaceutically acceptable liquid carriers e.g. pyrogen-free water; isotonic saline, i.e. a solution of 0.9% NaCl, or buffered (aqueous) solutions, e.g. phosphate, citrate etc. buffered solutions, vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid, etc. Particularly for injection and/or infusion of the pharmaceutical composition as used herein, a buffer, preferably an aqueous buffer, and/or 0.9% NaCl may be used.

If the pharmaceutical composition as used herein is provided in solid form, the pharmaceutically acceptable carrier will typically comprise one or more (compatible) pharmaceutically acceptable solid carriers. The composition may comprise as (compatible) pharmaceutically acceptable solid carriers e.g. one or more compatible solid or liquid fillers or diluents or encapsulating compounds may be used as well, which are suitable for administration to a person. Some examples of such (compatible) pharmaceutically acceptable solid carriers are e.g. sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulphate, etc.

The precise nature of the (compatible) pharmaceutically acceptable carrier or other material may depend on the route of administration. The choice of a (compatible) pharmaceutically acceptable carrier may thus be determined in principle by the manner in which the pharmaceutical composition as used according to the invention is administered. Various possible routes of administration are listed in the list "Route of Administration" of the FDA (cf. FDA: Data Standards Manual—Drug Nomenclature Monographs—Monograph Number: C-DRG-00301; Version Number 004), which is incorporated by reference herein. Further guidance for selecting an appropriate route of administration, in particular for non-human animals, can be found in Turner P V et al. (2011) Journal of the American Association for Laboratory Animal Science, Vol. 50, No 5, p. 600-613, which is also incorporated by reference herein. Preferred examples for routes for administration include, for example, parenteral routes (e.g. via injection), such as intravenous, intramuscular, subcutaneous, intradermal, or transdermal routes, etc., enteral routes, such as oral, or rectal routes, etc., topical routes, such as nasal, or intranasal routes, etc., or other routes, such as epidermal routes or patch delivery. Also contemplated (in particular for eye related diseases) are instillation, intravitreal, and subconjunctival administration. Likewise, administration may occur intratympanical, for example, whenever ear related diseases are treated.

The pharmaceutical composition as used according to the invention can be administered, for example, systemically. In general, routes for systemic administration include, for example, parenteral routes (e.g. via injection and/or infusion), such as intravenous, intra-arterial, intraosseous, intramuscular, subcutaneous, intradermal, transdermal, or transmucosal routes, etc., and enteral routes (e.g. as tablets, capsules, suppositories, via feeding tubes, gastrostomy), such as oral, gastrointestinal or rectal routes, etc. By systemic administration a system-wide action can be achieved and systemic administration is often very convenient, however, depending on the circumstances it may also trigger unwanted "side-effects" and/or higher concentrations of the JNK inhibitor according to the invention may be necessary as compared to local administration. Systemic administration is in general applicable for the prevention and/or treatment of the diseases/disorders mentioned herein due to its system-wide action. Preferred routes of systemic administration are intravenous, intramuscular, subcutaneous, oral and rectal administration, whereby intravenous and oral administration are particularly preferred.

The pharmaceutical composition as used according to the invention can also be administered, for example, locally, for example topically. Topical administration typically refers to application to body surfaces such as the skin or mucous membranes, whereas the more general term "local administration" additionally comprises application in and/or into specific parts of the body. Topical application is particularly preferred for the treatment and/or prevention of diseases and/or disorders of the skin and/or subcutaneous tissue as defined herein as well as for certain diseases of the mouth and/or diseases relating to or are accessible by mucous membranes.

Routes for local administration include, for example, inhalational routes, such as nasal, or intranasal routes, ophtalamic and otic drugs, e.g. eye drops and ear drops, administration through the mucous membranes in the body, etc., or other routes, such as epidermal routes, epicutaneous routes (application to the skin) or patch delivery and other local application, e.g. injection and/or infusion, into the organ or tissue to be treated etc. In local administration side effects are typically largely avoided. It is of note, that certain routes of administration may provide both, a local and a systemic effect, for example inhalation.

Routes for administration for the pharmaceutical composition as used according to the invention can be chosen according to the desired location of the application depending on the disorder/disease to be prevented or treated.

For example, an enteral administration refers to the gastrointestinal tract as application location and includes oral (p.o.), gastrointestinal and rectal administration, whereby these are typically systemic administration routes, which are applicable to the prevention/treatment of the diseases mentioned herein in general. In addition, enteral administration is preferred to prevent and/or treat diseases/disorders of the gastrointestinal tract as mentioned herein, for example inflammatory diseases of the gastrointestinal tract, metabolic diseases, cancer and tumor diseases, in particular of the gastrointestinal tract etc. For example, the oral route is usually the most convenient for a patient and carries the lowest cost. Therefore, oral administration is preferred for convenient systemic administration, if applicable. Pharmaceutical compositions for oral administration may be in tablet, capsule, powder or liquid form. A tablet may include a solid carrier as defined above, such as gelatin, and optionally an adjuvant. Liquid pharmaceutical compositions for oral administration generally may include a liquid carrier as defined above, such as water, petroleum, animal or vegetable oils, mineral oil or synthetic oil. Physiological saline solution, dextrose or other saccharide solution or glycols such as ethylene glycol, propylene glycol or polyethylene glycol may be included.

Furthermore, enteral administration also includes application locations in the proximal gastrointestinal tract without reaching the intestines, for example sublingual, sublabial, buccal or intragigingval application. Such routes of administration are preferred for applications in stomatology, i.e. disease/disorders of the mouth which may be treated and/or prevented with the JNK inhibitors as disclosed herein, for example pulpitis in general, in particular acute pulpitis, chronic pulpitis, hyperplastic pulpitis, ulcerative pulpitis, irreversible pulpitis and/or reversible pulpitis; periimplantitis; periodontitis in general, in particular chronic periodontitis, complex periodontitis, simplex periodontitis, aggressive periodontitis, and/or apical periodontitis, e.g. of pulpal origin; periodontosis, in particular juvenile periodontosis; gingivitis in general, in particular acute gingivitis, chronic gingivitis, plaque-induced gingivitis, and/or non-plaque-induced gingivitis; pericoronitis, in particular acute and chronic pericoronitis; sialadenitis (sialoadenitis); parotitis, in particular infectious parotitis and autoimmune parotitis; stomatitis in general, in particular aphthous stomatitis (e.g., minor or major), Bednar's aphthae, periadenitis mucosa necrotica recurrens, recurrent aphthous ulcer, stomatitis herpetiformis, gangrenous stomatitis, denture stomatitis, ulcerative stomatitis, vesicular stomatitis and/or gingivostomatitis; mucositis, in particular mucositis due to antineoplastic therapy, due to (other) drugs, or due to radiation, ulcerative mucositis and/or oral mucositis; cheilitis in general, in particular chapped lips, actinic cheilitis, angular cheilitis, eczematous cheilitis, infectious cheilitis, granulomatous cheilitis, drug-related cheilitis, exfoliative cheilitis, cheilitis glandularis, and/or plasma cell cheilitis; cellulitis (bacterial infection), in particular of mouth and/or lips; desquamative disorders, in particular desquamative gingivitis; and/or temporomandibular joint disorder. Particularly preferred diseases to be treated and/or prevented according to the invention by these routes of administration are selected from periodontitis, in particular chronic periodontitis, mucositis, oral desquamative disorders, oral liquen planus, pemphigus vulgaris, pulpitis, stomatitis, temporomandibular joint disorder, and peri-implantitis.

For example, intragingival administration, e.g. by injection into the gums (gingiva), is preferred in stomatology applications, for example for preventing and/or treating periodontitis. For example, disorders/diseases of the mouth, in particular periodontitis, may be prevented or treated by sublingual, sublabial, buccal or intragingival application, in particular intragingival application, of the pharmaceutical composition as defined above comprising a dose (per kg body weight) of 100 ng/kg to 100 mg/kg, preferably 10 µg/kg to 10 mg/kg, more preferably of the JNK inhibitor according to the present invention.

Alternatively, the diseases of the mouth mentioned herein may also be treated and/or prevented by systemic and, preferably, topical administration of the JNK inhibitor as disclosed herein or the respective pharmaceutical composition.

In addition, enteral administration also includes strictly enteral administration, i.e. directly into the intestines, which can be used for systemic as well as for local administration.

Moreover, the JNK inhibitor according to the present invention, used in the prevention and/or treatment of diseases and/or disorders according to the present invention may be administered to the central nervous system (CNS). Such routes of administration include in particular epidural (peridural), intra-CSF (intra-cerebrospinal fluid), intracerebroventricular (intraventricular), intrathecal and intracerebral administration, for example administration into specific brain regions, whereby problems relating to the blood-brain-barrier can be avoided. Such CNS routes of administration are preferred if the disease/disorder to be treated is a neural, a neurological and/or a neurodegenerative disease as specified herein.

In addition, the JNK inhibitor according to the present invention, used in the prevention and/or treatment of diseases and/or disorders according to the present invention may be administered at, in or onto the eye. Such routes of administration include eye drops applied topically, for example onto the conjunctiva, and, intravitreous (IVT), subconjunctival, and posterior juxtascleral administration, e.g. by injection, infusion and/or instillation and/or localized, sustained-release drug delivery (for example in case of the subconjunctval route), whereby eyedrops (for topical application), intravitreous (IVT) and subconjunctival routes of administration are particularly preferred. The subconjunctival route is safer and less invasive than the intravitreal route, however, the intravitreal route involves less systemic exposure than the subconjunctival route due to the presence of conjunctival and orbital blood vessels and tissue.

Local administration onto/in the eye is particularly preferred for eye-related diseases/disorders to be treated and/or prevented as disclosed herein, for example age-related macular degeneration (AMD), in particular in the wet and dry form; angioid streaks; anterior ischemic optic neuropathy; anterior uveitis; cataract, in particular age related cataract; central exudative chorioretinopathy; central serous chorioretinopathy; chalazion; choriodermia; chorioiditis; choroidal sclerosis; conjunctivitis; cyclitis; diabetic retinopathy; dry eye syndrome; endophthalmitis; episcleritis; eye infection; fundus albipunctatus; gyrate atrophy of choroid and retina; hordeolum; inflammatory diseases of the blephara; inflammatory diseases of the choroid; inflammatory diseases of the ciliary body; inflammatory diseases of the conjunctiva; inflammatory diseases of the cornea; inflammatory diseases of the iris; inflammatory diseases of the lacrimal gland; inflammatory diseases of the orbital bone; inflammatory diseases of the sclera; inflammatory diseases of the vitreous body; inflammatory diseases of the uvea; inflammatory diseases of the retina; intermediate uveitis; iritis; keratitis; Leber's disease; multifocal chorioditis; myositis of the eye muscle; neovascular maculopathy (e.g. caused by high myopia, tilted disc syndrome, choroidal osteoma or the like); NMDA induced retinotoxicity; non-chronic or chronic inflammatory eye diseases; Oguchi's disease; optic nerve disease; orbital phlegmon; panophtalmitis; panuveitis; post capsule opacification; posterior capsule opacification (PCO) (a cataract after-surgery complication); posterior uveitis; intraocular inflammation, in particular post-surgery intraocular inflammation; proliferative vitreoretinopathy; retinal artery occlusion; retinal detachment, retinal diseases; retinal injuries; retinal macroaneurysm; retinal pigment epithelium detachment; retinal vein occlusion; retinitis; retinitis pigmentosa; retinitis *punctata albescens*; retinopathy, in particular retinopathy of prematurity and diabetic retinopathy; scleritis; Stargardt's disease; treatment of inflamed ocular wounds and/or ocular wound edges; treatment of intraocular inflammation after eye surgery or trauma; uveitis; vitelliform macular dystrophy; etc.

For the treatment of dry eye, it is preferred to address aqueous tear-deficient dry or evaporative dry eye diseases. Aqueous tear-deficient dry eye may refer to Sjögren syndrome dry eye or Non-Sjögren syndrome dry eye. Non-Sjögren syndrome dry eye may be caused by primary or secondary lacrimal gland dysfunction or obstruction of the lacrimal gland ducts. Evaporative dry eye may have intrinsic, e.g. Meibomian gland dysfunction, low blink rate or disorders of lid aperture, or extrinsic causes, e.g. ocular surface disorder, lens wear or allegergic rhinitis. In particular Sjögrens or non-Sjögrens dry eye syndrome are to be treated by the present invention.

In particular, dry eye syndrome, uveitis, in particular anterior and/or posterior uveitis, age-related macular degeneration (AMD), in particular the wet and the dry form of AMD, retinopathy, in particular retinopathy of prematurity and diabetic retinopathy, and post-surgery or post-trauma eye inflammation, in particular post-surgery or post-trauma intraocular inflammation, are prevented and/or treated by the JNK inhibitor used according to the present invention by local administration in and/or onto the eye, preferably by instillation, e.g. eye drops, and/or intravitreal and/or subconjunctival administration, e.g. by injection or instillation. Instillation, e.g. eyedrops, and/or subconjunctval administration, e.g. by injection, are thereby preferred routes of administration For these routes of administration, in particular for instillation, e.g. eyedrops, intravitreal and/or subconjunctival administration, the respective pharmaceutical composition according to the present invention, preferably comprises a dose per eye in the range of 10 ng to 100 mg, more preferably in the range of 100 ng to 10 mg, even more preferably in the range of 1 µg to 5 mg, and particularly preferable in the range of 100 µg to 1 mg, for example 0.1, 0.2, or 0.4 mg, of the JNK inhibitor according to the present invention, preferably of the JNK inhibitor according to a sequence of SEQ ID NO. 172. One single administration or more administrations, in particular two, three, four or five, administrations of such dose(s) are preferred, whereby subsequent dose(s) may be administered on different days of the treatment schedule.

For example for intravitreal and/or subconjunctival administration in humans a single dose (per eye) of the JNK inhibitor is preferably in the range of 1 µg to 5 mg, preferably 50 µg to 1.5 mg, more preferably 500 µg to 1 µg, most preferably 800 µg to 1 mg. The injection volume, in particular for subconjunctival injection, may be for example 100 µl to 500 µl, e.g. 250 µl.

For instillation, e.g. eye drops, in humans a single dose (per eye) of the JNK inhibitor is preferably in the range of 1 µg to 5 mg, preferably 10 µg to 1.5 mg, more preferably 50 µg to 1 mg, most preferably 100 µg to 600 µg. In the treatment and/or prevention by way of instillation, a single dose or repeated doses may be administered, preferably daily, for example daily 2 to 4 times per day, preferably daily 3 times a day, for several weeks, preferably 2 to 4 weeks, more preferably 3 weeks. Such an administration is for example particularly useful to treat and/or prevent dry eye syndrome.

For topical ocular administration, in particular as eyedrops, which may be applied to both eyes or to one eye only, depending on the need, the pharmaceutical composition comprising the JNK inhibitor according to the invention is typically a solution, preferably an ophthalamic solution, e.g. comprising (sterile) 0.9% NaCl. Such a pharmaceutical composition comprises in particular 0.001%-10% of the JNK inhibitor as described herein, preferably 0.01%-5% of the JNK inhibitor as described herein, more preferably 0.05%-2% of the JNK inhibitor as described herein, even more preferably 0.1%-1% of the JNK inhibitor as described herein. The eyedrops may be administered once or repeatedly, whereby repeated administration is preferred. In general, the administration depends on the need and may for example be on demand. In repeated administration, subsequent dose(s) may be administered on different days of the treatment schedule, whereby on the same day a single dose or more than one single doses, in particular two, three, four or five, preferably two or three doses may be administered, whereby such repeated administration is preferably spaced by intervals of one or more hour(s), e.g. two, three, four, five, six, seven or eight hours.

In addition, eye diseases as described herein may of course also be treated and/or prevented by systemic application of the JNK inhibitor according to the invention (which also applies to the other diseases/disorders as described herein). The dose for systemic administration in eye diseases, in particular for intravenous administration, ranges preferably from 0.001 mg/kg to 10 mg/kg, more preferably from 0.01 mg/kg to 5 mg/kg, even more preferably from 0.1 mg/kg to 2 mg/kg. Such doses are for example particularly useful to treat and/or prevent uveitis, whereby the treatment schedule may comprises a single dose or repeated doses, whereby subsequent dose(s) may be administered on different days of the treatment schedule.

For example, if more than a single dose is applied, in particular intravenously, in the treatment and/or prevention of uveitis, the doses are typically spaced by intervals of at least one day, preferably by intervals of at least two days, more preferably by intervals of at least three days, even more preferably by intervals of at least four days, at least five days, or at least six days, particularly preferably by intervals of at least a week, most preferably by intervals of at least ten days.

Other routes of administration for the use of the JNK inhibitor according to the present invention, which are typically chosen according to the disease to be prevented and/or treated and the respective pharmacokinetics, include—but are not limited to—epicutaneous application (onto the skin) and/or intralesional application (into a skin lesion), for example for skin diseases as defined herein (mentioned herein), in particular selected from psoriasis, eczema, dermatitis, acne, mouth ulcers, erythema, lichen plan, sarcoidose, vascularitis, and adult linear IgA disease; nasal administration, for example for diseases of the respiratory system and in particular lung diseases, for example acute respiratory distress syndrome (ARDS), asthma, chronic illnesses involving the respiratory system, chronic obstructive pulmonary disease (COPD), cystic fibrosis, inflammatory lung diseases, pneumonia, and pulmonary fibrosis; intraarticular administration (into a joint space), for example in arthritis, in particular juvenile idiopathic arthritis, psoriatic arthritis and rheumatoid arthritis, and arthrosis, and osteoarthritis; intravesical administration (i.e. into the urinary bladder), for example for diseases of the urinary system, in particular the urinary bladder; intracardiac administration, intracavernous administration, intravaginal administration, and intradermal administration.

In general, the method of administration depends on various factors as mentioned above, for example the selected pharmaceutical carrier and the nature of the pharmaceutical preparation (e.g. as a liquid, tablet etc.) as well as the route of administration. For example, the pharmaceutical composition comprising the JNK inhibitor according to the invention may be prepared as a liquid, for example as a solution of the JNK inhibitor according to the invention in 0.9% NaCl. A liquid pharmaceutical composition can be administered by various methods, for example as a spray (e.g., for inhalational, intranasal etc. routes), as a fluid for topical application, by injection, including bolus injection, by infusion, for example by using a pump, by instillation, but also p.o., e.g. as drops or drinking solution, in a patch delivery system etc. Accordingly, for the administration different devices may be used, in particular for injection and/or infusion, e.g. a syringe (including a pre-filled syringe); an injection device (e.g. the INJECT-EASET™ and GENJECTT™ device); an infusion pump (such as e.g. Accu-Chek™); an injector pen (such as the GENPENT™); a needleless device (e.g. MEDDECTOR™ and BIOJECTOR™); or an autoinjector.

The suitable amount of the pharmaceutical composition to be used can be determined by routine experiments with animal models. Such models include, without implying any limitation, for example rabbit, sheep, mouse, rat, dog, gerbil, pig, and non-human primate models. Preferred unit dose forms for administration, in particular for injection and/or infusion include sterile solutions of water, physiological saline or mixtures thereof. The pH of such solutions should be adjusted to about 7.4. Suitable carriers for administration, in particular for injection and/or infusion include hydrogels, devices for controlled or delayed release, polylactic acid and collagen matrices. Suitable pharmaceutically acceptable carriers for topical application include those, which are suitable for use in lotions, creams, gels and the like. If the compound is to be administered per orally, tablets, capsules and the like are the preferred unit dose form. The pharmaceutically acceptable carriers for the preparation of unit dose forms, which can be used for oral administration are well known in the prior art. The choice thereof will depend on secondary considerations such as taste, costs and storability, which are not critical for the purposes of the present invention, and can be made without difficulty by a person skilled in the art.

For intravenous, intramuscular, intraperitoneal, cutaneous or subcutaneous injection and/or infusion, or injection and/or infusion at the site of affliction, i.e. local injection/infusion, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, in particular 0.9% NaCl, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "prophylactically effective amount or a "therapeutically effective amount" (as the case may be), this being sufficient to show benefit to the individual. The actual amount administered, and rate and time-course of administration, will depend on the nature and severity of what is being treated. For example, for i.v. administration in humans, single doses of up to 1 mg per kg body weight are preferred, more preferably up to 500 μg per kg body weight, even more preferably up to 100 μg per kg body weight, for example in the range of 100 ng to 1 mg per kg body weight, more specifically in the range of 1 μg to 500 μg per kg body weight, even more specifically in the range of 5 μg to 100 μg per kg body weight. Such doses may be administered for example as injection and/or infusion, in particular as infusion, whereby the duration of the infusion varies for example between 1 to 90 min, preferably 10 to 70 min, more preferably 30 to 60 min.

In addition, the pharmaceutical composition as used according to the present invention may additionally—i.e. in addition to any one or more of the JNK inhibitors as defined herein, and/or variants, fragments or derivatives thereof, nucleic acids, cells or cells transfected with a vector and/or nucleic acids as defined above—also comprise optionally a further "active component", which is also useful in the respective disease. In this context, the pharmaceutical composition according to the present invention may also combined in the therapy of the diseases according to the present invention with a further pharmaceutical composition comprising a further "active component". For example, a pharmaceutical composition comprising a JNK inhibitor according to the present invention may be used in post-surgery intraocular inflammation as stand-alone therapy or in combination with corticosteroids, preferably glucocorticoids, e.g. dexamethasone. Moreover, e.g. a pharmaceutical composition comprising a JNK inhibitor and/or chimeric peptide according to the present invention may preferably be used in the prevention and/or treatment of Alzheimer's Disease and/or Mild Cognitive Impairment, in particular MCI due to Alzheimer's disease, as stand-alone therapy or in combination with PKR inhibitors and, optionally, in addition to the JNK inhibitor according to the present invention and the PKR inhibitor with a amyloid lowering agent. PKR inhibitors are in particular peptides, e.g. "SC1481" by Polypeptide Group. Amyloid lowering agents include β-secretase (BACE1) inhibitors, γ-secretase inhibitors (GSI) and modulators (GSM). Non-limiting examples of such amyloid lowering agents. which are currently in clinical trials may be retrieved from Vassar R. (2014) BACE1 inhibitor drugs in clinical trials for Alzheimer's disease. Alzheimers Res Ther.; 6(9):89 and/or from Jia Q, Deng Y, Qing H (2014) Potential therapeutic strategies for Alzheimer's disease targeting or beyond β-amyloid: insights from clinical trials. Biomed Res Int. 2014; 2014:837157; for example Pioglitazone, CTS-21166, MK8931, LY2886721, AZD3293, E2609, NIC5-15, Begacestat, CHF 5074, EVP-0962, Atorvastatin, Simvastatin, Etazolate, Epigallocatechin-3-gallate (EGCg), Scylloinositol (ELND005/AZD103), Tramiprosate (3 APS), PBT2, Affitope AD02, and Affitope AD03. In the case of a combination therapy, separate pharmaceutical compositions for the active components to be combined are preferred for better individual dosing, however for convenience also a single pharmaceutical composition comprising the active components to be combined is conceivable. In the case of separate pharmaceutical compositions for the active components to be combined the administration of the JNK inhibitor according to the present invention may be before, during (concomitant or overlapping administration) or after the administration of the other active component comprised in a separate pharmaceutical composition, for example the PKR inhibitor, the amyloid lowering agent or the glucocorticoid. Administration "before" the administration of the JNK inhibitor preferably means within 24 h, more preferably within 12 h, even more preferably within 3 h, particularly preferably within 1 h and most preferably within 30 min before the administration of the JNK inhibitor starts. Administration "after" the administration of the JNK inhibitor preferably means within 24 h, more preferably within 12 h, even more preferably within 3 h, particularly preferably within 1 h and most preferably within 30 min after the administration of the JNK inhibitor is finished.

Particularly preferred embodiments of the use of the JNK inhibitor according to the present invention—for example a JNK inhibitor comprising or consisting of an inhibitory (poly)peptide sequence according to any of sequences of SEQ ID NOs: 2 to 27, potentially comprising an additional transporter sequence, whereby any of the sequences according to any one of SEQ ID NOs: 171-190, or a variant thereof as defined herein, are preferred and the sequence according to SEQ ID NO: 172, or a variant thereof as defined herein, are particularly preferred—include (but are not limited to) the prevention and/or treatment of the following diseases/disorders:

(i) diseases of the mouth and/or the jaw bone, in particular inflammatory diseases of the mouth and/or the jaw bone selected from (i) pulpitis in general, in particular acute pulpitis, chronic pulpitis, hyperplastic pulpitis, ulcerative pulpitis, irreversible pulpitis and/or reversible pulpitis; (ii) periimplantitis; (iii) periodontitis in general, in particular chronic periodontitis, complex periodontitis, simplex periodontitis, aggressive periodontitis, and/or apical periodontitis, e.g. of pulpal origin; periodontosis, in particular juvenile periodontosis; (iv) gingivitis in general, in particular acute gingivitis, chronic gingivitis, plaque-induced gingivitis, and/or non-plaque-induced gingivitis; (v) pericoronitis, in particular acute and chronic pericoronitis; sialadenitis (sialoadenitis); parotitis, in particular infectious parotitis and autoimmune parotitis; (vi) stomatitis in general, in particular aphthous stomatitis (e.g., minor or major), Bednar's aphthae, periadenitis mucosa necrotica recurrens, recurrent aphthous ulcer, stomatitis herpetiformis, gangrenous stomatitis, denture stomatitis, ulcerative stomatitis, vesicular stomatitis and/or gingivostomatitis; (vii) mucositis, in particular mucositis due to antineoplastic therapy, due to (other) drugs, or due to radiation, ulcerative mucositis and/or oral mucositis; (viii) cheilitis in general, in particular chapped lips, actinic cheilitis, angular cheilitis, eczematous cheilitis, infectious cheilitis, granulomatous cheilitis, drug-related cheilitis, exfoliative cheilitis, cheilitis glandularis, and/or plasma cell cheilitis; and (ix) cellulitis (bacterial infection), in particular of mouth and/or lips; desquamative disorders, in particular desquamative gingivitis; and/or temporomandibular joint disorder, whereby periodontitis, periimplantitis, gingivitis, stomatitis and mucositis are preferred and periodontitis is particularly preferred; wherein for the treatment and/or prevention of the diseases of the mouth and/or the jaw bone the JNK inhibitor is preferably applied in doses (per kg body weight) in the range of 100 µg/kg to 100 mg/kg, more preferably 1 mg/kg to 10 mg/kg, even more preferably 2 mg/kg to 5 mg/kg, and which is preferably applied intragingivally or topically, particularly preferably intragingivally;

(ii) nephrological diseases (kidney diseases), in particular selected from (i) glomerulonephritis, for example nonproliferative glomerulonephritis, in particular minimal change disease, focal segmental glomerulosclerosis, focal segmental glomerular hyalinosis and/or sclerosis, focal glomerulonephritis, membranous glomerulonephritis, and/or thin basement membrane disease, and proliferative glomerulonephritis, in particular membrano-proliferative glomerulonephritis, mesangio-proliferative glomerulonephritis, endocapillary proliferative glomerulonephritis, mesangiocapillary proliferative glomerulonephritis, dense deposit disease (membranoproliferative glomerulonephritis type II), extracapillary glomerulonephritis (crescentic glomerulonephritis), rapidly progressive glomerulonephritis (RPGN), in particular Type I RPGN, Type II RPGN, Type III RPGN, and Type IV RPGN, acute proliferate glomerulonephritis, post-infectious glomerulonephritis, and/or IgA nephropathy (Berger's disease); acute nephritic syndrome; rapidly progressive nephritic syndrome; recurrent and persistent hematuria; chronic nephritic syndrome; nephrotic syndrome; proteinuria with specified morphological lesion; glomerulitis; glomerulopathy; glomerulosclerosis; (ii) acute kidney injury ("AKI", also called "acute renal failure" or "acute kidney failure") in general, in particular prerenal AKI, intrinsic AKI, postrenal AKI, AKI with tubular necrosis for example acute tubular necrosis, renal tubular necrosis, AKI with cortical necrosis for example acute cortical necrosis and renal cortical necrosis, AKI with medullary necrosis, for example medullary (papillary) necrosis, acute medullary (papillary) necrosis and chronic medullary (papillary) necrosis, or other AKI; or (iii) nephropathy, in particular selected from membranous nephropathy, diabetic nephropathy, IgA nephropathy, hereditary nephropathy, analgesic nephropathy, CFHR5 nephropathy, contrast-induced nephropathy, amyloid nephropathy, reflux nephropathy and/or Mesoamerican nephropathydiabetic nephropathy, diabetic nephropathy, whereby preferably the disorder/disease to be prevented and/or treated is glomerulonephritis or acute kidney injury; wherein for the treatment and/or prevention of the nephrological diseases (kidney diseases) the JNK inhibitor is preferably applied in doses (per kg body weight) in the range of 10 µg/kg to 100 mg/kg, more preferably 100 µg/kg to 10 mg/kg, even more preferably 1 mg/kg to 5 mg/kg, if applicable repeatedly, for example daily or weekly for several, e.g. 2, 3, 4, 5, 6, 7, 8, 9, or 10 days and/or weeks, and which is preferably applied systemically, e.g. i.v. or s.c.;

(iii) diseases of the eye, in particular (i) dry eye syndrome; (ii) uveitis, in particular anterior, intermediate and/or posterior uveitis, sympathetic uveitis and/or panuveitis, preferably anterior and/or posterior uveitis; (iii) age-related macular degeneration (AMD), including exudative and/or non-exudative age-related macular degeneration, preferably the wet or the dry form of age-related macular degeneration; (iv) retinopathy, in particular selected from diabetic retinopathy, (arterial hypertension induced) hypertensive retinopathy, exudative retinopathy, radiation induced retinopathy, sun-induced solar retinopathy, trauma-induced retinopathy, e.g. Purtscher's retinopathy, retinopathy of prematurity (ROP) and/or hyperviscosity-related retinopathy, non-diabetic proliferative retinopathy, and/or proliferative vitreo-retinopathy, whereby diabetic retinopathy and retinopathy of prematurity (ROP) are preferred and diabetic retinopathy is particularly preferred; and/or (v) post-surgery inflammation of the eye, in particular after the surgery performed on and/or in the eye, for example after cataract surgery, laser eye surgery, glaucoma surgery, refractive surgery, corneal surgery, vitreo-retinal surgery, eye muscle surgery, oculoplastic surgery, and/or surgery involving the lacrimal apparatus, in particular after complex eye surgery and/or after uncomplicated eye surgery, whereby post-surgery intraocular inflammation is preferred; wherein for the treatment and/or prevention of the diseases of the eye the JNK inhibitor is preferably applied in doses in the range of 0.01 µg/eye to 10 mg/eye, more preferably 0.1 µg/eye to 5 mg/eye, even more preferably 1 µg/eye to 2 mg/eye, particularly preferably 50 µg/eye to 1.5 mg/eye, most preferably 100 µg/eye to 1 mg/eye, preferably by a single application, e.g. injection or instillation, however, if necessary repeatedly, for example daily, every 2 or 3 days or weekly, for several, e.g. 2, 3, 4, 5, 6, 7, 8, 9, or 10, weeks, and which is preferably applied in or onto the eye, preferably intravitreally or subconjunctivally, more preferably subconjunctivally; and/or the JNK inhibitor is preferably applied as eye drops, which may be applied to both eyes or to one eye only, wherein the pharmaceutical composition comprising the JNK inhibitor according to the invention is typically a solution, preferably an ophthalmic solution, e.g. comprising (sterile) 0.9% NaCl and wherein a pharmaceutical composition comprises in particular 0.001%-10% of the JNK inhibitor as described herein, preferably 0.01%-5% of the JNK inhibitor as described herein, more preferably 0.05%-2% of the JNK inhibitor as described herein, even more preferably 0.1%-1% of the JNK inhibitor as described herein, in particular for treating and/or preventing dry eye syndrome; and/or the JNK inhibitor is preferably applied systemically, in particular intravenously, whereby the dose ranges preferably from 0.001 mg/kg to 10 mg/kg, more preferably from 0.01 mg/kg to 5 mg/kg, even more preferably from 0.1 mg/kg to 2 mg/kg, whereby such administration is for example particularly useful to treat and/or prevent uveitis, whereby the treatment schedule may comprises a single dose or repeated doses, whereby subsequent dose(s) may be administered on different days of the treatment schedule.

(iv) diseases of the skin, in particular papulosquamous disorders, in particular selected from psoriasis in general, for example psoriasis vulgaris, nummular psoriasis, plaque psoriasis, generalized pustular psoriasis, impetigo herpetiformis, Von Zumbusch's disease, acrodermatitis continua, guttate psoriasis, arthropathis psoriasis, distal interphalangeal psoriatic arthropathy, psoriatic arthritis mutilans, psoriatic spondylitis, psoriatic juvenile arthropathy, psoriatic arthropathy in general, and/or flexural psoriasis; parapsoriasis in general, for example large-plaque parapsoriasis, small-plaque parapsoriasis, retiform parapsoriasis, *pityriasis lichenoides* and lymphomatoid papulosis; *pityriasis rosea*; lichen planus and other papulosquamous disorders for example *pityriasis rubra* pilaris, lichen *nitidus*, lichen *striatus*, lichen *ruber moniliformis*, and infantile popular acrodermatitis. Preferably, the disorder/disease to be prevented and/or treated is psoriasis, for example psoriasis vulgaris, nummular psoriasis, plaque psoriasis, generalized pustular psoriasis, impetigo herpetiformis, Von Zumbusch's disease, acrodermatitis continua, guttate psoriasis, arthropathis psoriasis, distal interphalangeal psoriatic arthropathy, psoriatic arthritis mutilans, psoriatic spondylitis, psoriatic juvenile arthropathy, psoriatic arthropathy in general, and/or flexural psoriasis; wherein for the treatment and/or prevention of the skin diseases the JNK inhibitor is preferably applied in doses (per kg body weight) in the range of 1 µg/kg to 100 mg/kg, more preferably 10 µg/kg to 10 mg/kg, even more preferably 50 µg/kg to 5 mg/kg, particularly preferably 100 µg/kg to 1 mg/kg, if applicable repeatedly, for example daily or weekly, preferably daily, for several, e.g. 2, 3, 4, 5, 6, 7, 8, 9, or 10 days and/or weeks, and which is preferably applied systemically, e.g. i.v., p.o. or s.c., and/or topically, epicutaneously and/or intralesionally (e.g. into skin lesion).

(v) arthritis and diseases/disorders of the joint, in particular selected from arthritis in general, osteoarthritis (degenerative joint disease), septic arthritis, rheumatoid arthritis, psoriatic arthritis, and related autoimmune diseases and arthritis; wherein for the treatment and/or prevention of the skin diseases the JNK inhibitor is preferably applied in doses (per kg body weight) in the range of 1 µg/kg to 100 mg/kg, more preferably 10 µg/kg to 50 mg/kg, even more preferably 50 µg/kg to 10 mg/kg, particularly preferably 100 µg/kg to 5 mg/kg, if applicable repeatedly, for example daily or weekly for several, e.g. 2, 3, 4, 5, 6, 7, 8, 9, 10 or more days and/or weeks, and which is preferably applied systemically, e.g. i.v., p.o. or s.c., particularly preferably i.v.

(vi) cancer and tumor diseases, in particular selected from (i) liver cancer and liver carcinoma in general, in particular liver metastases, liver cell carcinoma, hepatocellular carcinoma, hepatoma, intrahepatic bile duct carcinoma, cholangiocarcinoma, hepatoblastoma, angiosarcoma (of liver), and other specified or unspecified sarcomas and carcinomas of the liver; (ii) prostate cancer and/or prostate carcinoma; and/or (iii) colon cancer and colon carcinoma in general, in particular cecum carcinoma, appendix carcinoma, ascending colon carcinoma, hepatic flexure carcinoma, transverse colon carcinoma, splenic flexure carcinoma, descending colon carcinoma, sigmoid colon carcinoma, carcinoma of overlapping sites of colon and/or malignant carcinoid tumors of the colon, wherein for the treatment and/or prevention of the cancer and tumor diseases the JNK inhibitor is preferably applied in doses (per kg body weight) in the range of 1 µg/kg to 100 mg/kg, more preferably 10 µg/kg to 50 mg/kg, even more preferably 0.1 mg/kg to 20 mg/kg, particularly preferably 0.1 mg/kg to 5 mg/kg [doses mice!], if applicable repeatedly, for example daily, every 2 or 3 days or weekly, for several, e.g. 2, 3, 4, 5, 6, 7, 8, 9, or 10, weeks, and which is preferably applied systemically, e.g. p.o., i.v. or s.c.

(vii) diseases and/or disorders of the urinary system, in particular ureteritis; urinary tract infection (bladder infection, acute cystitis); cystitis in general, in particular interstitial cystitis, Hunner's ulcer, trigonitis and/or hemorrhagic cystitis; urethritis, in particular nongonococcal urethritis or gonococcal urethritis; painful bladder syndrome; IC/PBS; urethral syndrome; and/or retroperitoneal fibrosis; preferably IC/PBS; wherein for the treatment and/or prevention of the diseases and/or disorders of the urinary system, preferably for the treatment and/or prevention of IC/PBS, the JNK inhibitor is preferably applied (i) systemically, more preferably intravenously, e.g. by intravenous injection, in doses of (per kg body weight) in the range of 100 ng/kg to 10 mg/kg, more preferably 1 µg/kg to 5 mg/kg, even more preferably 10 µg/kg to 2 mg/kg, particularly preferably 0.1 mg/kg to 1 mg/kg, most preferably 0.2 mg/kg to 0.5 mg/kg, preferably administered in one single dose, however, if applicable also preferably administered repeatedly, for example daily, every 2 or 3 days or weekly, for several, e.g. 2, 3, 4, 5, 6, 7, 8, 9, or 10, weeks; or the JNK inhibitor is also preferably applied (ii) intravesically, more preferably by intravesical infusion, preferably at a concentration of 10 µg/ml-1000 mg/ml, more preferably 50 µg/ml-500 mg/ml, even more preferably 100 µg/ml-100 mg/ml, and particularly preferably 0.5 mg/ml-50 mg/ml, preferably in single doses of 0.1-1000 mg, more preferably 0.5-500 mg, even more preferably 1-100 mg, and particularly preferably 2-10 mg, preferably administered in one single dose, however, if applicable also preferably administered repeatedly, for example daily, every 2 or 3 days or weekly, for several, e.g. 2, 3, 4, 5, 6, 7, 8, 9, or 10, weeks.

(viii) neural, neuronal or neurodegenerative disorders, in particular neurodegenerative disease, preferably Alzheimer's disease, for example Alzheimer's disease with early onset, Alzheimer's disease with late onset, Alzheimer's dementia senile and presenile forms, and/or Mild Cognitive Impairment, in particular Mild Cognitive Impairment due to Alzheimer's Disease, wherein for the treatment and/or prevention of the neural, neuronal or neurodegenerative disorders the JNK inhibitor is preferably applied in doses (per kg body weight) in the range of 1 µg/kg to 100 mg/kg, more preferably 10 µg/kg to 50 mg/kg, even more preferably 100 µg/kg to 10 mg/kg, and particularly preferably 500 µg/kg to 1 mg/kg, whereby the JNK inhibitor is preferably administered, if applicable, once or repeatedly, preferably weekly (once per week) for several, e.g. 2, 3, 4, 5, 6, 7, 8, 9, or 10, or more weeks, every second week (once per two weeks) for several, e.g. 2, 3, 4, 5, 6, 7, 8, 9, or 10, or more weeks, monthly (once per month) for several, e.g. 2, 3, 4, 5, 6, 7, 8, 9, or 10, or more months, every sixth week (once per every six weeks) for several, e.g. 2, 3, 4, 5, 6, 7, 8, 9, or 10, or more months, every second month (once per two months) for several, e.g. 2, 3, 4, 5, 6, 7, 8, 9, or 10, or more months or every third month (once per three months) for several, e.g. 2, 3, 4, 5, 6, 7, 8, 9, or 10, or more weeks, more preferably weekly (once per week) for several, e.g. 2, 3, 4, 5, 6, 7, 8, 9, or 10, or more weeks, every second week (once per two weeks) for several, e.g. 2, 3, 4, 5, 6, 7, 8, 9, or 10, or more weeks, monthly (once per month) for several, e.g. 2, 3, 4, 5, 6, 7, 8, 9, or 10, or more months, even more preferably monthly (once per month) for several, e.g. 2, 3, 4, 5, 6, 7, 8, 9, or 10, or more months, and which is preferably applied systemically, e.g. i.v., p.o., i.m., s.c. or intra-CSF (intracerebrospinal fluid) moreover, for treating and/or preventing neural, neuronal or neurodegenerative disorders, in particular neurodegenerative disease, preferably Alzheimer's disease, for example Alzheimer's disease with early onset, Alzheimer's disease with late onset, Alzheimer's dementia senile and presenile forms, and/or Mild Cognitive Impairment, in particular Mild Cognitive Impairment due to Alzheimer's Disease, the JNK inhibitors of the present invention may be administered as stand-alone therapy, however, the JNK inhibitors of the present invention may also be administered in combination with other medications, e.g. with a PKR inhibitor, e.g. "SC1481" by Polypeptide Group, and, optionally, in addition to the JNK inhibitor according to the present invention and the PKR inhibitor with a amyloid lowering agent, whereby amyloid lowering agents include β-secretase (BACE1) inhibitors, γ-secretase inhibitors (GSI) and modulators (GSM) and examples of such inhibitors, which are currently in clinical trials may be retrieved from Vassar R. (2014) BACE1 inhibitor drugs in clinical trials for Alzheimer's disease. Alzheimers Res Ther.; 6(9):89 or from Jia Q, Deng Y, Qing H (2014) Potential therapeutic strategies for Alzheimer's disease targeting or beyond β-amyloid: insights from clinical trials. Biomed Res Int. 2014; 2014: 837157.

Prevention and/or treatment of a disease as defined herein typically includes administration of a pharmaceutical composition as defined above. The JNK inhibitors of the present invention will modulate the JNK activity in the subject. The term "modulate" includes in particular the suppression of phosphorylation of c-jun, ATF2 or NFAT4 in any of the diseases disclosed herein, for example, by using at least one JNK inhibitor comprising or consisting of an inhibitory (poly)peptide sequence according to any of sequences of SEQ ID NOs: 2 to 27, potentially comprising an additional transporter sequence, whereby—if a transporter sequence is attached—any of the sequences according to any one of SEQ ID NOs: 171-190, or a variant thereof as defined herein, are preferred, and the sequence according to SEQ ID NO: 172, or a variant thereof as defined herein, is particularly preferred, as a competitive inhibitor of the natural c-jun, ATF2 and NFAT4 binding site in a cell. The term "modulate" also includes suppression of hetero- and homomeric complexes of transcription factors made up of, without being limited thereto, c-jun, ATF2, or NFAT4 and their related partners, such as for example the AP-1 complex that is made up of c-jun, AFT2 and c-fos.

Treatment of a subject with the pharmaceutical composition as disclosed above may be typically accomplished by administering (in vivo) an ("therapeutically effective") amount of said pharmaceutical composition to a subject, wherein the subject may be e.g. a human subject or an animal, whereby a human is particularly preferred. The animal is preferably a non-human mammal, e.g., a non-human primate, mouse, rat, dog, cat, cow, horse or pig. The term "therapeutically effective" means that the active component of the pharmaceutical composition is of sufficient quantity to ameliorate the diseases and disorders as discussed herein.

According to another preferred embodiment, the JNK inhibitor of the present invention, for example, a JNK inhibitor comprising or consisting of an inhibitory (poly) peptide sequence according to any of sequences of SEQ ID NOs: 2 to 27, potentially comprising an additional transporter sequence, whereby—if a transporter sequence is attached—any of the sequences according to any one of SEQ ID NOs: 171-190, or a variant thereof as defined herein, are preferred, and the sequence according to SEQ ID NO: 172, or a variant thereof as defined herein, is particularly preferred, may be utilized for the treatment of a tissue or organ prior to its transplantation. Preferably, a solution for the isolation, transport, perfusion, implantation or the like of an organ and/or tissue to be transplanted comprises the JNK inhibitor according to the present invention, preferably in a concentration in the range of 1 to 1000 µM, more preferably in the range of 10 to 500 µM, even more preferably in the range of 50 to 150 µM. For this aspect of the invention, the transplant is a kidney, heart, lung, pancreas, in particular pancreatic islets (also called islets of Langerhans), liver, blood cell, bone marrow, cornea, accidental severed limb, in particular fingers, hand, foot, face, nose, bone, cardiac valve, blood vessel or intestine transplant, preferably a kidney, heart, pancreas, in particular pancreatic islets (also called islets of Langerhans), or skin transplant. For example, the JNK inhibitor according to the invention may be contained in the solution for the isolation of pancreatic islets. Such a solution may be for example injected into the pancreatic duct prior to isolation. Moreover, it is preferred if a solution containing the JNK inhibitor according to the invention is applied in isolation, transport, perfusion, transplantation or the like of an organ and/or tissue, in particular if the time of ischemia exceeds 15 min, more preferably, if the time of ischemia exceeds 20 min, even more preferably if the time of ischemia is at least 30 min. These ischemia times may apply to warm and/or cold ischemia time, however, it is particularly preferred if they apply exclusively to warm ischemia time (WIT), whereby WIT refers to the length of time that elapses between a donor's death, in particular from the time of cross-clamping or of asystole in non-heart-beating donors, until cold perfusion is commenced and to ischemia during implantation, from removal of the organ from ice until reperfusion.

Diseases and Disorders

The present invention is directed to specific uses (or methods of use) of the above disclosed JNK inhibitors or pharmaceutical compositions containing the same in a method for treatment of the human or animal body by therapy, in particular of the human body. As mentioned above JNK signalling is involved in a multitude of diverse disease states and disorder and inhibition of said signalling has proposed and successfully tested for many of these. The inventors of the present invention found that the JNK inhibitors disclosed herein are effective JNK inhibitors for the treatment of the diseases as disclosed in the following.

Treatment of a human or animal body by therapy, as used herein, refers to any kind of therapeutic treatment of a respective subject. It includes for example prevention of onset of the disease or symptoms (prophylaxis), i.e. typically prior to manifestation of the disease in the patient. The term also includes the "mere" treatment of symptoms of a given disease, i.e. the treatment will ameliorate pathogenesis by reducing disease-associated symptoms, without necessarily curing the underlying cause of the disease and symptoms. Certainly, curing the underlying cause of the disease is also encompassed by the term. The term also encompasses a treatment which delays or even stops progression of the respective disease.

In one embodiment the JNK inhibitors according to the present invention may be administered for example prophylactically prior to potential onset of a foreseeable disorder, e.g. prior to a planned surgical intervention or planned exposure to stressful stimuli. A surgical intervention could for example bear the risk of inflammation of the respective wound or neighbouring tissue. Exposure to stressful stimuli like radiation could lead to apoptosis of affected tissue and cells. In such scenario, the JNK inhibitors according to the present invention may, for example, be administered at least once up to about 4 weeks in advance. The JNK inhibitors may for example be administered at least 24 hours, at least 48 hours, at least 1 week, at least 2 weeks or 4 weeks in advance.

The diseases and disorders to be treated and/or prevented with the JNK inhibitors as disclosed herein may be acute or chronic.

While the JNK inhibitors of the present invention may be used in general for the treatment and/or prevention of diseases of various organs, such as diseases of the eye, diseases of the bone, neural diseases, neuronal diseases, neurodegenerative diseases, diseases of the skin, immune and/or autoimmune diseases, diseases of the eye, diseases of the mouth, diseases of the kidney, diseases of the urinary system, inflammatory diseases, metabolic diseases, cardiovascular diseases, proliferative diseases (in particular cancers and tumors), diseases of the ear, diseases of the intestine, diseases of the respiratory system (e.g. lung diseases), infectious diseases, and various other diseases, the present invention specifically refers to the following diseases:

Among the disease to be treated and/or prevented by the inventive molecules, skin diseases and diseases of the subcutaneous tissue are to be mentioned, in particular inflammatory skin diseases, more specifically skin diseases selected from the group consisting of eczema, Psoriasis, dermatitis, acne, mouth ulcers, erythema, Lichen plan, sarcoidosis, vascularitis and adult linear IgA disease. Dermatitis encompasses e.g. atopic dermatitis or contact dermatitis. In particular, the skin diseases and diseases of the subcutaneous tissue to be treated and/or prevented with the JNK inhibitor as described herein can be selected from papulosquamous disorders in general, in particular psoriasis in general, for example psoriasis vulgaris, nummular psoriasis, plaque psoriasis, generalized pustular psoriasis, impetigo herpetiformis, Von Zumbusch's disease, acrodermatitis continua, guttate psoriasis, arthropathis psoriasis, distal interphalangeal psoriatic arthropathy, psoriatic arthritis mutilans, psoriatic spondylitis, psoriatic juvenile arthropathy, psoriatic arthropathy in general, and/or flexural psoriasis, parapsoriasis in general, for example large-plaque parapsoriasis, small-plaque parapsoriasis, retiform parapsoriasis, *pityriasis* lichenoides and lymphomatoid papulosis; *pityriasis rosea*; lichen planus and other papulosquamous disorders for example *pityriasis rubra* pilaris, lichen *nitidus*, lichen *striatus*, lichen *ruber moniliformis*, and infantile popular acrodermatitis; eczema; dermatitis in general, in particular atopic dermatitis for example Besnier's prurigo, atopic or diffuse neurodermatitis, flexural eczema, infantile eczema, intrinsic eczema, allergic eczema, other atopic dermatitis, seborrheic dermatitis for example seborrhea capitis, seborrheic infantile dermatitis, other seborrheic dermatitis, diaper dermatitis for example diaper erythema, diaper rash and psoriasiform diaper rash, allergic contact dermatitis, in particular due to metals, due to adhesives, due to cosmetics, due to drugs in contact with skin, due to dyes, due to other chemical products, due to food in contact with skin, due to plants except food, due to animal dander, and/or due to other agents, irritant contact dermatitis, in particular due to detergents, due to oils and greases, due to solvents, due to cosmetics, due to drugs in contact with skin, due to other chemical products, due to food in contact with skin, due to plants except food, due to metal, and/or due to other agents, unspecified contact dermatitis, exfoliative dermatitis, dermatitis for example general and localized skin eruption due to substances taken internally, in particular due to drugs and medicaments, due to ingested food, due to other substances, nummular dermatitis, dermatitis gangrenosa, dermatitis herpetiformis, dry skin dermatitis, factitial dermatitis, perioral dermatitis, radiation-related disorders of the skin and subcutaneous tissue, stasis dermatitis, Lichen simplex chronicus and prurigo, pruritus, dyshidrosis, cutaneous autosensitization, infective dermatitis, erythema intertrigo and/or *pityriasis* alba; cellulitis (bacterial infection involving the skin); lymphangitis, in particular acute or chronic lymphangitis; panniculitis in general, in particular lobular panniculitis without vasculitis, for example acute panniculitis, previously termed Weber-Christian disease and systemic nodular panniculitis, lobular panniculitis with vasculitis, septal panniculitis without vasculitis and/or septal panniculitis with vasculitis; lymphadenitis, in particular acute lymphadenitis; pilonidal cyst and sinus; pyoderma in general, in particular pyoderma gangrenosum, pyoderma vegetans, dermatitis gangrenosa, purulent dermatitis, septic dermatitis and suppurative dermatitis; erythrasma; omphalitis; pemphigus, in particular pemphigus vulgaris, pemphigus vegetans, pemphigus foliaceous, Brazilian pemphigus, pemphigus erythematosus, drug-induced pemphigus, IgA pemphigus, for example subcorneal pustular dermatosis and intraepidermal neutrophilic IgA dermatosis, and/or paraneoplastic pemphigus; acne in general, in particular acne vulgaris, acne conglobata, acne varioliformis, acne necrotica miliaris, acne *tropica*, infantile acne acné excoriée des jeunes filles, Picker's acne, and/or acne keloid; mouth and other skin ulcers; urticaria in general, in particular allergic urticaria, idiopathic urticarial, urticarial due to cold and heat, dermatographic urticarial, vibratory urticarial, cholinergic urticarial, and/or contact urticarial; erythema in general, in particular erythema multiforme for example nonbullous erythema multiforme, Stevens-Johnson syndrome, toxic epidermal necrolysis (Lyell), and Stevens-Johnson syndrome-toxic epidermal necrolysis overlap syndrome, erythema nodosum, toxic erythema, erythema annulare centrifugum, erythema *marginatum* and/or other chronic figurate erythema; sunburn and other acute skin changes due to ultraviolet radiation; skin changes due to chronic exposure to nonionizing radiation; radiodermatitis; folliculitis; perifolliculitis; pseudofolliculitis barbae; hidradenititis suppurativa; sarcoidose; vascularitis; adult linear IgA disease; rosacea, in particular perioral dermatitis, rhinophyma, and other rosacea; and/or follicular cysts of skin and subcutaneous tissue, in particular epidermal cyst, pilar cyst, trichodermal cyst, steatocystoma multiplex, sebaceous cyst and/or other follicular cysts.

Examples for preferred skin diseases which can be treated with the JNK inhibitors of the present invention are psoriasis and lupus erythematosus. In more general terms, skin diseases and diseases of the subcutaneous tissue, which can preferably be treated and/or prevented with the JNK inhibitors as disclosed herein are papulosquamous disorders. These include psoriasis, parapsoriasis, *pityriasis rosea*, lichen planus and other papulosquamous disorders for example *pityriasis rubra* pilaris, lichen *nitidus*, lichen *striatus*, lichen *ruber moniliformis*, and infantile popular acrodermatitis. Preferably the disease to be treated and/or prevented by the JNK inhibitor according to the invention is selected from the group of psoriasis and parapsoriasis, whereby psoriasis is particularly preferred. Examples for psoriasis include psoriasis vulgaris, nummular psoriasis, plaque psoriasis, generalized pustular psoriasis, impetigo herpetiformis, Von Zumbusch's disease, acrodermatitis continua, guttate psoriasis, arthropathis psoriasis, distal interphalangeal psoriatic arthropathy, psoriatic arthritis mutilans, psoriatic spondylitis, psoriatic juvenile arthropathy, psoriatic arthropathy in general, and/or flexural psoriasis. Examples for parapsoriasis include large-plaque parapsoriasis, small-plaque parapsoriasis, retiform parapsoriasis, pityriasis lichenoides and lymphomatoid papulosis.

(Anti-inflammatory) treatment upon tissue or organ transplantation, is treatable by the inventive molecules in particular upon heart, kidney, and skin (tissue), lung, pancreas, liver, blood cells (e.g. any kind of blood cell, such as platelets, white blood cells, red blood cells), bone marrow, cornea, accidental severed limbs (fingers, hand, foot, face, nose etc.), bones of whatever type, cardiac valve, blood vessels, segments of the intestine or the intestine as such. Such a treatment is e.g. considered appropriate whenever e.g. a graft vs. host or host vs graft reaction occurs upon organ/tissue transplantation. The use of the inventive molecules may also be employed whenever transplantation surgery is carried, in particular in case of skin (or, pancreas, liver, lung, heart, kidney) graft vs. host or host vs. skin (or, pancreas, liver, lung, heart, kidney) graft reaction.

Among neurodegenerative diseases, in particular those associated with chronic inflammation, tauopathies and amyloidoses and prion diseases are addressed by the inventive molecules. Other such neurodegenerative disease refer to the various forms of dementia, e.g. frontotemporal dementia and dementia with lewy bodies, schizophrenia and bipolar disorder, spinocerebellar ataxia, spinocerebellar atrophy, multiple system atrophy, motor neuron disease, corticobasal degeneration, progressive supranuclear palsy or hereditary spastic paraparesis. Another field of indication is pain (e.g. neuropathic, incident, breakthrough, psychogenic, phantom, chronic or acute forms of pain). Another field of use is the treatment of bladder diseases, in particular for treating loss of bladder function (e.g. urinary incontinence, overactive bladder, interstitial cystitis or bladder cancer) or stomatitis.

The inventive molecules are used for the treatment of fibrotic diseases or fibrosis as well, in particular lung, heart, liver, bone marrow, mediastinum, retroperitoneum, skin, intestine, joint, and shoulder fibrosis.

While inflammatory diseases of the mouth and the jaw/mandible are treatable in general by the inventive molecules, gingivitis, osteonecrosis (e.g. of the jaw bone), peri-implantitis, pulpitis, and periodontitis are particularly suitable for the use of these inventive molecules for therapeutic purposes. In particular, diseases and/or disorders of the mouth or the jaw bone to be treated and/or prevented with the JNK inhibitor as described herein can be selected from pulpitis in general, in particular acute pulpitis, chronic pulpitis, hyperplastic pulpitis, ulcerative pulpitis, irreversible pulpitis and/or reversible pulpitis; periimplantitis; periodontitis in general, in particular chronic periodontitis, complex periodontitis, simplex periodontitis, aggressive periodontitis, and/or apical periodontitis, e.g. of pulpal origin; periodontosis, in particular juvenile periodontosis; gingivitis in general, in particular acute gingivitis, chronic gingivitis, plaque-induced gingivitis, and/or non-plaque-induced gingivitis; pericoronitis, in particular acute and chronic pericoronitis; sialadenitis (sialoadenitis); parotitis, in particular infectious parotitis and autoimmune parotitis; stomatitis in general, in particular aphthous stomatitis (e.g., minor or major), Bednar's aphthae, periadenitis mucosa necrotica recurrens, recurrent aphthous ulcer, stomatitis herpetiformis, gangrenous stomatitis, denture stomatitis, ulcerative stomatitis, vesicular stomatitis and/or gingivostomatitis; mucositis, in particular mucositis due to antineoplastic therapy, due to (other) drugs, or due to radiation, ulcerative mucositis and/or oral mucositis; cheilitis in general, in particular chapped lips, actinic cheilitis, angular cheilitis, eczematous cheilitis, infectious cheilitis, granulomatous cheilitis, drug-related cheilitis, exfoliative cheilitis, cheilitis glandularis, and/or plasma cell cheilitis; cellulitis (bacterial infection), in particular of mouth and/or lips; desquamative disorders, in particular desquamative gingivitis; and/or temporomandibular joint disorder.

In addition, polypes are effectively treatable by using the inventive molecules.

Also inflammatory or non-inflammatory pathophysiologies of the kidney are effectively treated by using the inventive molecules. In particular, the disease is selected from the group consisting of glomerulonephritis in general, in particular membrano-proliferative glomerulonephritis, mesangio-proliferative glomerulonephritis, rapidly progressive glomerulonephritis, acute kidney injury ("AKI", also called "acute renal failure" or "acute kidney failure") in general, in particular prerenal AKI, intrinsic AKI, postrenal AKI, AKI with tubular necrosis for example acute tubular necrosis, renal tubular necrosis, AKI with cortical necrosis for example acute cortical necrosis and renal cortical necrosis, AKI with medullary necrosis, for example medullary (papillary) necrosis, acute medullary (papillary) necrosis and chronic medullary (papillary) necrosis, or other AKI; nephrophathies in general, in particular membranous nephropathy or diabetic nephropathy, nephritis in general, in particular lupus nephritis, pyelonephritis, interstitial nephritis, tubulointerstitial nephritis, chronic nephritis or acute nephritis, and minimal change disease and focal segmental glomerulosclerosis. Moreover, diseases and/or disorders of the kidney (nephrological diseases) to be treated and/or prevented with the JNK inhibitor as described herein can be selected from glomerulonephritis in general, for example nonproliferative glomerulonephritis, in particular minimal change disease, focal segmental glomerulosclerosis, focal segmental glomerular hyalinosis and/or sclerosis, focal glomerulonephritis, membranous glomerulonephritis, and/or thin basement membrane disease, and proliferative glomerulonephritis, in particular membrano-proliferative glomerulonephritis, mesangio-proliferative glomerulonephritis, endocapillary proliferative glomerulonephritis, mesangiocapillary proliferative glomerulonephritis, dense deposit disease (membranoproliferative glomerulonephritis type II), extracapillary glomerulonephritis (crescentic glomerulonephritis), rapidly progressive glomerulonephritis (RPGN), in particular Type I RPGN, Type II RPGN, Type III RPGN, and Type IV RPGN, acute proliferate glomerulonephritis, post-infectious glomerulonephritis, and/or IgA nephropathy (Berger's disease); acute nephritic syndrome; rapidly progressive nephritic syndrome; recurrent and persistent hematuria; chronic nephritic syndrome; nephrotic syndrome; proteinuria with specified morphological lesion; glomerulitis; glomerulopathy; glomerulosclerosis; acute kidney injury ("AKI", also called "acute renal failure" or "acute kidney failure") in general, in particular prerenal AKI, intrinsic AKI, postrenal AKI, AKI with tubular necrosis for example acute tubular necrosis, renal tubular necrosis, AKI with cortical necrosis for example acute cortical necrosis and renal cortical necrosis, AKI with medullary necrosis, for example medullary (papillary) necrosis, acute medullary (papillary) necrosis and chronic medullary (papillary) necrosis, or other AKI; chronic kidney disease; nephropathies in general, in particular membranous nephropathy, diabetic nephropathy, IgA nephropathy, hereditary nephropathy, analgesic nephropathy, CFHR5 nephropathy, contrast-induced nephropathy, amyloid nephropathy, reflux nephropathy and/or Mesoamerican nephropathy; nephritis in general, in particular lupus nephritis, pyelonephritis, interstitial nephritis, tubulointerstitial nephritis, chronic nephritis or acute nephritis, diffuse proliferative nephritis, and/or focal proloferative nephritis, tubulo-interstitial nephritis, infectious interstitial nephritis, pyelitis, pyelonephrititis, interstitial nephritis; tubulopathy, tubulitis, in particular RTA (RTA1 and RTA2), Fanconi syndrome, Bartter syndrome, Gitelman syndrome, Liddle's syndrome, nephrogenic diabetes insipidus, renal papillary necrosis, hydronephrosis, pyonephrosis and/or acute tubular necrosis chronic kidney disease (CKD); Goodpasture syndrome (anti-glomerular basement antibody disease); granulomatosis with polyangiitis; microscopic polyangiitis; and/or Churg-Strauss syndrome.

Glomerulonephritis refers to several renal diseases, whereby many of the diseases are characterised by inflammation either of the glomeruli or small blood vessels in the kidneys, but not all diseases necessarily have an inflammatory component. Acute kidney injury ("AKI", also called "acute renal failure" or "acute kidney failure") is an abrupt loss of kidney function, which is often investigated in a renal ischemia/reperfusion injury model. Nephropathies, i.e. damage to or disease of a kidney, includes also nephrosis, which is non-inflammatory nephropathy, and nephritis, which is inflammatory kidney disease.

Among the diseases or disorders which are effectively treated by the inventive molecules, a larger number of diseases or disorders may be linked to inflammatory processes, but do not necessarily have to be associated with such inflammatory processes. The following diseases or disorders are specifically disclosed in this regard as being treatable by the use of the inventive molecules: Addison's disease, Agammaglobulinemia, Alopecia areata, Amytrophic lateral sclerosis, Antiphospholipid syndrome, Atopic allergy, Autoimmune aplastic anemia, Autoimmune cardiomyopathy, Autoimmune enteropathy, Autoimmune hemolytic anemia, Autoimmune inner ear, disease, Autoimmune lymphoproliferative syndrome, Autoimmune polyendocrine syndrome, Autoimmune progesterone dermatitis, Idiopathic thrombocytopenic purpura, Autoimmune urticaria, Balo concentric sclerosis, Bullous pemphigoid, Castleman's disease, Cicatricial pemphigoid, Cold agglutinin disease, Complement component 2 deficiency associated disease, Cushing's syndrome, Dagos disease, Adiposis dolorosa, Eosinophilic pneumonia, Epidermolysis bullosa acquisita, Hemolytic disease of the newborn, Cryoglobulinemia, Evans syndrome, Fibrodysplasia ossificans progressive, Gastrointestinal pemphigoid, Goodpasture's syndrome, Hashimoto's encephalopathy, Gestational pemphigoid, Hughes-stovin syndrome, Hypogammaglobulinemia, Lambert-eaton myasthenic syndrome, Lichen sclerosus, Morphea, Pityriasis lichenoides et varioliformis acuta, Myasthenia gravis, Narcolepsy, Neuromyotonia, Opsoclonus myoclonus syndrome, Paraneoplastic cerebellar degeneration, Paroxysmal nocturnal hemoglobinuria, Parry-romberg syndrome, Pernicious anemia, POEMS syndrome, Pyoderma gangrenosum, Pure red cell aplasia, Raynaud's phenomenon, Restless legs syndrome, Retroperitoneal fibrosis, Autoimmune polyendocrine syndrome type 2, Stiff person syndrome, Susac's syndrome, Febrile neutrophilic dermatosis, Sydenham's chorea, Thrombocytopenia, and vitiligo.

While any kind of inflammatory eye disease may be treated by the use of the inventive molecules, the following eye-related diseases are specifically disclosed: inflammation after corneal surgery, non-infective keratitis, chorioretinal inflammation, and sympathetic ophthalmia. In more general terms, the JNK inhibitors as described herein can be used to treat and/or prevent inflammatory and non-inflammatory diseases of the eye, in particular selected from uveitis, in particular anterior, intermediate and/or posterior uveitis, sympathetic uveitis and/or panuveitis; scleritis in general, in particular anterior scleritis, brawny scleritis, posterior scleritis, and scleritis with corneal involvement; episcleritis in general, in particular episcleritis periodica *fugax* and nodular episcleritis; retinitis; conjunctivitis in general, in particular acute conjunctivitis, mucopurulent conjunctivitis, atopic conjunctivitis, toxic conjunctivitis, pseudomembranous conjunctivitis, serous conjunctivitis, chronic conjunctivitis, giant pupillary conjunctivitis, follicular conjunctivitis vernal conjunctivitis, blepharoconjunctivitis, and/or pingueculitis; non-infectious keratitis in general, in particular corneal ulcer, superficial keratitis, macular keratitis, filamentary keratitis, photokeratitis, punctate keratitis, keratoconjunctivitis, for example exposure keratoconjunctivitis, Dry Eye Syndrome (keratoconjunctivitis sicca), neurotrophic keratoconjunctivitis, ophthalmia *nodosa*, phlyctenular keratoconjunctivitis, vernal keratoconjunctivitis and other keratoconjunctivitis, interstitial and deep keratitis, sclerosing keratitis, corneal neovascularization and other keratitis; iridocyclitis in general, in particular acute iridocyclitis, subacute iridocyclitis and chronic iridocyclitis, primary iridocyclitis, recurrent iridocyclitis and secondary iridocyclitis, lens-induced iridocyclitis, Fuchs' heterochromic cyclitis, Vogt-Koyanagi syndrome; iritis; chorioretinal inflammation in general, in particular focal and disseminated chorioretinal inflammation, chorioretinitis, choroiditis, retinitis, retinochoroiditis, posterior cyclitis, Harada's disease, chorioretinal inflammation in infectious and parasitic diseases; post-surgery inflammation of the eye, in particular whereby the surgery was performed on and/or in the eye, for example after cataract surgery, laser eye surgery, glaucoma surgery, refractive surgery, corneal surgery, vitreo-retinal surgery, eye muscle surgery, oculoplastic surgery, and surgery involving the lacrimal apparatus, in particular post-surgery intraocular inflammation, preferably post-surgery intraocular inflammation after complex eye surgery and/or after uncomplicated eye surgery, for example inflammation of postprocedural bleb; inflammatory diseases damaging the retina of the eye; retinal vasculitis, in particular Eales disease and retinal perivasculitis; retinopathy in general, in particular diabetic retinopathy, (arterial hypertension induced) hypertensive retinopathy, exudative retinopathy, radiation induced retinopathy, sun-induced solar retinopathy, trauma-induced retinopathy, e.g. Purtscher's retinopathy, retinopathy of prematurity (ROP) and/or hyperviscosity-related retinopathy, non-diabetic proliferative retinopathy, and/or proliferative vitreo-retinopathy; blebitis; endophthalmitis; sympathetic ophthalmia; hordeolum; chalazion; blepharitis; dermatitis and other inflammations of the eyelid; dacryoadenititis; canaliculitis, in particular acute and chronic lacrimal canaliculitis; dacryocystitis; inflammation of the orbit, in particular cellulitis of orbit, periostitis of orbit, tenonitis of orbit, granuloma of orbit and orbital myositis; purulent and parasitic endophthalmitis; and diseases and/or disorders relating to degeneration of macula and/or posterior pole in general, in particular age-related macular degeneration (AMD), in particular the wet or the dry form of age-related macular degeneration, exudative and/or non-exudative age-related macular degeneration, and cataract.

The "dry" form of advanced AMD, results from atrophy of the retinal pigment epithelial layer below the retina, which causes vision loss through loss of photoreceptors (rods and cones) in the central part of the eye. Neovascular, the "wet" form of advanced AMD, causes vision loss due to abnormal blood vessel growth (choroidal neovascularization) in the choriocapillaris, through Bruch's membrane, ultimately leading to blood and protein leakage below the macula. Bleeding, leaking, and scarring from these blood vessels eventually cause irreversible damage to the photoreceptors and rapid vision loss, if left untreated. The inventive molecules are suitable for treating both forms of AMD.

In particular, the JNK inhibitors of the present invention can be used to treat and/or prevent Dry eye syndrome (DES). Dry eye syndrome (DES), also called keratitis sicca, xerophthalmia, keratoconjunctivitis sicca (KCS) or cornea sicca, is an eye disease caused by eye dryness, which, in turn, is caused by either decreased tear production or increased tear film evaporation. Typical symptoms of dry eye syndrome are dryness, burning and a sandy-gritty eye irritation. Dry eye syndrome is often associated with ocular surface inflammation. If dry eye syndrome is left untreated or becomes severe, it can produce complications that can cause eye damage, resulting in impaired vision or even in the loss of vision. Untreated dry eye syndrome can in particular lead to pathological cases in the eye epithelium, squamous metaplasia, loss of goblet cells, thickening of the corneal surface, corneal erosion, punctate keratopathy, epithelial defects, corneal ulceration, corneal neovascularization, corneal scarring, corneal thinning, and even corneal perforation. The JNK inhibitors according to the present invention may be utilized in treatment and/or prevention of dry eye syndrome, e.g. due to aging, diabetes, contact lenses or other causes and/or after eye surgery or trauma, in particular after Lasik (laser-assisted in situ keratomileusis), commonly referred to simply as laser eye surgery.

The standard treatment of dry eye may involve the administration of artificial tears, cyclosporine (in particular cyclosporine A; e.g. Restasis®); autologous serum eye drops; lubricating tear ointments and/or the administration of (cortico-)steroids, for example in the form of drops or eye ointments. Therefore, the present invention also relates to the use of the JNK inhibitor as described herein in a method of treatment of dry eye syndrome, wherein the method comprises the combined administration of the JNK inhibitor as defined herein together with a standard treatment for dry eye, in particular with any one of the above mentioned treatments. Particularly preferred is the combination with cyclosporine A and most preferably with artificial tears. Combined administration comprises the parallel administration and/or subsequent administration (either first the JNK inhibitor described herein and then the (cortico)steroids or vice versa). Certainly, subsequent and parallel administration may also be combined, e.g. the treatment is started with JNK inhibitors described herein and at a later point in time in the course of the treatment (cortico)steroids are given in parallel, or vice versa.

In particular, the JNK inhibitors of the present invention can be used to treat and/or prevent inflammatory diseases of the sclera, the cornea, the iris, the ciliary body, the retina and/or the choroid of the eye. Preferably, the JNK inhibitors of the present invention can be used to treat and/or prevent uveitis, i.e. an inflammation of the uvea. The uvea consists of the middle, pigmented vascular structures of the eye and includes the iris, the ciliary body, and the choroid. Typically, uveitis is classified as anterior uveitis, intermediate uveitis, posterior uveitis, and/or panuveitis, whereby the latter is the inflammation of all the layers of the uvea. Furthermore, uveitis includes sympathetic ophthalmia (sympathetic uveitis), which is a bilateral diffuse granulomatous uveitis of both eyes following trauma to one eye. Anterior uveitis, which is particularly preferred to be treated with the JNK inhibitors of the present invention, includes iridocyclitis and iritis. Iritis is the inflammation of the anterior chamber and iris. Iridocyclitis presents the same symptoms as iritis, but also includes inflammation in the vitreous cavity. Examples of iridocyclitis to be prevented and/or treated with the JNK inhibitors of the present invention include—but are not limited to—acute iridocyclitis, subacute iridocyclitis and chronic iridocyclitis, primary iridocyclitis, recurrent iridocyclitis and secondary iridocyclitis, lens-induced iridocyclitis, Fuchs' heterochromic cyclitis, and Vogt-Koyanagi syndrome. Intermediate uveitis, also known as pars planitis, in particular includes vitritis, which is inflammation of cells in the vitreous cavity, sometimes with "snowbanking" or deposition of inflammatory material on the pars plana. Posterior uveitis includes in particular chorioretinitis, which is the inflammation of the retina and choroid, and chorioditis (choroid only). In more general terms, the JNK inhibitors as disclosed herein can be used to treat and/or prevent chorioretinal inflammation in general, for example focal and/or disseminated chorioretinal inflammation, chorioretinitis, chorioditis, retinochoroiditis, posterior cyclitis, Harada's disease, chorioretinal inflammation in infectious and parasitic diseases and/or retinitis, i.e. an inflammation of the retina. Inflammatory diseases damaging the retina of the eye in general are included, in addition to retinitis in particular retinal vasculitis, for example Eales disease and retinal perivasculitis. Further inflammatory diseases of the sclera, the cornea, the iris, the ciliary body, the retina and/or the choroid of the eye to be treated and/or prevented with the JNK inhibitors as disclosed herein include scleritis, i.e. an inflammation of the sclera, for example anterior scleritis, brawny scleritis, posterior scleritis, scleritis with corneal involvement and scleromalacia perforans; episcleritis, in particular episcleritis periodica *fugax* and nodular episcleritis; and keratitis, which is an inflammation of the cornea, in particular corneal ulcer, superficial keratitis, macular keratitis, filamentary keratitis, photokeratitis, punctate keratitis, keratoconjunctivitis, for example exposure keratoconjunctivitis, keratoconjunctivitis sicca (dry eyes), neurotrophic keratoconjunctivitis, ophthalmia *nodosa*, phlyctenular keratoconjunctivitis, vernal keratoconjunctivitis and other keratoconjunctivitis, interstitial and deep keratitis, sclerosing keratitis, corneal neovascularization and other keratitis.

In addition, the JNK inhibitors as disclosed herein are particularly useful to treat and/or prevent post-surgery (or "post-procedural") or post-trauma inflammation of the eye. "Post-surgery" refers in particular to a surgery performed on and/or in the eye, for example cataract surgery, laser eye surgery, glaucoma surgery, refractive surgery, corneal surgery, vitreo-retinal surgery, eye muscle surgery, oculoplastic surgery, and/or surgery involving the lacrimal apparatus. Preferably, the surgery referred to in "post-surgery" is a complex eye surgery and/or an uncomplicated eye surgery. Particularly preferred is the use of JNK inhibitors as disclosed herein to treat and/or prevent post-surgery or post-trauma intraocular inflammation, which may be for example (but not limited to) inflammation of postprocedural bleb.

Another particularly preferred eye disease to be treated and/or prevented with the JNK inhibitors according to the invention is retinopathy. Non-limiting examples of retinopathy include diabetic retinopathy, hypertensive retinopathy (e.g., arterial hypertension induced), exudative retinopathy, radiation induced retinopathy, sun-induced solar retinopathy, trauma-induced retinopathy, e.g. Purtscher's retinopathy, retinopathy of prematurity (ROP) and/or hyperviscosity-related retinopathy, non-diabetic proliferative retinopathy, and/or proliferative vitreo-retinopathy. The JNK inhibitors as disclosed herein are particularly preferred for the treatment and/or prevention of diabetic retinopathy and retinopathy of prematurity, respectively.

Retinopathy of prematurity (ROP), previously known as retrolental fibroplasia (RLF), is a disease of the eye affecting prematurely-born babies generally having received intensive neonatal care. It is thought to be caused by disorganized growth of retinal blood vessels which may result in scarring and retinal detachment. ROP can be mild and may resolve spontaneously, but it may lead to blindness in serious cases. As such, all preterm babies are at risk for ROP, and very low birth weight is an additional risk factor. Both oxygen toxicity and relative hypoxia can contribute to the development of ROP. The inventive molecules are suitable for treating ROP.

Furthermore, the inventive molecules are particularly suitable to treat all forms of retinopathy, in particular diabetes mellitus induced retinopathy, arterial hypertension induced hypertensive retinopathy, radiation induced retinopathy (due to exposure to ionizing radiation), sun-induced solar retinopathy (exposure to sunlight), trauma-induced retinopathy (e.g. Purtscher's retinopathy) and hyperviscosity-related retinopathy as seen in disorders which cause paraproteinemia).

In addition, the JNK inhibitors as disclosed herein are particularly useful to treat and/or prevent arthritis and related disease and/or disorders of joint. Arthritis is a form of joint disorder that involves inflammation of one or more joints. There are over 100 different forms of arthritis. The most common form, osteoarthritis (degenerative joint disease), is a result of trauma to the joint, infection of the joint, or age. Other arthritis forms are rheumatoid arthritis, psoriatic arthritis, and related autoimmune diseases. Septic arthritis is caused by joint infection. There are several diseases where joint pain is primary, and is considered the main feature. Generally when a person has "arthritis" it means that they have one of these diseases, which include osteoarthritis, rheumatoid arthritis, gout and pseudogout, septic arthritis, ankylosing spondylitis, juvenile idiopathic arthritis, Still's disease. Joint pain can also be a symptom of other diseases. In this case, the arthritis is considered to be secondary to the main disease; these include psoriasis (Psoriatic arthritis), reactive arthritis, Ehlers-Danlos Syndrome, haemochromatosis, hepatitis, Lyme disease, Sjogren's disease, Hashimoto's Thyroiditis, Inflammatory bowel disease (including Crohn's disease and ulcerative colitis), Henoch-Schönlein purpura, Hyperimmunoglobulinemia D with recurrent fever, Sarcoidosis, Whipple's disease, TNF receptor associated periodic syndrome, Wegener's granulomatosis (and many other vasculitis syndromes), Familial Mediterranean fever and sSystemic lupus erythematosus. An undifferentiated arthritis is an arthritis that does not fit into well-known clinical disease categories, possibly being an early stage of a definite rheumatic disease.

In particular, diseases and/or disorders arthritis relating to arthritis, which may be treated and/or prevented with the JNK inhibitors as disclosed herein, can be selected from pyogenic arthritis, in particular staphylococcal arthritis and polyarthritis, pneumococcal arthritis and polyarthritis, other streptococcal arthritis and polyarthritis, and arthritis and polyarthritis due to other bacteria; direct infections of joint in infectious and parasitic diseases in general; postinfective and reactive arthropathies, in particular arthropathy following intestinal bypass, postdysenteric arthropathy, postimmunozation arthropathy, Reiter's disease, and other reactive arthropathies; inflammatory polyarthropathies, in particular rheumatoid arthritis with rheumatoid factor, for example Felty's syndrome, rheumatoid lung disease with rheumatoid arthritis, rheumatoid vasculitis with rheumatoid arthritis, rheumatoid heart disease with rheumatoid arthritis, rheumatoid myopathy with rheumatoid arthritis, rheumatoid polyneuropathy with rheumatoid arthritis, rheumatoid arthritis with involvement of other organs and systems, rheumatoid arthritis with rheumatoid factor without organ or systems involvement; other rheumatoid arthritis, for example rheumatoid arthritis without rheumatoid factor, Adult-onset Still's disease, rheumatoid bursitis, rheumatoid nodule, inflammatory polyarthropathy; enteropathic arthropathies; juvenile arthritis, for example unspecified juvenile rheumatoid arthritis, juvenile ankylosing spondylitis, juvenile rheumatoid arthritis with systemic onset, juvenile rheumatoid polyarthritis (seronegative), and pauciarticular juvenile rheumatoid arthritis; chronic gout, for example idiopathic chronic gout, lead-induced chronic gout, drug-induced chronic gout, chronic gout due to renal impairment; gout, for example idiopathic gout, lead-induced gout, drug-induced gout, gout due to renal impairment; other crystal arthropathies, for example familial and other chondrocalcinosis; other arthropathies for example Kaschin-Beck disease, Villonodular synovitis (pigmented), palindromic rheumatism, intermittent hydrathrosis, traumatic arthropathy; other arthritis, for example polyarthritis and monoarthritis; other arthropathies, for example Charcôt's joint; osteoarthritis, in particular polyosteoarthritis, for example primary generalized (osteo)arthritis, Heberden's nodes, Bouchard's nodes, secondary multiple arthritis and erosive arthritis, osteoarthritis of the hip, osteoarthritis of the knee, osteoarthritis of first carpometacarpal joint, primary, secondary and post-traumatic osteoarthritis; and other joint disorders, in particular acquired deformities of fingers and toes, for example Mallet finger, Boutonniere deformitiy, swan-neck deformity, Hallux valgus, disorders of patella, internal derangement of knee, ankylosis of joint, protrusio acetabuli; and other joint disorders, for example hemathrosis, fistula of joint, flial joint, and osteophyte.

A further class of inflammatory-associated diseases to be treated by the use of the inventive molecules is the following: acute disseminated encephalomyelitis, antisynthetase syndrome, autoimmune hepatitis, autoimmune peripheral neuropathy, pancreatitis, in particular autoimmune pancreatitis, Bickerstaffs encephalitis, Blau syndrome, Coeliac disease, Chagas disease, chronic inflammatory demyelinating polyneuropathy, osteomyelitis, in particular chronic recurrent multifocal osteomyelitis, Churg-Strauss syndrome, Cogan syndrome, giant-cell arteritis, CREST syndrome, vasculitis, in particular cutaneous small-vessel vasculitis or urticarial vasculitis, dermatitis, in particular dermatitis herpetiformis, dermatomyositis, systemic scleroderma, Dressler's syndrome, drug-induced lupus erythematosus, discoid lupus erythematosus, enthesitis, eosinophilic fasciitis, gastroenteritis, in particular, eosinophilic gastroenteritis, erythema nodosum, idiopathic pulmonary fibrosis, gastritis, Grave's disease, Guillain-barré syndrome, Hashimoto's thyroiditis, Henoch-Schonlein purpura, Hidradenitis suppurativa, idiopathic inflammatory demyelinating diseases, myositis, in particular inclusion body myositis, cystitis, Kawasaki disease, Lichen planus, lupoid hepatitis, Majeed syndrome, Ménière's disease, Microscopic polyangiitis, mixed connective tissue disease, myelitis, in particular neuromyelitis, e.g. neuromyelitis optica, thyroiditis, in particular Ord's thyroiditis, rheumatism, in particular palindromic rheumatism, Parsonage-Turner syndrome, perivenous encephalomyelitis, polyarteritis *nodosa*, polymyalgia rheumatica, polymyositis, cirrhosis, in particular primary biliary cirrhosis, cholangitis, in particular primary sclerosing cholangitis, progressive inflammatory neuropathy, Rasmussen's encephalitis, chondritis, in particular polychondritis, e.g. relapsing polychondritis, reactive arthritis (Reiter disease), rheumatic fever, sarcoidosis, Schnitzler syndrome, serum sickness, spondylitis, in particular ankylosing spondylitis, spondyloarthropathy, Takayasu's arteritis, Tolosa-Hunt syndrome, transverse myelitis, and granulomatosis, in particular Wegener's granulomatosis.

In the most preferred embodiment of the present invention, the inventive molecules are used for the treatment of the following diseases or disorders: persistent or acute inflammatory diseases of the skin, in particular psoriasis, dry eye disease (Dry Eye Syndrome), uveitis, persistent or acute inflammatory diseases damaging the retina of the eye, retinopathy, in particular diabetic retinopathy or retinopathies caused by other diseases, age-related macular degeneration (AMD), in particular the wet or the dry form of age-related macular degeneration, retinopathy of prematurity (ROP), persistent or acute inflammatory diseases of the mouth, in particular peri-implantitis, pulpitis, periodontitis, anti-inflammatory treatment upon tissue or organ transplantation, in particular upon heart, kidney, and skin (tissue) transplantation, graft rejection upon heart, kidney or skin (tissue) transplantation, inflammatory brain diseases and/or tauopathies, in particular for the treatment of Alzheimer's disease in general, for example Alzheimer's disease with early onset, Alzheimer's disease with late onset, Alzheimer's dementia senile and presenile forms, metabolic disorders, diseases of the kidney, in particular glomerulonephritis and acute kidney injury, and arthrosis/arthritis, in particular reactive arthritis, rheumatoid arthrosis, juvenile idiopathic arthritis, and psoriatic arthritis.

Thus, in a particularly preferred embodiment, the disorder/disease to be prevented and/or treated is a neurodegenerative disease, in particular tauopathies, preferably Alzheimer's disease, for example Alzheimer's disease with early onset, Alzheimer's disease with late onset, Alzheimer's dementia senile and presenile forms.

Alzheimer's disease (AD) is a devastating neurodegenerative disorder that leads to progressive cognitive decline with memory loss and dementia. Neuropathological lesions are characterized by extracellular deposition of senile plaques, formed by β-amyloid (Aβ) peptide, and intracellular neurofibrillary tangles (NFTs), composed of hyperphosphorylated tau proteins (Duyckaerts et al., 2009, Acta Neuropathol 118: 5-36). According to the amyloid cascade hypothesis, neurodegeneration in AD could be linked to an abnormal amyloid precursor protein (APP) processing through the activity of the beta-site APP cleaving enzyme 1 (BACE1) and presenilin 1, leading to the production of toxic Aβ oligomers that accumulate in fibrillar Aβ peptides before forming Aβ plaques. Aβ accumulations can lead to synaptic dysfunction, altered kinase activities resulting in NFTs formation, neuronal loss and dementia (Hardy and Higgiins, 1992, Science 256: 184-5). AD pathogenesis is thus believed to be triggered by the accumulation of Aβ, whereby Aβ self-aggregates into oligomers, which can be of various sizes, and forms diffuse and neuritic plaques in the parenchyma and blood vessels. Aβ oligomers and plaques are potent synaptotoxins, block proteasome function, inhibit mitochondrial activity, alter intracellular $Ca^+$ levels and stimulate inflammatory processes. Loss of the normal physiological functions of Aβ is also thought to contribute to neuronal dysfunction. Aβ interacts with the signalling pathways that regulate the phosphorylation of the microtubule-associated protein tau. Hyperphosphorylation of tau disrupts its normal function in regulating axonal transport and leads to the accumulation of neurofibrillary tangles (NFTs) and toxic species of soluble tau. Furthermore, degradation of hyperphosphorylated tau by the proteasome is inhibited by the actions of Aβ. These two proteins and their associated signalling pathways therefore represent important therapeutic targets for AD.

C-Jun N-terminal kinases (JNKs) are serine-threonine protein kinases, coded by three genes JNK1, JNK2, and JNK3, expressed as ten different isoforms by mRNA alternative splicing, each isoforms being expressed as a short form (46 kDa) and a long form (54 kDa) (Davis., 2000, Cell 103: 239-52). While JNK1 and JNK2 are ubiquitous, JNKs is mainly expressed in the brain (Kyriakis and Avruch, 2001, Physiol Rev 81: 807-69). JNKs are activated by phosphorylation (pJNK) through MAPKinase activation by extracellular stimuli, such as ultraviolet stress. cytokines and AB peptides and they have multiple functions including gene expression regulation, cell proliferation and apoptosis (Dhanasekaran and Reddy, 2008. Oncogene 27: 624-51).

According to the present invention, it is assumed that the JNK inhibitors according to the present invention reduce tau hyperphosphorylation and, thus, neuronal loss. Therefore, the JNK inhibitors according to the present invention can be useful for treating and/or preventing tauopathies. Tauopathies are a class of neurodegenerative diseases associated with the pathological aggregation of tau protein in the human brain. The best-known tauopathy is Alzheimer's disease (AD), wherein tau protein is deposited within neurons in the form of neurofibrillary tangles (NFTs), which are formed by hyperphosphorylation of tau protein. The degree of NFT involvement in AD is defined by Braak stages. Braak stages I and II are used when NFT involvement is confined mainly to the transentorhinal region of the brain, stages III and IV when there is also involvement of limbic regions such as the hippocampus, and V and VI when there is extensive neocortical involvement. This should not be confused with the degree of senile plaque involvement, which progresses differently. Thus, the JNK inhibitors can be used according to the present invention for treating and/or preventing tauopathies, in particular Alzheimer's disease with NFT involvement, for example AD with Braak stage I, AD with Braak stage II, AD with Braak stage III, AD with Braak stage IV and/or AD with Braak stage V.

Further tauopathies, i.e. conditions in which neurofibrillary tangles (NFTs) are commonly observed, and which can thus be treated and/or prevented by the JNK inhibitors according to the present invention, include progressive supranuclear palsy although with straight filament rather than PHF (paired helical filaments) tau; dementia pugilistica (chronic traumatic encephalopathy); frontotemporal dementia and parkinsonism linked to chromosome 17, however without detectable β-amyloid plaques; Lytico-Bodig disease (Parkinson-dementia complex of Guam); tangle-predominant dementia, with NFTs similar to AD, but without plaques; ganglioglioma and gangliocytoma; meningioangiomatosis; subacute sclerosing panencephalitis; and/or lead encephalopathy, tuberous sclerosis, Hallervorden-Spatz disease, and lipofiscinosis. Further tauopathies, which can be treated and/or prevented by the JNK inhibitors according to the present invention, include Pick's disease; corticobasal degeneration; Argyrophilic grain disease (AGD); frontotemporal dementia and frontotemporal lobar degeneration. In Pick's disease and corticobasal degeneration tau proteins are deposited in the form of inclusion bodies within swollen or "ballooned" neurons. Argyrophilic grain disease (AGD), another type of dementia, which is sometimes considered as a type of Alzheimer disease and which may co-exist with other tauopathies such as progressive supranuclear palsy, corticobasal degeneration, and also Pick's disease, is marked by the presence of abundant argyrophilic grains and coiled bodies on microscopic examination of brain tissue. The non-Alzheimer's tauopathies are sometimes grouped together as "Pick's complex".

It is also preferred according to the present invention, that the disorder/disease to be prevented and/or treated by the JNK inhibitor according to the present invention is Mild Cognitive Impairment (MCI), in particular MCI due to Alzheimer's Disease. Typically, Mild Cognitive Impairment (MCI) is different from Alzheimer's Disease, i.e. Mild Cognitive Impairment (MCI) is typically not Alzheimer's Disease, but is a disease on its own classified by ICD-10 in F06.7. In ICD-10 (F06.7), MCI is described as a disorder characterized by impairment of memory, learning difficulties, and reduced ability to concentrate on a task for more than brief periods. There is often a marked feeling of mental fatigue when mental tasks are attempted, and new learning is found to be subjectively difficult even when objectively successful. None of these symptoms is so severe that a diagnosis of either dementia (F00-F03) or delirium (F05.-) can be made. The disorder may precede, accompany, or follow a wide variety of infections and physical disorders, both cerebral and systemic, but direct evidence of cerebral involvement is not necessarily present. It can be differentiated from postencephalitic syndrome (F07.1) and postconcussional syndrome (F07.2) by its different etiology, more restricted range of generally milder symptoms, and usually shorter duration. Mild cognitive impairment (MCI), in particular MCI due to Alzheimer's Disease, causes a slight but noticeable and measurable decline in cognitive abilities, including memory and thinking skills. MCI involves the onset and evolution of cognitive impairments whatever type beyond those expected based on the age and education of the individual, but which are not significant enough to interfere with their daily activities. The diagnosis of MCI is described for example by Albert M S, DeKosky S T, Dickson D, Dubois B, Feldman H H, Fox N C, Gamst A, Holtzman D M, Jagust W J, Petersen R C, Snyder P J, Carrillo M C, Thies B, Phelps C H (2011) The diagnosis of mild cognitive impairment due to Alzheimer's disease: recommendations from the National Institute on Aging-Alzheimer's Association workgroups on diagnostic guidelines for Alzheimer's disease; Alzheimers Dement.; 7(3):270-9. MCI may be at the onset of whatever type of dementia or represents an ephemeric form of cognitive impairment which may disappear over time without resulting in a clinical manifestation of dementia. A person with MCI is at an increased risk of developing Alzheimer's or another dementia, in particular at an increased risk of developing Alzheimer's Disease, without however necessarily developing dementia, in particular Alzheimer's Disease. No medications are currently approved by the U.S. Food and Drug Administration (FDA) to treat Mild Cognitive Impairment. Drugs approved to treat symptoms of Alzheimer's Disease have not shown any lasting benefit in delaying or preventing progression of MCI to dementia.

The JNK inhibitors of the present invention may also be used for the treatment of diseases and/or disorders of the urinary system in particular selected from ureteritis; urinary tract infection (bladder infection, acute cystitis); cystitis in general, in particular interstitial cystitis, Hunner's ulcer, trigonitis and/or hemorrhagic cystitis; urethritis, in particular nongonococcal urethritis or gonococcal urethritis; painful bladder syndrome; IC/PBS; urethral syndrome; and/or retroperitoneal fibrosis, preferably cystitis in general, in particular interstitial cystitis. In this context it is noted that interstitial cystitis (IC) varies very much in symptoms and severity and, thus, most researchers believe it is not one, but several diseases. In recent years, scientists have started to use the terms "bladder pain syndrome" (BPS) or "painful bladder syndrome" (PBS) to describe cases with painful urinary symptoms that may not meet the strictest definition of IC. The term "IC/PBS" includes all cases of urinary pain that can't be attributed to other causes, such as infection or urinary stones. The term interstitial cystitis, or IC, is typically used alone when describing cases that meet all of the IC criteria, for example as established by the National Institute of Diabetes and Digestive and Kidney Diseases (NIDDK).

The JNK inhibitors of the present invention may also be used for the treatment of metabolic disorders, for example for the treatment of diabetes (type 1 or type 2, in particular type 1), Fabry disease, Gaucher disease, hypothermia, hyperthermia hypoxia, lipid histiocytosis, lipidoses, metachromatic leukodystrophy, mucopolysaccharidosis, Niemann-Pick disease, obesity, and Wolman's disease. Moe generally, metabolic disorders may be of hereditary form or may be acquired disorders of carbohydrate metabolism, e.g., glycogen storage disease, disorders of amino acid metabolism, e.g., phenylketonuria, maple syrup urine disease, glutaric acidemia type 1, Urea Cycle Disorder or Urea Cycle Defects, e.g., Carbamoyl phosphate synthetase I deficiency, disorders of organic acid metabolism (organic acidurias), e.g., alcaptonuria, disorders of fatty acid oxidation and mitochondrial metabolism, e.g., Medium-chain acyl-coenzyme A dehydrogenase deficiency (often shortened to MCADD.), disorders of porphyrin metabolism, e.g. acute intermittent *porphyria*, disorders of purine or pyrimidine metabolism, e.g., Lesch-Nyhan syndrome, Disorders of steroid metabolism, e.g., lipoid congenital adrenal hyperplasia, or congenital adrenal hyperplasia, disorders of mitochondrial function, e.g., Kearns-Sayre syndrome, disorders of peroxisomal function. e.g., Zellweger syndrome, or Lysosomal storage disorders, e.g., Gaucher's disease or Niemann Pick disease.

The JNK inhibitors of the present invention may also be used for the treatment of neoplasms in particular cancer (malignant neoplasms) and/or tumor diseases, in particular selected from solid tumors in general; hematologic tumors in general, in particular leukemia, for example acute lymphocytic leukemia (L1, L2, L3), acute lymphoid leukaemia (ALL), acute myelogenous leukemia (AML), chronic lymphocytic leukaemia (CLL), chronic myeloid leukaemia (CML), promyelocytic leukemia (M3), monocytic leukemia, myeloblastic leukemia (M1), myeloblastic leukemia (M2), megakaryoblastic leukemia (M7) and myelomonocytic leukemia (M4); myeloma, for example multiple myeloma; lymphomas, for example non-Hodgkin's lymphomas, mycosis fungoides, Burkitt's lymphoma, and Hodgkin's syndrome; pancreatic cancer, in particular pancreatic carcinoma; ovarian cancer, in particular ovarian carcinoma; liver cancer and liver carcinoma in general, in particular liver metastases, liver cell carcinoma, hepatocellular carcinoma, hepatoma, intrahepatic bile duct carcinoma, cholangiocarcinoma, hepatoblastoma, angiosarcoma (of liver), and other specified or unspecified sarcomas and carcinomas of the liver; skin cancer; melanoma, in particular malignant melanoma; squamous cell carcinoma; glioblastoma; colon cancer and colon carcinoma in general, in particular cecum carcinoma, appendix carcinoma, ascending colon carcinoma, hepatic flexure carcinoma, transverse colon carcinoma, splenic flexure carcinoma, descending colon carcinoma, sigmoid colon carcinoma, carcinoma of overlapping sites of colon and/or malignant carcinoid tumors of the colon; prostate cancer and prostate tumours, in particular prostate carcinoma; and further cancer and/or tumor diseases, in particular selected from acusticus neurinoma lung carcinomas; adenocarcinomas; anal carcinoma; bronchial carcinoma; cervix carcinoma; cervical cancer; astrocytoma; basalioma; cancer with Bcr-Abl transformation; bladder cancer; blastomas; bone cancer; brain metastases; brain tumours; breast cancer; carcinoids; cervical cancer; corpus carcinoma; craniopharyngeomas; CUP syndrome; virus-induced tumours; EBV-induced B cell lymphoma; endometrium carcinoma; erytholeukemia (M6); esophagus cancer; gallbladder cancer; gastrointestinal cancer; gastrointestinal stromal tumors; gastrointestinal tumours; genitourinary cancer; glaucoma; gliomas; head/neck tumours; hepatitis B-induced tumours; hepatocell or hepatocellular carcinomas; hepatocarcinomas; hepatomas; herpes virus-induced tumours; HTLV-1-induced lymphomas; HTLV-2-induced lymphomas; insulinomas; intestinal cancer; Kaposi's sarcoma; kidney cancer; kidney carcinomas; laryngeal cancer; leukemia; lid tumour; lung cancer; lymphoid cancer; mammary carcinomas; mantle cell lymphoma; neurinoma; medulloblastoma; meningioma; mesothelioma; non-small cell carcinoma; non-small cell carcinoma of the lung; oesophageal cancer; oesophageal carcinoma; oligodendroglioma; papilloma virus-induced carcinomas; penis cancer; pituitary tumour; plasmocytoma; rectal tumours; rectum carcinoma; renal-cell carcinoma; retinoblastoma; sarcomas; Schneeberger's disease; small cell lung carcinomas; small intestine cancer; small intestine tumours; soft tissue tumours; spinalioma; squamous cell carcinoma; stomach cancer; testicular cancer; throat cancer; thymoma; thyroid cancer; thyroid carcinoma; tongue cancer; undifferentiated AML (MO); urethral cancer; uterine cancer; vaginal cancer; Von Hippel Lindau disease; vulval cancer; Wilms' Tumor; Xeroderma pigmentosum.

A person skilled in the art will readily realize that the above mentioned disease states and disorders may belong to more than one of the above mentioned disease classes. For example, bronchial carcinoma is certainly not only a proliferative disease but would also belong in the group of diseases of the respiratory system including lung diseases. Thus, the above mentioned classification of individual diseases is not considered to be limiting or concluding but is considered to of exemplary nature only. It does not preclude that individual disease states recited in one class are factually also suitable examples for the application of the JNK inhibitors of the present invention as treatment in another class of disease states. A person skilled in the art will readily be capable of assigning the different disease states and disorders to matching classifications.

Finally, as mentioned above, the present invention contemplates the use of a JNK inhibitor as defined herein for the treatment and/or prevention of various diseases states and disorders. The present invention does not contemplate to use the JNK inhibitors as defined herein for immunizing non-human animals, e.g. for the production of monoclonal antibodies. Such methods are herein not considered to be methods for treatment of the animal body by therapy.

Tissue and Organ Transplantation

According to another aspect the present invention provides a JNK inhibitor as defined herein for the (in vitro) treatment of a tissue or organ transplant prior to its transplantation. The term "prior to its transplantation" comprises the time of isolation and the time of perfusion/transport. Thus, the treatment of a tissue or organ transplant "prior to its transplantation" refers for example to treatment during the isolation and/or during perfusion and/or during transport. In particular, a solution used for isolation of of a tissue or organ transplant as well as a solution used for perfusion, transport and/or otherwise treatment of a tissue or organ transplant can preferably contain the JNK inhibitor according to the invention.

In transplantation the tolerable cold ischemia time (CIT) and the tolerable warm ischemia time (WIT) play critical roles. CIT is the length of time that elapses between an organ being removed from the donor, in particular the time of perfusion/treatment of an organ by cold solutions, to its transplantation into the recipient. WIT is in general a term used to describe ischemia of cells and tissues under normothermic conditions. In particular WIT refers to the length of time that elapses between a donor's death, in particular from the time of cross-clamping or of asystole in non-heart-beating donors, until cold perfusion is commenced. Additionally, WIT may also refer to ischemia during implantation, from removal of the organ from ice until reperfusion. In allotransplantation usually, a transplant originating from a brain-dead donor is typically not subjected to WIT, but has 8-12 hrs of CIT (time needed for transportation from the procurement hospital to the isolation lab), whereas a transplant from a non-heart beating donor is typically exposed to a longer WIT and also 8-12 hrs of CIT. However, such transplantation is currently not used routinely because of concerns about damage due to the WIT. In autotransplantation, WIT may occur, however, CIT is usually limited (typically 1-2 hrs, for example in islet autotransplantation in patients with chronic pancreatitis).

Depending on the donor, the organ and/or tissue is not perfused with blood for a variable amount of time prior to its transplantation, leading to ischemia. Ischemia is an inevitable event accompanying transplantation, for example kidney transplantation. Ischemic changes start with brain death, which is associated with severe hemodynamic disturbances: increasing intracranial pressure results in bradycardia and decreased cardiac output; the Cushing reflex causes tachycardia and increased blood pressure; and after a short period of stabilization, systemic vascular resistance declines with hypotension leading to cardiac arrest. Free radical-mediated injury releases proinflammatory cytokines and activates innate immunity. It has been suggested that all of these changes—the early innate response and the ischemic tissue damage play roles in the development of adaptive responses, which in turn may lead to transplant rejection. Hypothermic storage of the organ and/or tissue of various durations before transplantation add to ischemic tissue damage. The final stage of ischemic injury occurs during reperfusion. Reperfusion injury, the effector phase of ischemic injury, develops hours or days after the initial insult. Repair and regeneration processes occur together with cellular apoptosis, autophagy, and necrosis; the fate of the organ depends on whether cell death or regeneration prevails. The whole process has been described as the ischemia-reperfusion (I-R) injury. It has a profound influence on not only the early but also the late function of a transplanted organ or tissue. Prevention of I-R injury can thus already be started before organ recovery by donor pretreatment.

It was found that transplants may be (pre-)treated by the JNK inhibitors according to the present invention in order to improve their viability and functionality until transplanted to the host. For that aspect of the invention, the transplant is in particular a kidney, heart, lung, pancreas, in particular pancreatic islets (also called islets of Langerhans), liver, blood cell, bone marrow, cornea, accidental severed limb, in particular fingers, hand, foot, face, nose, bone, cardiac valve, blood vessel or intestine transplant, preferably a kidney, heart, pancreas, in particular pancreatic islets (also called islets of Langerhans), or skin transplant.

Moreover, in a further aspect, the present invention provides a JNK inhibitor as defined herein for the treatment of a tissue or organ transplant, or an animal or human who received a tissue or organ transplant during or after transplantation. The term "after transplantation" refers in particular to reperfusion of the organ or tissue, for example a kidney, whereby reperfusion begins for example by unclamping the respective blood flow. The treatment with a JNK inhibitor according to the present invention after transplantation refers in particular to the time interval of up to four hours after reperfusion, preferably up to two hours after reperfusion, more preferably up to one hour after reperfusion and/or at the day(s) subsequent to transplantation. For the treatment after transplantation, for example after kidney transplantation, the JNK inhibitor according to the present invention may be administered for example to an animal or human who received a tissue or organ transplant as pharmaceutical composition as described herein, for example systemically, in particular intravenously, in a dose in the range of 0.01-10 mg/kg, preferably in the range of 0.1-5 mg/kg, more preferably in the range of 0.5-2 mg/kg at a single dose or repeated doses.

For that aspect of the invention, the transplant is in particular a kidney, heart, lung, pancreas, in particular pancreatic islets (also called islets of Langerhans), liver, blood cell, bone marrow, cornea, accidental severed limb, in particular fingers, hand, foot, face, nose, bone, cardiac valve, blood vessel or intestine transplant, preferably a kidney, heart, pancreas, in particular pancreatic islets (also called islets of Langerhans), or skin transplant.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

All references cited herein are herewith incorporated by reference.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

EXAMPLES

In the following, particular examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: Synthesis of JNK Inhibitor SEQ ID NO: 172

As illustrative example, synthesis of the JNK inhibitor with SEQ ID NO: 172 is set out below. A person skilled in the art will know that said synthesis may also be used for and easily adapted to the synthesis of any other JNK inhibitor according to the present invention.

The JNK inhibitor with SEQ ID NO: 172 was manufactured by solid-phase peptide synthesis using the Fmoc (9-fluorenylmethyloxycarbonyl) strategy. The linker between the peptide and the resin was the Rink amide linker (p-[Fmoc-2,3-dimethoxybenzyl]-phenoxyacetic acid). The peptide was synthesized by successive Fmoc deprotection and Fmoc-amino acid coupling cycles. At the end of the synthesis, the completed peptide was cleaved by trifluoroacetic acid (TFA) directly to yield the crude C-terminal amide, which was then purified by preparative reverse phase HPLC. The purified fractions were pooled in a homogeneous batch that is treated by ion exchange chromatography to obtain its acetate salt. The peptide was then freeze-dried.

1.1 Solid Phase Synthesis of the Peptide

Except when noted, the manufacturing took place at room temperature (22° C.±7° C.) in an air-filtered environment. The scale of synthesis was 0.7 mmoles of the starting amino acid on the resin, for an expected yield of about 1 g of purified peptide. Synthesis was performed manually in a 30-50 mL reactor equipped with a fritted disk with mechanical stirring and/or nitrogen bubbling.

1.2 Preparation of the Resin

The p-methylbenzhydrylamide resin (MBHA-resin) was first washed with dichloromethane/dimethylformamide/diisoproplyethylamine under nitrogen. The washed resin was then coupled to the Rink amide linker (p-[Fmox-2,4-dimethoxybenzyl]-phenoxyacetic acid) in PyBOB(benzotriazole-1-yl-oxy-tris-pyrrolidino-phosphonium hexafluorophosphate)/diisopropyl-ethylamine/1-hydroxybenzotriazole to yield Fmoc-Rink amide-MBHA resin.

1.3 Coupling of Amino Acids

Amino acids were coupled to the resin using the following cycle: The Fmoc-Rink amide-MBHA resin was deprotected by washing it in 35% (v/v) piperidine/dimethylformamide, followed by dimethylformamide. The deprotection reaction took approximately 16 minutes. Fmoc-protected amino acids (e.g., 2 eq of amino acid and HOBt (1-hydroxybenzotriazole) in dimethylformamide/dichloromethane (50/50) were added to the resin followed by addition of 2 eq of the coupling agent diisopropylcarbodiimide (DIC). The coupling reaction took from one hour to overnight depending upon the respective amino acid being added. Volumes were calculated on a basis of 0.5 mL/100 mg of peptide-resin and adjusted after each cycle. After coupling, the resin was washed 3 times with DMF. Completeness of coupling was tested by the ninhydrin test (or Kaiser test 1) on primary amines and the chloranyl test 2 on secondary amines. On some occasions, the chloranyl test may be associated with a ninhydrin test as a security control. In case the coupling test indicated incompleteness of reaction, coupling was repeated with a lower excess (0.5-1 eq) of amino acid, PYBOP, HOBT in dimethylformamide/dichloromethane and diisopropylethylamine. Functionality of the resin was measured and generally 0.6-0.2 meq/g, depending on the original loading of the resin. After the last amino acid has been coupled, the peptide-resin was deprotected as usual and then washed 5 times with DCM before drying in an oven under vacuum at 30° C. After the peptide-resin had dried, the yield of the solid-phase synthesis was calculated as the ratio of the weight increase of the peptide resin compared to the theoretical weight increase calculated from the initial loading of the resin. The yield may be close to 100%.

1.4 Cleavage and Deprotection

The peptide was cleaved from the resin in a mixture of trifluoroacetic acid/1,2-ethanedithiol/thioanisole/water/phenol (88/2.2/4.4/4.4/7 v/v), also called TFA/K reagent, for 4 hours at room temperature. The reaction volume was 1 mL/100 mg of peptide resin. During addition of the resin to the reagent, the mixture temperature was regulated to stay below 30° C.

1.5 Extraction of the Peptide from the Resin:

The peptide was extracted from the resin by filtration through a fritted disc. After concentration on a rotavapor to ⅓ of its volume, the peptide was precipitated by cold t-butyl methyl ether and filtered. The crude peptide was then dried under vacuum at 30° C.

1.6 Preparative HPLC Purification:

The crude peptide was then purified by reverse-phase HPLC to a purity of ≥95%. The purified fractions were concentrated on a rotavaporator and freeze-dried.

1.7 Ion Exchange Chromatography

The concentrated freeze-dried pools of purified peptide with the sequence of SEQ ID NO: 172 was dissolved in water and purified by ion exchange chromatography on Dowex acetate, 50-100 mesh resin.

The required starting reagents for the synthesis were:

|  | CAS Registry Number | Chemical Name | Molecular Weight |
|---|---|---|---|
| Fmoc-Rink amide linker | 145069-56-3 | p-[Fmoc-2,4-dimethoxybenzyl]-phenoxyacetic acid | 539.6 |
| Fmoc-D-Ala-OH, H$_2$O | 79990-15-1 | N-alpha-Fmoc-D-alanine | 311.3 |
| Fmoc-Arg(Pbf)-OH | 154445-77-9 | N-alpha-Fmoc-N [2,2,4,6,7-pentamethyldihydrobenzofuran-5-sulfonyl]-arginine | 648.8 |
| Fmoc-D-Arg(Pbf)-OH | 187618-60-6 | N-alpha-Fmoc-N [2,2,4,6,7-pentamethyldihydrobenzofuran-5-sulfonyl]-D-arginine | 648.8 |
| Fmoc-Asn(Trt)-OH | 132388-59-1 | N-alpha-Fmoc-N-beta-trityl-asparagine | 596.7 |
| Fmoc-Gln(Trt)-OH | 132327-80-1 | N-alpha-Fmoc-N-delta-trityl-glutamine | 610.7 |
| Fmoc-Leu-OH | 35661-60-0 | N-alpha-Fmoc-leucine | 353.4 |
| Fmoc-Lys(Boc)-OH | 71989-26-9 | N-alpha-Fmoc-N epsilon-Boc-L-lysine | 468.5 |
| Fmoc-D-Lys(Boc)-OH | 143824-78-6 | N-alpha-Fmoc-N epsilon-Boc-D-lysine | 468.5 |
| Fmoc-D-Phe-OH | 86123-10-6 | N-alpha-Fmoc-D-phenylalanine | 387.4 |
| Fmoc-Pro-OH | 71989-31-6 | N-alpha-Fmoc-proline | 337.4 |
| Fmoc-Thr(tBu)-OH | 71989-35-0 | N-alpha-Fmoc-O-t-butyl-threonine | 397.5 |

Other JNK inhibitors of the present invention may be prepared in similar manner.

Example 2: Inhibitory Efficacy of Selected JNK Inhibitors According to the Present Invention In the following a standard operating procedure will be set forth describing how the Inhibitory efficacy of JNK inhibitors according to the present invention was measured. The method allows to measure in vitro, in a non radioactive standardized assay, the ability of a candidate compound to decrease the phosphorylation of the c-Jun specific substrate by JNK. Moreover, it will be illustrated how to determine the inhibitory effect (IC50) and the Ki of a chosen compound for JNK. The method is suitable to verify whether a candidate compound does or does not inhibit JNK activity. And a person skilled in the art will certainly understand how to adapt the below methods for his specific purposes and needs.

2.1 Material

AlphaScreen Reagent and Plate:

His-JNK1 (ref 14-327, Upstate, 10 μg in 100 μl: concentration: 2.2 μM) 5 nM final His-JNK2 (ref 14-329, Upstate, 10 μg in 100 μl: concentration: 2 μM) 5 nM final His-JNK3 (ref 14-501, Upstate, 10 μg in 100 μl: concentration: 1.88 μM) 5 nM final Anti-Phospho-cJun (ref 06-828, Upstate, lot DAM1503356, concentration: 44.5 μM) 10 nM final Biotin-cJun (29-67):
sequence: Biotin—SNPKILKQSMTLNLADPVGSLK-PHLRAKNSDLLTSPDVG (SEQ ID NO: 198), lot 100509 (mw 4382.11, P 99.28%) dissolved in H$_2$O, concentration: 10 mM) 30 nM final ATP (refAS001A, Invitrogen, lot 50860B, concentration 100 mM)) 5 µM final SAD beads (ref 6760617M, PerkinElmer, lot 540-460-A, concentration 5 mg/ml) 20 µg/ml final AprotA beads (ref 6760617M, PerkinElmer, lot 540-460-A, concentration 5 mg/ml) 20 µg/ml final Optiplate 384 well white plate (ref 6007299, PerkinElmer, lot 654280/2008)

96 well plate for peptide dilution (ref 82.1581, Sarstedt)

TopSeals-A (ref 6005185, Perkin Elmer, Lot 65673)

Bioluminescent energy transfer reading

The bioluminescent energy transfer was read on the Fusion Alpha Plate reader (Perkin Elmer).

Pipette:

An electronic EDP3 pipette 20-300 (Ref 17007243; Rainin) was used to fill in the plate with the Enzyme-Antibody mix, the Substrate-ATP mix and the Beads.

A PIPETMAN® Ultra multichannel 8×20 (Ref 21040; Gilson) was used to fill in the plate with the inhibitory compounds.

Buffer and Solutions

Kinase Buffer: 20 mM Tris-base pH 7.4, 10 mM MgCl, 1 mM DTT, 100 µM Na$_3$VO$_4$, 0.01% Tween, (1% DMSO)

Stop Buffer: 20 mM Tris-base pH 7.4, 200 mM NaCl, 80 mM EDTA-K (pH de 8 with KOH instead of NaOH), 0.3% BSA JNK dilution Kinase buffer: 50 mM Tris-base pH 7.4, 150 mM NaCl, 0.1 mM EGTA, 0.03% Brij-35, 270 mM sucrose, 0.1% 3-mercaptoethanol.

2.2 Method

To assess inhibitory effect of the peptides, a standard AlphaScreen assay (see for example Guenat et al. J Biomol Screen, 2006; 11: pages 1015-1026) was performed. The different components were prepared and subsequently mixed as indicated. The plates were sealed and incubated as following:

| | | |
|---|---|---|
| 5 µl | JNK + Antibody | |
| 5 µl | TP kinase +/− inhibitor | Pre-incubation 30 min |
| 5 µl | Biotin-cJun + ATP | Incubation 60 min at 24° C. |
| 10 µl | Beads SAD + A protA | Incubation 60 min in the dark at 24° C. |

To avoid contamination, the mixes were added with the pipette in different corner of the well. After the filling in of the plate with each mix, the plate was tapped (Keep one side fix and let the opposite side tap the table) to let the mix go down the walls of the wells.

The bioluminescent energy transfer was read on the Fusion Alpha Plate reader (Perkin Elmer).

All compounds should at least be tested in triplicate in 3 independent experiments for each isoform of JNK. Possibly concentrations of the compounds to be tested were 0, 0.03 nM, 0.1 nM, 0.3 nM, 1 nM, 3 nM, 10 nM, 30 nM, 100 nM, 300 nM, 1 µM, 3 µM, 10 µM, 30 µM, and 100 µM. Controls were samples either without JNK or without substrate (c-Jun).

Mix Preparation

JNK1, JNK2 and JNK3 5 nM

Biotin-cJun 30 nM

ATP 5 µM; Anti phospho-cJun (S63) 10 nM

Bille SAD/AprotA 20 µg/ml

Antibody [final]=10 nM (anti Phospho cJun (S63))

Detection part: [Mix]×5 (5 µl in final volume of 25 µl)

[Stock]=44.5 µM (ref 06-828, Upstate, Lot DAM1503356)

10 nM→50 nM in Kinase Buffer

JNK1, JNK2 and JNK3 [final]=5 nM

Reaction part: [Mix]×3 (5 µl in final volume of 15 µl)

[Stock]=2.2 µM for JNK1 (ref 14-327, Upstate, lot D7KN022CU)

2.0 µM for JNK2 (ref 14-329, Upstate, lot 33221CU)

1.88 µM for JNK3 (ref 14-501, Upstate, lot D7CN041CU)

5 nM→15 nM in Antibody Buffer

Inhibitor:

Reaction part: [Mix]×3 (5 µl in final volume of 15 µl)

[Stock]=10 mM

100 µM→300 µM in Kinase Buffer

30 µM→90 µM in Kinase Buffer

10 µM→30 µM in Kinase Buffer

. . .

0.03 nM→0.09 nM in Kinase Buffer

And 0 nM→Kinase Buffer

Two series of 10 times serial dilutions were performed in a 96 well plate, one beginning with 300 µM to 0 nM, the second with 90 µM to 0.03 nM. The peptides are added in the 384 plates with an 8 channels multipipette (ref F14401, Gilson, 8×20).

ATP [final]=5 µM

Reaction part: [Mix]×3 (5 µl in final volume of 15 µl)

[Stock]=100 mM (ref AS001A, Invitrogen, lot 50860B)

5 µM→15 µM in Kinase Buffer

Biotin c-Jun [final]=30 nM

Reaction part: [Mix]×3 (5 µl in final volume of 15 µl)

[Stock]=10 mM 30 nM→30 nM in ATP Buffer

Beads SAD/A ProtA [final]=20 µg/ml (Light sensitive)

Detection part: [Mix]×2.5 (10 µl in final volume of 25 µl)

[Stock]=5 mg/ml→20 µg/ml 50 µg/ml in STOP Buffer

Mix in the dark room (green Light) or in the darkness.

Analysis of the IC50 Curves:

The analysis was performed by the GraphPad Prism4 software with the following equation: Sigmoidal dose-response (No constraint).

$$Y=Bottom+(Top-Bottom)/(1+10^{\wedge}((\text{Log } EC50-X)))$$

The outliers data were avoided using Grugg's test.

Comparison of the IC50:

The analysis was performed by the GraphPad Prism4 software with the following test: One way ANOVA test followed by a Tukey's Multiple Comparison Test. P<0.05 was considerate as significant.

The Km of the ATP for JNK and the Km of biotin-cJun specific peptide were determined in the report AlphaScreen standardization assay The mathematical relation between Ki and IC50 (Ki=IC50/(1+([Substrate]/Km of the substrate)) may be used to calculate the Ki values.

Example 3: Internalization Experiments and Analysis 3.1 Materials and Methods for Uptake Experiments a) Cell Line:

The cell line used for this experiment was HL-60 (Ref CCL-240, ATCC, Lot 116523)

b) Culture Medium and Plates

RPMI (Ref 21875-091, Invitrogen, Lot 8296) or DMEM (Ref 41965, Invitrogen, Lot 13481) complemented with:

10% FBS (Ref A64906-0098, PAA, Lot A15-151): decomplemented at 56° C., 30 min, on Apr. 4, 2008.

1 mM Sodium Pyruvate (Ref S8636, Sigma, Lot 56K2386)

Penicillin (100 unit/ml)/Streptomycin (100 µg/ml) (Ref P4333, Sigma, Lot 106K2321)

PBS 10× (Ref 70011, Invitrogen, Lot 8277): diluted to 1× with sterile $H_2O$

Trypsine-0.05% EDTA (Ref L-11660, PAA, Lot L66007-1194)

6 well culture plates (Ref 140675, Nunc, Lot 102613)

24 well culture plates (Ref 142475, Nunc, Lot 095849)

96 well culture plates (Ref 167008, Nunc, Lot 083310)

96 well plates for protein dosing (Ref 82.1581, Sarstedt)

96 well plates for fluorescence measurement (Ref 6005279, Perkin Elmer)

c) Solutions

Poly-D-lysine coating solution (Sigma P9011 Lot 095K5104): 25 µg/ml final diluted in PBS 1×

Acidic wash buffer: 0.2M Glycin, 0.15M NaCl, pH 3.0

Ripa lysis buffer: 10 mM $NaH_2PO_4$ pH 7.2, 150 mM NaCl, 1% Triton X-100, 1 mM EDTA pH 8.0, 200 µM $Na_3VO_2$, 0.1% SDS, 1× protease inhibitor cocktail (Ref 11873580001, Roche, Lot 13732700)

d) Microscopy and Fluorescence Plate Reader

Cells were observed and counted using an inverted microscope (Axiovert 40 CFL; Zeiss; 20×). The fluorescence was read with the Fusion Alpha Plate reader (Perkin Elmer).

e) Method

FITC marked peptide internalization was studied on suspension cells. Cells were plated into poly-DL-lysine coated dishes at a concentration of $1\times10^6$ cells/ml. Plates were then incubated for 24 h at 37° C., 5% $CO_2$ and 100% relative humidity prior to the addition of a known concentration of peptide. After peptide addition, the cells were incubated 30 min, 1, 6 or 24 h at 37° C., 5% $CO_2$ and 100% relative humidity. Cells were then washed twice with an acidic buffer (Glycin 0.2 M, NaCl 0.15 M, pH 3.0) in order to remove the cell-surface adsorbed peptide (see Kameyama et al., (2007), *Biopolymers*, 88, 98-107). The acidic buffer was used as peptides rich in basic amino acids adsorb strongly on the cell surfaces, which often results in overestimation of internalized peptide. The cell wash using an acidic buffer was thus employed to remove the cell-surface adsorbed peptides. The acid wash was carried out in determining cellular uptake of Fab/cell-permeating peptide conjugates, followed by two PBS washes. Cells were broken by the addition of the RIPA lysis buffer. The relative amount of internalized peptide was then determined by fluorescence after background subtraction and protein content normalization.

The steps are thus: 1. Cell culture
2. Acidic wash and cellular extracts
3. Analysis of peptide internalization with a fluorescence plate reader f) Cell Culture and Peptide Treatment The 6 well culture plates are coated with 3 ml of Poly-D-Lys (Sigma P9011; 25 µg/ml in PBS), the 24 well plates with 600 µl and the 96 well plates with 125 µl and incubated for 4 h at 37° C., $CO_2$ 5% and 100% relative humidity.

After 4 hours the dishes were washed twice with 3.5 ml PBS, 700 µl or 150 µl PBS for the 6, 24 or 96 well plates, respectively.

The cells were plated into the dishes in 2.4 ml medium (RPMI) at plating densities of 1'000'000 cells/ml for suspension cells. After inoculation, the plates were incubated at 37° C., 5% $CO_2$ and 100% relative humidity for 24 hours prior to the addition of the peptide. Adherent cells should be at a density of 90-95% the day of treatment and were plated in DMEM:

| well | Surface of culture ($cm^2$) | Medium | Nb adherent cells | Nb suspension cells |
|---|---|---|---|---|
| 96 well | 0.3 | 100-200 µl | 8'000-30'000 | 100'000 |
| 24 well | 2 | 500-1000 µl | 100'000-200'000 | 500'000-1'000'000 |
| 35 mm (P35)/ 6 well | 10 | 2.4 ml | 250'000-2'100'000 | 2'400'000 |
| 60 mm (P60) | 20 | 3.5 ml | $15 * 10^5$ | 1'000'000/ml |
| 10 cm (P100) | 60 | 10 ml | $15\text{-}60 * 10^5$ | |

The cells were treated with the desired concentration of FITC labeled peptide (stock solution at a concentration of 10 mM in $H_2O$).

Following peptide addition, the cells were incubated 0 to 24 hours (e.g. 30 min, 1, 6 or 24 hours) at 37° C., $CO_2$ 5% and 100% relative humidity.

Acidic Wash and Cellular Extracts:

The extracts were cooled on ice.

Suspension cells (or cells, which don attach well to the dish): Transfer the cells in <<Falcon 15 ml». To recover the maximum of cells, wash the dish with 1 ml of PBS.

Harvest the cells 2 min at 2400 rpm max.

Suspend the cells in 1 ml cold PBS.

Transfer the cells into a coated "Eppendorf tube" (coated with 1 ml of poly D-Lys for 4 hours and washed twice with 1 ml PBS).

Wash three times with 1 ml of cold acidic wash buffer and centrifuge 2 min at 2400 rpm max. Beware of the spreading of the cells in the "eppendorf".

Wash twice with 1 ml cold PBS to neutralize.

Add 50 µl of lysis RIPA Buffer.

Incubate 30 min-1 h on ice with agitation.

Adherent Cells:

Wash three times with 3 ml, 1 ml or 200 µl (for 6, 24 or 96 well plates, respectively) of cold acidic wash buffer. Beware of the cells who detach from the dish.

Wash twice with 1 ml cold PBS (for 6, 24 or 96 well plates, respectively) to neutralize.

Add 50 µl of lysis RIPA buffer.

Incubate 30 min-1 h on ice with agitation.

Scrap the cells with a cold scrapper. The 24 and 96 well plates were directly centrifuged at 4000 rpm at 4° for 15 min to remove the cellular debris. Then the supernatants (100 or 50 ml respectively for the 24 or 96 well plates) were directly transferred in a dark 96 well plated. The plates were read by a fluorescence plate reader (Fusion Alpha, Perkin Elmer).

Transfer the lysate in a coated "eppendorf" (coated with 1 ml of poly D-Lys for 4 hours and wash twice with 1 ml PBS).

The lysed cells were then centrifuged 30 min at 10000 g at 4° C. to remove the cellular debris.

Remove the supernatant and store it at −80° C. in a coated "Eppendorf tube" (coated with 1 ml of poly D-Lys for 4 hours and washed twice with 1 ml PBS).

Analysis of Peptide Internalization with a Fluorescence Plate Reader:

The content of each protein extract was determined by a standard BCA assay (Kit No 23225, Pierce), following the instructions of the manufacturer.

The relative fluorescence of each sample is determined after reading 10 μl of each sample in a fluorescence plate reader (Fusion Alpha, Perkin Elmer), background subtraction and normalization by protein concentration.

3.2 Uptake Experiments

The time dependent internalization (uptake) of FITC-labeled TAT derived transporter constructs into cells of the HL-60 cell line was carried out as described above using sequences transporter peptides of SEQ ID NOs: 52-96, 43, and 45-47. These sequences are listed below in Table 4.

TABLE 4

Transporter sequence tested in uptake experiments

Figure 6A:
FIG. 6A-6B: shows internalization experiments using TAT derived transporter constructs with D-amino acid/L-amino acid pattern as denoted in SEQ ID NO: 30. The rat transporter sequences analyzed correspond to SEQ ID NOs: 52-94 plus SEQ ID NOs: 45, 47, 46, 43 and 99 (FIG. 6A) and SEQ ID NOs: 100-147 (FIG. 6B). As can be seen, all transporters with the consensus sequence rXXXrXXXr (SEQ ID NO: 31) showed a higher internalization capability than the L-TAT transporter (SEQ ID NO: 43). Hela cells were incubated 24 hours in 96 well plate with 10 mM of the respective transporters. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction.
Figure 6B:
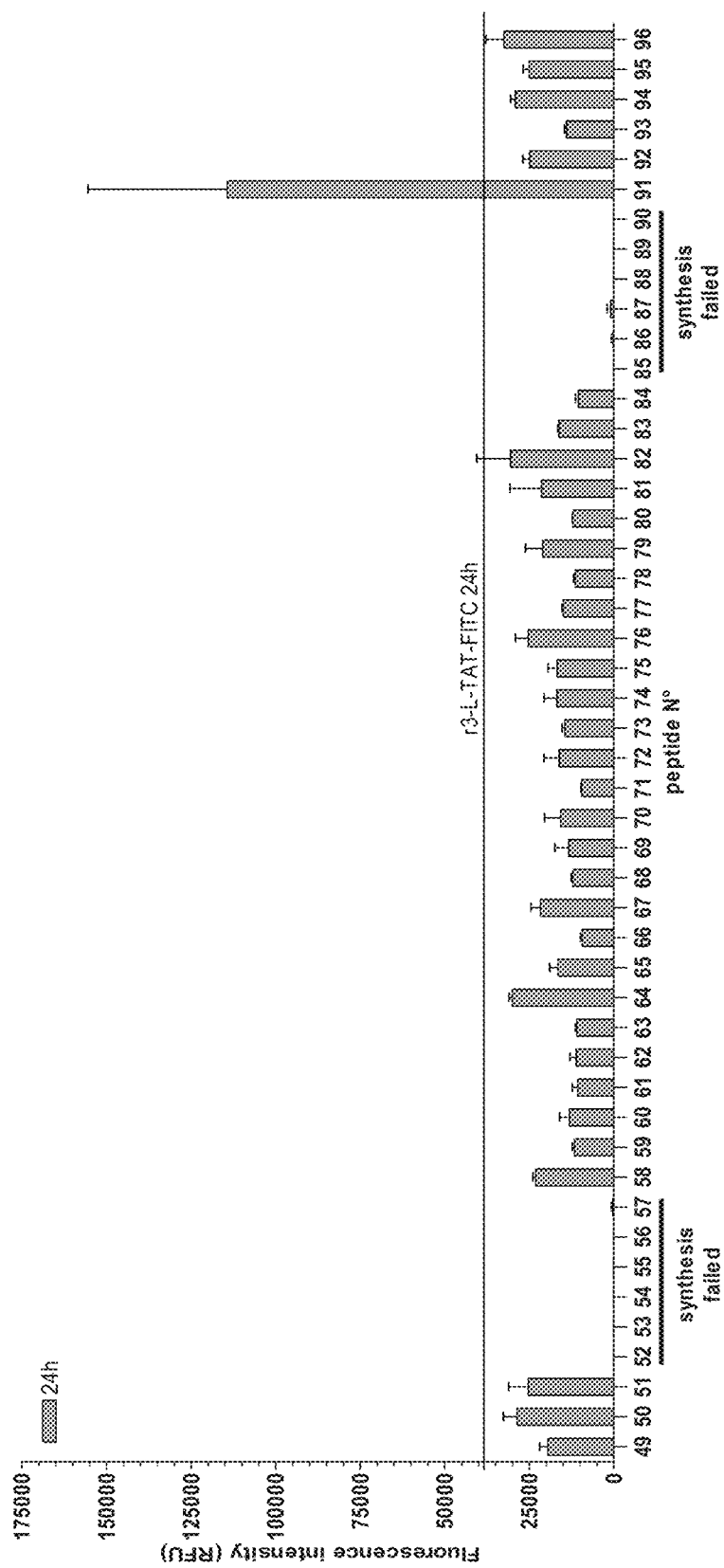
Figure 7A:
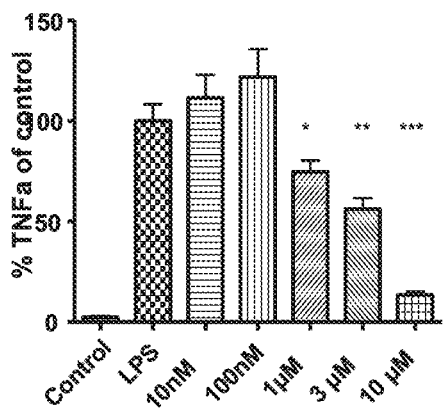
FIG. 7A-7D The JNK inhibitor with the sequence of SEQ ID NO: 172 blocks LPS-induced cytokine and chemokine release in THP1-PMA-differentiated macrophages.
Figure 7B:
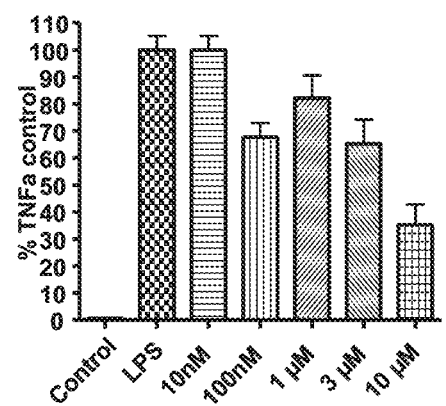
Figure 7C:
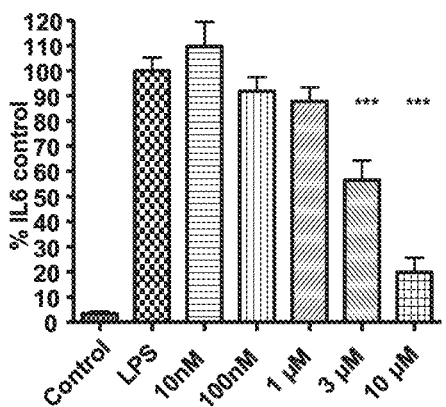
Figure 7D:
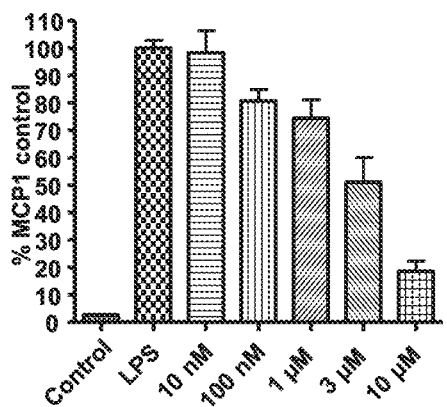
Figure 8:
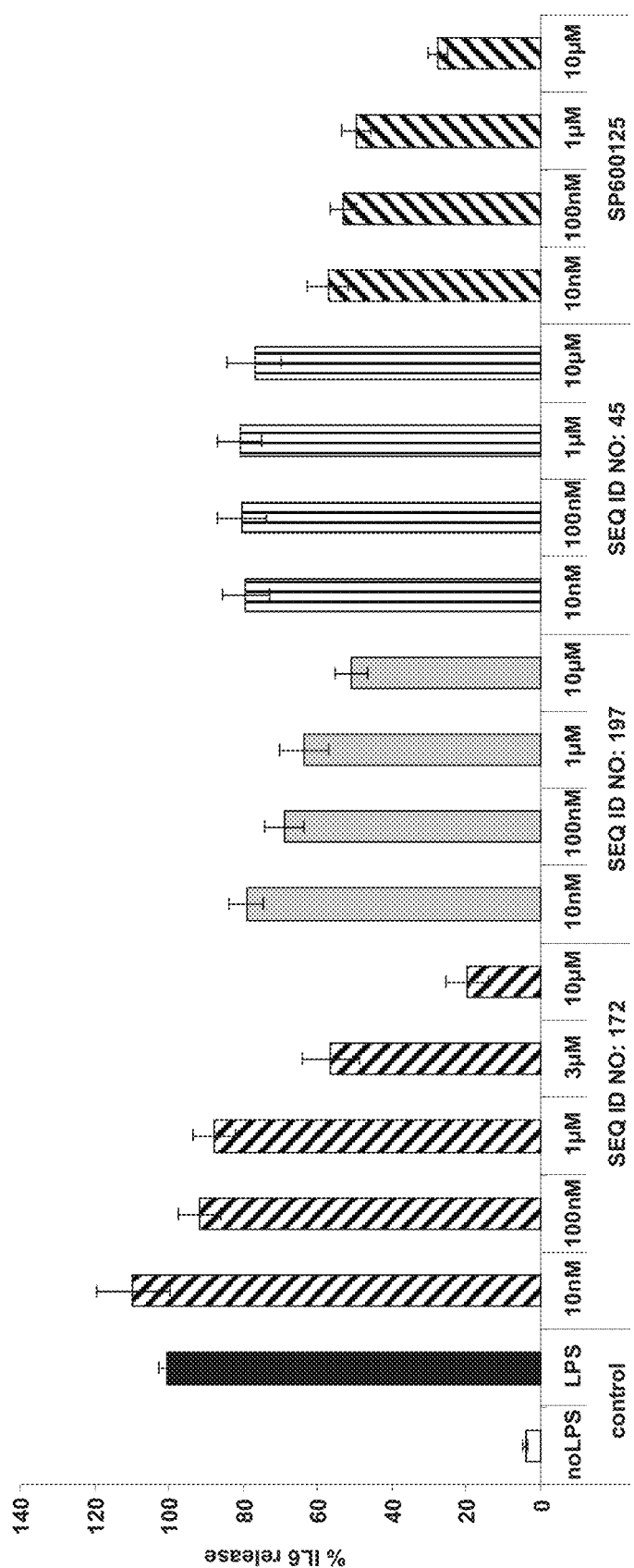
FIG. 8 The JNK inhibitor of SEQ ID NO: 172 blocks LPS-induced IL6 release in THP1 differentiated macrophages with higher potency than D-TAT-IB1 (SEQ ID NO: 197), dTAT (SEQ ID NO: 45) and SP 600125. LPS was added for 6 h (10 ng/ml).
Figure 9:
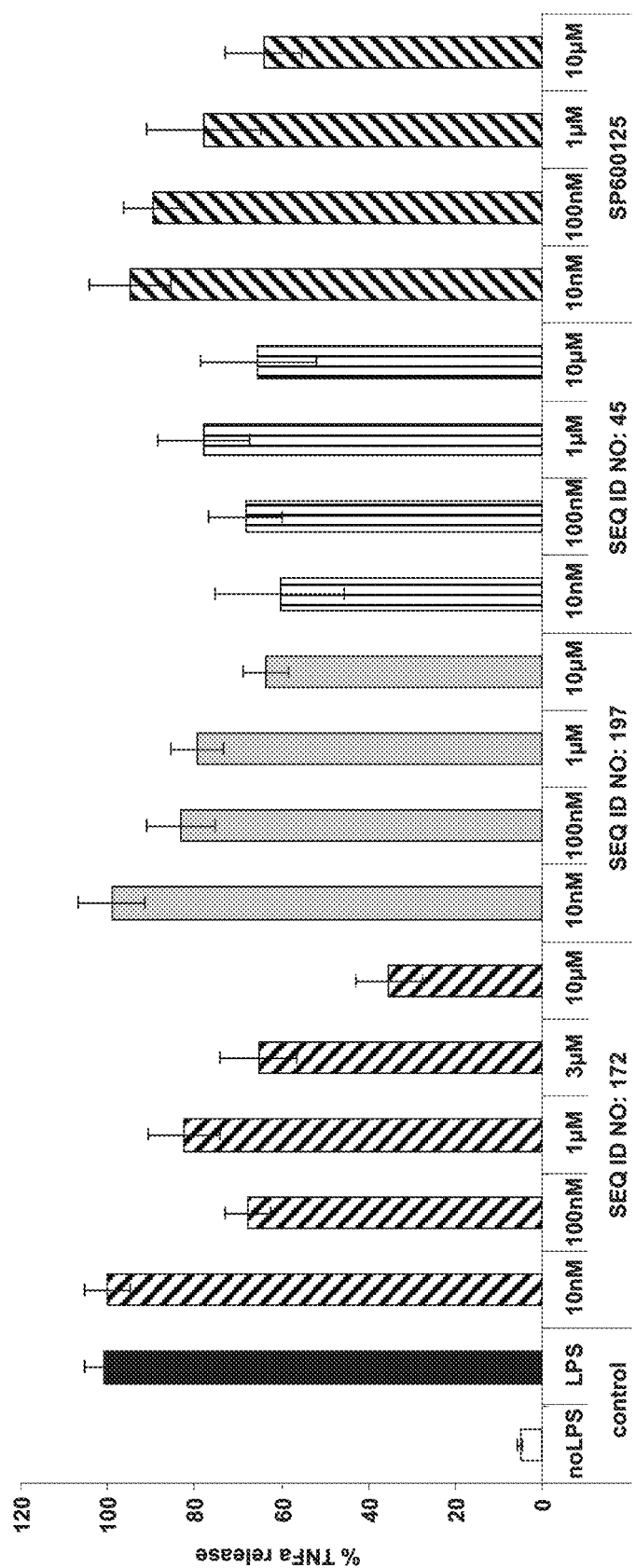
FIG. 9 The JNK inhibitor of SEQ ID NO: 172 blocks LPS-induced TNFα release in THP1 differentiated macrophages with higher potency than D-TAT-IB1 (SEQ ID NO: 197), dTAT (SEQ ID NO: 45) and SP 600125. LPS was added for 6 h (10 ng/ml).
Figure 10:
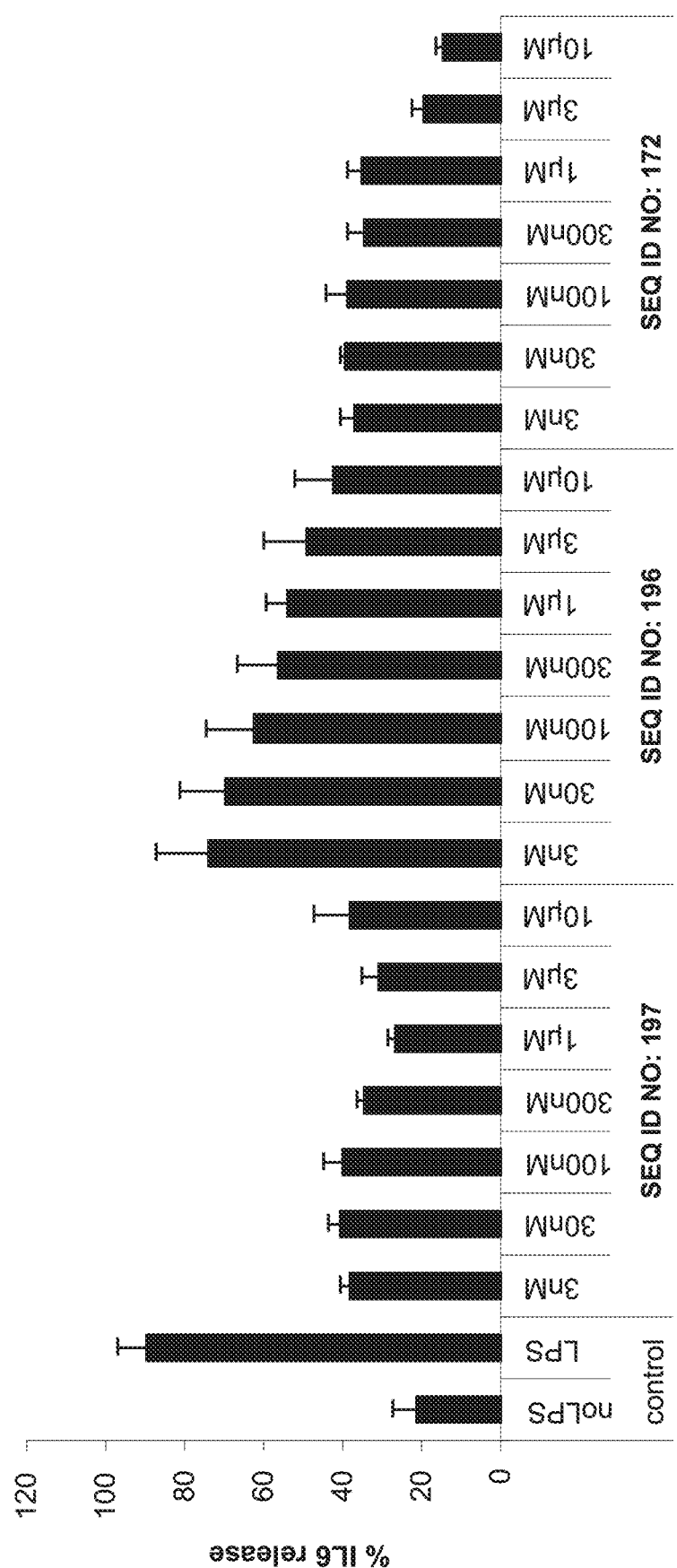
FIG. 10 The JNK inhibitor of SEQ ID NO: 172 blocks LPS-induced IL-6 release in PMA differentiated macrophages with higher potency than D-TAT-IB1 (SEQ ID NO: 197) and L-TAT-IB1 (SEQ ID NO: 196). LPS was added for 6 h.
Figure 11:
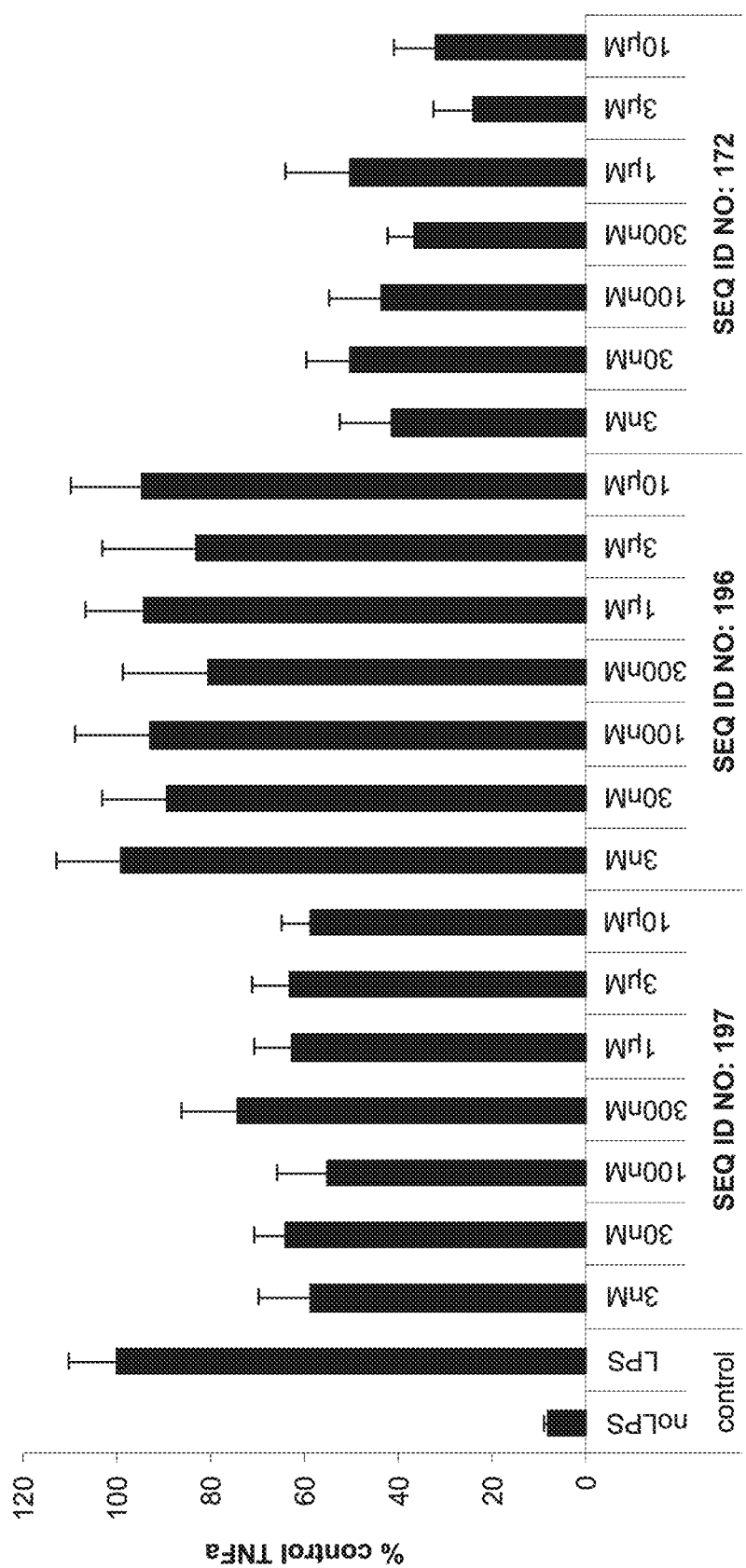
FIG. 11 The JNK inhibitor of SEQ ID NO: 172 blocks LPS-induced TNFα release in PMA differentiated macrophages with higher potency than D-TAT-IB1 (SEQ ID NO: 197) and L-TAT-IB1 (SEQ ID NO: 196).
Figure 12:
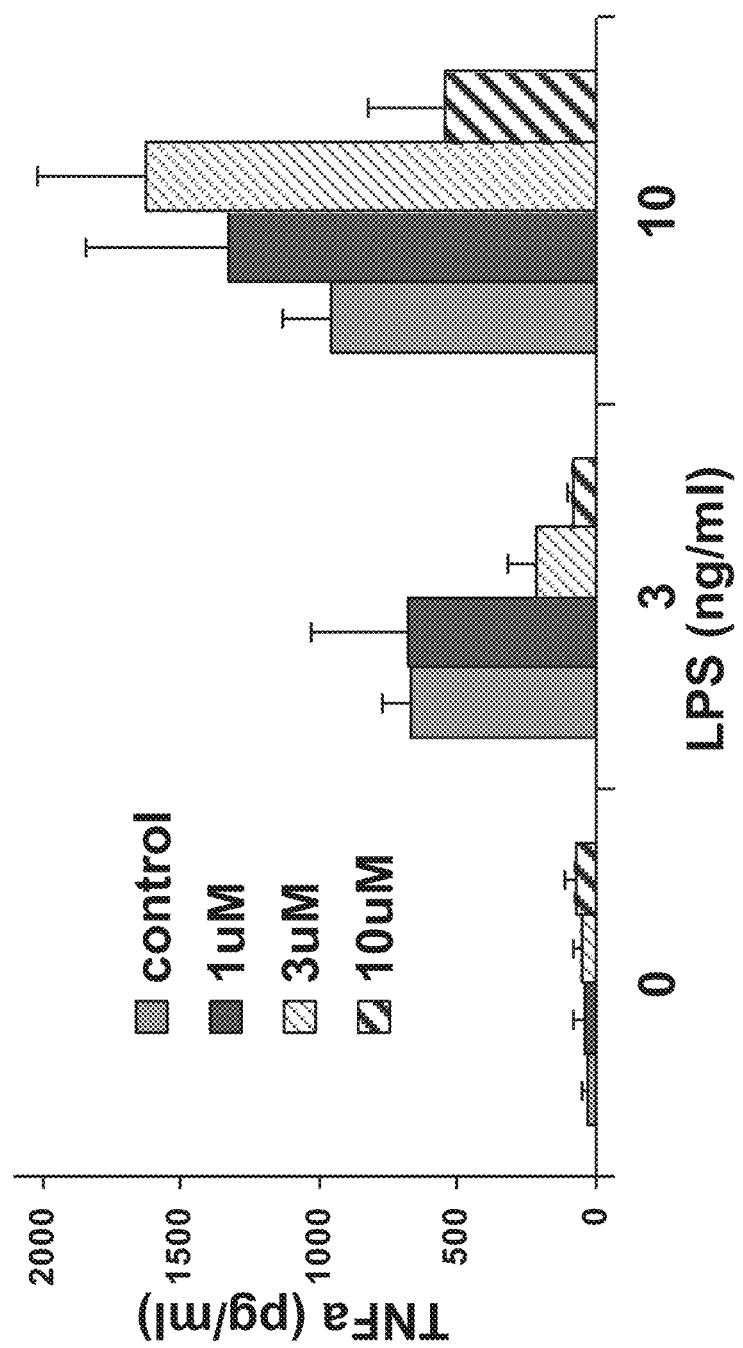
FIG. 12 The JNK inhibitor of SEQ ID NO: 172 blocks LPS-induced TNFα release in Primary Rat Whole Blood Cells at 3 ng/ml. Given are the results for the control, 1 μM of SEQ ID NO: 172, 3 μM of SEQ ID NO: 172, and 10 μM of SEQ ID NO: 172 at different levels of LPS (ng/ml).
Figure 13:
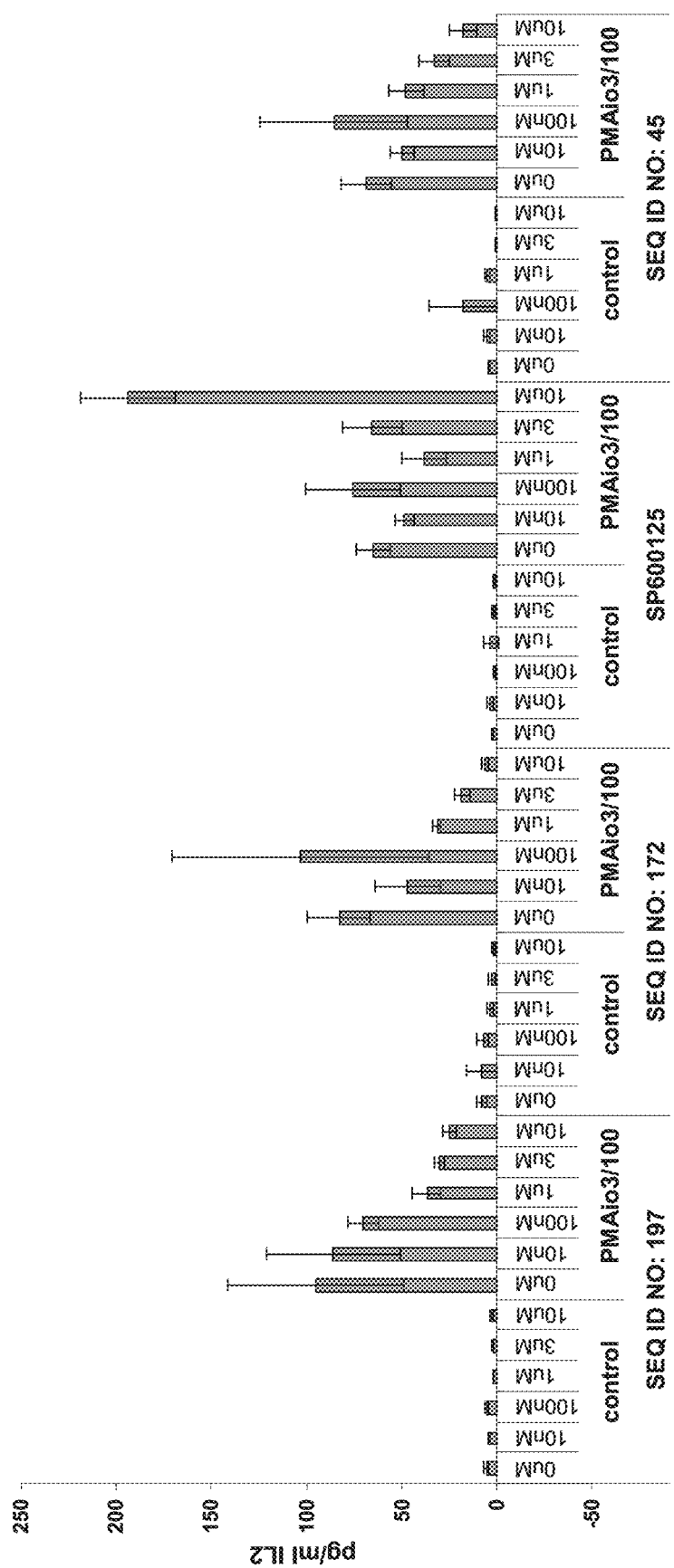
FIG. 13 The JNK inhibitor of SEQ ID NO: 172 blocks IL-2 secretion by primary human T-cells in response to PMA/Ionomycin.
Figure 14:
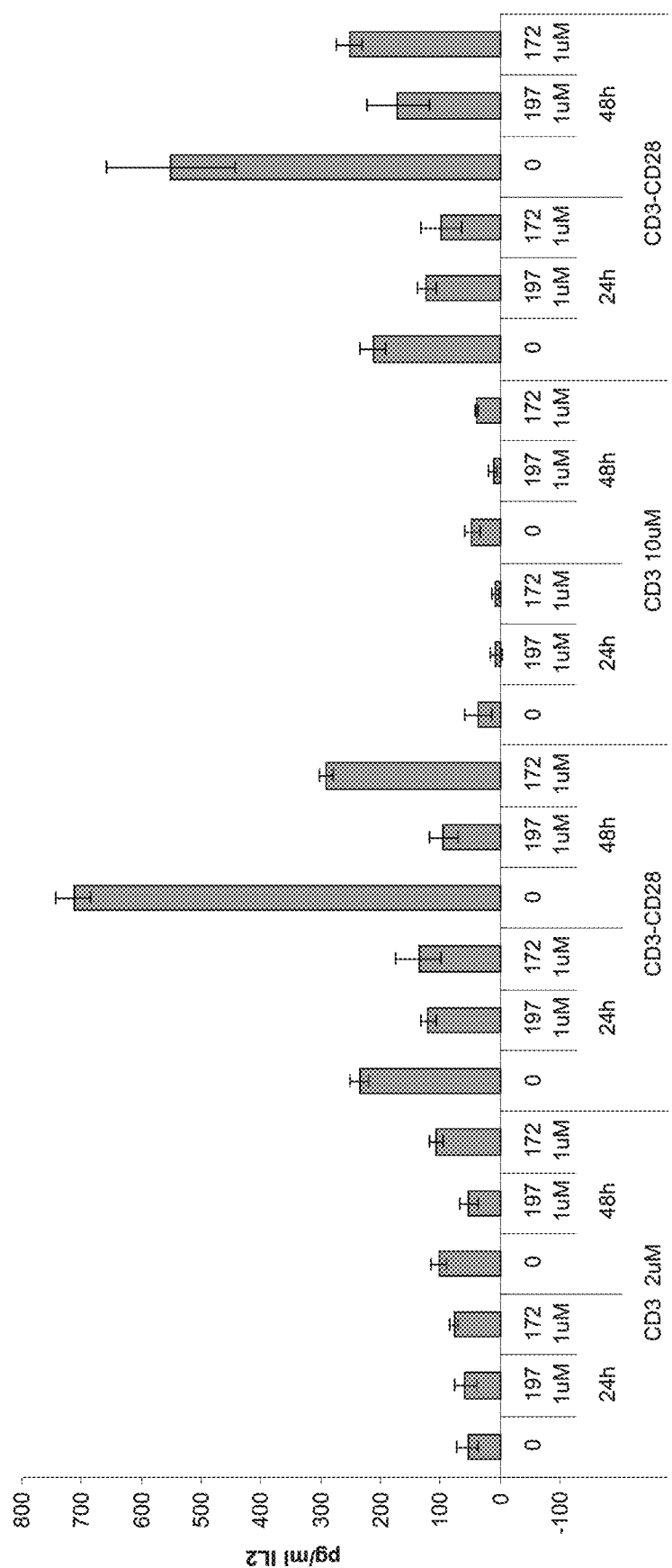
FIG. 14 The JNK inhibitor of SEQ ID NO: 172 blocks IL-2 secretion by primary human T-cells in response to CD3/CD28 stimulation. The JNK inhibitors used are indicated by their SEQ ID NO: 172 and 197.
Figure 15:
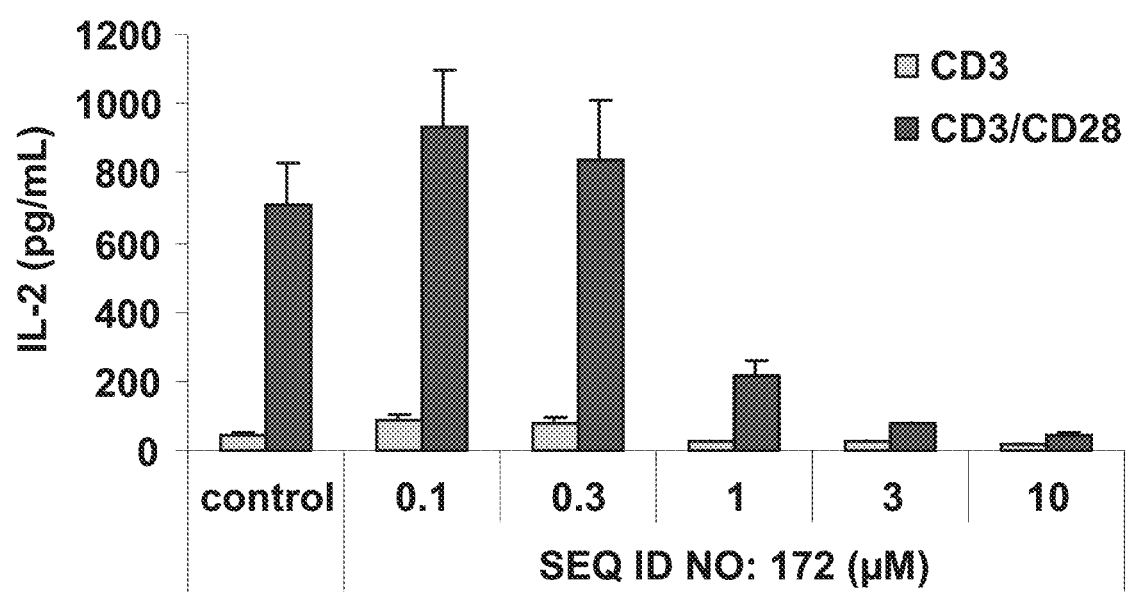
FIG. 15 Dose-dependent inhibition by JNK inhibitor with SEQ ID NO: 172 of CDs/CD28-induced IL-2 release in primary rat lymph-nodes purified T cells. Control rat were sacrificed and lymph-nodes were harvested. T cells further were purified (using magnetic negative selection) and plated into 96-well plates at 200.000 cells/well. Cells were treated with anti-rat CD3 and anti-rat CD28 antibodies (2 μg/mL). JNK inhibitor with SEQ ID NO: 172 was added to the cultures 1 h before CD3/CD28 treatment and IL-2 release was assessed in supernatant 24 h after treatment.
Figure 16:
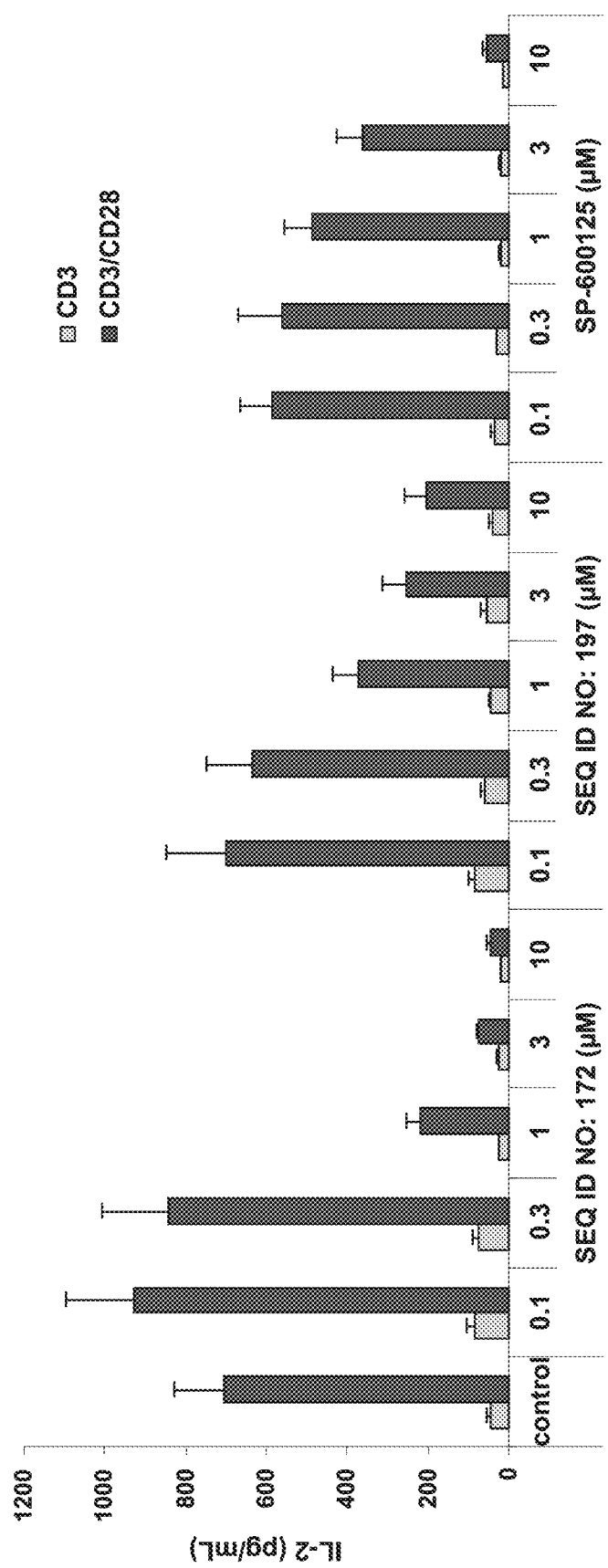
FIG. 16 Dose-dependent inhibition of CD3/CD28-induced IL-2 release in primary rat lymph nodes purified T cells: Comparison of several JNK inhibitors, namely SEQ ID NOs: 172, 197 and SP600125.
Figure 17:
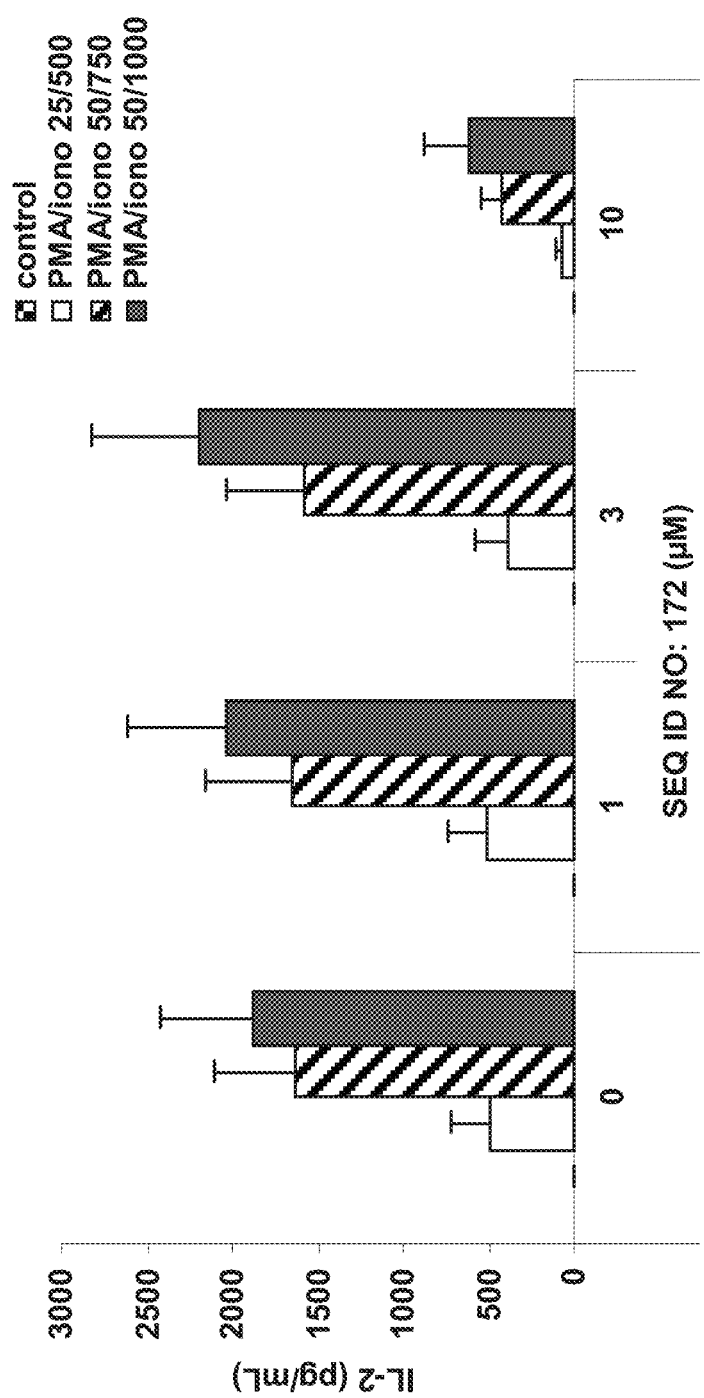
FIG. 17 Dose dependent inhibition of IL-2 release in rat whole blood stimulated with PMA+ionomycin. JNK inhibitor with SEQ ID NO: 172 was added at three different concentrations, namely 1, 3 and 10 μM 1 h before stimulation with PMA+ionomycin. Three doses of activators were added (25/500 ng/mL, 50/750 ng/mL and 50/1000 ng/mL) for 4 h. IL-2 release was assessed in supernatant. JNK inhibitor with SEQ ID NO: 172 at 10 μM did efficiently reduce PMA-iono-induced IL-2 release at the three tested activator concentrations.
Figure 18:
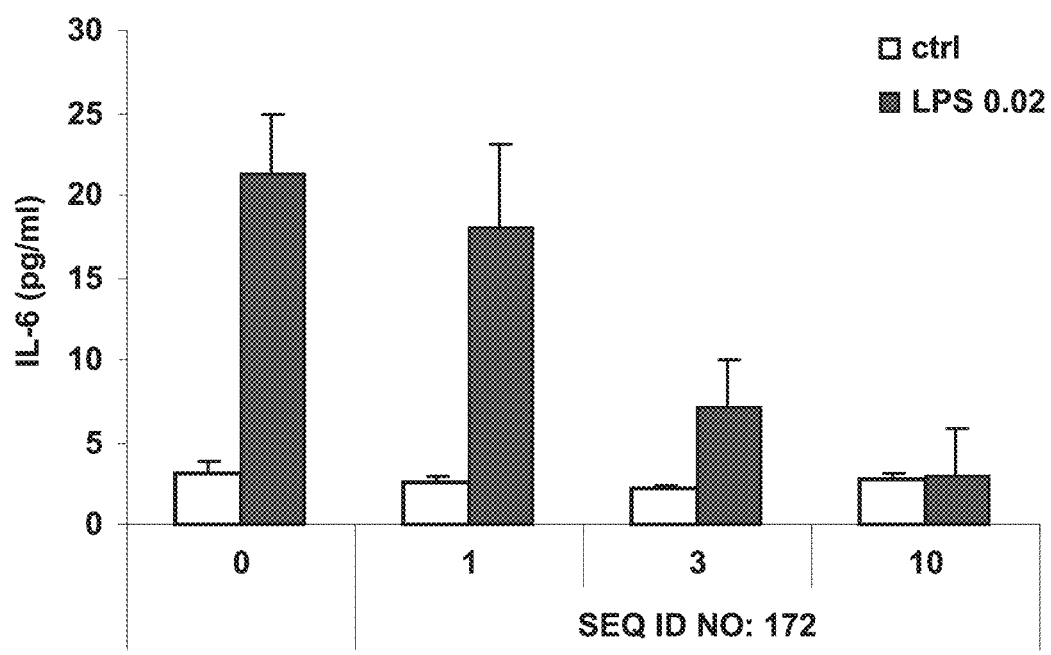
FIG. 18 JNK inhibition and IL-6 release in human whole blood. The JNK inhibitor with SEQ ID NO: 172 was added at three different concentrations, namely 1, 3 and 10 μM 1 h before whole blood stimulation with LPS (0.02 ng/mL) for 4 hours. The JNK inhibitor with SEQ ID NO: 172 did reduce the LPS-induced IL-6 release in a dose-dependent manner.
Figure 19:
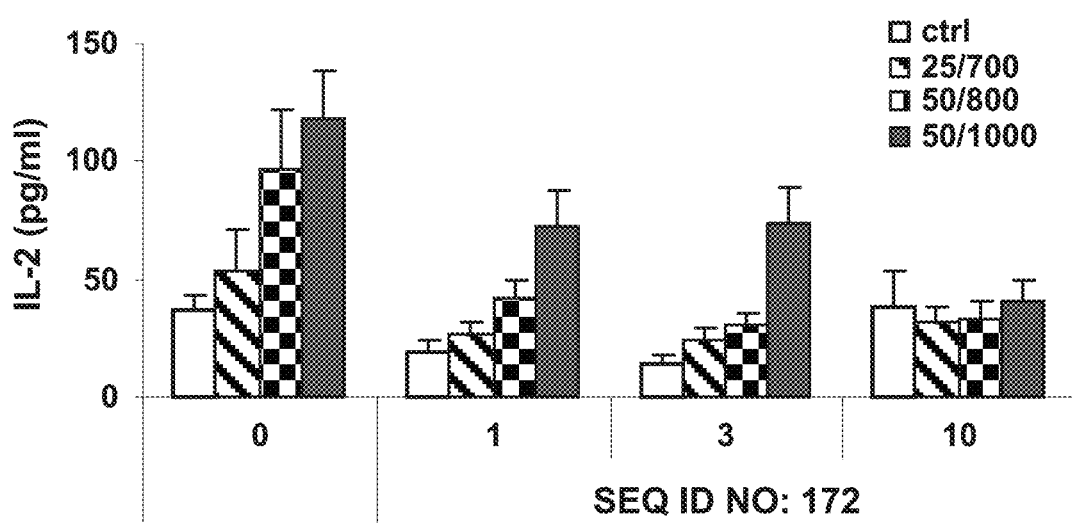
FIG. 19 JNK inhibition and IL-2 release in human whole blood. The JNK inhibitor with SEQ ID NO: 172 was added at three different concentrations, namely 1, 3 and 10 μM 1 h before whole blood stimulation with PMA+ionomycin (25/700 ng/mL, 50/800 ng/mL and 50/1000 ng/mL) for 4 hours. The JNK inhibitor with SEQ ID NO: 172 did reduce the PMA+ionomycin-induced IL-2 release in a dose-dependent manner.
Figure 20:
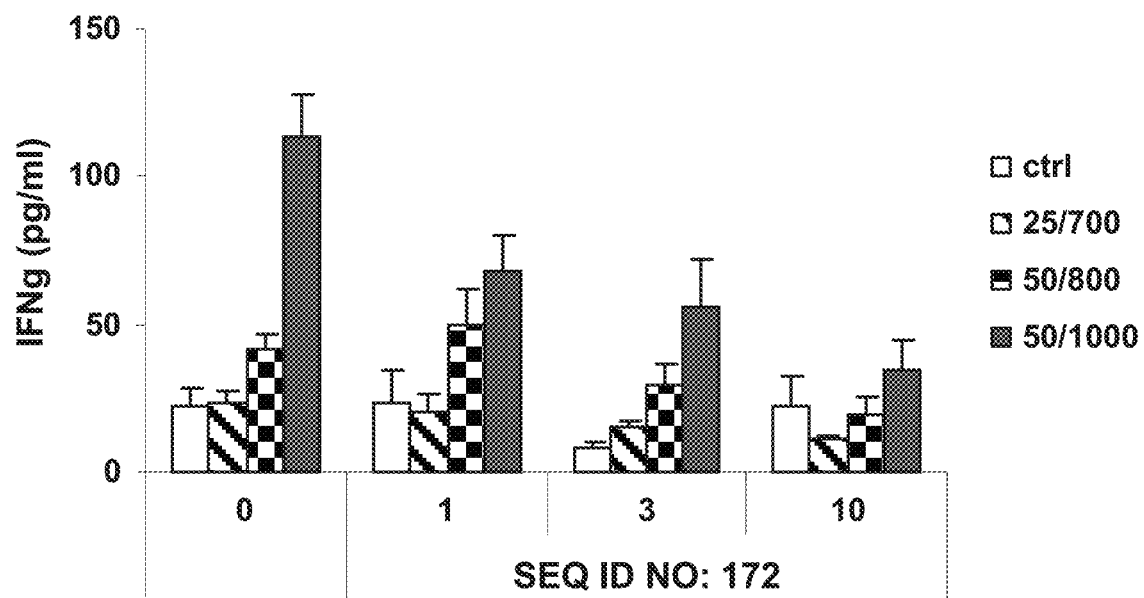
FIG. 20 JNK inhibition and IFN-γ release in human whole blood. The JNK inhibitor with SEQ ID NO: 172 was added at three different concentrations, namely 1, 3 and 10 μM 1 h before whole blood stimulation with PMA+ionomycin (25/700 ng/mL, 50/800 ng/mL and 50/1000 ng/mL) for 4 hours. The JNK inhibitor with SEQ ID NO: 172 did reduce the PMA+ionomycin-induced IFN-γ release in a dose-dependent manner.
Figure 21:
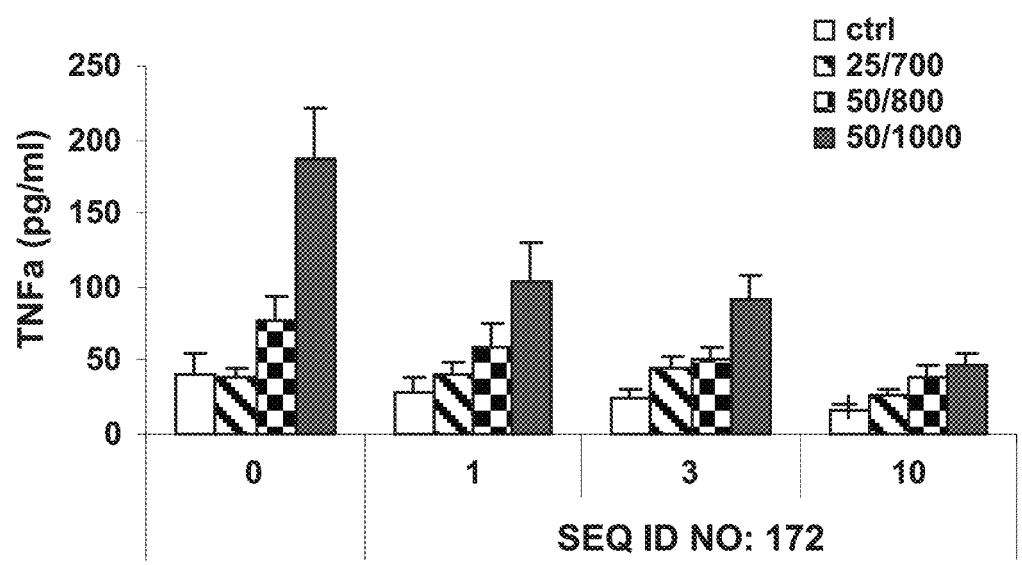
FIG. 21 JNK inhibition and TNF-α release in human whole blood. The JNK inhibitor with SEQ ID NO: 172 was added at three different concentrations, namely 1, 3 and 10 μM 1 h before whole blood stimulation with PMA+ionomycin (25/700 ng/mL, 50/800 ng/ml and 50/1000 ng/mL) for 4 hours. The JNK inhibitor with SEQ ID NO: 172 did reduce the PMA+ionomycin-induced TNF-α release in a dose-dependent manner.
Figure 22:
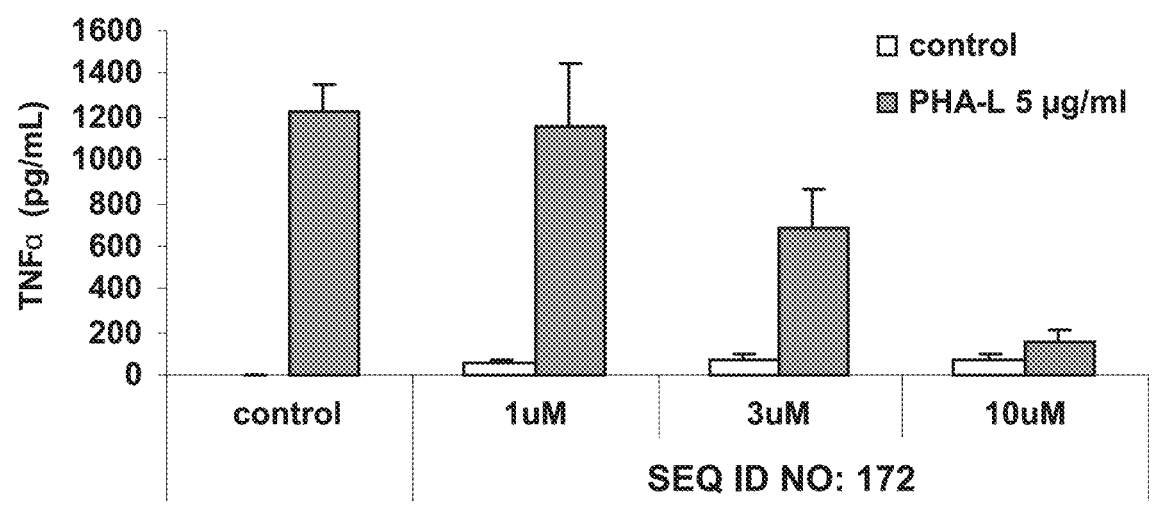
FIG. 22 JNK inhibition and TNF-α release in human whole blood. The JNK inhibitor with SEQ ID NO: 172 was added at three different concentrations, namely 1, 3 and 10 μM 1 h before whole blood stimulation with PHA-L (5 μg/mL) for 3 days. The JNK inhibitor with SEQ ID NO: 172 did reduce the PHA-L-induced TNF-α release in a dose-dependent manner.
Figure 23:
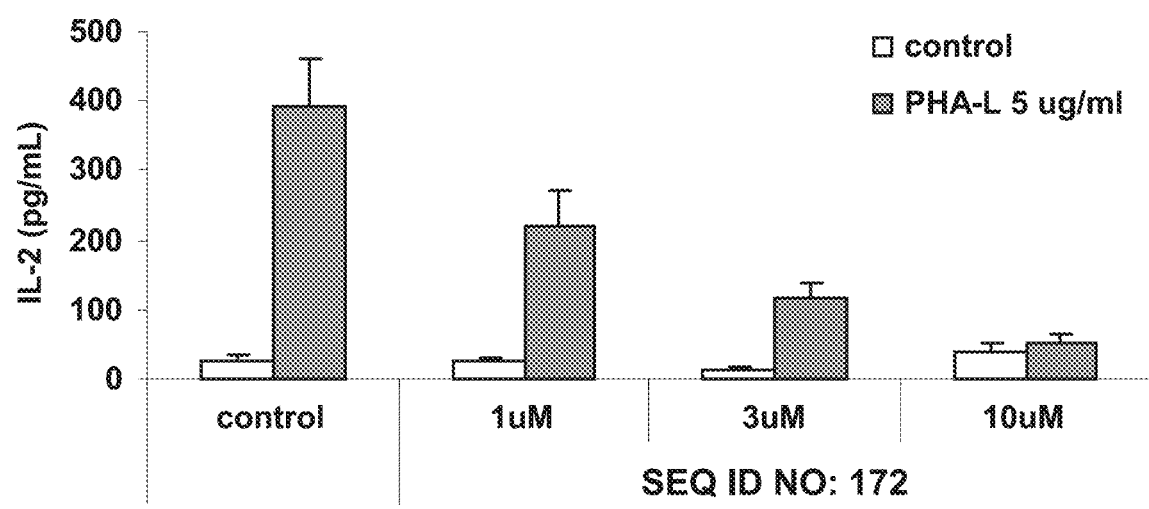
FIG. 23 JNK inhibition and IL-2 release in human whole blood. The JNK inhibitor with SEQ ID NO: 172 was added at three different concentrations, namely 1, 3 and 10 μM 1 h before whole blood stimulation with PHA-L (5 μg/mL) for 3 days. The JNK inhibitor with SEQ ID NO: 172 did reduce the PHA-L-induced IL-2 release in a dose-dependent manner.
Figure 24:
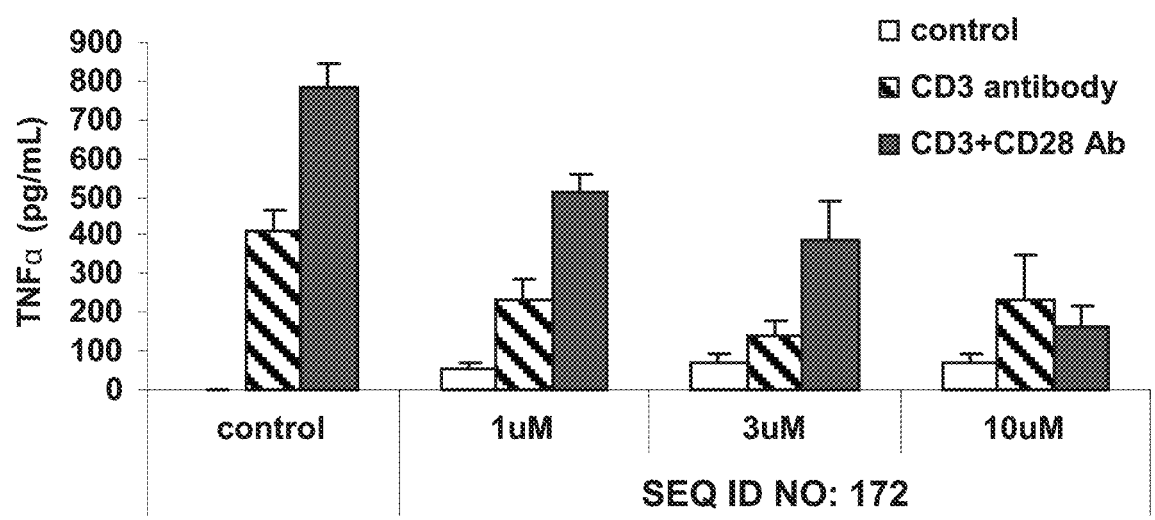
FIG. 24 JNK inhibition and TNF-α release in human whole blood. The JNK inhibitor with SEQ ID NO: 172 was added at three different concentrations, namely 1, 3 and 10 μM 1 h before whole blood stimulation with CD3+/−CD28 antibodies (2 μg/mL) for 3 days. The JNK inhibitor with SEQ ID NO: 172 did reduce the CD3/CD28-induced TNF-α release in a dose-dependent manner.
Figure 25:
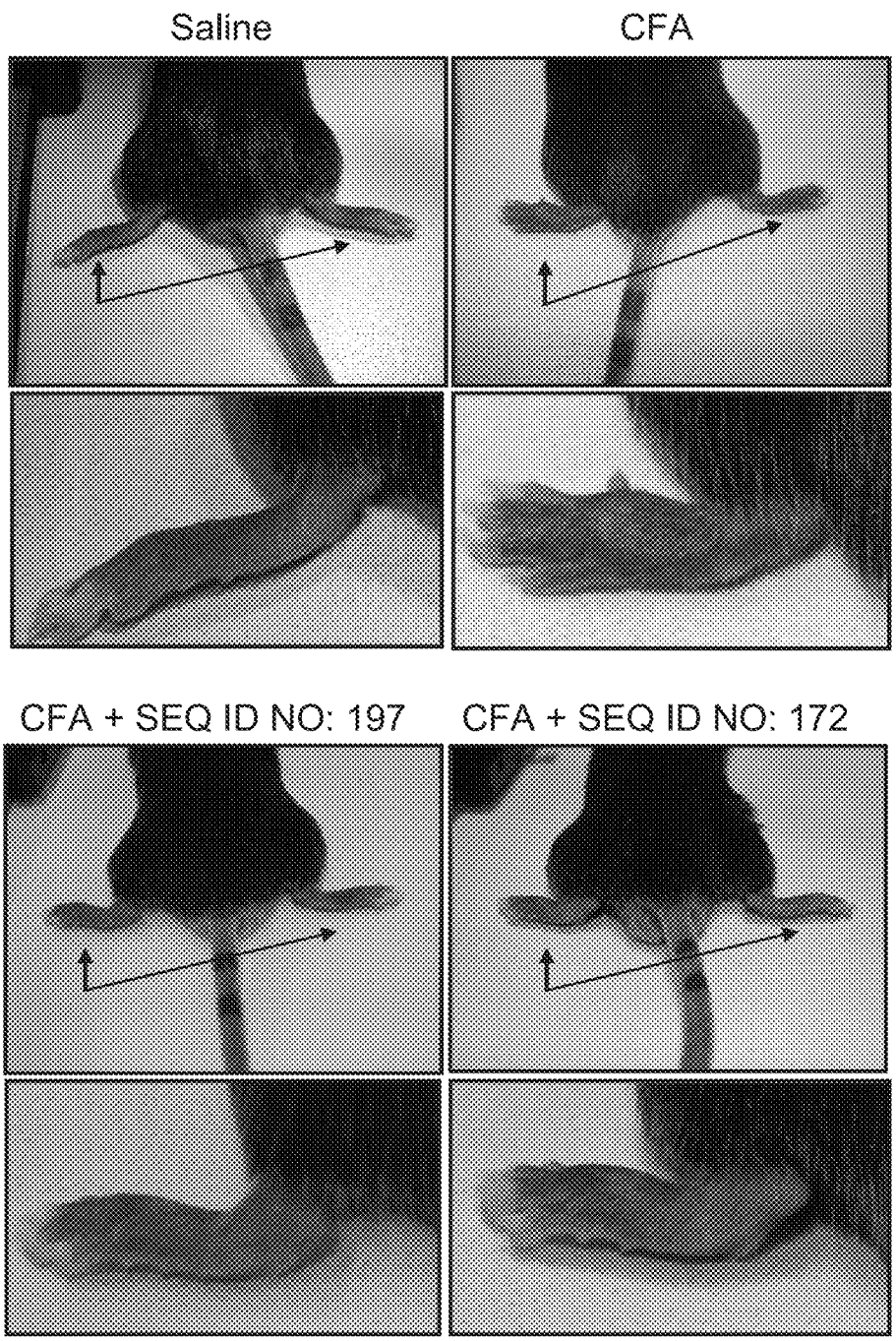
FIG. 25 Photograhic illustration of in vivo anti-inflammatory properties of the JNK inhibitors with SEQ ID NO: 197 (10 μg/kg) and SEQ ID NO: 172 (10 μg/kg) after CFA (complete Freund's adjuvant) induced paw swelling. Paw swelling was induced in the left hind paw, the right hind paw was not treated.
Figure 26:
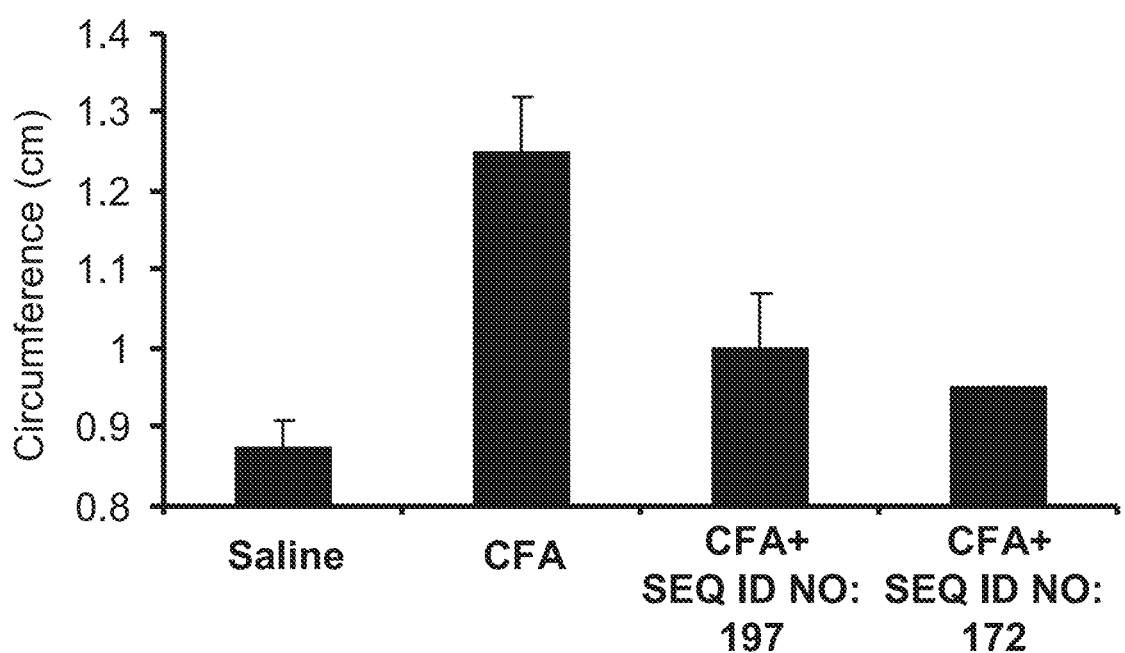
FIG. 26 Graphical representation of in vivo anti-inflammatory properties of the JNK inhibitors with SEQ ID NO: 197 (10 μg/kg, n=4) and SEQ ID NO: 172 (10 μg/kg, n=3) after CFA (complete Freund's adjuvant) induced paw swelling. Indicated is the measured circumference of the left hind paw after treatment.
Figure 27:
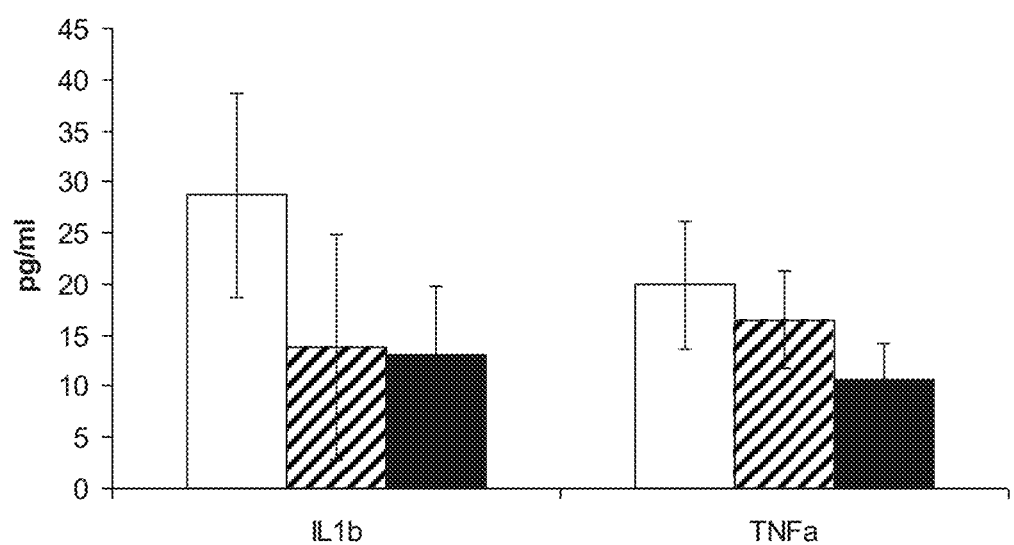
FIG. 27 Graphical representation of in vivo anti-inflammatory properties of the JNK inhibitors with SEQ ID NO: 197 (10 μg/kg) and SEQ ID NO: 172 (10 μg/kg) after CFA (complete Freund's adjuvant) induced paw swelling. Indicated is the measured in vivo cytokine release one hour after CFA induced paw swelling.
Figure 28:
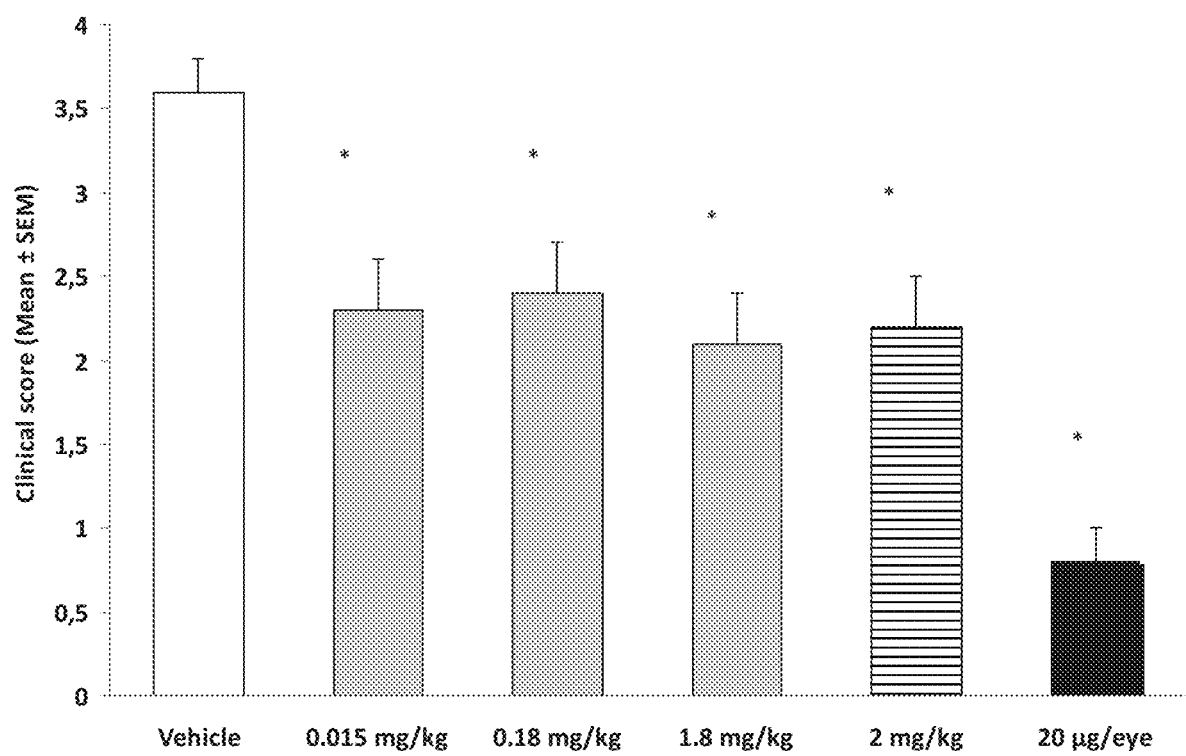
FIG. 28 Clinical evaluation of administration of different amounts of the JNK inhibitor according to SEQ ID NO: 172 in albino rats after intravenous administration (endotoxin-induced uveitis model, EIU). Form left to right: Vehicle, 0.015 mg/kg (i.v.) of SEQ ID NO: 172; 0.18 mg/kg (i.v.) of SEQ ID NO: 172; 1.8 mg/kg (i.v.) of SEQ ID NO: 172, 2 mg/kg (i.v.) of SEQ ID NO: 197 and 20 μg dexamethasone (administered directly by subconjunctival injection to the eye). Indicated is the clinical score (mean and the SEM).
Figure 29:
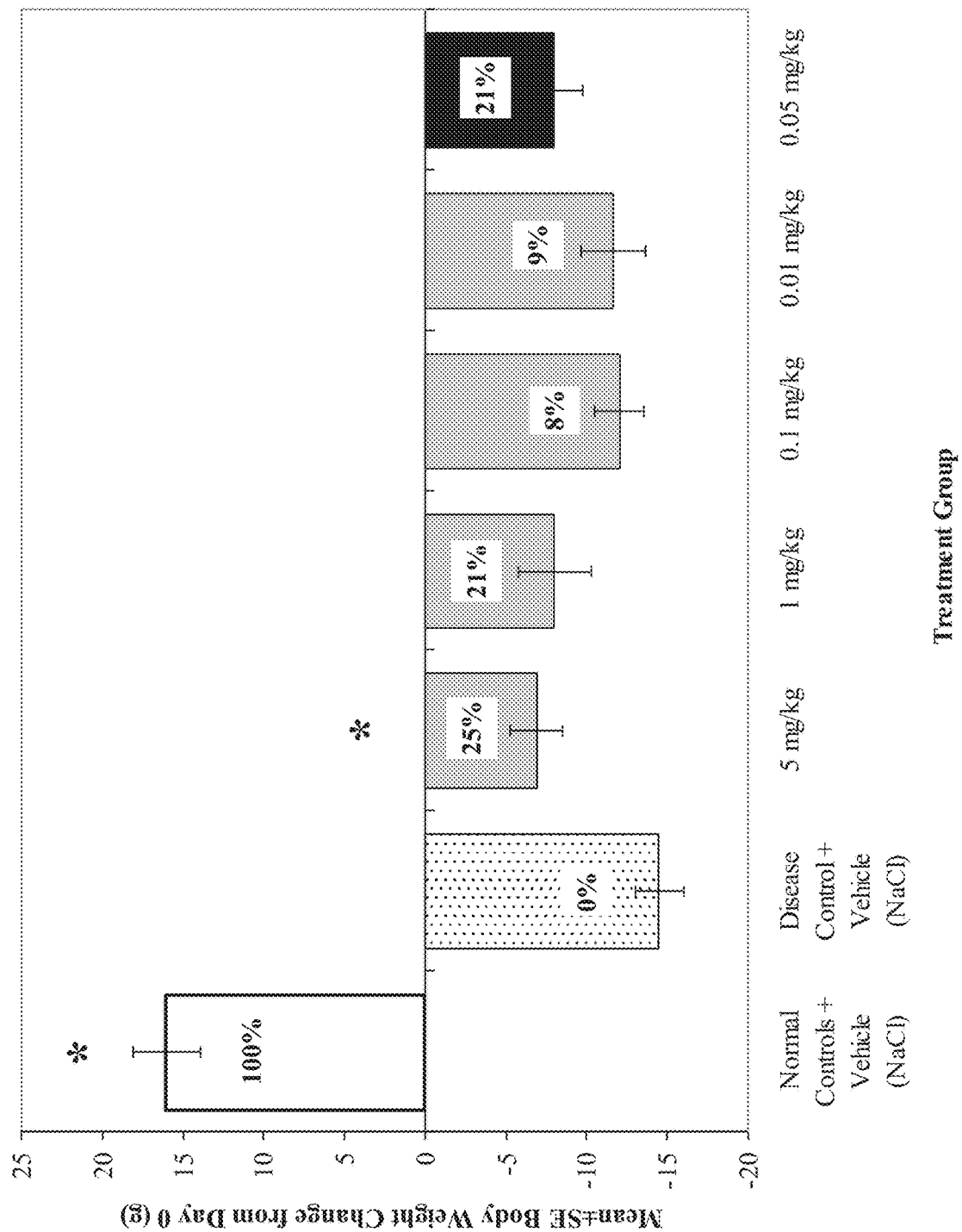
FIG. 29 Responsive effects of the JNK inhibitor of SEQ ID NO: 172 after daily intravenous administration in 14 day rat chronic established Type II collagen arthritis (RTTC/SOL-1). Shown is the body weight change from day 0 to day 14. From left to right: Normal control+Vehicle (NaCl), Disease Control+Vehicle (NaCl), 5 mg/kg (i.v.) of SEQ ID NO: 172; 1 mg/kg (i.v.) of SEQ ID NO: 172; 0.1 mg/kg (i.v.) of SEQ ID NO: 172, 0.01 mg/kg (i.v.) of SEQ ID NO: 172, 0.05 mg/kg (i.v.) of dexamethasone. Indicated is the clinical score (mean and the SEM). n=4/normal group, n=8/treatment group; *p≤0.05 1-way ANOVA to disease control+Vehicle (NaCl)
Figure 30:
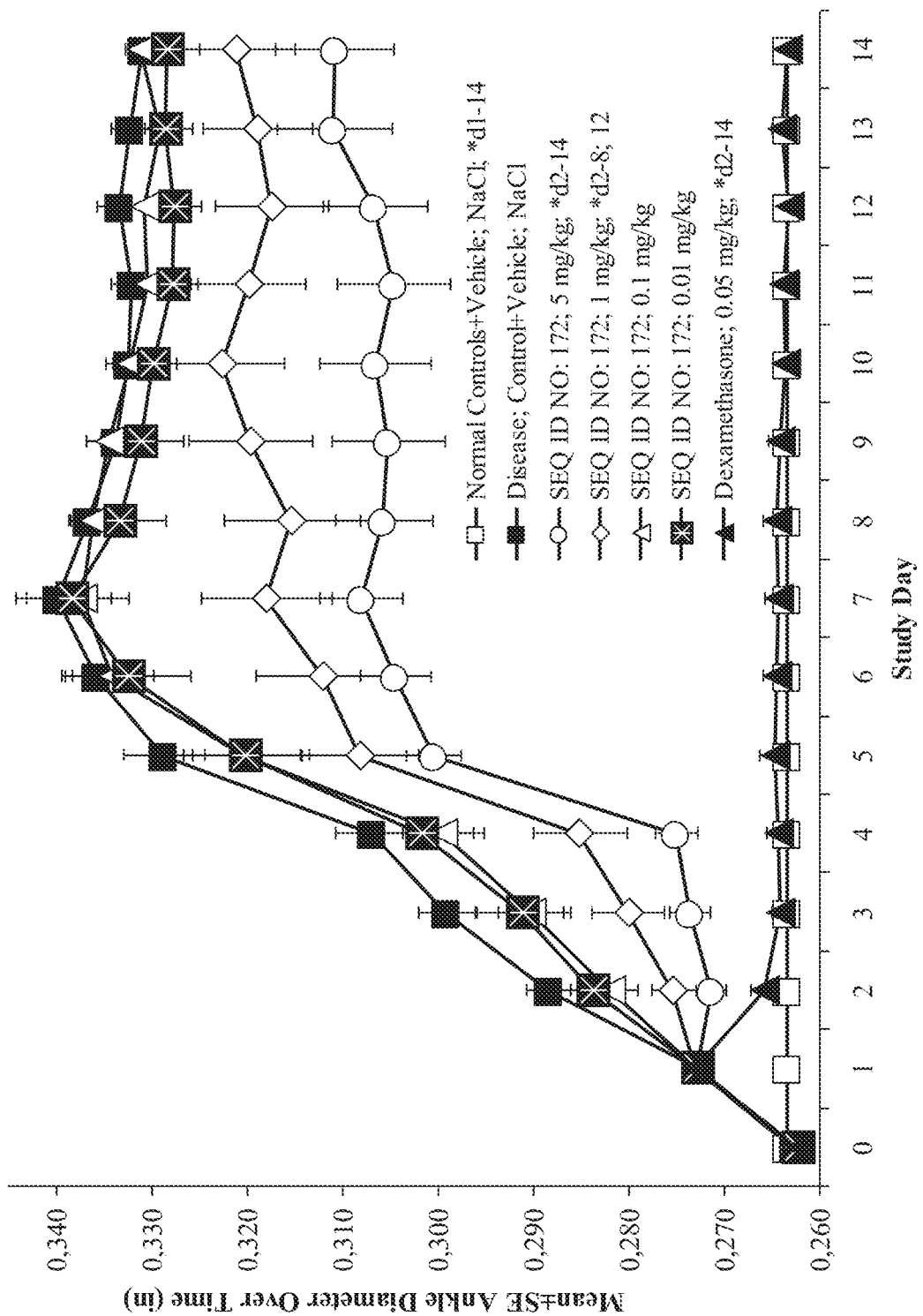
FIG. 30 Responsive effects of the JNK inhibitor of SEQ ID NO: 172 after daily intravenous administration in 14 day rat chronic established Type II collagen arthritis (RTTC/SOL-1). Shown is the ankle diameter (in) over time. n=4/normal group, n=8/treatment group; *p≤0.05 2-way RM ANOVA to disease control+Vehicle (NaCl).
Figure 31:
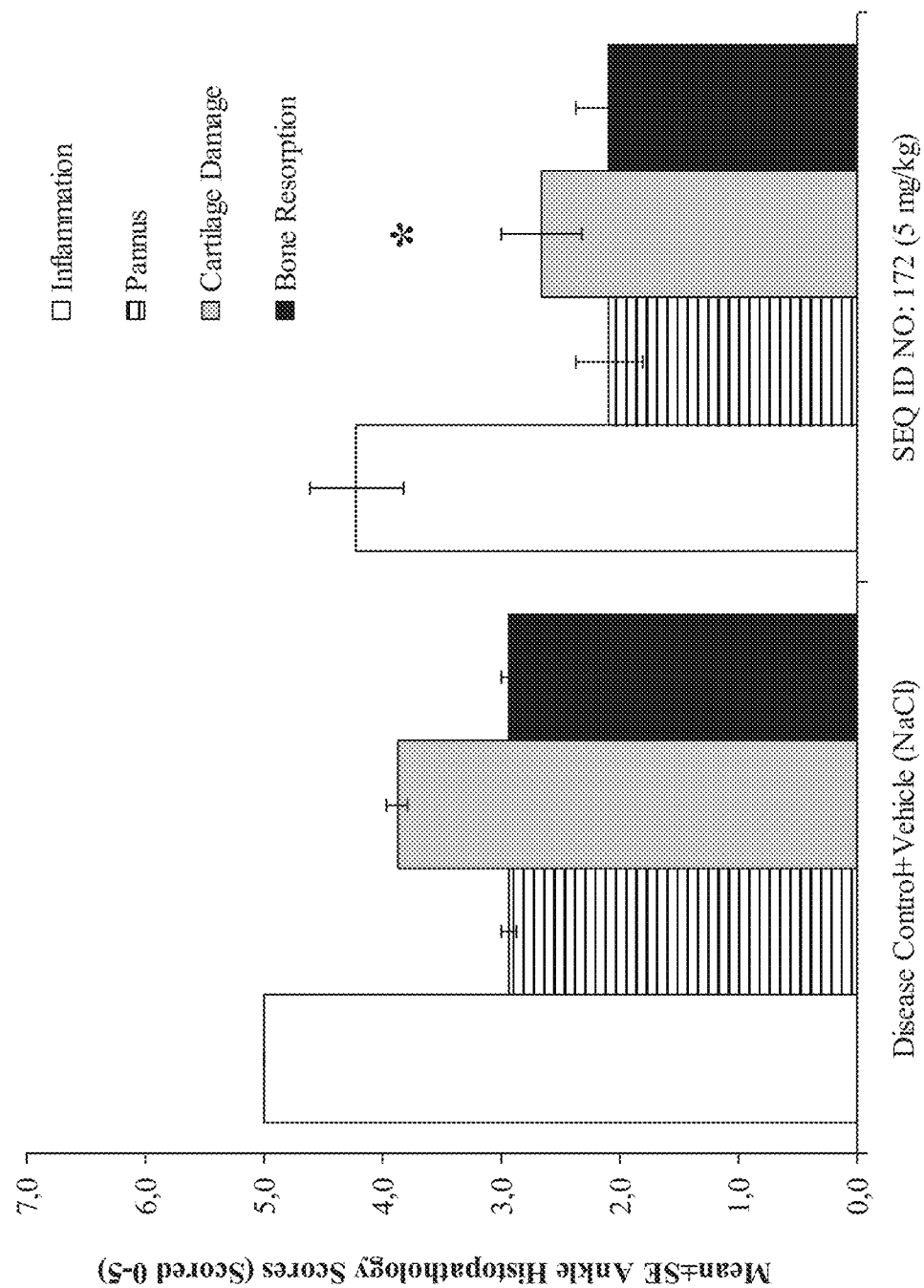
FIG. 31 Responsive effects of the JNK inhibitor of SEQ ID NO: 172 after daily intravenous administration in 14 day rat chronic established Type II collagen arthritis (RTTC/SOL-1). Illustrated are the ankle histopathology scores regarding inflammation, pannus, cartilage damage and bone resorption. n=8 in the treatment group. *p≤0.05 Mann-Whitney U test to disease control+Vehicle (NaCl).
Figure 32:
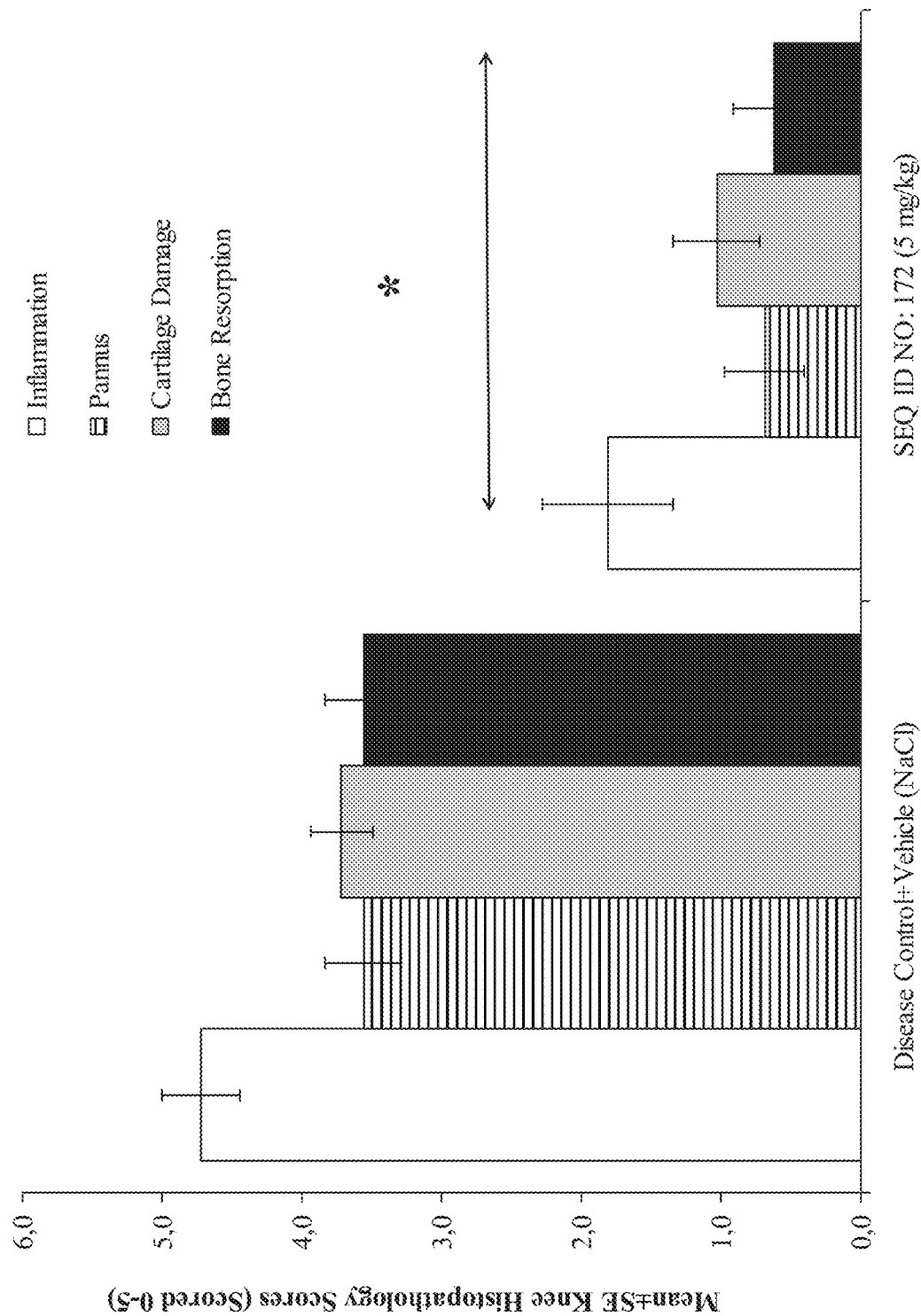
FIG. 32 Responsive effects of the JNK inhibitor of SEQ ID NO: 172 after daily intravenous administration in 14 day rat chronic established Type II collagen arthritis (RTTC/SOL-1). Illustrated are the knee histopathology scores regarding inflammation, pannus, cartilage damage and bone resorption. n=8 in the treatment group. *p≤0.05 Mann-Whitney U test to disease control+Vehicle (NaCl).
Figure 33:
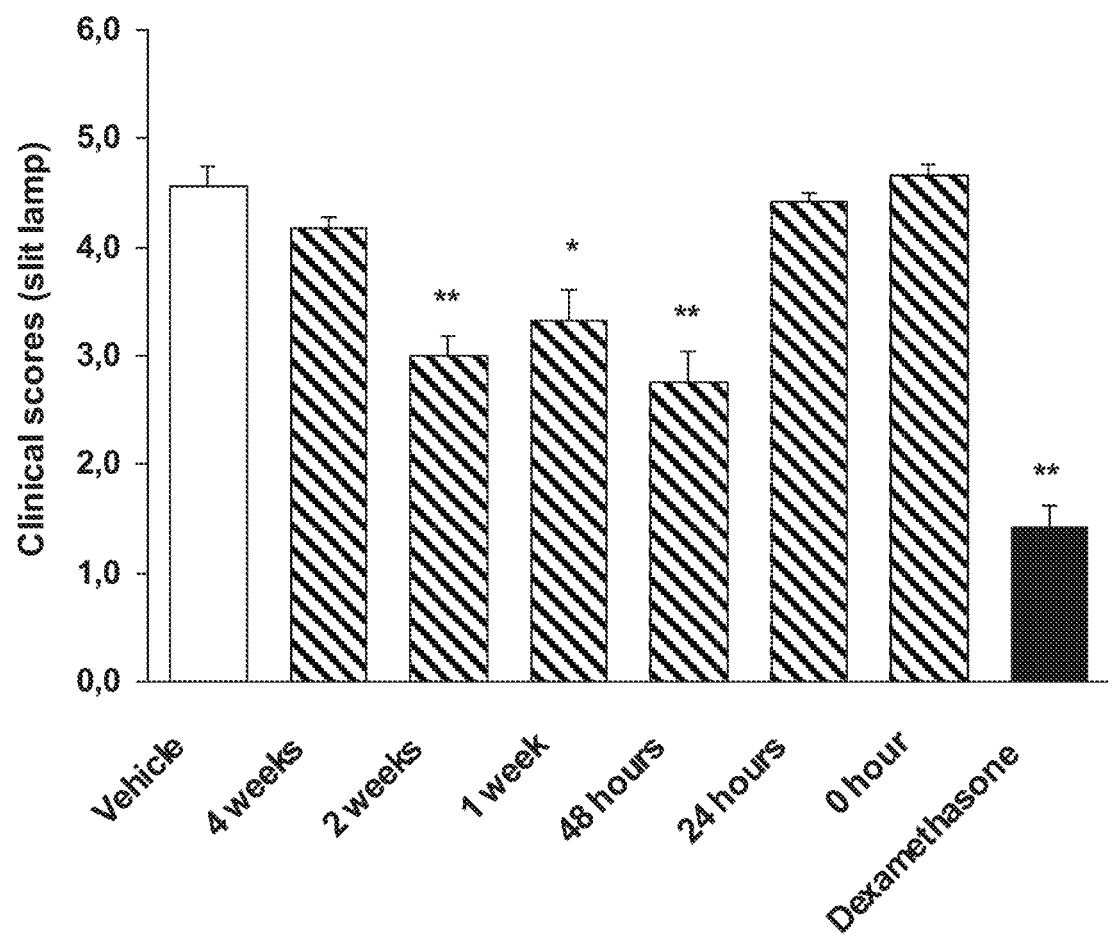
FIG. 33 Clinical scoring by slit lamp 24 hours after EIU induction and administration of JNK inhibitor according to SEQ ID NO: 172 (1 mg/kg i.v.) at different times prior to EIU induction. From left to right: Vehicle (0 hours); SEQ ID NO: 172 4 weeks prior to EIU induction; SEQ ID NO: 172 2 weeks prior to EIU induction; SEQ ID NO: 172 1 week prior to EIU induction; SEQ ID NO: 172 48 hours prior to EIU induction; SEQ ID NO: 172 24 hours prior to EIU induction; SEQ ID NO: 172 0 hours prior to EIU induction; Dexamethasone (2 mg/kg i.v.) 0 hours prior to EIU induction. Mean±SEM. *p≤0.05 versus vehicle, **p≤0.01 versus vehicle.
Figure 34:
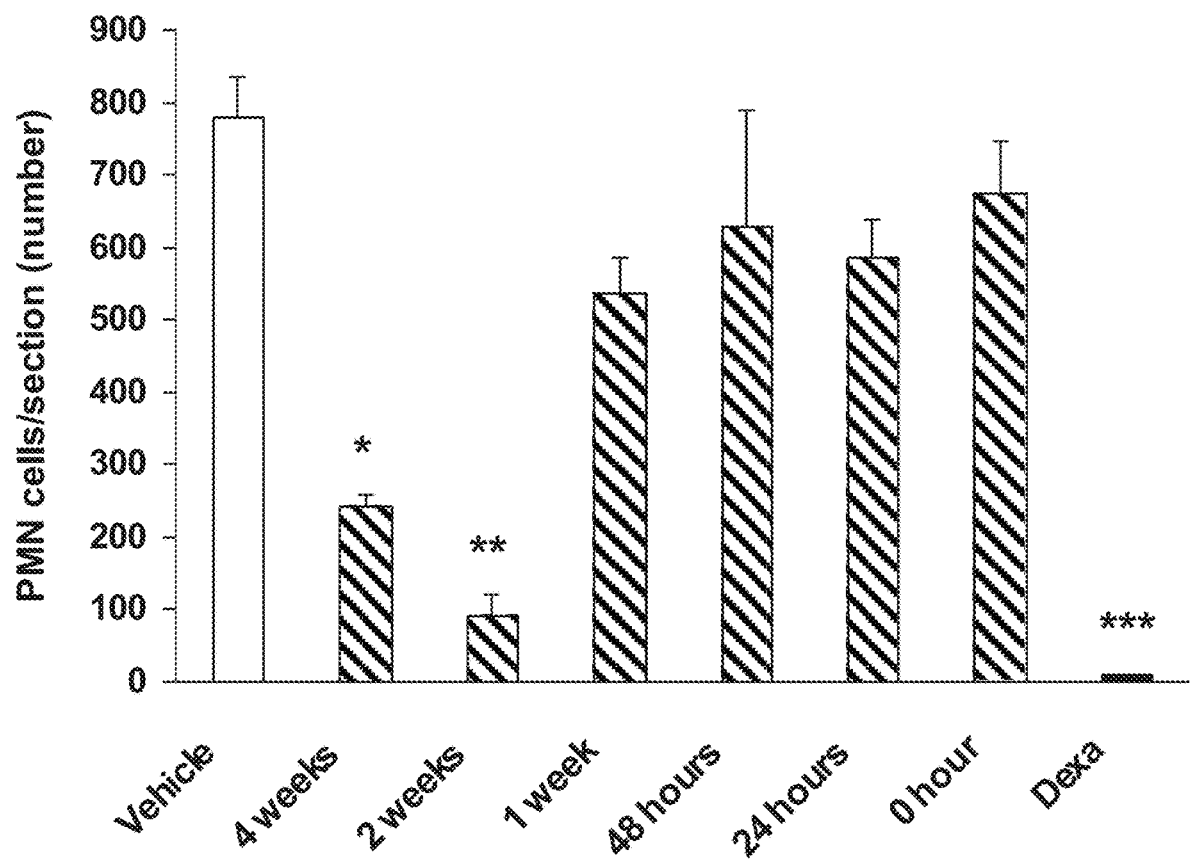
FIG. 34 Number of PMN cells per section quantified 24 hours after EIU induction and administration of JNK inhibitor according to SEQ ID NO: 172 (1 mg/kg i.v.) at different times prior to EIU induction. From left to right: Vehicle (0 hours); SEQ ID NO: 172 4 weeks prior to EIU induction; SEQ ID NO: 172 2 weeks prior to EIU induction; SEQ ID NO: 172 1 week prior to EIU induction; SEQ ID NO: 172 48 hours prior to EIU induction; SEQ ID NO: 172 24 hours prior to EIU induction; SEQ ID NO: 172 0 hours prior to EIU induction; Dexamethasone (2 mg/kg i.v.) 0 hours prior to EIU induction. Mean±SEM. *p≤0.05 versus vehicle, **p≤0.01 versus vehicle.
Figure 35:
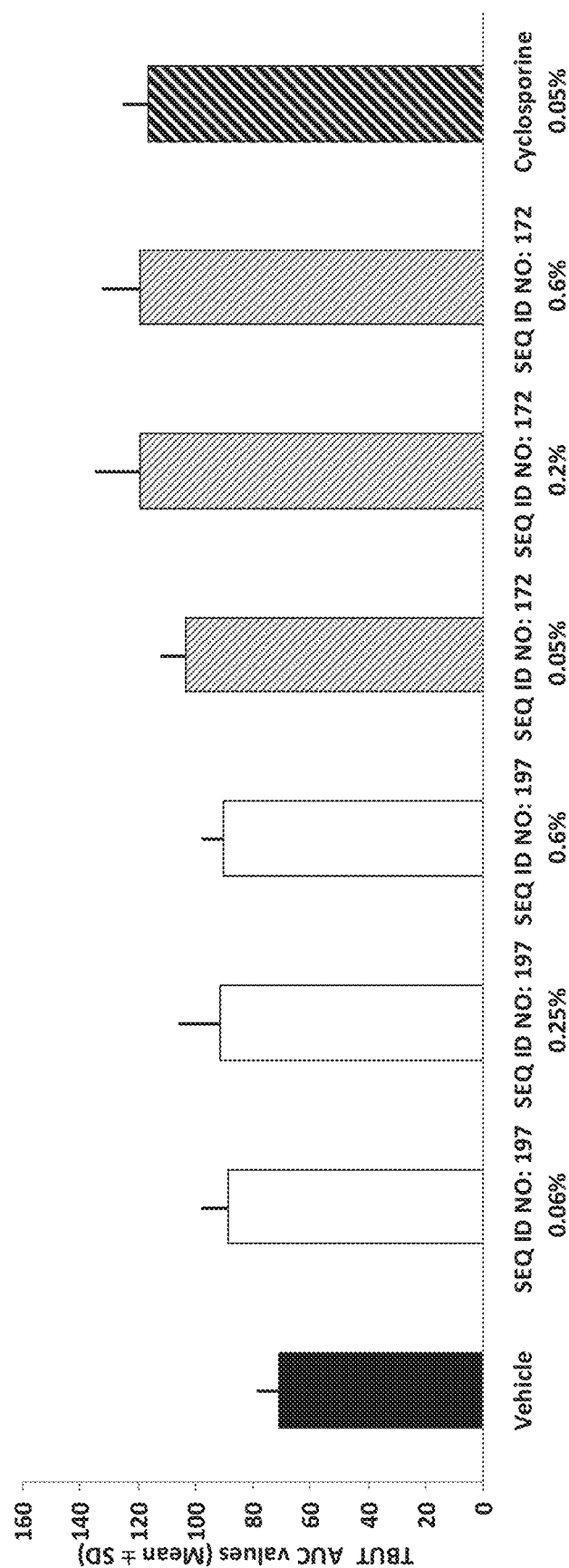
FIG. 35 shows the mean calculated TBUT AUC values for animals with scopolamine-induced dry eye syndrome. Shown are the results for animals treated with vehicle, 3 different concentrations of an all-D-retro-inverso JNK-inhibitor (poly-)peptide with the sequence of SEQ ID NO: 197, 3 different concentrations of a JNK-inhibitor (poly-)peptide with the sequence of SEQ ID NO: 172, and the results for animals treated with cyclosporine.
Figure 36:
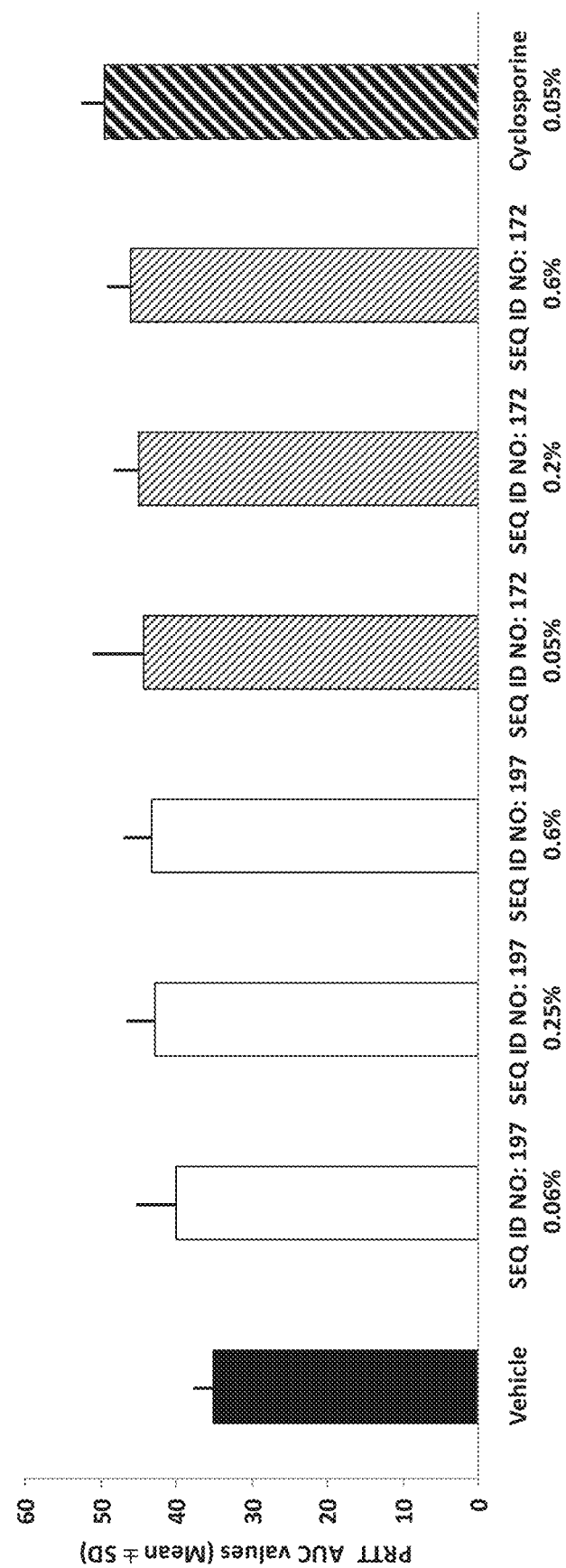
FIG. 36 shows the mean calculated PRTT AUCs for animals with scopolamine induced Dry Eye (Day 7-21). Shown are the results for animals treated with vehicle, 3 different concentrations of an all-D-retro-inverso JNK-inhibitor (poly-)peptide with the sequence of SEQ ID NO: 197, 3 different concentrations of a JNK-inhibitor (poly-)peptide with the sequence of SEQ ID NO: 172, and the results for animals treated with cyclosporine.
Figure 37:
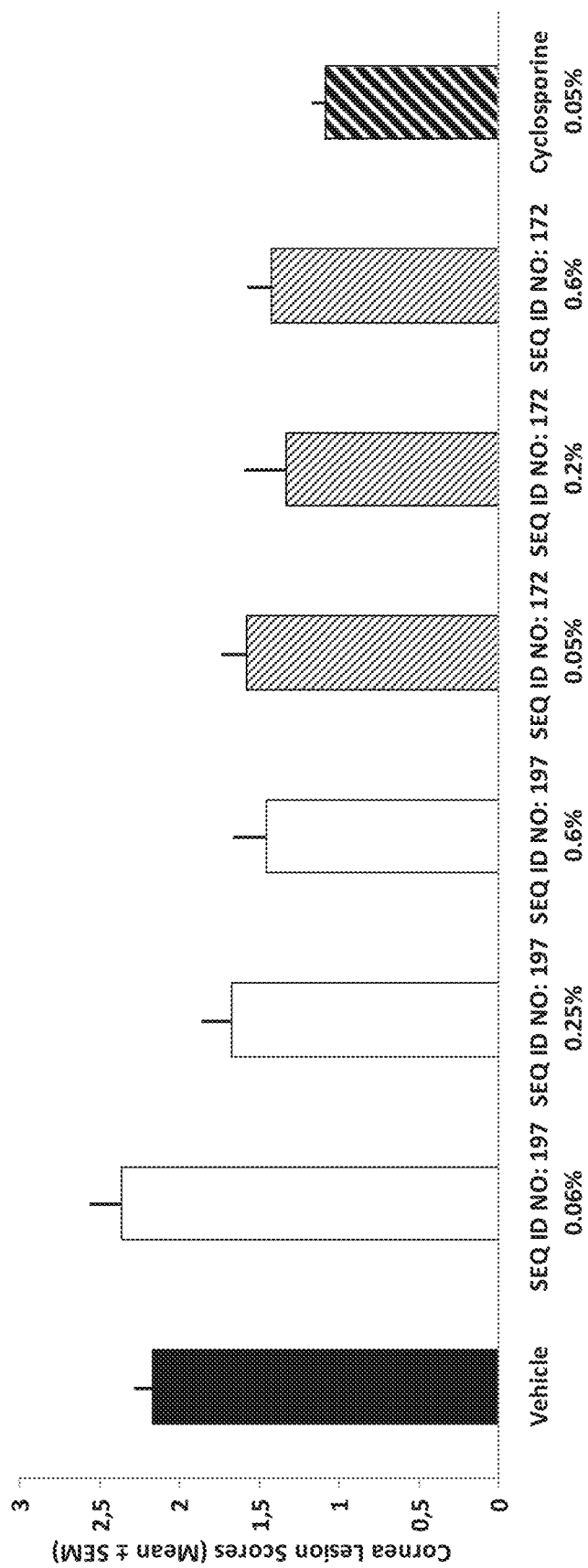
FIG. 37 shows the mean histological Cornea Lesion Scores for animals with scopolamine induced dry eye syndrome. Shown are the results for animals treated with vehicle, 3 different concentrations of an all-D-retro-inverso JNK-inhibitor (poly-)peptide with the sequence of SEQ ID NO: 197, 3 different concentrations of a JNK-inhibitor (poly-)peptide with the sequence of SEQ ID NO: 172, and the results for animals treated with cyclosporine.

| SEQ ID NO: | peptide No: abbreviation in FIG. 6 | | | | | | | | | | |
|---|---|---|---|---|---|---|---|---|---|---|---|
| 46 | r3-L-TAT | H2N | dR | K | K | R | dR | Q | R | R | dR | CONH2 |
| 52 | 1 | H2N | dR | A | K | R | dR | Q | R | R | dR | CONH2 |
| 53 | 2 | H2N | dR | K | A | R | dR | Q | R | R | dR | CONH2 |
| 54 | 3 | H2N | dR | K | K | A | dR | Q | R | R | dR | CONH2 |
| 55 | 4 | H2N | dR | K | K | R | dR | A | R | R | dR | CONH2 |
| 56 | 5 | H2N | dR | K | K | R | dR | Q | A | R | dR | CONH2 |
| 57 | 6 | H2N | dR | K | K | R | dR | Q | R | A | dR | CONH2 |
| 58 | 7 | H2N | dR | D | K | R | dR | Q | R | R | dR | CONH2 |
| 59 | 8 | H2N | dR | K | D | R | dR | Q | R | R | dR | CONH2 |
| 60 | 9 | H2N | dR | K | K | D | dR | Q | R | R | dR | CONH2 |
| 61 | 10 | H2N | dR | K | K | R | dR | D | R | R | dR | CONH2 |
| 62 | 11 | H2N | dR | K | K | R | dR | Q | D | R | dR | CONH2 |
| 63 | 12 | H2N | dR | K | K | R | dR | Q | R | D | dR | CONH2 |
| 64 | 13 | H2N | dR | E | K | R | dR | Q | R | R | dR | CONH2 |
| 65 | 14 | H2N | dR | K | E | R | dR | Q | R | R | dR | CONH2 |
| 66 | 15 | H2N | dR | K | K | E | dR | Q | R | R | dR | CONH2 |
| 67 | 16 | H2N | dR | K | K | R | dR | E | R | R | dR | CONH2 |
| 68 | 17 | H2N | dR | K | K | R | dR | Q | E | R | dR | CONH2 |
| 69 | 18 | H2N | dR | K | K | R | dR | Q | R | E | dR | CONH2 |
| 70 | 19 | H2N | dR | F | K | R | dR | Q | R | R | dR | CONH2 |
| 71 | 20 | H2N | dR | K | F | R | dR | Q | R | R | dR | CONH2 |
| 72 | 21 | H2N | dR | K | K | F | dR | Q | R | R | dR | CONH2 |
| 73 | 22 | H2N | dR | K | K | R | dR | F | R | R | dR | CONH2 |
| 74 | 23 | H2N | dR | K | K | R | dR | Q | F | R | dR | CONH2 |
| 75 | 24 | H2N | dR | K | K | R | dR | Q | R | F | dR | CONH2 |
| 76 | 25 | H2N | dR | R | K | R | dR | Q | R | R | dR | CONH2 |
| 77 | 26 | H2N | dR | K | R | R | dR | Q | R | R | dR | CONH2 |
| 78 | 27 | H2N | dR | K | K | K | dR | Q | R | R | dR | CONH2 |
| 79 | 28 | H2N | dR | K | K | R | dR | R | R | R | dR | CONH2 |
| 80 | 29 | H2N | dR | K | K | R | dR | Q | K | R | dR | CONH2 |
| 81 | 30 | H2N | dR | K | K | R | dR | Q | R | K | dR | CONH2 |
| 82 | 31 | H2N | dR | H | K | R | dR | Q | R | R | dR | CONH2 |
| 83 | 32 | H2N | dR | K | H | R | dR | Q | R | R | dR | CONH2 |
| 84 | 33 | H2N | dR | K | K | H | dR | Q | R | R | dR | CONH2 |
| 85 | 34 | H2N | dR | K | K | R | dR | H | R | R | dR | CONH2 |
| 86 | 35 | H2N | dR | K | K | R | dR | Q | H | R | dR | CONH2 |
| 87 | 36 | H2N | dR | K | K | R | dR | Q | R | H | dR | CONH2 |
| 88 | 37 | H2N | dR | I | K | R | dR | Q | R | R | dR | CONH2 |
| 89 | 38 | H2N | dR | K | I | R | dR | Q | R | R | dR | CONH2 |
| 90 | 39 | H2N | dR | K | K | I | dR | Q | R | R | dR | CONH2 |
| 91 | 40 | H2N | dR | K | K | R | dR | I | R | R | dR | CONH2 |
| 92 | 41 | H2N | dR | K | K | R | dR | Q | I | R | dR | CONH2 |
| 93 | 42 | H2N | dR | K | K | R | dR | Q | R | I | dR | CONH2 |
| 94 | 43 | H2N | dR | L | K | R | dR | Q | R | R | dR | CONH2 |
| 45 | 44 (D-TAT) | H2N | dR | dR | dR | dQ | dR | dR | dK | dK | dR | CONH2 |
| 47 | 45 (r3-L-TATi) | H2N | dR | R | R | Q | dR | R | K | K | dR | CONH2 |
| 46 | 46 (r3-L-TAT) | H2N | dR | K | K | R | dR | Q | R | R | dR | CONH2 |
| 43 | 47 (L-TAT) | H2N | R | K | K | R | R | Q | R | R | R | CONH2 |
| 99 | 48 | H2N | dR | K | K | R | dR | Q | R | L | dR | CONH2 |
| 100 | 49 | H2N | dR | M | K | R | dR | Q | R | R | dR | CONH2 |
| 101 | 50 | H2N | dR | K | M | R | dR | Q | R | R | dR | CONH2 |
| 102 | 51 | H2N | dR | K | K | M | dR | Q | R | R | dR | CONH2 |
| 103 | 52 | H2N | dR | K | K | R | dR | M | R | R | dR | CONH2 |
| 104 | 53 | H2N | dR | K | K | R | dR | Q | M | R | dR | CONH2 |
| 105 | 54 | H2N | dR | K | K | R | dR | Q | R | M | dR | CONH2 |
| 106 | 55 | H2N | dR | N | K | R | dR | Q | R | R | dR | CONH2 |
| 107 | 56 | H2N | dR | K | N | R | dR | Q | R | R | dR | CONH2 |
| 108 | 57 | H2N | dR | K | K | N | dR | Q | R | R | dR | CONH2 |
| 109 | 58 | H2N | dR | K | K | R | dR | N | R | R | dR | CONH2 |
| 110 | 59 | H2N | dR | K | K | R | dR | Q | N | R | dR | CONH2 |
| 111 | 60 | H2N | dR | K | K | R | dR | Q | R | N | dR | CONH2 |

TABLE 4-continued

Transporter sequence tested in uptake experiments

| SEQ ID NO: | peptide No: abbreviation in FIG. 6 | | | | | | | | | | |
|---|---|---|---|---|---|---|---|---|---|---|---|
| 112 | 61 | H2N | dR | Q | K | R | dR | Q | R | R | dR CONH2 |
| 113 | 62 | H2N | dR | K | Q | R | dR | Q | R | R | dR CONH2 |
| 114 | 63 | H2N | dR | K | K | Q | dR | Q | R | R | dR CONH2 |
| 115 | 64 | H2N | dR | K | K | R | dR | K | R | R | dR CONH2 |
| 116 | 65 | H2N | dR | K | K | R | dR | Q | Q | R | dR CONH2 |
| 117 | 66 | H2N | dR | K | K | R | dR | Q | R | Q | dR CONH2 |
| 118 | 67 | H2N | dR | S | K | R | dR | Q | R | R | dR CONH2 |
| 119 | 68 | H2N | dR | K | S | R | dR | Q | R | R | dR CONH2 |
| 120 | 69 | H2N | dR | K | K | S | dR | Q | R | R | dR CONH2 |
| 121 | 70 | H2N | dR | K | K | R | dR | S | R | R | dR CONH2 |
| 122 | 71 | H2N | dR | K | K | R | dR | Q | S | R | dR CONH2 |
| 123 | 72 | H2N | dR | K | K | R | dR | Q | R | S | dR CONH2 |
| 124 | 73 | H2N | dR | T | K | R | dR | Q | R | R | dR CONH2 |
| 125 | 74 | H2N | dR | K | T | R | dR | Q | R | R | dR CONH2 |
| 126 | 75 | H2N | dR | K | K | T | dR | Q | R | R | dR CONH2 |
| 127 | 76 | H2N | dR | K | K | R | dR | T | R | R | dR CONH2 |
| 128 | 77 | H2N | dR | K | K | R | dR | Q | T | R | dR CONH2 |
| 129 | 78 | H2N | dR | K | K | R | dR | Q | R | T | dR CONH2 |
| 130 | 79 | H2N | dR | V | K | R | dR | Q | R | R | dR CONH2 |
| 131 | 80 | H2N | dR | K | V | R | dR | Q | R | R | dR CONH2 |
| 132 | 81 | H2N | dR | K | K | V | dR | Q | R | R | dR CONH2 |
| 133 | 82 | H2N | dR | K | K | R | dR | V | R | R | dR CONH2 |
| 134 | 83 | H2N | dR | K | K | R | dR | Q | V | R | dR CONH2 |
| 135 | 84 | H2N | dR | K | K | R | dR | Q | R | V | dR CONH2 |
| 136 | 85 | H2N | dR | W | K | R | dR | Q | R | R | dR CONH2 |
| 137 | 86 | H2N | dR | K | W | R | dR | Q | R | R | dR CONH2 |
| 138 | 87 | H2N | dR | K | K | W | dR | Q | R | R | dR CONH2 |
| 139 | 88 | H2N | dR | K | K | R | dR | W | R | R | dR CONH2 |
| 140 | 89 | H2N | dR | K | K | R | dR | Q | W | R | dR CONH2 |
| 141 | 90 | H2N | dR | K | K | R | dR | Q | R | W | dR CONH2 |
| 142 | 91 | H2N | dR | Y | K | R | dR | Q | R | R | dR CONH2 |
| 143 | 92 | H2N | dR | K | Y | R | dR | Q | R | R | dR CONH2 |
| 144 | 93 | H2N | dR | K | K | Y | dR | Q | R | R | dR CONH2 |
| 145 | 94 | H2N | dR | K | K | R | dR | Y | R | R | dR CONH2 |
| 146 | 95 | H2N | dR | K | K | R | dR | Q | Y | R | dR CONH2 |
| 147 | 96 | H2N | dR | K | K | R | dR | S | R | Y | dR CONH2 |

In the above table D amino acids are indicated by a small "d" prior to the respective amino acid residue (e.g. dR=D-Arg).

For a few sequences synthesis failed in the first approach due to technical reasons. These sequences are abbreviated in FIG. 6 as 1, 2, 3, 4, 5, 6, 7, 8, 43, 52, 53, 54, 55, 56, 57, 85, 86, 87, 88, 89, and 90. All the remaining sequences were used in the internalization experiments.

The results are shown in FIG. 6.

As can be seen in FIG. 6, after 24 hours of incubation, all transporters with the consensus sequence rXXXrXXXr (SEQ ID NO: 31) showed a higher internalization capability than the L-TAT transporter (SEQ ID NO: 43). Hela cells were incubated 24 hours in 96 well plate with 10 mM of the r3-L-TAT-derived transporters. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction As can be seen in FIG. 6, one position appears to be critical for highest transporter activity and for improved kinetics of transport activity: Y in position 2 (peptide No 91 corresponding to SEQ ID NO: 142).

The conclusion from the results of this experiment is as follows:

After 24 hours incubation, all transporters with the consensus sequence rXXXrXXXr (SEQ ID NO: 31) (see Table 2 for a selection of possible sequences) showed a higher internalization capability than the L-TAT transporter (SEQ ID NO: 43) (FIG. 6). Those results fully validate the consensus sequence rXXXrXXXr (SEQ ID NO: 31).

One position is critical for highest transporter activity and (FIG. 6): Y in position 2 (sequence 91 corresponding to SEQ ID NO: 142).

Accordingly, such TAT derived sequences as shown in Table 4 are preferred, which exhibit an Y in position 2, particularly when the sequence exhibits 9 aa and has the consensus sequence rXXXrXXXr (SEQ ID NO: 31).

Example 4: Measurement of Cytokine and Chemokine Release

In the following the procedure will be set forth describing how the released amount of several human cytokines after ligand induced secretion from human cells (Blood, WBC, PBMC, purified primary lymphocytes, cell lines, . . . ) was measured.

The technique used is a Sandwich ELISA, which allows measuring the amount of antigen between two layers of antibodies (i.e. capture and detection antibody). The antigen to be measured must contain at least two antigenic sites capable of binding to antibody, since at least two antibodies act in the sandwich. Either monoclonal or polyclonal antibodies can be used as the capture and detection antibodies in Sandwich ELISA systems. Monoclonal antibodies recognize a single epitope that allows fine detection and quantification of small differences in antigen. A polyclonal is often used as the capture antibody to pull down as much of the antigen as possible. The advantage of Sandwich ELISA is that the sample does not have to be purified before analysis, and the assay can be very sensitive (up to 2 to 5 times more sensitive than direct or indirect).

The method may be used to determine the effect of the JNK inhibitors of the present invention in vitro/cell culture. At non toxic doses, compound efficacy is indicated by the decrease of the cytokine levels (the variation of optical density (absorbance at 450 nm)) as compared to non-treated samples and is monitored by ELISA. Results are express in ng/ml.

4.1 Material
96 well plate:
  for collecting the supernatants (Ref 82.1581, Sarstedt)
  for ELISA (F96 maxisorp, Ref 442404, Nunc)
TopSeal-A: 96 well microplate seals (Ref 600585, PerkinElmer).
ELISA reagent
  Coating buffer ELISA: 0.1M NaCarbonate pH 9.5 (=7.13 g $NaHCO_3$ (ref 71627, Fluka)+1.59 g $Na_2CO_3$ (ref 71345, Fluka) in 1 litre H2O, pH to 9.5 with NaOH concentrated)
  Wash buffer ELISA: PBS 1×+0.01% Tween20. Prepare 1 litre PBS 1× (PBS10×: ref 70011, GIBCO) and add 100 ul of Tween20 (ref P1379, Sigma) slowly while mixing with magnetic agitator)
  Assay diluent: PBS 1×+10% FBS (Ref A15-151, PAA, decomplemented at 56° C., 30 min).
  DAKO TMB (ref S1599, DAKO): commercial substrate solution
  Stop Solution: 1M $H_3PO_4$ (→ for 200 ml=177 ml $H_2O$+23 ml $H_3PO_4$ 85% (ref 345245, Aldrich).
ELISA Kit (reagent for 20 plates)
  IFN-γ: Human IFN-γ ELISA set, BD OptEIA™ (ref 555142, DB).
  IL-1β: Human IL-1β ELISA set II, BD OptEIA™ (ref 557953, BD)
  IL-10: Human IL-10 ELISA set II, BD OptEIA™ (ref 555157, DB).
  IL-12: Human IL-12 (p70) ELISA set, BD OptEIA™ (ref 555183, DB).
  IL-15: Human IL-15 ELISA Set, BD OptEIA™ (ref 559268, DB).
  IL-2: Human IL-2 ELISA set, BD OptEIA™ (ref 555190, DB).
  IL-4: Human IL-4 ELISA set, BD OptEIA™ (ref 555194, DB).
  IL-5: Human IL-5 ELISA set, BD OptEIA™ (ref 555202, DB).
  IL-6: Human IL-6 ELISA setI, BD OptEIA™ (ref 555220, DB).
  IL-8: Human IL-8 ELISA set, BD OptEIA™ (ref 555244, DB).
  MCP-1: Human MCP-1 ELISA set, BD OptEIA™ (ref 555179, BD)
  TNF-α: Kit human TNF ELISA set, BD OptEIA™ (ref 555212, DB).
Absorbance reading: The absorbance was read on the Fusion Alpha Plate reader (Perkin Elmer).
Repeating pipettes, digital pipettes or multichannel pipettes.

4.2 Method
Preparation of the Samples
The samples are culture medium supernatant from cultured human cells (typically whole blood, WBC, PBMC, Purified subtype of WBC, cancerous cell lines). Remove any particulate material by centrifugation (400 g 5 min 4° C.) and assay immediately or store samples at ≤−20° C. Avoid repeated freeze-thaw cycles.
One hour before using, defrost the samples on ice and centrifuge them. At step 11, dilute the samples in assay diluent directly into the plate (add first assay diluent, then the samples and pipette up and down):
Preparation of Standard
After warming lyophilized standard to room temperature, carefully open vial to avoid loss of material. Reconstitute lyophilized standard with the proposed volume of deionized water to yield a stock standard. Allow the standard to equilibrate for at least 15 minutes before making dilutions. Vortex gently to mix. After reconstitution, immediately aliquot standard stock in polypropylene vials at 50 µl per vial and freeze at −20° C. for up to 6 months. If necessary, store at 2-8° C. for up to 8 hours prior to aliquotting/freezing. Do not leave reconstituted standard at room temperature.

Immediately before use, prepare a ten point standard curve using 2-fold serial dilutions in reagent Diluent. A high standard of 4000 pg/ml is recommended.
Preparation of Detector Mix
One-step incubation of Biotin/SAv reagents. Add required volume of Detection Antibody to Assay Diluent. Within 15 minutes prior to use, add required quantity of Enzyme Reagent, vortex or mix well. For recommended dilutions, see lot-specific Instruction/Analysis Certificate. Discard any remaining Working Detector after use.
Coating with Capture Antibody
1. Coat the wells of a PVC microtiter plate with 100 µL per well of Capture Antibody diluted in Coating Buffer. For recommended antibody coating dilution, see lot-specific Instruction/Analysis Certificate.
2. Cover the plate with an adhesive plastic and incubate overnight at 4° C.
3. Remove the coating solution and wash the plate by filling the wells with 15001 wash buffer.
4. The solutions or washes are removed by flicking the plate over a sink.
5. Repeat the process two times for a total of three washes.
6. After the last wash, remove any remaining wash buffer by patting the plate on a paper towel.
Blocking
7. Block the remaining protein-binding sites in the coated wells by adding 100 µl reagent Diluent per well.
8. Cover the plate with an adhesive plastic and incubate for 1 h at room temperature.
9. During the incubation, start preparing the standard.
Adding Samples
10. Do one wash as in step 3 with 150 µl of wash buffer. The plates are now ready for sample addition.
11. Add 50 µl of appropriately diluted samples in assay diluent to each well. For accurate quantitative results, always compare signal of unknown samples against those of a standard curve. Standards (triplicates) and blank must be run with each cytokine to ensure accuracy.
12. Cover the plate with an adhesive plastic and incubate for 2 h at room temperature.

Incubation with Detection Antibody and Secondary Antibody
13. Wash the plate four times with 150 μl wash buffer like step 3.
14. Add 50 μl of detector MIX (detection antibody+ Secondary Streptavidin-HRP antibody in assay diluent) to each well at recommended dilutions (see lot-specific Instruction/Analysis Certificate).
15. Cover the plate with an adhesive plastic and incubate for 1 h at room temperature light protect.
16. Wash the plate six times with 150 μl wash buffer as in step 3.
17. Add 50 μl DAKO TMB solution to each well, incubate for 15-20 min at room temperature, in the dark, not sealed.
18. Add 50 μl of stop solution to each well. Gently tap the plate to ensure thorough mixing.
19. Mix the plate 5 min at 500 rpm on a plate mixer.
20. Read the optical density at 450 nm. (Program: Cytokine_ELISA on Fusion Alpha Plate reader).

Data Analysis

Average the triplicate readings for each standard control and each sample. Subtract the average zero standard optical density (O.D). Create a standard curve plotting the log of the cytokine concentration versus the log of the O.D and the best fit line can be determined by regression analysis. If samples have been diluted, the concentration read from the standard curve must be multiplied by the dilution factor. A standard curve should be generated for each set of samples assayed. The outliers data were avoided using Grugg's test. Then the data which weren't in the interval of two times the SD, were discard. The independent experiments are taken into account if the positive control showed data as previously observed. The independent experiments are pooled (N>3).

The data are presented in pg/ml of cytokine release or in %, compared to the induced condition without inhibitor treatment.

Example 5: THP1 Differentiation—Stimulation for Cytokine Release

In the following the procedure will be set forth describing how cytokine production from human PMA differentiated THP1 cells challenged by LPS for 6 h was induced in order to test the ability of JNK inhibitors of the present invention, in particular of a JNK inhibitor with SEQ ID NO: 172, to reduce stimulation-induced cytokine release. THP1 cells were stimulated ex-vivo by different ligands for the readout of cytokine release. At non toxic doses, JNK inhibitor efficacy is indicated by the decrease of the cytokine levels as compared to non-treated samples and is monitored by ELISA. The toxicity of the compound are evaluated by the reduction of a tretazolium salt (MTS) to formazan, giving a purple colour.

Procedure:
a. Material
Cell Line: THP-1 (Ref TIB-202, ATCC, lot 57731475)
Culture medium, reagent and plates
RPMI (Ref 21875-091, Invitrogen) complemented with:
10% FBS (Ref A15-151, PAA): decomplemented at 56° C., 30 min.
10 mM Hepes (Ref H0887, Sigma)
50 M β-mercaptoethanol (Ref 63690, Fluka: stock at 14.3M): add 560 μl of 50 mM aliquots in PBS stocked at −20° C.)
1 mM Sodium Pyruvate (Ref S8636, Sigma)
Penicilline (100 unit/ml)/Streptomycine (100 g/ml) (Ref P4333, Sigma)
The RPMI medium is then filtrated with a 0.22 M filter (Ref SCGPU05RE, Millipore).
PBS 10× (Ref 70011, Invitrogen): diluted to 1× with sterile $H_2O$
DMSO: Ref41444, Fluka
PMA (phorbol 12-myristate 13-acetate, Ref P1585, Sigma, concentration 1 mM=616.8 ug/ml in DMSO at −20° C.). Use directly at a final concentration of 100 nM in RPMI (1 ul in 10 ml of medium).
LPS ultrapure (Lipopolysaccharide, Ref tlrl-eklps, Invivogen, concentration 5 mg/ml): Stock solution of LPS: 3 g/ml in PBS at 4° C. Use directly to prepare a 4× concentrated solution of 40 ng/ml in RPMI medium (min 1800 μl/plate; for 5 plates: 125 μl of LPS 3 g/ml+9250 μl RPMI). 96 well plate:
for adherent cell culture (Ref 167008, Nunc)
for collecting the supernatants (Ref 82.1581, Sarstedt)
for ELISA (F96 maxisorp, Ref 442404, Nunc)
Coating solutions: poly-D-lysine (Ref P9011, Sigma): 25 g/ml final diluted in PBS 1×
ELISA reagent and kits
Coating buffer ELISA: 0.1M NaCarbonate pH 9.5 (=7.13 g $NaHCO_3$ (ref 71627, Fluka)+1.59 g $Na_2CO_3$ (ref 71345, Fluka) in 1 liter H2O, pH to 9.5 with NaOH concentrated)
Wash buffer ELISA: PBS 1×+0.01% Tween20 (refP1379, Sigma, lot 094K0052)(=prepare 1 liter PBS 1× and add 100 ul of Tween20 slowly while mixing with magnetic agitator)
Assay diluent: PBS 1×+10% FBS (Ref A15-151, PAA, decomplemented at 56° C., 30 min).
DAKO TMB (ref S1599, DAKO): commercial substrate solution
Stop Solution: 1M $H_3PO_4$ (→ for 200 ml=177 ml $H_2O$+23 ml $H_3PO_4$ 85% (ref 345245, Aldrich).
TNF-α: Kit human TNF ELISA set, BD OptEIA (ref 555212, DB).
Cytotoxicity measurement: CellTiter 96 reagent (ref G3581, Promega)
Control compound: SP600125 (ref ALX-270-339-M025, Alexis, concentration: 20 mM DMSO)
Absorbance reading: The absorbance was read on the Fusion Alpha Plate reader (Perkin Elmer).
Repeating pipettes, digital pipettes or multichannel pipettes.
TopSeal-A: 96 well microplate seals (Ref 600585, PerkinElmer).
b. Method
Well Coating
The plates had been coated with 200 μl of poly D-Lysine (1×) and incubated 2 hours at 37° C., $CO_2$ 5% and 100% relative humidity.
Cell Plating
After 2 hours the wells were washed twice with 200 l PBS 1× (use immediately or leave with 200 l of PBS 1× at 37° C. till use, but no more than 3 days).
The cells were counted. The desired number of cells was taken and resuspended in the amount of media necessary to get a dilution of 1'000'000 cells/ml. 100 nM of PMA was added to induce the differentiation of the THP1 from suspension monocytes to adherent macrophages. The cells were plated into the wells in 100 l medium at plating densities of 100'000 cells/well. After inoculation, the plates were incubated at 37° C., 5% CO2 and 100% relative humidity 3 days to let them differentiate, prior to the addition of experimental drugs.

Cell Treatment

After 3 days, the adherent cells were observed with the microscope. The media containing PMA was aspirated and replaced by 100 1 of fresh RPMI media without PMA (no washing step with PBS 1×).

Experimental drug were prepared at the concentration of 10 mM in $H_2O$ or DMSO and stored at −80° C. Prior to each daily use, one aliquot of JNK inhibitor was defrost and diluted to reach a 4× concentrated solution (120 M) in RPMI medium and then to the desired concentration in RPMI. The SP600125 was diluted to reach a 4× concentrated solution (40 M) in RPMI medium and then to the desired concentration in RPMI containing 0.8% DMSO.

The plates were treated with 50 µl of medium or a solution of 4× the final desired drug concentration (0, 100 nM, 1, 3, 10 or 30 M final for JNK compound or at 0, 10, 100 nM, 1, 3 or 10 M final for the SP600125 positive control). Following drug addition, the plates were incubated for an additional 1 h at 37° C., 5% $CO_2$ and 100% relative humidity.

After 1 hour, the secretion of TNFα was induced by the addition of 50 1 of a 4× concentrated dilution of LPS ultrapure (3 ng/ml final).

Assay

After 6 hours, 100 1 of the supernatant were transferred to new 96 well plates. Those plates were sealed and stored at −20° till the analysis by ELISA (e.g. see example 4) of the secretion of the cytokines.

The cytotoxic effect of the compounds was evaluated by MTS absorbance (e.g. see example 4) and cells were observed using an inverted microscope (Axiovert 40 CFL; Zeiss; 10×).

Data Analysis

Analyses of the data are performed as indicated in the ELISA (see example 4). Briefly, for ELISA: Average the triplicate readings for each standard control and each sample. Subtract the average zero standard optical density (O.D). Create a standard curve plotting the log of the cytokine concentration versus the log of the O.D and the best fit line can be determined by regression analysis. If samples have been diluted, the concentration read from the standard curve must be multiplied by the dilution factor. A standard curve should be generated for each set of samples assayed. The outliers data were avoid using Grugg's test. Then the data which weren't in the interval of two times the SD, were discard. The independent experiments are taken into account if the positive control showed data as previously observed. The independent experiments are pooled (N>3).

For the Cytotoxicity effect evaluation: on each plate of each independent experiment taken into account for the cytokine release experiment analysis, the average of the absorbance of the medium alone was considerate as the background and subtracted to each absorbance value. The average of triplicate of the non treated cells of each compound was considerate as the 100% viability. The average of triplicate of each compound was normalized by its 100%. The outliers data were avoid using Grugg's test. Then the data which weren't in the interval of two times the SD, were discard. The independent experiments are pooled (N>3).

All statistical comparisons of conditions were performed by the GraphPad Prism4 software with the following test: One way ANOVA test followed by a Tukey's Multiple Comparison Test. $P<0.05$ was considerate as significant.

Example 6: JNK Inhibitor of SEQ ID NO: 172 and TNFα Release in Primary Rat or Human Whole Blood Cells Whole blood is collected from anesthetized rat or human healthy volunteers using a venipuncture connected to a pre-labeled vacuum tube containing sodium citrate. Tubes are gently mixed by inversion 7-8 times; and are then kept at RT until stimulation. JNK inhibitor of SEQ ID NO: 172 is prepared 6 times concentrated in PBS, and 30 µl/well of mix is added into 96-well plate. Whole blood is diluted by 1:2 in PBS and 120 µl of diluted blood is added in each well where either PBS alone or JNK inhibitor of SEQ ID NO: 172 has been previously added. Whole blood is incubated at 37° C.; 85 rpm (Stuart Orbital incubator SI500) for 60 min. Activators (LPS) are the prepared, 30 µl/well of LPS, 6 times concentrated. After 60 min incubation, LPS is added to the blood, blood is mixed by pipetting up and down, and then kept for 4 h under agitation (85 rpm), at 37° C. After the 4 h incubation, the plates are centrifuged at about 770 g, 4° C. for 15 min in a pre-cooled centrifuge. Supernatants are finally collected and kept at −20° C. until cytokine measurement. Cytokine (IL-6, IL-2, IFNγ and TNFα) were then measured using standard Elisa kits (e.g. from R&D Systems: DuoSet Elisas; or from BD Biosciences: BD Opteia Set Elisa). Results are expressed as pg/ml of supernatant of the measured cytokine.

A similar experiment was conducted with PMA+ionomycin instead of LPS as activator/stimulant.

Example 7: Half-Life of Specific JNK Inhibitors Disclosed Herein

The JNK inhibitors with the sequence of SEQ ID NOs: 196, 197, and 172 (0.1 mM final concentration) were digested in human serum (10 and 50% in PBS 1×). The experiment was performed as described by Tugyi et al. (Proc Natl Acad Sci USA, 2005, 413-418). The remaining intact peptide was quantified by UPLC-MS. Stability was assessed for SEQ ID NOs: 196, 197, and 172 identically but in two separate assays. While the JNK inhibitor with SEQ ID NO: 196 was totally degraded into amino acids residues within 6 hours, the JNK inhibitor with SEQ ID NO: 172 was completely degraded only after 14 days. The JNK inhibitor with SEQ ID NO: 197 was still stable after 30 days.

Example 8: Dose-Dependent Inhibition by JNK Inhibitor with Sequence of SEQ ID NO: 172 of CD3/CD28-Induced IL-2 Release in Rat Primary T-Cells Control animal were sacrificed, lymph nodes (LN) were harvested and kept in complete RPMI medium. LN were smashed with complete RPMI on 70 µm filter using a 5 ml piston. A few drops of media were added to keep strainer wet. Cells were centrifuged for 7 min at 450 g and 4° C. Pellet was resuspended in 5 ml fresh medium. Cells were passed again through cell strainer. An aliquot of cells was counted, while cells were centrifuged again 10 min at 1400 rpm and 4° C. Cells were resuspended in MACS buffer (80 µl of MACS buffer per $10^7$ cells). 10 µl of anti-rat MHC microbeads were added per 10 million cells, cells were incubated for 15 min at 4°-8° C. Cells were washed with 15 ml MACS buffer and centrifuge for 7 min at 700 g and 4° C. Pellet was resuspended in 500 µl MACS buffer per $10^8$ cells. One LS column was placed in the magnetic field of the MACS separator per animal. Column was first rinsed with 3 ml of MACS buffer. One tube was placed below the column in ice to collect cells=T cells (negative selection so we collect what is eluted). Cell suspension was added and elute was collected on ice. Column was washed 3 times with 3 mL MACS buffer. Eluted T cells were centrifuges for 7 min at 700 g and 4° C. Resuspended cells were counted and plated at density of 200000 cells/well in 100 µl of complete medium. Plates were pre-coated the day before experiment with 2 µg/mL of CD3 antibody, and the day of experiment plates were washed three times with PBS. Cells were treated with 100 µl of (poly-)peptide JNK inhibitor (SEQ ID NO: 172), two times concentrated for 1 h before ligand activation. After 1 h of pre-treatment with (poly-)peptide JNK inhibitor (SEQ ID NO: 172), cells were then stimulated with 2 µg/mL of anti CD28 antibody for 24 h. After 24 h of stimulation, supernatant were collected and stored at −20° C. until analysis. Cytokines were then measured using standard Elisa kits. Results are expressed as pg/ml of supernatant of the measured cytokine.

In a further experiment, essentially the same protocol as set forth above was used, but in addition to the (poly-)peptide JNK inhibitors with SEQ ID NO: 172, JNK inhibitors with the sequence of SEQ ID NO: 197 and the drug molecule SP600125 were also tested thus allowing to compare the effects of these inhibitors on the inhibition of CD3/CD28-induced IL-2 release.

Example 9: JNK Inhibitor and TNFα/IL-2 Release in Human Whole Blood

Whole blood from human healthy volunteers was collected using a venipuncture connected to a pre-labeled vacuum tube containing sodium citrate. Tubes are gently mixed by inversion 7-8 times; and are then kept at RT until stimulation. 350 µl of RPMI+P/S were added into 1.2 ml-96-well plate. 10 times concentrated of SEQ ID NO: 172 was prepared in RPMI+P/S (50 µl per well). 50 µl was added into 1.2 ml-96 well plates. 50 µl of whole blood was then added in each well where either medium alone or JNK inhibitor has been previously added. Whole blood was incubated at 37° C., 5% CO2 for 60 min. 50 µl/well of ligands diluted in RPMI+P/S was prepared, corresponding to the final dilution 10 times concentrated. After 60 min of incubation, ligand was added; wells were then mixed by pipetting up and down the blood. Whole blood was incubated for 3 days at 37° C. (wells were mixed by pipetting each well up and down once per day). At the end of incubation, plates were mixed and then centrifuged at 2500 rpm, 4° C. for 15 min in a pre-cooled centrifuge. Cytokine were then measured using standard Elisa kits. Results are expressed as pg/ml of supernatant of the measured cytokine.

A similar experiment was carried out with slight modifications. In the case of CD3/CD8 stimulation, CD3 antibody was coated at 2 µg/mL in PBS overnight at 4° C. The day of experiment, wells were washed three times with PBS and left in PBS until use at 37° C. CD28 antibody was added 1 h after SEQ ID NO: 172 at final concentration of 2 µg/mL; supernatants were collected after 3 days of stimulation.

Example 10: Anti-Inflammatory Potency in a Rat Model of Endotoxins Induced Uveitis (EIU)

The anti-inflammatory potency of the JNK inhibitor of SEQ ID NO: 172 was tested in albino rats following intravenous administration (EIU/LPS model). The aim of this study was to determine the effects of single intravenous injections of SEQ ID NO: 172 (0.015, 0.18, and 1.80 mg/kg) on the inflammatory response in an endotoxins-induced uveitis albino rat model and to compare these affects to those obtained with prior art JNK inhibitor of SEQ ID NO: 197 (2 mg/kg). As a further control served phosphate sodic dexamethasone ("reference") and vehicle (0.9% NaCl).

Sixty (60) male Lewis rats were randomly divided into six (6) groups often (10) animals each. 0.9% NaCl (vehicle, "control"), SEQ ID NO: 197 at 2 mg/kg and SEQ ID NO: 172 at three concentrations (1.80 mg/kg, 0.18 mg/kg and 0.015 mg/kg) were administered by intravenous injection just before EIU induction (on the day of induction). Accordingly, phosphate sodic dexamethasone (20 Dg/eye, 5 µl; "reference") was administered by a single sub-conjunctival injection in both eyes just before EIU induction (on the day of induction). EIU was induced by footpad injection of lipopolysaccharide (LPS, 1 mg/kg). 24 hours after LPS injection, inflammatory response was evaluated by clinical scoring.

The intensity of clinical ocular inflammation was scored on a scale from 0 to 4 for each eye:

| Grade 0 | no inflammation |
| --- | --- |
| Grade 1 | slight iris and conjunctival vasodilation |
| Grade 2 | moderate iris and conjunctival vasodilation with flare |
| Grade 3 | intense iris and conjunctival vasodilation with flare |
| Grade 4 | intense inflammatory reaction |

(+1) fibrin formation and seclusion of pupils

Twenty-four hours after LPS induction, clinical scores for the vehicle-treated rats were 3.6±0.2 (mean±SEM, n=20) with a median of 4 (range, 2-5). A significant reduction (p<0.001) in the severity of the ocular inflammation was detected 24 hours after induction and intravenous treatment with SEQ ID NO: 197 (2 mg/kg) (mean score: 2.2±0.3, median: 2), corresponding to a 40% decrease of EIU scores compared with the score observed in vehicle group. Intravenous treatment with SEQ ID NO: 172, at approximately the same dose (1.80 mg/kg) reduced also significantly the severity of the ocular inflammation by 42% (mean score: 2.1±0.3, median: 2, p=0.001). The lower doses (0.18 and 0.015 mg/kg) reduced by 33% (mean score: 2.4±0.3, median: 2) and 36% (mean score: 2.3±0.3, median: 2) the inflammation, respectively. The reduction was significant with p<0.001.

A sub-conjunctival treatment with dexamethasone (20 Dg/eye), used as positive control drug also significantly reduced the clinical scores by 79% (mean score: 0.8±0.2, median: 0.5, p<0.001).

Under these experimental conditions, it can be stated that a single intravenous injection of SEQ ID NO: 197 at 2 mg/kg partially prevented the endotoxin-induced inflammation observed in the anterior chamber. In comparison, SEQ ID NO: 172 intravenously injected at 0.015, 0.18, 1.80 mg/kg also reduced the endotoxin-induced inflammation in the anterior chamber.

Example 11: Dose-Responsive Effects after Intravenous Administration of JNK Inhibitor after 14 Days in a Rat Model of Chronic Established Type II Collagen Arthritis Rat collagen arthritis is an experimental model of polyarthritis that has been widely used for preclinical testing of numerous anti-arthritic agents that are either under preclinical or clinical investigation or are currently used as therapeutics in this disease. The hallmarks of this model are reliable onset and progression of robust, easily measurable polyarticular inflammation, marked cartilage destruction in association with pannus formation, and mild to moderate bone resorption and periosteal bone proliferation.

Intravenous (IV) efficacy of the JNK inhibitor of SEQ ID NO: 172 administered daily (QD) for 14 days (arthritis d1-14) for inhibition of the inflammation (paw swelling), cartilage destruction, and bone resorption that occurs in established type II collagen arthritis in rats was determined in said experimental model.

Animals (8/group for arthritis) were anesthetized with isoflurane and injected with 300 □l of Freund's Incomplete Adjuvant (Difco, Detroit, Mich.) containing 2 mg/ml bovine type II collagen (Elastin Products, Owensville, Mo.) at the base of the tail and 2 sites on the back on days 0 and 6. On day to of the study (arthritis d0), onset of arthritis occurred and rats were randomized into treatment groups. Randomization into each group was done after ankle joint swelling was obviously established in at least one hind paw.

Female Lewis rats with established type II collagen arthritis were treated daily (QD) on arthritis days 1-14 by the intravenous (IV) route with vehicle (0.9% NaCl), SEQ ID NO: 172 (0.00, 0.1, 1, or 5 mg/kg), or the reference compound dexamethasone (Dex, 0.05 mg/kg). Animals were terminated on arthritis day 14. Efficacy evaluation was based on animal body weights, daily ankle caliper measurements, ankle diameter expressed as area under the curve (AUC), terminal hind paw weights, and histopathologic evaluation of ankles and knees of selected groups.

Scoring of Joints Collagen arthritic ankles and knees are given scores of 0-5 for inflammation, pannus formation and bone resorption according to the following criteria:

Knee and/or Ankle Inflammation

| | |
|---|---|
| 0 | Normal |
| 0.5 | Minimal focal inflammation |
| 1 | Minimal infiltration of inflammatory cells in synovium/periarticular tissue |
| 2 | Mild infiltration |
| 3 | Moderate infiltration with moderate edema |
| 4 | Marked infiltration with marked edema |
| 5 | Severe infiltration with severe edema |

Ankle Pannus

| | |
|---|---|
| 0 | Normal |
| 0.5 | Minimal infiltration of pannus in cartilage and subchondral bone, affects only marginal zones and affects only a few joints |
| 1 | Minimal infiltration of pannus in cartilage and subchondral bone, primarily affects marginal zones |
| 2 | Mild infiltration (<¼ of tibia or tarsals at marginal zones) |
| 3 | Moderate infiltration (¼ to ⅓ of tibia or small tarsals affected at marginal zones) |
| 4 | Marked infiltration (½ to ¾ of tibia or tarsals affected at marginal zones) |
| 5 | Severe infiltration (>¾ of tibia or tarsals affected at marginal zones, severe distortion of overall architecture) |

Knee Pannus

| | |
|---|---|
| 0 | Normal |
| 0.5 | Minimal infiltration of pannus in cartilage and subchondral bone, affects only marginal zones and affects only a few joints |
| 1 | Minimal infiltration of pannus in cartilage and subchondral bone, approximately 1-10% of cartilage surface or subchondral bone affected |
| 2 | Mild infiltration (extends over up to ¼ of surface or subchondral area of tibia or femur), approximately 11-25% of cartilage surface or subchondral bone affected |
| 3 | Moderate infiltration (extends over >¼ but <½ of surface or subchondral area of tibia or femur) approximately 26-50% of cartilage surface or subchondral bone affected |
| 4 | Marked infiltration (extends over ½ to ¾ of tibial or femoral surface) approximately 51-75% of cartilage surface or subchondral bone affected |
| 5 | Severe infiltration approximately 76-100% of cartilage surface or subchondral bone affected |

Ankle Cartilage Damage (Emphasis on Small Tarsals)

| | |
|---|---|
| 0 | Normal |
| 0.5 | Minimal decrease in T blue staining, affects only marginal zones and affects only a few joints |
| 1 | Minimal = minimal to mild loss of toluidine blue staining with no obvious chondrocyte loss or collagen disruption |
| 2 | Mild = mild loss of toluidine blue staining with focal mild (superficial) chondrocyte loss and/or collagen disruption |
| 3 | Moderate = moderate loss of toluidine blue staining with multifocal moderate (depth to middle zone) chondrocyte loss and/or collagen disruption, smaller tarsals affected to ½ to ¾ depth with rare areas of full thickness loss |
| 4 | Marked = marked loss of toluidine blue staining with multifocal marked (depth to deep zone) chondrocyte loss and/or collagen disruption, 1 or 2 small tarsals surfaces have full thickness loss of cartilage |
| 5 | Severe = severe diffuse loss of toluidine blue staining with multifocal severe (depth to tide mark) chondrocyte loss and/or collagen disruption affecting more than 2 cartilage surfaces |

Knee Cartilage Damage

| | |
|---|---|
| 0 | Normal |
| 0.5 | Minimal decrease in T blue staining, affects only marginal zones |
| 1 | Minimal = minimal to mild loss of toluidine blue staining with no obvious chondrocyte loss or collagen disruption |
| 2 | Mild = mild loss of toluidine blue staining with focal mild (superficial) chondrocyte loss and/or collagen disruption, may have few small areas of 50% depth of cartilage affected |
| 3 | Moderate = moderate loss of toluidine blue staining with multifocal to diffuse moderate (depth to middle zone) chondrocyte loss and/or collagen disruption, may have 1-2 small areas of full thickness loss affecting less than ¼ of the total width of a surface and not more than 25% of the total width of all surfaces |
| 4 | Marked = marked loss of toluidine blue staining with multifocal to diffuse marked (depth to deep zone) chondrocyte loss and/or collagen disruption or 1 surface with near total loss and partial loss on others, total overall loss less than 50% of width of all surfaces combined |
| 5 | Severe = severe diffuse loss of toluidine blue staining with multifocal severe (depth to tide mark) chondrocyte loss and/or collagen disruption on both femurs and/or tibias, total overall loss greater than 50% of width of all surfaces combined |

Ankle Bone Resorption

| | |
|---|---|
| 0 | Normal |
| 0.5 | Minimal resorption affects only marginal zones and affects only a few joints |
| 1 | Minimal = small areas of resorption, not readily apparent on low magnification, rare osteoclasts |
| 2 | Mild = more numerous areas of resorption, not readily apparent on low magnification, osteoclasts more numerous, <¼ of tibia or tarsals at marginal zones resorbed □ |
| 3 | Moderate = obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones |

-continued

4 Marked = Full thickness defects in cortical bone, often with distortion of profile of remaining cortical surface, marked loss of medullary bone, numerous osteoclasts, ½ to ¾ of tibia or tarsals affected at marginal zones
5 Severe = Full thickness defects in cortical bone, often with distortion of profile of remaining cortical surface, marked loss of medullary bone, numerous osteoclasts, >¾ of tibia or tarsals affected at marginal zones, severe distortion of overall architecture Knee Bone Resorption 0 Normal
0.5 Minimal resorption affects only marginal zones
1 Minimal = small areas of resorption, not readily apparent on low magnification, approximately 1-10% of total joint width of subchondral bone affected
2 Mild = more numerous areas of resorption, definite loss of subchondral bone, approximately 11-25% of total joint width of subchondral bone affected
3 Moderate = obvious resorption of subchondral bone approximately 26-50% of total joint width of subchondral bone affected
4 Marked = obvious resorption of subchondral bone approximately 51-75% of total joint width of subchondral bone affected
5 Severe = distortion of entire joint due to destruction approximately 76-100% of total joint width of subchondral bone affected Results:

Disease severity in the disease control group increased from days 1 to 5 with day 4-5 having the greatest daily increase. Then the incremental increases were smaller to the peak at day 7. From that point forward, acute swelling generally decreased and caliper measures were decreased. The treatment groups followed this general pattern as well.

Body weight loss was observed in all disease groups whereas the normal control group had a weight increase. Body weight loss was significantly (25%, p<0.05 by ANOVA) inhibited for rats treated with 5 mg/kg SEQ ID NO: 172 as compared to vehicle treated disease controls. When compared to disease controls using a Student's t-test, inhibition of body weight loss was also significant for rats treated with 1 mg/kg SEQ ID NO: 172 (21%, p<0.05) or Dex (21%, p<0.05). Results of treatment with SEQ ID NO: 172 were dose responsive for this parameter.

Daily ankle diameter measurements were significantly (p<0.05 by 2-way RM ANOVA) reduced toward normal for rats treated with 5 mg/kg SEQ ID NO: 172 (p<0.05 days 4-12) or Dex (p<0.05 d3-14) as compared to disease controls.

Ankle diameter AUC was significantly (p<0.05 by ANOVA) reduced toward normal for rats treated with 5 mg/kg SEQ ID NO: 172 (43% reduction), 1 mg/kg SEQ ID NO: 172 (27%), or Dex (97%) as compared to disease controls. Results of treatment with SEQ ID NO: 172 were dose responsive for this parameter.

Final paw weights were significantly (p<0.05 by ANOVA) reduced toward normal for rats treated with 5 mg/kg SEQ ID NO: 172 (26% reduction) or Dex (114%) as compared to disease controls. Results of treatment with SEQ ID NO: 172 were dose responsive for this parameter.

Relative liver weights were not significantly (by ANOVA) affected for rats in any treatment group as compared to disease controls.

Spleen weights relative to body weight were significantly (p<0.05 by ANOVA) reduced for rats treated with Dex as compared to disease controls. Relative spleen weights for Dex treated rats were also significantly reduced as compared to normal controls. Relative spleen weights were not significantly affected for rats treated with SEQ ID NO: 172.

Thymus weights relative to body weight were significantly (p<0.05 by ANOVA) reduced for rats treated with Dex as compared to disease controls. Relative thymus weights for Dex treated rats were also significantly reduced as compared to normal controls. Relative thymus weights were not significantly affected for rats treated with SEQ ID NO: 172.

All ankle histopathology parameters were significantly (by Mann-Whitney U test) reduced toward normal for rats treated with 5 mg/kg SEQ ID NO: 172 (25% reduction of summed scores) as compared to disease controls.

All knee histopathology parameters were significantly (by Mann-Whitney U test) reduced toward normal for rats treated with 5 mg/kg SEQ ID NO: 172 (73% reduction of summed scores) as compared to disease controls.

Results of this study indicated that daily intravenous treatment with SEQ ID NO: 172 (5 mg/kg) had significant beneficial effect on the clinical and histopathology parameters associated with established type II collagen arthritis in rats. Treatment with SEQ ID NO: 172 (1 mg/kg) resulted in significantly reduced ankle diameter AUC. The beneficial effect on ankle diameter was observed up to day 12 despite the reduction of swelling after day 7 in disease control animals. Results of treatment with SEQ ID NO: 172 were dose responsive.

Treatment with SEQ ID NO: 172 had no adverse effect on organ weights unlike dexamethasone.

Example 12: Effect of the all-D-Retro-Inverso JNK-Inhibitor (Poly-)Peptide of SEQ ID NO: 197 and the JNK Inhibitor (Poly-)Peptide of SEQ ID NO: 172 at Three Doses in a Scopolamine-Induced Model of Dry Eye in Mice Study Concept The objective of this study was to assess the effects of two different compounds, the all-D-retro-inverso JNK-inhibitor (poly-)peptide of SEQ ID NO: 197 and the JNK inhibitor (poly-)peptide of SEQ ID NO: 172, at three dose levels in a mouse model of scopolamine-induced dry eye.

The peptides of SEQ ID NO: 197 and SEQ ID NO: 172 were tested for efficacy in this murine model of dry eye. The peptides were both tested at a low, medium and a high dose. For the peptide of SEQ ID NO: 197 the concentrations measured in the formulation samples for low, medium and high dose levels were 0.06% (w/v), 0.25% (w/v) and 0.6% (w/v), respectively, and for SEQ ID NO: 172 the concentrations measured in the formulation samples for the low, medium and high dose levels, were 0.05% (w/v), 0.2% (w/v) and 0.6% (w/v), respectively. The vehicle, which also served as the negative control, was 0.9% Sodium Chloride for Injection USP.

The study consisted of a total of 9 groups of female C57BL/6 mice, comprising 8 groups of 12 mice each and an additional group of 4 mice. Bilateral short-term dry eye was induced by a combination of scopolamine hydrobromide (Sigma-Aldrich Corp., St. Louis, Mo.) injection (subcutaneous (SC), four times daily, 0.5 mg/dose, Days 0-21) and by exposing mice to the drying environment of constant air draft. Starting on Day 1, mice of Groups 1-8 were treated three times daily (TID) for 21 days with bilateral topical ocular (oculus uterque; OU) administration (5 µL/eye/dose) of vehicle (0.9% sterile saline; negative control article); the peptide of SEQ ID NO: 197 (0.06%, 0.25% and 0.6%), the peptide of SEQ ID NO: 172 (0.05%, 0.2% and 0.6%); or cyclosporine (0.05%; positive control, an immunosuppressant drug used to reduce the activity of the immune system). Mice of Group 9 were maintained as un-induced, (no dry eye) untreated controls.

During the in-life (treatment) period, clinical observations were recorded once daily; slit-lamp examination (SLE) with corneal fluorescein staining, tear break-up time test (TBUT), and phenol red thread test (PRTT) were performed three times per week. Necropsies were performed on Day 22; eyes, eye lids, conjunctivae, and lacrimal glands were collected from both eyes of each animal. Tissues from the right eyes (oculus dexter, OD) were fixed and then evaluated microscopically. Tissues from the left eyes (oculus sinister; OS) were flash-frozen in liquid nitrogen and stored frozen at $-80°$ C. for possible subsequent analyses.

TABLE 5

Experimental Design

| Group | Number of animals (females) | Induction of Dry Eye (QID, SC) Days 0 to 21 | Treatment (TID, OU, 5 μL/eye) Days 1 to 21 |
|---|---|---|---|
| 1 | 12 | Scopolamine (200 μL of 2.5 mg/mL sol., 0.5 mg/dose) | Vehicle |
| 2 | 12 | | SEQ ID NO: 197 (0.06%) |
| 3 | 12 | | SEQ ID NO: 197 (0.25%) |
| 4 | 12 | | SEQ ID NO: 197 (0.6%) |
| 5 | 12 | | SEQ ID NO: 172 (0.05%) |
| 6 | 12 | | SEQ ID NO: 172 (0.2%) |
| 7 | 12 | | SEQ ID NO: 172 (0.6%) |
| 8 | 12 | | Restasis ®* (0.05%) |
| 9 | 4 | No dry eye induction | No treatment |

*Cyclosporine

Methods

1. Dose Preparation

The (poly-)peptide of SEQ ID NO: 197 was obtained from Polypeptide Laboratories (France) as a 1.5-mL clear plastic microfuge vial containing 300.65 mg of dry powder.

The (poly-)peptide of SEQ ID NO: 172 was obtained from Polypeptide Laboratories (France) as a 1.5-mL clear plastic microfuge vial containing 302.7 mg of dry powder.

Prior to the start of the study, the (poly-)peptides of SEQ ID NO: 172 and of SEQ ID NO: 197 were formulated in sterile saline (vehicle). Dosing solutions at each concentration were sterilized using 0.2-μm filters, aliquoted to multiple pre-labeled vials, and frozen at $-20°$ C. The concentrations measured in the formulation samples for the peptide of SEQ ID NO: 197 were 0.058%, 0.25% and 0.624%, rounded to 0.06%, 0.25% and 0.6%. The concentrations measured in the formulation samples for the peptide of SEQ ID NO: 172 were 0.053%, 0.217% and 0.562%, rounded to 0.05, 0.2% and 0.6%.

On each day of dosing, one set of dosing solutions was thawed and used for that day's dose administrations. The controls (vehicle, cyclosporine) were provided ready to dose; no dose preparation was necessary.

2. Slit-Lamp Examinations (SLE)

Prior to entry into the study, each animal underwent a SLE and indirect ophthalmic examination using topically-applied fluorescein. Ocular findings were recorded using the Draize scale ocular scoring. SLE and Draize scoring were repeated three times a week during the in-life period.

3. Tear Break-Up Time (TBUT) Test and Subsequent Corneal Examination

The TBUT test was conducted three times weekly by measuring the time elapsed in seconds between a complete blink after application of fluorescein to the cornea and the appearance of the first random dry spot in the tear film. To perform the TBUT, 0.1% liquid sodium fluorescein was dropped into the conjunctival sac, the eyelids were manually closed three times and then held open revealing a continuous fluorescein-containing tear film covering the cornea, and the time (in seconds) required for the film to break (appearance of a dry spot or streak) was recorded. At least ninety seconds later, corneal epithelial damage was graded using a slit-lamp with a cobalt blue filter after another drop of 0.1% fluorescein was reapplied to the cornea; the cornea then was scored per the Draize ocular scale.

4. Phenol Red Thread Tear Test (PRTT)

Tear production was measured three times a week in both eyes using PRTT test strips (Zone-Quick; Menicon, Nagoya, Japan). Prior to the first treatment of the day, a thread was applied to the lateral canthus of the conjunctival fornix of each eye for 30 seconds under slit-lamp biomicroscopy. Tear migration up the tread (i.e., the length of the wetted cotton thread) was measured using a millimeter scale.

5. Necropsy and Pathology

At necropsy on Day 22, both eyes from each animal, including the globes, lacrimal glands, eyelids, and conjunctivae, were excised. The right eye and associated tissues were fixed by overnight submersion in modified Davidson's solution followed by transfer to 10% neutral buffered formalin (NBF). The fixed tissues of the right eye were dehydrated, embedded in paraffin, sectioned at 3 to 5-μm thicknesses, and slide-mounted tissues were stained with hematoxylin and eosin (H & E). Stained slides were evaluated via light microscopy. Detailed and complete histopathologic assessment was conducted on all parts of the eye, with at least two section levels being examined histopathologically for each right eye. Special attention was paid to the cornea, epithelia (including goblet cells) of the conjunctiva and cornea, as well as the lacrimal gland. These tissues were scored for injury based upon a 0-4 scale, with 0 being normal, 1 being minimal, 2 being mild, 3 being moderate, and 4 being severe. For each cornea, scores were based on corneal epithelium thickness, and corneal inflammation. Conjunctivae were scored for erosion and inflammation as well as presence or absence of goblet cells.

Results

Four-times daily SC administration of scopolamine (0.5 mg/dose) induced a dry eye syndrome in female C57BL/6 mice characterized by a decrease in the volume of aqueous tear production and changes in the physiochemical properties of the tears rendering them less capable of maintaining a stable tear film able to effectively lubricate and protect the eye.

1. Tear Break-Up Time (TBUT) Teat and Corneal Examination

The tear break-up time tests (TBUTs) were performed prior to the induction of dry eye, and again on Days 2, 4, 7, 9, 11, 14, 16, 18 and 21 after dry eye induction. After initiation of dosing with scopolamine (dry eye induction) TBUT mean values began to decrease in all animals, but appeared to decrease more slowly in Group 6 (mid-dose of SEQ ID NO: 172). The TBUT mean nadir for Groups 5, 6, 7 (low, mid and high-dose of the peptide of SEQ ID NO: 172), and Group 8 (cyclosporine) occurred on Day 7, reaching similar values (6.6±0.4, 6.7±0.4, 6.7±0.3, and 6.4±0.4 s, respectively). Subsequently, the TBUT means of these groups increased to a peak on Day 9. Groups 6 and 7 (SEQ ID NO: 172 mid and high-dose groups) TBUT means rose to higher values (10.0±0.7 s and 9.9±0.8 s, respectively) than Group 8, the cyclosporine group (8.5±0.3 s), while the peak TBUT mean of Group 5, the low-dose of SEQ ID NO: 172 (8.0±0.4 s) was slightly below that of Group 8 (cyclosporine). TBUT means for the mid and high-dose of SEQ ID NO: 197-treated animals, Groups 3 and 4, continued to decline after onset of dosing, reaching a nadir on Day 9, while the low-dose Group 2 increased on Day 9. The low, medium and high-dose TBUT means of SEQ ID NO: 172-treated animals (Groups 2, 3 and 4, respectively) were above the vehicle group and generally below the low, mid and high-dose group means of SEQ ID NO: 172-treated animals.

When the area under the curve (AUC) for TBUT values from Day 7 to Day 21 was used to compare the various treatments with the vehicle control, treatment with mid, low and high-dose of the peptide of SEQ ID NO: 172 (0.05%, 0.2% and 0.6%, respectively), Groups 5, 6, and 7, as well as animals treated with cyclosporine (0.05%), Group 8, showed significant increases in the TBUT AUC (Kruskal-Wallis nonparametric ANOVA). The peptide of SEQ ID NO: 172 appeared to produce a dose-dependent increase in TBUT, with the mid and high-doses often producing similar effects. Furthermore, there were no significant differences in TBUT AUC between the cyclosporine-treated group, the groups treated with three dose levels of SEQ ID NO: 172 and the un-induced group (Groups 5, 6, 7, 8, and 9). This finding suggests that all three doses of the peptide of SEQ ID NO: 172 and cyclosporine were approximately equally effective in improving or reversing the ophthalmological changes that underlie the TBUT changes in this dry eye model.

Groups treated with low, mid and high dose levels of the peptide of SEQ ID NO: 197 (Groups 2-4) showed slight generally dose-dependent increases in TBUT which started to increase approximately two days later than animals treated with SEQ ID NO: 172 or cyclosporine.

TABLE 6

Mean Calculated TBUT AUC Values:

| Group | TBUT AUC |
|---|---|
| Group 1 | 71.19 |
| Group 2 | 88.54 |
| Group 3 | 91.19 |
| Group 4 | 89.98 |
| Group 5 | 102.98 |
| Group 6 | 119.08 |
| Group 7 | 119.31 |
| Group 8 | 116.1 |
| Group 9 | 124.54 |

2. Phenol Red Thread Tear Test (PRTT)

PRTT tests were performed prior to the induction of dry eye, and again on Days 2, 4, 7, 9, 11, 14, 16, 18 and 21. PRTT values from Day 0 to Day 4 decreased in all mice that had dry eye induced, indicating a decrease in tear production after the administration of scopolamine and exposure to a drying environment of increased air draft created by the blowers. The nadir in PRTT in most groups occurred at approximately Day 7. PRTT kept decreasing in the vehicle control group (Group 1) reaching a nadir on Day 14. After the nadir, there was an increase in all dry eye groups. These findings indicate that initiation of scopolamine treatment one day earlier than initiation of compound treatment was sufficient to initiate physiological changes in the eye associated with dry eye syndrome. Even the cyclosporine-treated group showed a decrease in PRTT similar to other groups through approximately Day 7, then increased to a peak on Days 11-14, followed by a slight decrease. In the last PRTT test (Day 21) cyclosporine (Group 8), and Groups 6 and 7 all had similar PRTT values suggesting that both the mid and high-dose of the peptide of SEQ ID NO: 172 treatments have therapeutic effects similar to cyclosporine in increasing the aqueous tear production in this murine dry eye model.

Animals treated with the low, mid or high-dose of the peptide of SEQ ID NO: 172 produced significantly more aqueous tears compared to vehicle-treated animals. Thus, similar to TBUT, the peptide of SEQ ID NO: 172 produced generally dose-related significant increases in the production of aqueous tears in this model.

Groups treated with low, mid and high dose levels of the peptide of SEQ ID NO: 197 (0.06%, 0.25% and 0.6%, Groups 2, 3 and 4, respectively) showed generally dose-dependent increases in PRTT.

TABLE 7

Mean PRTT AUC Values

| Group | PRTT AUC |
|---|---|
| Group 1 | 35.02 |
| Group 2 | 39.96 |
| Group 3 | 42.79 |
| Group 4 | 43.17 |
| Group 5 | 44.38 |
| Group 6 | 44.85 |
| Group 7 | 46.10 |
| Group 8 | 49.44 |
| Group 9 | 113.63 |

3. Histopathology

In this study histologic changes were generally confined to the cornea. Findings in the cornea consisted of increased keratinization of the corneal epithelial surface, increased thickness of the corneal epithelium, increased cellularity of the corneal epithelium, mildly increased incidence of mitosis of the basal epithelial layer consistent with increased epithelial cell turnover. These findings are indicative of a physiologic adaptive response to corneal drying and corneal surface irritation. Surface ulceration, corneal stromal edema and inflammatory infiltrate into the cornea were not seen in this study. The eyes in Group 9, the untreated group (normal mice, no scopolamine treatment), were within normal limits. There was some minimal nonsuppurative inflammation of the eye lids scattered throughout all groups, but the conjunctiva, retina, lacrimal glands and other parts of the eye were within normal limits. Goblet cells appeared to be within limits in all groups. Goblet cells are a primary producer of mucin which helps the tears form a stronger more adhesive film.

Mild to moderate corneal changes were noted in all groups except the untreated normal eye group (Group 9) and were slightly more severe in Group 1, the vehicle-treated group and Group 2, the low dose of the peptide of SEQ ID NO: 197, in comparison to the other treatment groups. These findings were consistent with the positive beneficial effects of increased tear production on the cornea.

When histological scores of the various treatment groups were compared to the histological scores in the cyclosporine group to determine if any other treatments produced "similar score reductions" to cyclosporine, Groups 4, 6, and 7 were found to be not significantly different than the cyclosporine group scores. Thus, these three treatments, mid and high-dose of the peptide of SEQ ID NO: 172 and the high-dose of the peptide of SEQ ID NO: 197, were the most effective, after cyclosporine, in reducing/ameliorating the corneal changes associated with this murine dry eye model.

Example 13: Effect of a JNK Inhibitor on Adriamycin-Induced Nephropathy in Rats

Adriamycin treatment induces glomerular disease in rat and mice mimicking human focal segmental and glomerular sclerosis (FSGS). In this model, tubular and interstitial inflammatory lesions occur during the disease course, partly due to heavy proteinuria. In the absence of therapy, kidney disease progresses to terminal renal failure within eight weeks. Podocyte injury is one of the initial steps in the sequences leading to glomerulosclerosis. The aim of the study was to investigate whether a JNK inhibitor could prevent the development of renal lesions and the renal failure.

Methods 30 male Sprague-Dawley rats (Charles River) were used in this study (divided into 3 groups of ten rats). Nephropathy was induced by a single intravenous injection of Adriamycin to mg/kg on Day 0. The JNK inhibitor of SEQ ID NO: 172 (2 mg/kg; in NaCl 0.9%) or vehicle was administered intravenously into the tail vein on Day 0. The administration volume was 0.2 ml.

The table below summarizes the random allocation:

| Group N° | ADR (Day 0) | Treatment (Day 0) | Dose volume/ Route of administration | Dose concentration | Number of animals |
|---|---|---|---|---|---|
| 1 | 10 mg/kg | NaCl 0.9% | 0.2 ml, IV | 0 | 10 |
| 2 | 10 mg/kg | JNK inhibitor of SEQ ID NO: 172 2 mg/kg | 0.2 ml, IV | 1 mg/ml | 10 |
| 3 | NaCl 0.9% | NaCl 0.9% | 0.2 ml, IV | 0 | 10 |

Each day, the general behavior and the appearance of all animals were observed. The health of the animals was monitored (moribund animals, abnormal important loss of weight, major intolerance of the substance, etc. . . . ). No rats were removed.

Retroorbital blood was collected at Days 7, 14, 28, 42 and 56 from 4 rats per group. Serum creatinine concentrations, blood urea and protidemia were measured using appropriate kits from Advia Chemistry 1650 (Bayer Healthcare AG, Leverkusen, Germany).

Two rats per group were sacrificed on Days 7, 14, 28, 42 and 56 after anesthesia. After animal sacrifice, both kidneys were collected. For histopathological examination fixed tissue specimens were dehydrated in graded alcohol solutions, cleared in toluene, and embedded in paraffin. Sections (4 □m) were stained with periodic acid-Schiff (PAS), and Masson's trichrome staining was performed to detect collagen deposition. Glomerular and tubulointerstitial sclerosis were quantified under microscope.

Results were expressed in the form of individual and summarized data tables using Microsoft Excel® Software. Numerical results were expressed as mean±standard error of the mean (SEM). Due to the small number of animal tested, no statistical analyses was performed.

Figure 38A:
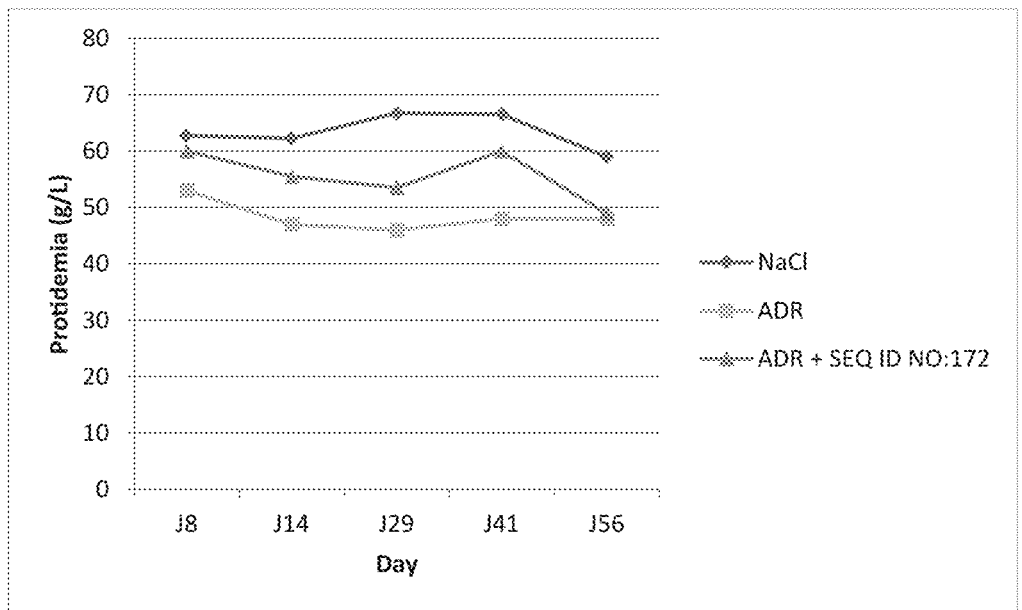
FIG. 38A-38B shows the renal function assessed by protidemia (FIG. 38A) and urea level (FIG. 38B) of rats in an Adriamycin (ADR)-induced nephropathy model on Days 8, 14, 29, 41 and 56 after ADR administration. Groups No. 1 ("ADR") and No. 2 ("ADR+JNK inhibitor SEQ Id NO: 172") have been treated on Day 0 with ADR to induce necropathy, whereas group No. 3 ("NaCl") received 0.9% NaCL. Moreover, group No. 2 ("ADR+JNK inhibitor SEQ Id NO: 172") has been treated on Day 0 with the JNK inhibitor SEQ ID NO: 172, whereas No. 1 and 3 received vehicle (0.9% NaCl).
Figure 38B:
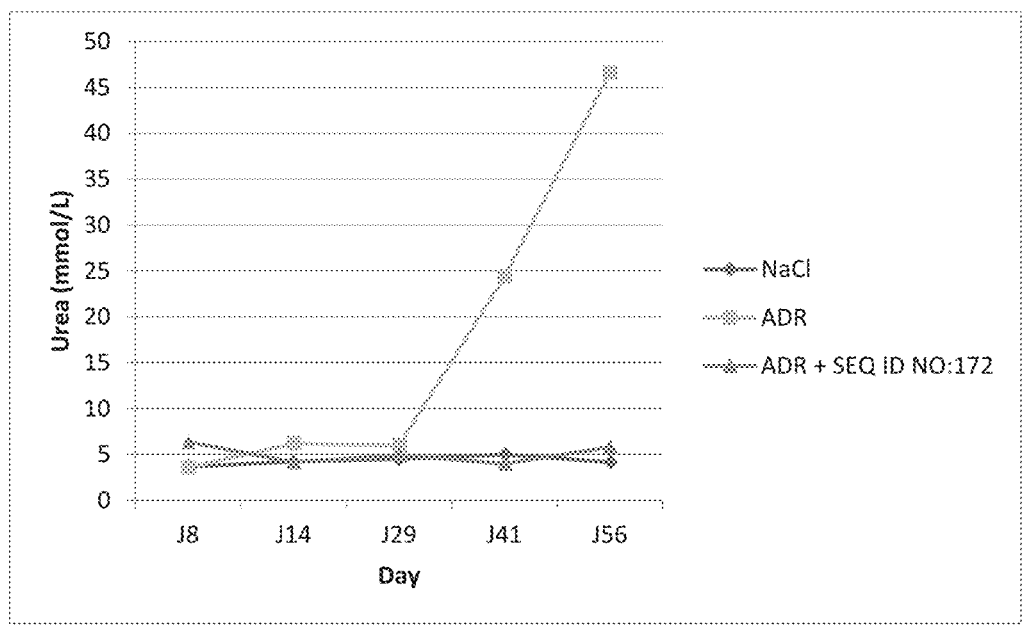

Results:

Effect of the JNK inhibitor of SEQ ID NO: 172 on renal function during the progression of the disease: Urea and creatinine serum levels were measured to study the renal function during the kidney disease course. Because creatinine interferes with the calorimetric dosage, only urea that is a fine indicator of renal function was analyzed. Whereas urea serum levels were remarkably stable in untreated rats (below 5 mmol/1), ADR induced progressive increase of urea levels, which sharply raised from Day 28 up to 25 mmol/l at Day 41, then 48 mmol/l at Day 56 reflecting terminal renal failure (FIG. 38 B). On the other hand, JNK inhibitor of SEQ ID NO: 172-treated rats exhibited an urea serum level below 10 mmol/l throughout the course of the disease (FIG. 38 B). These results suggest that JNK inhibitor of SEQ ID NO: 172 prevents the progression to renal disease and renal failure.

Figure 39:
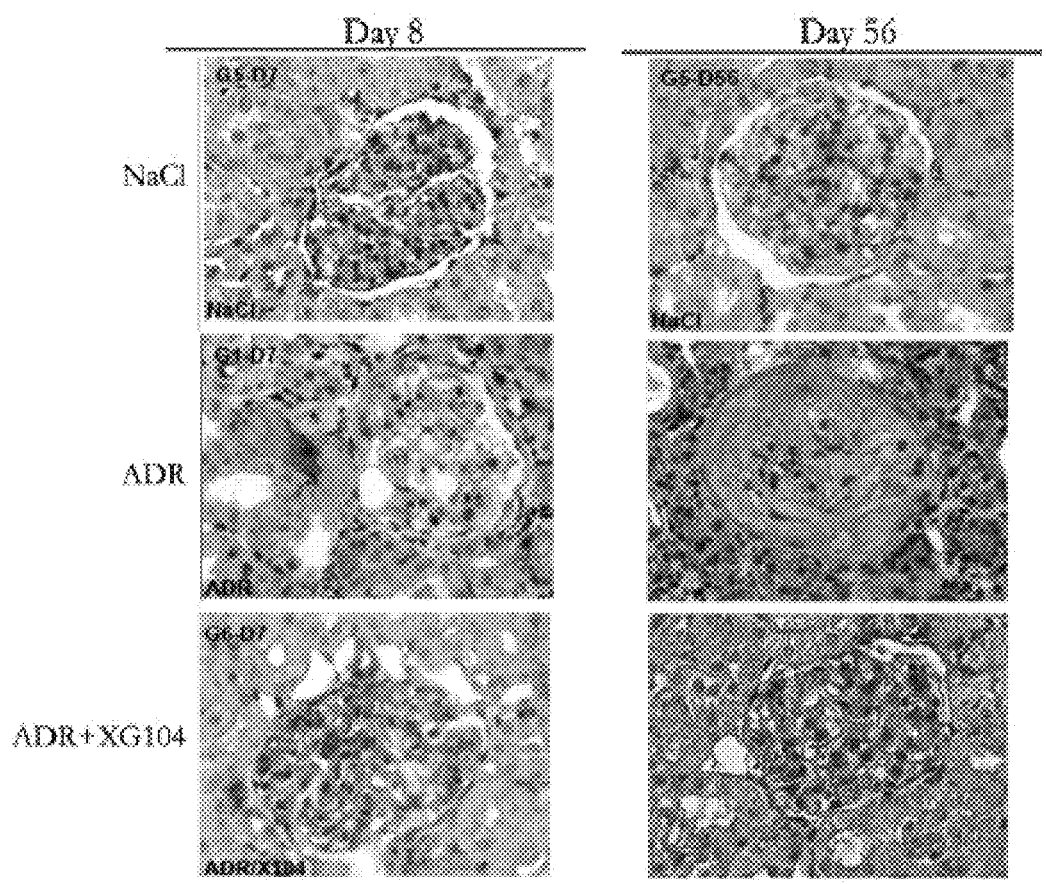
FIG. 39 shows kidney sections of the rats in the Adriamycin (ADR)-induced nephropathy model stained with periodic acid-Schiff (PAS) (original magnification ×40). For the sections shown in the left column, rats were sacrificed at Day 8 following ADR administration, whereas for the sections shown in the left column, rats were sacrificed at Day 56. ADR has been administered only to the groups "ADR" and "ADR+XG104", whereas the group "NaCl" received 0.9% NaCL only. The group "ADR+XG104" has been treated on Day 0 with the JNK inhibitor SEQ ID NO: 172 (i.e. "XG104" refers to the JNK inhibitor SEQ ID NO: 172), whereas the other groups ("ADR" and "NaCl") received vehicle (0.9% NaCl).
Figure 40:
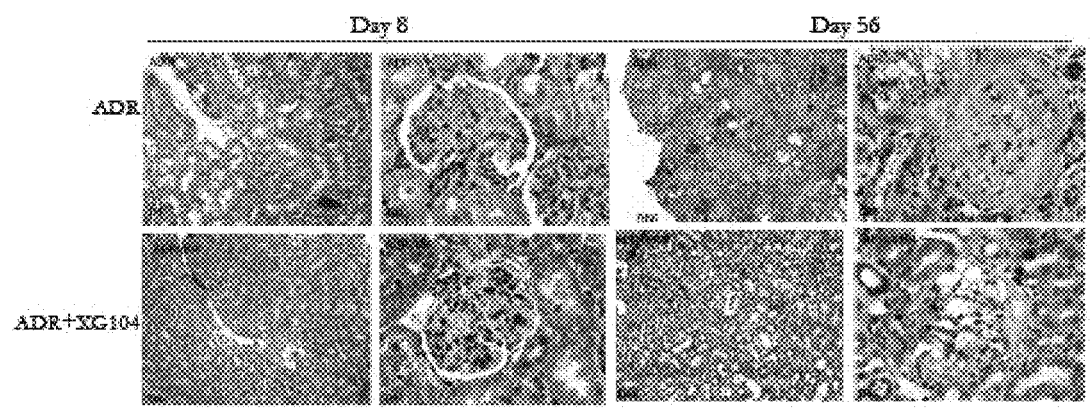
FIG. 40 shows the kidney fibrosis in ADR nephropathy evaluated with Masson's trichrome (blue) on Days 8 (left four panels) and 56 (right four panels) following ADR administration for the group "ADR" (upper panel), which has been treated with ADR and vehicle at Day 0 and for the group "ADR+XG104" (lower panel), which has been treated with ADR and the JNK inhibitor SEQ ID NO: 172 at Day 0. The original magnification ×10 is depicted in the left panels for the respective day and the original magnification ×40 is depicted in the right panels for the respective day.

Histopathological Findings (PAS and Masson Trichrome Staining):

ADR-induced structural changes were evaluated under light microscope. Saline-treated control rats showed morphologically normal glomeruli and tubules. On Day 8, light microscopic examination showed some areas with focal segmental glomerulosclerosis and proteinaceous casts in the ADR nephrosis group. In contrast, although some tubules were filled with proteins in JNK inhibitor of SEQ ID NO: 172-treated rats, glomeruli exhibited a normal architecture with absence or discrete mesangial hypercellularity, while the tubular structures and interstitium did not display pathological changes (FIG. 39). By Day 14, ADR treated rats exhibited progressive glomerulosclerosis, hyaline deposits, tubular dilation and cast formation. The degree of glomerulosclerosis was dramatically worsened in this group and became diffuse with obvious adhesion between the glomerular tufts and the Bowman's space in most glomeruli by Day 29 and 41, associated with severe tubular atrophy and interstitial fibrosis. At Day 56, diffuse glomerular sclerosis was observed in all glomeruli (FIG. 40). However, JNK inhibitor of SEQ ID NO: 172-treated rats had a relatively normal appearance at Day 8, and develop few focal and segmental glomerulosclerosis and tubulointerstitial fibrosis at Day 56 compared with ADR-treated rats. Altogether, these results strongly suggest that the JNK inhibitor of SEQ ID NO: 172 prevents the development of glomerular and tubulointerstitial fibrosis and may explain the preservation of renal function in this group.

The study results provide evidence that the JNK inhibitor of SEQ ID NO: 172 prevents the progression of glomerular and tubulointerstitial injuries induced by ADR. Moreover, this molecule preserves renal function.

Example 14: Evaluation of a JNK Inhibitor on Imiquimod-Induced Psoriasis in Mice Imiquimod (IMQ), a ligand for TLR7 and TLR8, is a potent immune response modifier. It has been demonstrated for potent antiviral and antitumor effects in many animal models. Van der Fits et al. (The Journal of Immunology 2009, 182, P. 5836-5845) have demonstrated that the topical application of IMQ in BALB/c mice induced psoriasis and closely resemble human psoriasis lesion.

Methods

Female BALB/cAnNCrl mice (Charles River, age 8 to 10 weeks at study start) have been assigned to the following groups (treatment schedule):

| Group | Dose (mg/kg) | Dose Volume (ml/kg) | Prep Conc. (mg/ml) | Dosing Duration (# Days) | Prep Frequency | Route | No. of animals |
|---|---|---|---|---|---|---|---|
| Vehicle | N/A | 5 | N/A | Days 1, 4, 7 | Days 1, 4, 7 | IV | 8 |
| SEQ ID NO: 172 | 0.02 | 5 | 0.004 | Days 1, 4, 7 | Days 1, 4, 7 | IV | 8 |
| SEQ ID NO: 172 | 0.2 | 5 | 0.04 | Days 1, 4, 7 | Days 1, 4, 7 | IV | 8 |
| SEQ ID NO: 172 | 2 | 5 | 0.4 | Days 1, 4, 7 | Days 1, 4, 7 | IV | 8 |
| Prednisolone | 10 | 10 | 1 | 7 | Daily | PO | 8 |
| Dexamethasone | 0.5 | 5 | 0.1 | Days 1, 4, 7 | Days 1, 4, 7 | IV | 6 |

Additionally, a group of five animals has not been treated ("Naïve" group).

To demonstrate whether topical application of IMQ induced skin inflammation is accompanied by structural features characteristic for psoriasis, IMQ cream (approx. 62.5 mg Imiquimod Cream 5%) has been applied on the back of shaved skin and to the right ear of the BALB/c mice for 6 consecutive days (days 2 through 7).

In this experiment, two positive controls have been utilized. Firstly, Prednisolone at 10 mg/kg (vehicle: 1% Hydroxyethylcellulose, 0.25% Polysorbate 80, and 0.05% Antifoam in purified water) has been dosed daily and orally (group "Prednisolone"). Secondly, Dexamethasone has been administered at 0.5 mg/kg (vehicle: sterile 0.9% NaCl) on days 1, 4 and 7 via intravenous route.

The JNK inhibitor of SEQ ID NO: 172 ("SEQ ID NO: 172") has been dissolved in 0.9% NaCl. To receive three different doses (cf. above, groups table) it has been serially diluted (1:10 fold). The JNK inhibitor of SEQ ID NO: 172 was readily soluble and did not fall out of solution. The three different doses of the JNK inhibitor of SEQ ID NO: 172 (0.02, 0.2 and 2 mg/kg) have been administered to the respective groups intravenously on days 1, 4 and 7.

Figure 41:
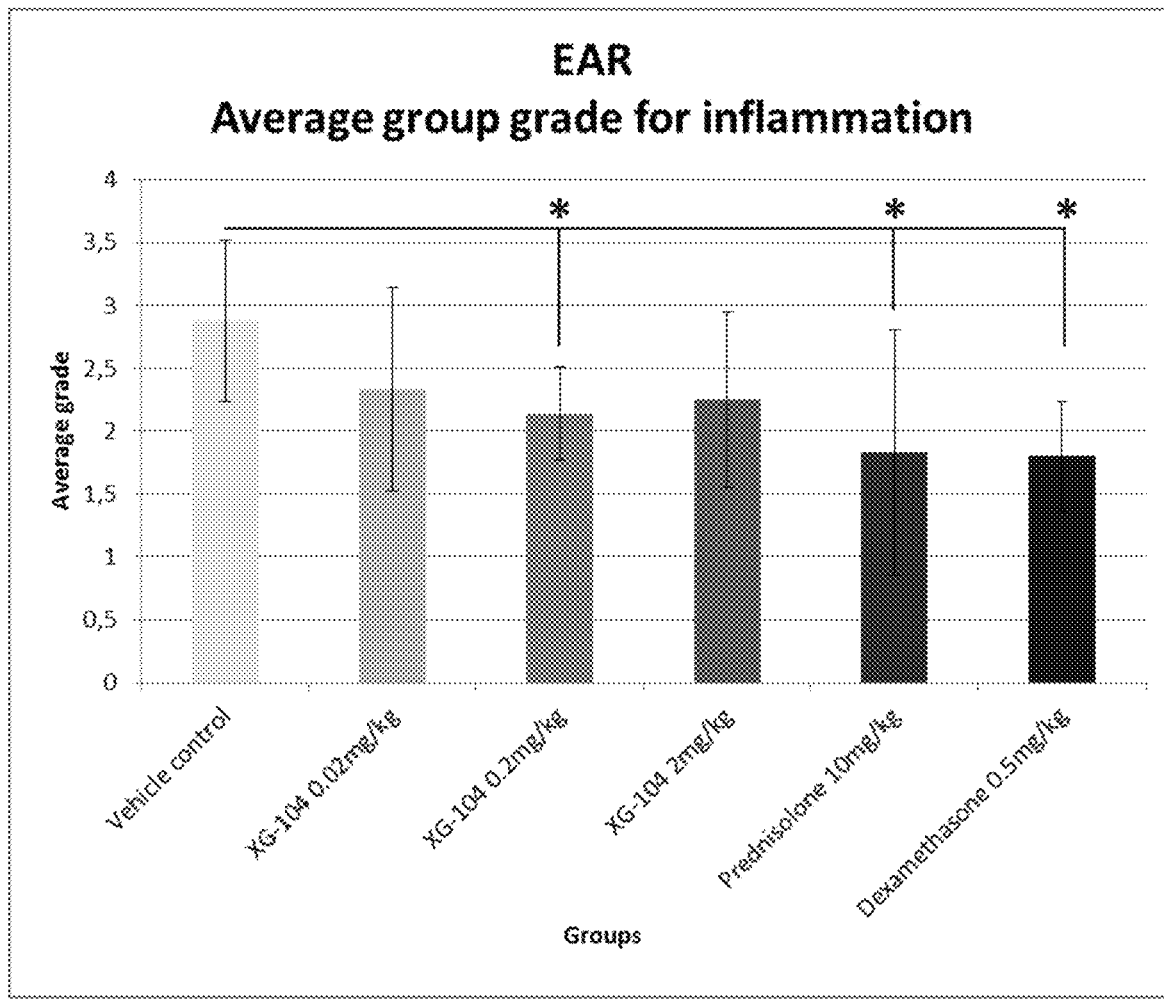
FIG. 41 shows the average group grade for inflammation of the ear in an imiquimod-induced psoriasis-model in mice after six consecutive days of imiquimod application. The "average grade" refers to the microscopic histopathology end-points (cf. Example 14). Three doses (0.02, 0.2 and 2 mg/kg) of the JNK inhibitor of SEQ ID NO: 172 have been tested (groups "XG-104 0.02 mg/kg, XG-104 0.2 mg/kg, and XG-104 2 mg/kg, respectively). Prednisolone and dexamethasone served as positive controls. The groups XG-104 0.2 mg/kg, prednisolone and dexamethasone showed significant differences from the vehicle control group.

On day 8, animals have been sacrificed and the tissue (ear) has been fixed in 10% neutral buffered formalin. For histopathology hematoxylin-and-eosin-stained sections (cross cut) have been prepared and microscopic evaluation on the collected tissues from all animals has been performed. Methods and end-points for histopathology were similarly described in the van der Fits (2009) paper in that inflammation, epidermal hyperplasia, epidermal hyperkeratosis (rather than parakeratosis) were observed and recorded for severity grade, whereby the respective methodology from Van der Fits et al. (The Journal of Immunology 2009, 182, P. 5836-5845) is hereby incorporated by reference. Histopathology grading scores were excluded for either skin or ear in animals with secondary inflammatory processes (full thickness epidermal ulcers). Scores were averaged by group and standard deviation and statistical significance were calculated. The graph in FIG. 41 shows group averages (+/−) standard deviation (SD) are depicted below. Formalin-fixed, paraffin embedded skin from the dorsal surface of the mouse (BALB/c) was stained with hematoxylin and eosin (H&E) stain and assessed microscopically. An important difference from the above reference and to describe in more detail the observations of the present study: Hyperkeratosis can be defined specifically as orthokeratotic (no retained nuclei) or parakeratotic (retained nuclei). Either can occur normally in various anatomical locations and depending on species; however, both conditions are well defined in particular disease states. The van der Fits paper describes their Imiquimod (IMQ)-induced psoriasis model as causing parakeratotic hyperkeratosis similar to what is seen in the human condition, and that was a defined end-point for this study. However, the Danilenko et al. (Veterinary Pathology 2008 45:563) has shown that many rodent psoriasis models have orthokeratotic hyperkeratosis. In reality, the same lesion can sometimes exhibit both types of hyperkeratosis, and the rodents in this study had primarily orthokeratotic hyperkeratosis with rare, multifocal parakeratosis. The more general term 'hyperkeratosis' was used for grading end-points and describe in the text what type was seen (primarily orthokeratotic). Another difference from the van der Fits paper, is that they describe human patients as having decreased granulation in their stratum *granulosum* layer of the epidermis (and in their study, the rodent skin was reportedly similar); however, in this study, and the Danilenko review, many rodent models of psoriasis exhibit increased (hypergranulosis) granulation in this layer or the layer itself is hyperplastic.

Microscopic Histopathology end-points were graded as such:
1=MI=minimal
2=SL=slight
3=MO=moderate
4=MA=marked
5=SE=severe
Results The JNK inhibitor of SEQ ID NO: 172 mid-dose group (statistically significant) and the JNK inhibitor of SEQ ID NO: 172 high-dose group had decreased inflammation of the ear compared to the vehicle-IMQ dose group (FIG. 41). Also the positive control groups, i.e. the Prednisolone group and the Dexamethasone group, showed decreased inflammation of the ear compared to the vehicle-IMQ dose group (both statistically significant, FIG. 41). In general, inflammation that was present in the dermis consisted of lymphocytes and macrophages admixed with fewer neutrophils. Inflammation in the epidermis, which was much less common, was primarily neutrophilic and was present in intracorneal layers (of orthokeratotic layers) and in the intraepidermis as Munro's microabscesses. Inflammation was not present in the naïve group.

Minimal decreases in epidermal hyperplasia of the ear were also observed for the JNK inhibitor of SEQ ID NO: 172 mid-dose group that was slightly below that observed for the Prednisolone and Dexamethasone groups. Although the JNK inhibitor of SEQ ID NO: 172 mid-dose and prednisolone groups were below that of the vehicle-IMQ dose group, they were not statistically significant. No overt differences were exhibited as a dose-response treated with JNK inhibitor of SEQ ID NO: 172 for ear with regards to epidermal hyperkeratosis, however the JNK inhibitor of SEQ ID NO: 172 low-dose group, Prednisolone, and Dexamethasone groups had minimally decreased average grades compared to the vehicle-IMQ dose group. The naïve group was microscopically normal.

Example 15: Effects of a JNK Inhibitor on Renal Ischemia/Reperfusion Lesions

Renal Ischemia/Reperfusion (Renal I/R) injury is a commonly employed model of acute kidney injury (AKI), also known as acute renal failure. In addition to the clinical relevance of studies that examine renal I/R injury to acute kidney injury, experimental renal I/R injury is also an important model that is used to assess the conditions that occur in patients receiving a kidney transplant. Depending upon the donor, transplanted kidneys are not perfused with blood for a variable amount of time prior to transplantation. Because AKI has such serious effects in patients, and all transplanted kidneys experience renal I/R injury to some extent, the clinical relevance and translational importance of this type of research to human health is extremely high. The aim of this study is thus to investigate the influence of the JNK inhibitor of SEQ ID NO: 172 on experimental renal ischemia/reperfusion in rats.

To this end, 26 male Wistar rats (age 5 to 6 weeks, Charles River) are assigned to the following groups:

| Group No | Pretreament (1 hour before clamping) | Treatment (1 hour after clamping) | Dose volume/ Route of administration | Concentration | Renal Ischemia time (min) | Number of animals |
|---|---|---|---|---|---|---|
| 1 | Heparine (5000 IU/kg) | NaCl 0.9% | 2 ml/kg, IV | 0 | | 6 |
| 2 | Heparine (5000 IU/kg) | JNK inhibitor SEQ ID NO: 172 2000 µg/kg | 2 ml/kg, IV | 1 mg/ml | 40 | 10 |
| 3 | Heparine (5000 IU/kg) | NaCl 0.9% | 2 ml/kg, IV | 0 | 40 | 10 |

Renal ischemia will be induced by clamping both renal pedicles with atraumatic clamp (induction of necropathy). One unique dose of the JNK inhibitor of SEQ ID NO: 172 (2000 µg/kg) will be administered intravenously (IV) into the tail vein on Day 0, one hour after clamping period (after reperfusion) both renal pedicles with atraumatic clamp. The administration volume will be 2 ml/kg. Heparin (5000 IU/kg) will be administered intraperitoneally 1 hour before clamping.

Each day, the general behavior and the appearance of all animals is observed. If animal health is not compatible with the continuation of the study (moribund animals, abnormal important loss of weight, major intolerance of the substance, etc. . . . ), animals will be ethically sacrificed under the responsibility of the Study Director. Individual rats are housed in metabolic cages (Techniplast, France). Urine is collected every 24 hours up to 72 hours. Blood samples are obtained from tail vein before, then at 24 and 72 hours after reperfusion. At the end of both periods (24 and 72 hours), 5 rats per group (3 for group 1) are sacrificed. After animal sacrifice, both kidneys are collected. Five rats per group (3 for group 1) are used at each time point (24 and 72 hours after reperfusion). For the evaluation of the renal function, serum creatinine (µmol/ml) or urea concentrations (mmol/mL) are measured with the appropriate kits (Bayer Healthcare AG, Leverkusen, Germany). For the evaluation of proteinuria and albuminuria, proteinuria and albuminuria are performed using appropriate kits from Advia Chemistry 1650 (Bayer Healthcare AG, Leverkusen, Germany).

Evaluation of histological lesions is performed 24 and 72 hours after reperfusion. For light microscopy, kidneys are incubated for 16 hours in Dubosq-Brazil, dehydrated, embedded in paraffin, cut into sections and stained with hematoxylin and eosin (H&E) or periodic acid-Schiff (PAS) reagent. Three sections will be analyzed for each staining.

For immunohistochemistry analysis, kidney samples are fixed for 16 hours in Dubosq Brazil, and subsequently dehydrated and embedded in paraffin. Antigen retrieval is performed by immersing the slides in boiling 0.01 M citrate buffer in a 500 W microwave oven for 15 min. The endogenous peroxidase activity is blocked with 0.3% $H_2O_2$ in methanol for 30 min. Slides are incubated with the blocking reagents consisting of the Avidin-biotin solution for 30 min and the normal blocking serum for 20 min. For immunodetection, the slides are incubated overnight with an antibody, then with a biotinylated secondary antibody. An avidin-biotinylated horseradish peroxidase complex (Vectastain ABC Reagent, Vector Laboratories; Burlingame, Calif.) and 3,3'-diaminobenzidine (Sigma Biochemicals; St Louis, Mo.) as a chromogen is applied for visualization of the immunoreaction. Slides are counterstained with hematoxylin. Omission of the primary antibody is considered as a negative control.

Immunofluorescence labeling is carried out on 4 mm thick cryostat sections of kidney tissue fixed in acetone for 10 min, air-dried for 30 min at room temperature, then incubated in PBS for 3 min and blocked in 1% BSA in PBS. The sections are incubated with the indicated antibodies for 1 hour at room temperature, washed in PBS and incubated with Red Texas-conjugated secondary antibodies. Sections are examined by fluorescence microscopy (Zeiss) for immunofluorescence analysis.

The expression of several markers specific of podocyte damage, inflammation and renal fibrosis (RelA, TGFβ, TNFα, Masson trichrome) is evaluated by immunohistochemistry and immunofluorescence. Quantitative transcription profile of TNF, IL6, CXCL1 (KC), CXCL2 (MIP-2) and MCP1 in kidneys are determined.

Example 16: Inhibitory Effects of a JNK Inhibitor on the Inflammatory Response in a Rat Periodontitis Model The aim of this study is to investigate the influence of the JNK inhibitor of SEQ ID NO: 172 on inflammation induced in a periodontitis model in the rat.

30 Sprague-Dawley rats (male, 42-56 days old) are used in this study (divided into 4 groups of ten rats). Experimental periodontitis is induced by a ligature placed around the $1^{st}$ molar (one molar per animal) on Day 0 for 10 days. One dose of 4 mg/kg of the JNK inhibitor of SEQ ID NO: 172 (in 0.9% NaCl as vehicle) is administered intragingivally (IGV) on day 10. The administration volume is 10 µl. Administrations are performed IGV in the attached gingiva surrounding the first molar.

The table below summarizes the random allocation:

| Group N° | Ligature (Day 0) | Treatment | Route of administration | Number of animals |
|---|---|---|---|---|
| 1 | — | — | IGV | 10 |
| 2 | Yes | NaCl 0.9% | IGV | 10 |
| 3 | Yes | SEQ ID NO: 172 4 mg/kg | IGV | 10 |

Each day, the general behavior and the appearance of all animals is observed. If animal health is not compatible with the continuation of the study (moribund animals, abnormal important loss of weight, major intolerance of the substance, etc. . . . ), animals are ethically sacrificed under the responsibility of the Study Director. Periodontitis inflammation aspect are analyzed by macroscopic observation of gingival tissue on days 0, 10 and 17. Plaque index and gingival inflammation index are measured on day 0, 10 and 17 as periodontal clinical indices using clinical scoring.

On day 17 the animals are sacrificed and samples are collected. Gingival tissue is excised for bio-molecular analysis on all animals. After euthanasia, mandibles are excised for histological evaluation. For the evaluation of inflammatory cells, quantification of inflammatory cells is performed by histomorphometric measurements. For the evaluation of inflammatory protein levels, the level of inflammatory proteins (p-JNK, TNF, IL-1, IL-10, MMP-8, MMP-9) are measured from gingival tissue homogenates. For the evaluation of tissue destruction, bone tissue destruction is evaluated on 3 animals per group by radiological analysis (micro-CT). Periodontal complex destruction is evaluated by histological analysis. For the evaluation of bone microarchitecture, bone trabecular measurements (thickness, separation) are evaluated by radiological analysis (micro-CT) on 3 animals per group on days 0, 10 and 17. For the identification of oral bacteria, bacterial population in dental pockets are identified by DNA probes (real time PCR) on 9 periodontopathogens on days 0, 10 and 17. For the collagen framework, measurements of total collagen amount are performed using Polarized-light microscopy. The collagen I/collagen III ratio is evaluated by histomorphometrical analysis.

Example 17: Evaluation of the Action Duration of the JNK Inhibitor According to SEQ ID NO: 172 ("XG-104") in the Endotoxin-Induced Uveitis (EIU) Model in Rats Twenty four (18) female Lewis rats (36 eyes) were randomly divided into 6 groups of 3 animals each. EIU was induced by a single footpad injection of 100 □l sterile pyrogen-free saline containing 200 □g of LPS (Lipopolysaccharides from *Salmonella typhimurium*, Sigma-Aldrich, France)(2 mg/ml).

Animals were treated 48 hours, 1 week, 2 weeks or 4 weeks before EIU induction by intravenous injection of the JNK inhibitor according to SEQ ID NO: 172 ("XG-104") at a single dose of 1 mg/kg (dose volume 1 ml/kg) in the tail vein. Dexamethasone 2 mg/kg or vehicle (NaCl 0.9%) were injected intravenously immediately before EIU induction.

The effect of the JNK inhibitor according to SEQ ID NO: 172 ("XG-104") on EIU was evaluated using clinical scoring and PMN cells quantification 24 hours after induction. Ocular examinations were performed by slit lamp at 24 hours i.e. at the clinical peak of the disease in this model.

The intensity of clinical ocular inflammation was scored on a scale from 0 to 5 for each eye:
Grade 0: no inflammation,
Grade 1: presence of a minimal iris and conjunctival vasodilatation but without the observation of flare or cells in the anterior chamber (AC),
Grade 2: presence of moderate iris and conjunctival vessel dilation but without evident flare or cells in the AC,
Grade 3: presence of intense iris vessels dilation, flare and less than 10 cells per slit lamp, field in the AC,
Grade 4: presence of more severe clinical signs than grade 3, with more than 10 cells in the AC with or without the formation of a hypopyon,
Grade 5: presence of intense inflammatory reaction, fibrin formation in the AC and total seclusion of the pupil.

Clinical evaluation was performed in a blinded manner.

For histology, eighteen eyeballs (one per animal) were collected and fixed for 1 h at room temperature in phosphate buffered saline (PBS) containing 4% paraformaldehyde before being rinsed overnight in PBS. The next day, samples were embedded in optimal cutting temperature (OTC) compound (Tissue-Tek®, Sakura Finetek, Zoeterwoude, Netherland) and the optic nerve level using a cryostat (Leica CM 3050S, France) and mounted on super-frost slides for histology. After nuclei staining with DAPI (Sigma-Aldrich, France), sections were mounted in PBS/Glycerol (1/1) and observed by fluorescence photomicroscopy (FXA Microphot, Nikon, USA). Digitized micrographs were obtained usinga digital camera (Spot, BFI Optilas, France). PMN cells identified by the shape of their nuclei stained with DAPI, were quantified on histological sections. The analysis was performed with 2 different sections per eye at the optic nerve head level.

Twenty-four hours after LPS induction, clinical scores for the vehicle-treated rats were 4.6±0.2 (mean±SEM, n=8). Reduction was calculated as (grade in vehicle-treated eye—grade in test item treated eye)/(grade in vehicle-treated eye). A significant reduction (*$p<0.05$, $p<0.01$) in the severity of the ocular inflammation was detected 24 hours after induction and intravenous treatment with the JNK inhibitor according to SEQ ID NO: 172 ("XG-104") (1 mg/kg) administered 48 hours before EIU induction (mean score: 2.8±0.3), corresponding to a 40% () decrease of EIU scores compared with the score observed in vehicle group, 24 hours after induction and intravenous treatment with the JNK inhibitor according to SEQ ID NO: 172 ("XG-104") (1 mg/kg) administered 1 week before EIU induction (mean score: 3.3±0.3), corresponding to a 27% (*) decrease of EIU scores compared with the score observed in vehicle group, and 24 hours after induction and intravenous treatment with the JNK inhibitor according to SEQ ID NO: 172 ("XG-104") (1 mg/kg) administered 2 weeks before EIU induction (mean score: 3.0±0.2), corresponding to a 35% (**) decrease of EIU scores compared with the score observed in vehicle group. However, no significant reduction was observed 24 hours after induction and intravenous treatment with the JNK inhibitor according to SEQ ID NO: 172 ("XG-104") (1 mg/kg) administered 4 weeks before EIU induction (mean score: 4.2±0.1), corresponding to a 9% decrease of EIU scores compared with the score observed in vehicle group.

A single intravenous treatment with dexamethasone (2 mg/kg) immediately before EIU induction used as positive control drug also significantly reduced the clinical scores by 69% (mean score: 1.4±0.2, $p<0.01$).

In the histological investigation the number of PMN cells was significantly decreased when the JNK inhibitor according to SEQ ID NO: 172 ("XG-104") was administered 4 weeks (p<0.05) and 2 weeks (p<0.01) before EIU induction. Accordingly, the number of PMN cells was significantly decreased when dexamethasone was administered immediately before EIU induction.

Conclusion: The aim of this study was to evaluate the action duration of the JNK inhibitor according to SEQ ID NO: 172 ("XG-104") (1 mg/kg) as an anti-inflammatory in the Endotoxin-Induced Uveitis (EIU) model in rats. The effect of XG-104 on EIU was evaluated using clinical scoring and PMN cells quantification 24 hours after induction. The mean clinical score of XG-104 treated eyes 48 hours, 1 week and 2 weeks after LPS challenge was statistically different from the mean score of vehicle group with 40%, 27% and 35% reduction, respectively. The number of PMN cells was significantly decreased when XG-104 was administered 2 and 4 weeks, respectively, before EIU induction with 88% and 69% reduction compared to vehicle treated group, respectively. Dexamethasone significantly reduced the clinical score and the PMN cells number when administered immediately before LPS challenge. The action duration of XG-104 was therefore demonstrated to be between 2 and 4 weeks.

Example 18: Effects of the JNK Inhibitor According to SEQ ID NO: 172 ("XG-104") on Renal Ischemia/Reperfusion Lesions Renal Ischemia/Reperfusion (Renal I/R) injury is a commonly employed model of acute kidney injury (AKI), also known as acute renal failure. In addition to the clinical relevance of studies that examine renal I/R injury to acute kidney injury, experimental renal I/R injury is also an important model that is used to assess the conditions that occur in patients receiving a kidney transplant. Depending upon the donor, transplanted kidneys are not perfused with blood for a variable amount of time prior to transplantation. Because AKI has such serious effects in patients, and all transplanted kidneys experience renal I/R injury to some extent, the clinical relevance and translational importance of this type of research to human health is extremely high. The aim of this study is thus to investigate the influence of the JNK inhibitor according to SEQ ID NO: 172 ("XG-104") on experimental renal ischemia/reperfusion in rats.

Twenty-six (26) male Wistar rats (age 5-6 weeks) were used in this study (divided into 2 groups of 10 rats and 1 group of 6 rats). Rats were housed in standard cages and had free access to food and tap water. Each day, the general behavior and the appearance of all animals were observed. The health of the animals was monitored (moribund animals, abnormal important loss of weight, major intolerance of the substance, etc. . . . ). No rats were removed.

Renal ischemia was induced by clamping both renal pedicles with atraumatic clamp. A single dose of 2 mg/kg of the JNK inhibitor according to SEQ ID NO: 172 (in 0.9% NaCl as vehicle) or vehicle, respectively, was administered by IV injection in the tail vein on Day 0, one hour after clamping period (after reperfusion) both renal pedicles with atraumatic clamp. The administration volume was 2 ml/kg. Heparin (5000 UI/kg) was administered intraperitoneally 1 hour before clamping (in all groups).

The table below summarizes the random allocation:

| Group N° | Treatment (1 hour after clamping) | Dose volume/ Route of administration | Concentration | Renal Ischemia time (min) | Number of animals |
|---|---|---|---|---|---|
| 1 | NaCl 0.9% | 2 mL/kg, IV | 0 | | 6 |
| 2 | NaCl 0.9% | 2 mL/kg, IV | 0 | 40 | 10 |
| 3 | XG-104 (2 mg/kg) | 2 mL/kg, IV | 1 mg/mL | 40 | 10 |

For sample collection, rats were housed individually in metabolic cages (Techniplast, France). Urine was collected at 72 hours. Blood samples were obtained from tail vein before and at 24 hours after reperfusion. After animal sacrifice, both kidneys were collected.

For evaluation of proteinuria and albuminuria appropriate kits from Advia Chemistry 1650 (Bayer Healthcare AG, Leverkusen, Germany) were used.

For evaluation of renal function, blood was collected from the tail vein at 24 hours after reperfusion. Serum creatinine (µmol/mL) and urea concentrations (mmol/mL) were measured using appropriate kits (Bayer Healthcare AG, Leverkusen, Germany).

Evaluation of histological lesions was performed at 24 and 72 hours after reperfusion.

For light microscopy, kidneys were be incubated for 16 hours in Dubosq-Brazil, dehydrated, embedded in paraffin, cut into sections and stained with hematoxylin and eosin (H&E) or with periodic acid-Schiff (PAS).

For immunohistochemistry, kidney samples were fixed for 16 hours in Dubosq Brazil, and subsequently dehydrated and embedded in paraffin. Antigen retrieval was performed by immersing the slides in boiling 0.01 M citrate buffer in a 500 W microwave oven for 15 min. The endogenous peroxidase activity was blocked with 0.3% $H_2O_2$ in methanol for 30 min. Slides were incubated with the blocking reagents consisting of the Avidin-biotin solution for 30 min and the normal blocking serum for 20 min. For immunodetection, the slides were incubated overnight with an antibody, then with a biotinylated secondary antibody. An avidinbiotinylated horseradish peroxidase complex (Vectastain ABC Reagent, Vector Laboratories; Burlingame, Calif.) and 3,3'-diaminobenzidine (Sigma Biochemicals; St Louis, Mo.) as a chromogen were applied for visualization of the immunoreaction. Slides were counterstained with hematoxylin. Omission of the primary antibody was considered as a negative control.

Immunofluorescence labeling was carried out on 4 mm thick cryostat sections of kidney tissue fixed in acetone for 10 min, air-dried for 30 min at room temperature, then incubated in PBS for 3 min and blocked in 1% BSA in PBS. The sections were incubated with the indicated antibodies for 1 hour at room temperature, washed in PBS and incubated with Red Texas-conjugated secondary antibodies. Sections will be examined by fluorescence microscopy (Zeiss).

Moreover, expression of several markers specific of podocyte damage, inflammation and renal fibrosis (RelA, TGF β, TNFα, Masson trichrome) were evaluated by immunohistochemistry and immunofluorescence. Quantitative transcription profile of TNFα, IL6, CXCL 1 (KC), CXCL2 (MIP-2) and MCP1 in kidneys were determined.

Figure 42:
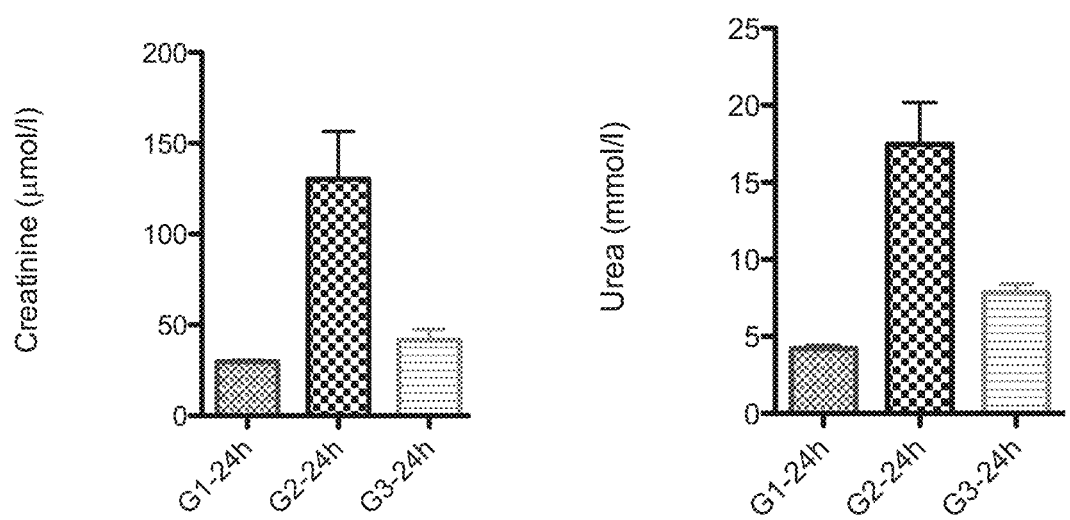
FIG. 42 Renal ischemia was induced in rats of group G2 and group G3 by clamping both renal pedicles with atraumatic clamp for 40 min, whereas in group G1 no ischemia was induced. Rats of group G3 received a single dose of 2 mg/kg of the JNK inhibitor according to SEQ ID NO. 172 ("XG-104") (in 0.9% NaCl as vehicle) and rats of groups G1 and G2 received vehicle, respectively, by IV injection in the tail vein on Day 0, one hour after clamping period (after reperfusion) both renal pedicles with atraumatic clamp. Serum creatinine and urea were increased in vehicle-treated ischemic rats (G2) 24 h following ischemia, as compared to vehicle-treated controls rats without ischemia (G1). On the other hand, XG-104-treated-ischemic rats (G3) exhibited lower serum creatinine and lower urea, relatively to untreated ischemic rats (G2).

Results:

Results are shown in FIG. 42. Serum creatinine and urea were increased in vehicle-treated ischemic rats (G2) 24 h following ischemia, as compared to vehicle-treated controls rats without ischemia (G1). On the other hand, ischemic rats treated with of the JNK inhibitor according to SEQ ID NO: 172 (G3) exhibited lower serum creatinine and lower urea, relatively to untreated ischemic rats (G2). These results suggest that the JNK inhibitor according to SEQ ID NO: 172 ("XG-104") may prevent the ischemia-induced renal failure.

Example 19: Antitumour Activity of the JNK Inhibitor According to SEQ ID NO: 172 ("XG-104") Against Human Liver Tumour Cell Lines The aim of this study is to determine the cytotoxic activity of the JNK inhibitor according to SEQ ID NO: 172 ("XG-104") against human hepatocarcinoma and human hepatoma cell lines using MTS assay.

The human hepatocarcinoma cell line HepG2 (origin: American Type Culture Collection, Manassas, Va., USA; the HepG2 cell line was established from the tumor tissue of a 15-year old Argentine boy with a hepatocellular carcinoma in 1975, there is no evidence of a Hepatitis B virus genome in this cell line) and the human hepatoma cell line PLC/PRF/5 (origin: American Type Culture Collection, Manassas, Va., USA; the PLC/PRF/5 cell line secrete hepatitis virus B surface antigen (HBsAg)) are used. Tumor cells are grown as monolayer at 37° C. in a humidified atmosphere (5% $CO_2$, 95% air). The culture medium is EMEM (ref: BE12-611F, Lonza) supplemented with 10% fetal bovine serum (ref: 3302, Pan), 0.1 mM NEAA (ref: BE13-114E, Lonza) and 1 mM NaPyr (ref: BE13-115E, Lonza). The cells are adherent to plastic flasks. For experimental use, tumor cells are detached from the culture flask by a 5-minute treatment with trypsin-versene (ref: BE02-007E, Lonza), in Hanks' medium without calcium or magnesium (ref: BE10-543F, Lonza) and neutralized by addition of complete culture medium. The cells are counted in a hemocytometer and their viability is assessed by 0.25% trypan blue exclusion assay.

Tumor cells are plated at the optimal seeding density in flat-bottom microtitration 96-well plates (ref 167008, Nunc, Dutscher, Brumath, France) and incubated in 190 □L drug-free culture medium at +37° C. in a humidified atmosphere containing 5% $CO_2$ for 24 hours before treatment.

Dilutions of the JNK inhibitor according to SEQ ID NO: 172 ("XG-104") as well as distribution to plates containing cells are performed manually. At treatment start 10 □L of the JNK inhibitor according to SEQ ID NO: 172 ("XG-104") dilutions are added to wells at the following final concentrations (for both cell lines): 0, $3.8 \times 10^{-4}$, $1.5 \times 10^{-3}$, $6.1 \times 10^{-3}$, $2.4 \times 10^{-2}$, $9.8 \times 10^{-2}$, 0.4, 1.6, 6.3, 25 and 100 □M. Then cells are incubated for 72 hours in 200 □L final volume of culture medium containing the JNK inhibitor according to SEQ ID NO: 172 ("XG-104") at +37° C. in a humidified atmosphere containing 5% $CO_2$. At the end of treatments, the cytotoxic activity is evaluated by a MTS assay.

The in vitro cytotoxic activity of the JNK inhibitor according to SEQ ID NO: 172 ("XG-104") is revealed by a MTS assay using tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). Like MTT, MTS is bioreduced by cells into a formazan product that is directly soluble in culture medium without processing, unlike MTT. At the end of cell treatment, 40 □L of a 0.22 □m freshly filtered combined solution of MTS (20 mL at 2 mg/mL, ref: Gll 11, Promega, Charbonnieres, France) and PMS (1 mL at 0.92 mg/mL, ref: P9625, Sigma) in Dulbecco's Phosphate Buffered Saline (DPBS, ref: 17-513F, Cambrex), are added in each well. Absorbance (Optical Density, OD) is measured at 490 nm in each well using a VICTOR3™ 1420 multilabeled counter (Wallac, PerkinElmer, Courtaboeuf, France).

Individual OD values of MTS assays are provided. Dose response for index of cytotoxicity (IC) is expressed as follows:

$$IC = (OD_{drug-exposed\ wells} / OD_{vehicle-exposed\ wells}) \times 100$$

whereby $IC_{50}$ refers to the drug concentration to obtain a 50% inhibition of cell proliferation. $IC_{50}$ represent drug concentration required to obtain 50% of cellular cytotoxicity. Dose-response curves are plotted using XLFit5 (IDBS, United Kingdom) and provided. The $IC_{50}$ determination values are calculated using the XLFit5 software from semi-log curves. Each individual $IC_{50}$ determination values are provided as well as mean±SD $IC_{50}$ values.

Figure 45A:
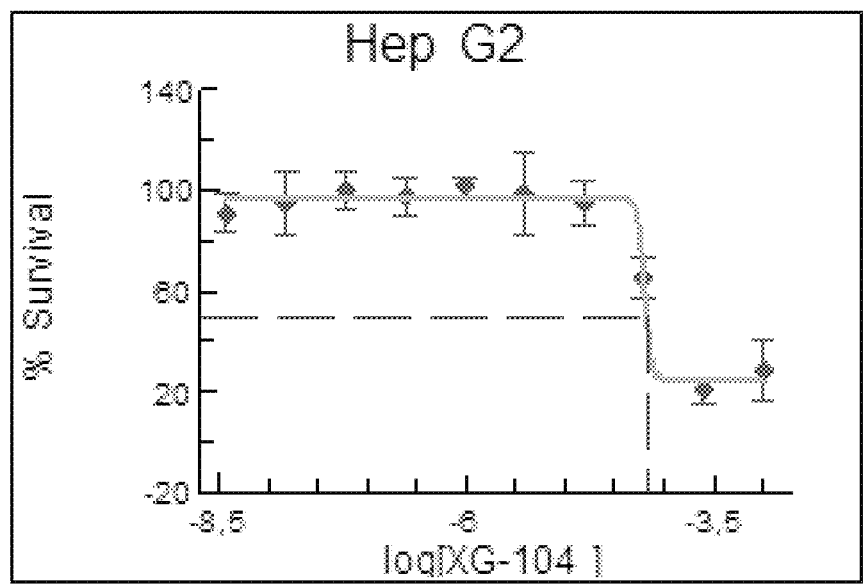
FIG. 45A and FIG. 45B show for Example 19 the results of the determination of of the cytotoxic activity of XG-104 against HepG2 (FIG. 45A) and PLC/PRF/5 (FIG. 45B) tumour cell lines using MTS assay.
Figure 45B:
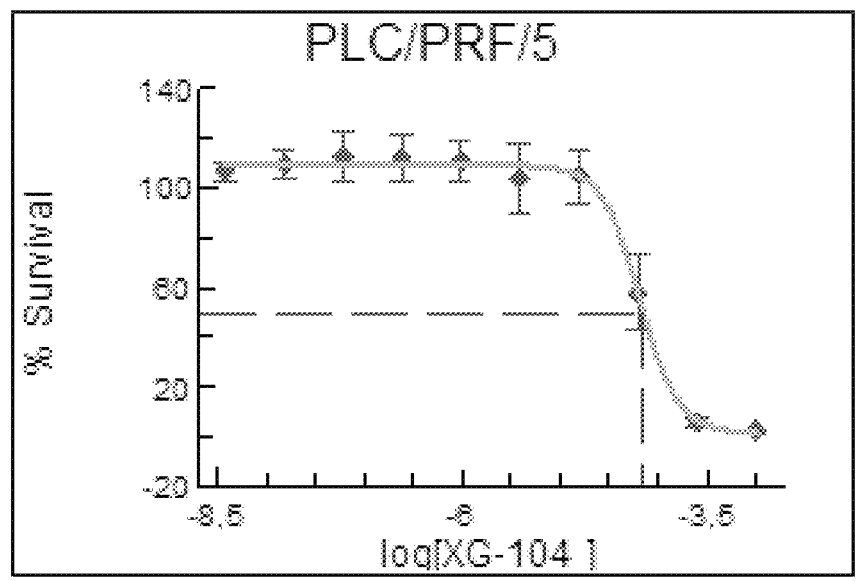

FIG. 45 shows the results of the determination of of the cytotoxic activity of XG-104 against HepG2 and PLC/PRF/5 tumour cell lines using MTS assay.

Example 20: Effects of the JNK Inhibitor According to SEQ ID NO: 172 ("XG-104") in a Mouse Model of Psoriasis The aim of this study is to evaluate the effects of the JNK inhibitor according to SEQ ID NO: 172 ("XG-104") in the BK5.STAT3C mouse model of psoriasis. This model uses heterozygous transgenic mice whose keratinocytes express a constitutively active form of Stat3.

Psoriasis is a chronic inflammatory skin disorder characterized by accelerated growth and altered differentiation of keratinocytes and angiogenesis with marked ectasia of blood vessels. It develops through interactions between the skin and immune system mediated by T cells, dendritic cells, and inflammatory cytokines. In vivo modelling of the disease has been achieved with varying degrees of success. While xenotransplantation models reflect the human disease the best, they are more elaborate and complex. One of the transgenic mouse models resembling human psoriasis the most is the K5.STAT3C model. K5.STAT3C mice express the constitutively active form of the transcription factor Stat3 in basal keratinocytes, and upon tape stripping develop skin lesions that histologically recapitulate hallmarks of psoriasis. As in human psoriasis, T cells played a critical role for the induction of the psoriatic phenotype. Here, an evaluation of efficacy for compound XG-104 was performed in the K5.STAT3C mouse model of psoriasis.

To this end, two independent experiments are performed, each with at least 15 mice per experiment (5 mice per group). In each experiment, BK5.STAT3C heterozygous transgenic mice (Tg(KRT5-Stat3*A661C*N663C)1Jdg, henceforth referred to as K5.STAT3C mice) were randomly allocated to the following experimental groups 1 and 2, and wild-type littermates were allocated to group 3:

| Group | n | Treatment | Dose Level (mg/kg) | Dose Conc. (mg/mL) | Dose Vol. (mL/kg) | Freq. | Route | Treatment Schedule |
|---|---|---|---|---|---|---|---|---|
| 1 | 5 (tg) | Vehicle | n/a | n/a | 10 | QD | IP | D 0-D 5 |
| 2 | 5 (tg) | XG-104 | 5 | 0.5 | 10 | QD | IP | D 0-D 5 |
| 3 | 5 (wt) | Vehicle | n/a | n/a | 10 | QD | IP | D 0-D 5 |

Group 1 (Vehicle, BK5.STAT3C transgenic mice):
Vehicle (0.9% NaCl) is given once a day (QD) by intraperitoneal injection from Day 0 to Day 5.
Group 2 (XG-104, BK5.STAT3C transgenic mice):
The JNK inhibitor according to SEQ ID NO: 172 ("XG-104") is given a day (QD) by intraperitoneal injection from Day 0 to Day 5.
Group 3 (Vehicle, FVB wild type mice)
Vehicle (0.9% NaCl) is given once a day (QD) by intraperitoneal injection from Day 0 to Day 5.

On Day 0, psoriasis is induced by tape striping (12-18 times) the back of the mouse after depilation. To this end, mice were anaesthetized using a Ketamine/Xylazine cocktail (100 mg/kg and 10 mg/kg respectively) intraperitoneally, shaved, depilated and skin injury was applied by 15 gentle strokes of tape stripping. Mice were treated with either vehicle (saline) or XG-104 right before anaesthesia on day 0 and once a day thereafter for 5 days. Mice were sacrificed after 5 days of experimentation by dislocation and lesions were excised for histological evaluation. Two independent experiments were performed with 5 mice per group (wt vehicle; tg vehicle; tg XG-104).

Animals are weighed once on day 0. All animals are observed for signs of ill health daily throughout the study. After termination of the study at day 5, approximately 1 cm$^2$ skin biopsy (lesions) is collected on the back of each mouse, embedded with Optimal Cutting Temperature (OCT)-containing moulds, frozen on dry ice, sectioned in 6 μm slices using a cryotome and stained with H&E. Epidermal thickness (acanthosis) is histologically measured blinded by two independent experimenters. One slide per mouse and 10 different zones of the sections are measured.

Figure 43A:
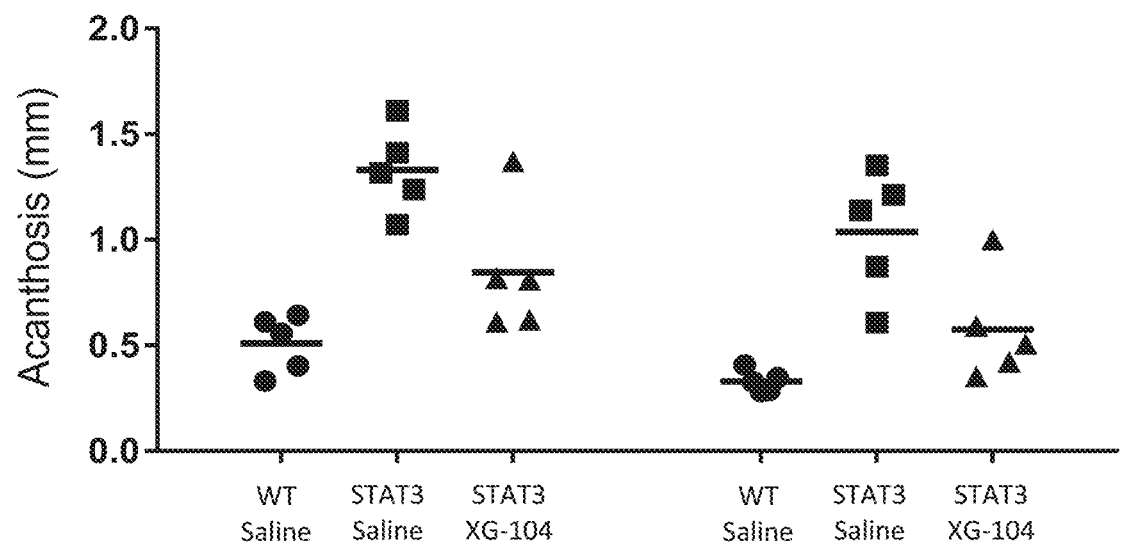
FIG. 43A and FIG. 43B show for Example 20 that XG-104 blocks the development of a psoriatic phenotype in vivo in the K5.STAT3c model for psoriasis. Wild type or K5STAT3c mice were treated with either vehicle (Saline) or XG-104 compound prior to tape stripping, followed by daily treatments of vehicle or XG-104. After five days, mice were sacrificed and biopsies taken from the lesion sites in order to quantify acanthosis (thickening of the epidermis). Quantification of acanthosis is shown for two independent experiments separately (FIG. 43A) and combined (FIG. 43B). Dots represent mean values from individual mice (A&B). A one-way ANOVA test was performed to analyze significance.
Figure 43B:
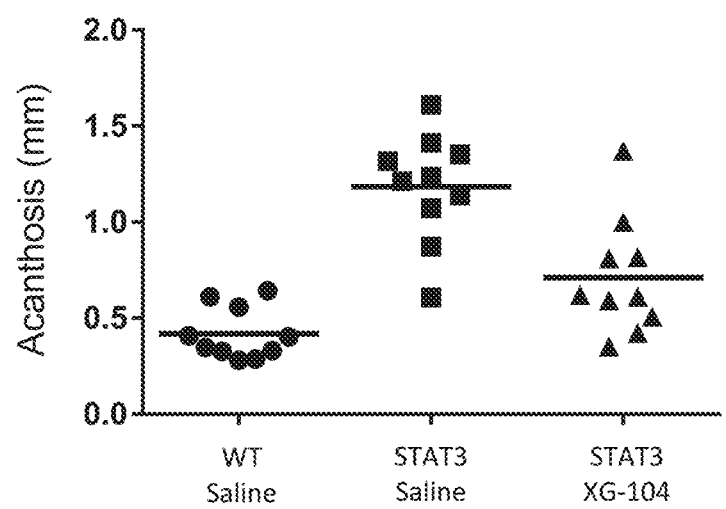
Figure 44:
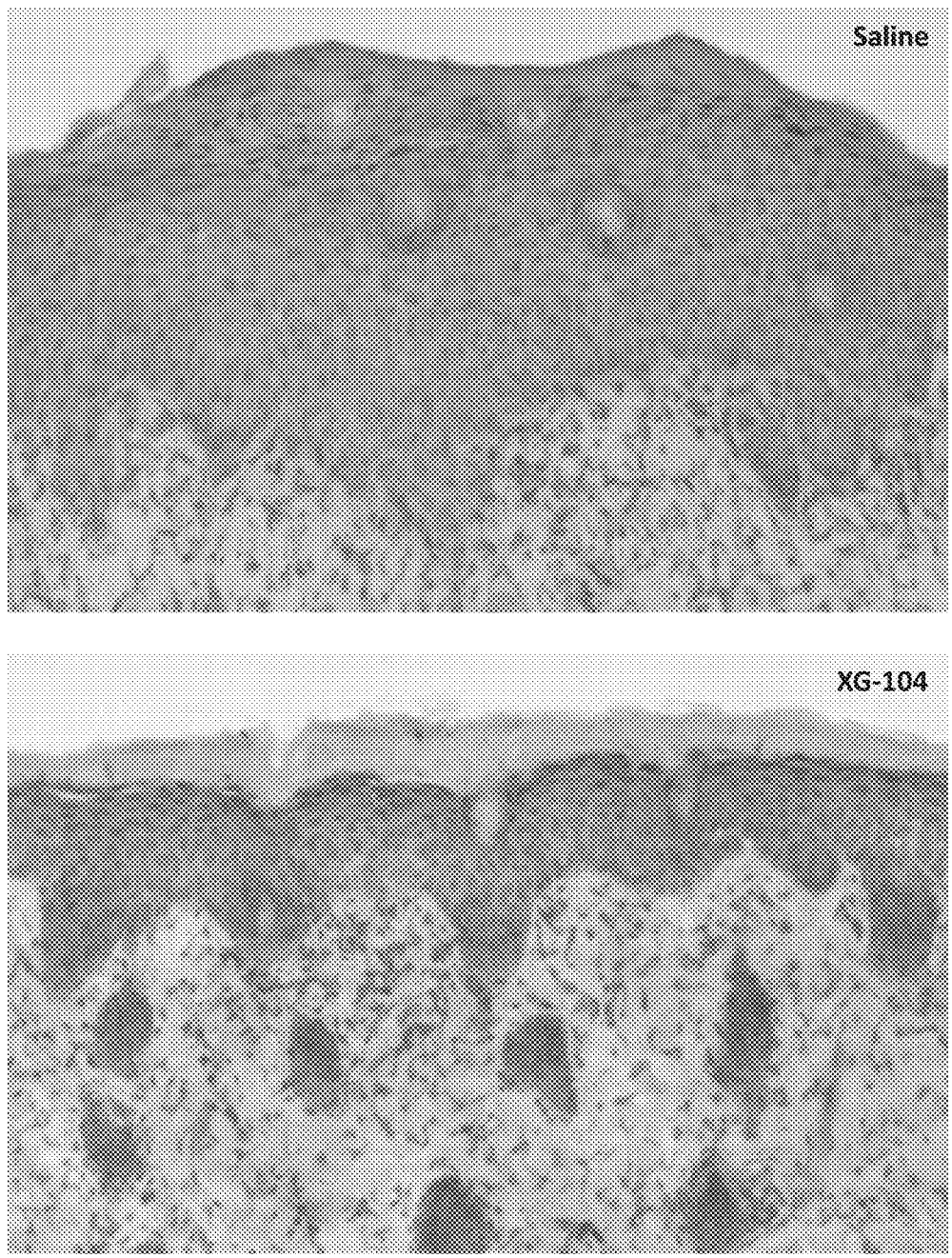
FIG. 44 shows for Example 20 representative histologies of K5.STAT3c mice treated with either Saline or XG-104, indicating that XG-104 blocks the development of a psoriatic phenotype in vivo in the K5.STAT3c model for psoriasis.

As compared to wild-type littermates, tape stripping induced a thickened epidermis (acanthosis) on all K5.STAT3C mice treated with vehicle, with prominent sites of parakeratosis (FIG. 43 A). Treatment with XG-104 significantly reduced the acanthosis in both experiments (FIG. 43 A). Pooling of the values of both experiments (FIG. 43 B), adds further power to the observations by increasing the statistical significance (p<0.001). Additionally, we observed absence of any parakeratosis (retention of nuclei in the corneal layer) over the extent of the skin biopsies in XG-104 treated mice as compared to mice treated with vehicle (FIG. 44). Taken together, these data show that XG-104 is able to efficiently inhibit the induction of a psoriatic phenotype in the K5.STAT3C mouse.

Thus, the results confirm that XG-104 treatment is sufficient to block the development of a psoriatic phenotype in the K5.STAT3C mouse for psoriasis.

Example 21: Safety, Tolerability and Pharmacokinetics of Single and Repeated Topical Doses of the JNK Inhibitor According to SEQ ID NO: 172 ("XG-104") Administered to Healthy Male Volunteers in a Randomized, Double Blind, Placebo Controlled at Each Dose Level Phase I Study The primary objective of the study was to assess determine the tolerability and safety of single and repeated instillations of ascending doses of XG-104 (the JNK inhibitor according to SEQ ID NO: 172) in healthy male volunteers. The secondary objective of the study was to assess the systemic pharmacokinetics of single and repeated instillations of ascending doses of XG-104 in healthy male volunteers.

XG-104 was prepared as solution for instillations (in NaCl 0.9%). NaCl 0.9% served as placebo. A total of 49 subjects were included in this study, 28 in the "Single dose part" of this study and 21 in the "Multiple dose part" of this study. In the single dose part, the 28 subjects included were randomised between one of the 5 groups: 5 subjects in each of the 4 XG-104 groups (0.1 mg, 0.2 mg, 0.4 mg, 0.8 mg) (0.2, 0.4, 0.8 and 1.6%, respectively) and 8 subjects in the placebo group. In the multiple dose part, the 21 subjects included were randomised between one of the 4 groups: 5 subjects in each of the 3 XG-104 groups (0.1 mg, 0.2 mg, 0.4 mg) and 6 subjects in the placebo group. All subjects completed the study.

In the "Single dose part" of this study, single topical doses of 0.1, 0.2, 0.4 and 0.8 mg (0.2, 0.4, 0.8 and 1.6%, respectively) of XG-104 were tested. A single administration of XG-104 or placebo was performed on day 1 (D1) (one drop in the right eye). In the single dose part, subjects were hospitalized for approximately 36 h, namely from day −1 (D−1) evening to D2 morning. On day 3 an ambulatory visit was performed and the study ended with a visit at D4.

In the "Multiple dose part" of this study, three dose levels were tested. Doses were chosen according to the results of the single dose part as follows: first group: 0.1 mg (0.2%), second group: 0.2 mg (0.4%), and third group: 0.4 mg (0.8%). XG-104 or placebo was administered tid ("ter in die"—three times daily), each time 1 drop in the right eye, from D1 to D21. The administration took place at around 8 a.m., 12 a.m. and 8 p.m. In the multiple dose part, subjects were hospitalized from D−1 evening to D22 morning, whereby the end of the study was a visit at D36 (±2). For more flexibility, subjects had the possibility to perform some visits in ambulatory. In that case visits were the following: hospitalization for approximately 36 h, D−1 evening to D2 morning, ambulatory visits from D2 to D7, hospitalization for approximately 36 h, D7 evening to D9 morning, ambulatory visits from D9 to D14, hospitalization for approximately 36 h, D14 evening to D16 morning, ambulatory visits from D16 to D20, and hospitalization for approximately 36 h, D20 evening to D22 morning. The end of the study was a visit at D36 (±2), accordingly.

The safety parameters evaluated included: physical examination; vital signs (BP, PR); 12-lead ECG (electrocardiogram); fundus of the eye, intraocular pressure, slit lamp examination, best-corrected visual acuity, redness; Schirmer's tear test, TBUT (tear film break-up time); clinical laboratory tests (haematology, haemostasis, clinical chemistry and urinalysis); adverse events; and assessment of tolerability.

The pharmacokinetic parameters evaluated included the following plasma parameters: $C_{max}$, $T_{max}$, $AUC_{0-12}$, $AUC_{0-24}$, $AUC_t$, $AUC_{inf}$, $Kel$, $t_{1/2}$, % AUCextra, $V_d/F$, $Cl/F$.

Results:
1. Pharmacokinetic Results:
In this study, six hundred human plasma samples were analyzed to quantify XG-104. All standard samples, QC samples and calibration curve parameters met the acceptance criteria. However, all concentration measured in specimen samples were below the LLOQ (lower limit of quantification: <40 ng/mL).

2. Safety Results:
2.1 Single Dose Part
During the overall study period, 15 out of 28 subjects reported the occurrence of 34 adverse events. 32 of these were treatment emergent adverse events (TEAEs) and 2 were non-emergent (blood creatine phosphokinase increased and neck pain). Among the TEAEs, 21 were experienced after XG-104 administration and 11 after placebo administration. All were of mild intensity. The most reported TEAEs were eye disorders: 17 reported on the right eye (treated) and 13 reported on the left eye (non-treated). Among TEAEs reported on the right eye, 3 were probably related (all in the XG-104 0.8 mg (1.6%) group) to study drug administration (conjunctivitis (2) and conjunctival hyperaemia (1)) and 14 were unrelated (punctate keratitis (12): 5 in the placebo group, 2 in the XG-104 0.1 mg (0.2%) group, 2 in the XG-104 0.2 mg (0.4%) group, 2 in the XG-104 0.4 mg (0.8%) group, 1 in the XG-104 0.8 mg (1.6%) group; and eye pruritus (1) in 0.1 mg (0.2%) and conjunctival hyperaemia (1) in 0.2 mg (0.4%) group). All TEAEs reported on the left eye were unrelated to study drug administration (punctate keratitis (12), conjunctival hyperaemia (1)). No serious adverse events were reported during this study. No clinically relevant findings were observed in clinical examination, vital signs or ECG parameters.

A single dose of XG-104 0.1 mg, 0.2 mg, 0.4 mg was well tolerated and a single dose of XG-104 0.8 mg (1.6%) was rather well tolerated (2 episodes of conjunctivitis). The choice for the three dose-levels in repeated doses was: 0.1 mg, 0.2 mg and 0.4 mg (0.2, 0.4 and 0.8%, respectively).

2.2 Multiple Dose Part
During the overall study period, 17 out of 21 subjects reported the occurrence of 66 adverse events. 65 of these were treatment emergent adverse events (TEAEs) and 1 was non-emergent (punctate keratitis). Among the TEAEs, 61 were experienced after XG-104 administration and 4 after placebo administration. All were of mild to moderate intensity. The most reported TEAEs were eye disorders: 44 reported on the right eye (treated) and 18 reported on the left eye (non-treated). Among TEAEs reported on the right eye, 3 were probably related to study drug administration (conjunctivas (2) in the XG-104 0.1 mg (0.2%) group and eyelid irritation (1) in the XG-104 0.2 mg (0.4%) group); 39 were unlikely related (conjunctival hyperaemia (21): 6 in the XG-104 0.1 mg (0.2%) group, 5 in the XG-104 0.2 mg (0.4%) group and 10 in the XG-104 0.4 mg (0.8%) group; punctate keratitis (17): 6 in the XG-104 0.1 mg (0.2%) group, 6 in the XG-104 0.2 mg (0.4%) group and 5 in the XG-104 0.4 mg (0.8%) group; conjunctivitis (1) in the XG-104 0.4 mg (0.8%) group); 2 were unrelated (punctate keratitis (2): 1 in the placebo group and 1 in the XG-104 0.2 mg (0.4%) group). Among TEAEs reported on the left eye, 12 were unlikely related to study drug administration (conjunctival hyperaemia (7): 2 in the XG-104 0.1 mg (0.2%) group, 3 in the XG-104 0.2 mg (0.4%) group and 2 in the XG-104 0.4 mg (0.8%) group; punctate keratitis (5): 2 in the XG-104 0.1 mg (0.2%) group, 1 in the XG-104 0.2 mg (0.4%) group and 2 in the XG-104 0.4 mg (0.8%) group); 6 were unrelated to study administration (punctate keratitis (6): 1 in the placebo group, 1 in the XG-104 0.1 mg (0.2%) group and 4 in the XG-104 0.2 mg (0.4%) group). Ophthalmic examination confirmed a global dose effect (lower abnormal examination in the placebo group) increasing between day 3 and day 20.

No serious adverse events were reported during this study. No clinically relevant findings were observed in clinical examination, biological parameters, vital signs or ECG parameters. A repeated dose t.i.d. of XG-104 (0.1 mg, 0.2 mg, 0.4 mg) in 21 healthy male subjects was well tolerated.

Example 22: Efficacy and Safety of a JNK Inhibitor for the Treatment of Dry Eye (Clinical Phase II)

A multicenter, randomized, double-masked, placebo-controlled, clinical phase II study served to assess the efficacy and safety of ophthalmic solutions of the JNK inhibitor according to SEQ ID NO: 172 ("XG-104") in the environment and during challenge in the controlled adverse environment (CAESM) model for the treatment of dry eye. The purpose of this study is to assess the efficacy and safety of ophthalmic solutions of the JNK inhibitor according to SEQ ID NO: 172 compared to placebo for the treatment of the signs and symptoms of dry eye after a four week TID treatment period.

The "Controlled Adverse Environment" model is an environment designed and constructed to provide an environmental challenge to aggravate a clinical condition under study. In general, a controlled adverse environment (CAE) design can be used to control the environment, the subjects' activities, or a combination of both during the clinical trial, thereby providing a stressful environment to exacerbate clinical symptoms and signs of dry eye. Such a stress test is especially valuable in establishing a pharmacological effect in a short period of time. Humidity, temperature, and airflow are environmental variables that can be monitored and manipulated. Activities can include visual tasks, and the blink rate and tear film stability can be monitored. Thus, the controlled adverse environment (CAESM) model is a clinical model that reproduces a standard ocular challenge (by regulation of humidity, temperature, airflow, lighting conditions, and visual tasking) for the investigation of treatments for dry eye. A key aspect of the CAE is its utility in distinguishing subpopulations of dry eye patients. Subjects challenged by environmental changes (such as those presented by the CAE) normally respond with some degree of physiological compensation, and previous studies have shown that the ability of these mechanisms to adequately compensate for environmental challenges is reduced in those with dry eye.

In this study the subjects are subjects who were diagnosed with dry eye (have a reported history for dry eye for at least six months prior to Visit 1, have a history of use or desire to use eye drops for dry eye symptoms within 6 months of Visit 1, report a score of 2 or higher in at least one symptom on the Ora Calibra™ Ocular Discomfort & 4-Symptom Questionnaire assessed pre-CAESM, at Visits 1 and 2, have a conjunctival redness score=1 on the Ora Calibra™ scale at Visits 1 and 2, have a total corneal fluorescein staining score=2 in at least one region according to the Ora Calibra™ Scale at Visits 1 and 2, pre-CAESM etc.).

Three different concentration of an ophthalmic solution of the JNK inhibitor according to SEQ ID NO: 172 ("XG- 104"), namely XG-104 0.2%, XG-104 0.4%, and XG-104 0.8% are compared versus placebo (vehicle: NaCl 0.9%) eye drops efficacy. Visits #1, 2, 3, and 4 are planned at days −7, 1, 15, and 29 respectively.

In particular corneal fluorescein staining in the inferior region change from Pre-CAESM to Post-CAESM, as measured by the Ora Calibra™ Scale, in the worst eye at baseline, preferably at visit 4 at day 29, and the worst dry eye symptom determined from subject diary data recorded preferably during the 1-week run-in period between Visit 1 and Visit 2, evaluated over the 7 days preceding Visit 4 (not including day of visit) during the treatment period, serve as primary outcome measures.

Secondary outcome measures are in particular (i) fluorescein staining (using Ora Calibra™ Scale and NEI Scale), preferably at visits 3 and 4 (pre- and post-CAESM; regions: central, superior, inferior (visit 3 preferably only as visit 4 is the primary endpoint), temporal, nasal, corneal sum, conjunctival sum and total), (ii) Lissamine green staining (using Ora Calibra™ Scale and NEI Scale), preferably at visits 3 and 4 (pre- and post-CAESM and change from pre- to post-CAESM; regions: central, superior, inferior, temporal, nasal, corneal sum, conjunctival sum, and total), (iii) tear film break-up time, preferably at visits 3 and 4 (pre- and post-CAESM), (iv) conjunctival redness using Ora Calibra™ Scale, preferably at visits 3 and 4 (pre- and post-CAESM), (v) lid margin redness using Ora Calibra™ Scale, preferably at visits 3 and 4 (pre- and post-CAESM), (vi) tear osmolarity, preferably at visits 2 and 4 (post-CAESM), (vii) blink rate, preferably at visits 3 and 4 (pre-CAESM) using Ora Calibra™ methodology, (viii) ocular protection index (OPI 2.0), preferably at visits 3 and 4 (pre-CAESM) using Ora Calibra™ methodology, (ix) unanesthetized Schirmer's Test, preferably at visits 3 and 4 (pre-CAESM), drop comfort and symptom assessment using Ora Calibra™ Scales after randomization, preferably at visits 2 and 3, (x) ocular surface disease index (OSDI), preferably at visits 3 and 4 (pre-CAESM), (xi) ocular discomfort using Ora Calibra™ Scale, preferably at visits 3 and 4 (pre and post-CAESM), (xii) ocular discomfort using Ora Calibra™ Discomfort and 4-Symptom Questionnaire, preferably at visits 3 and 4 (pre- and post-CAESM), (xiii) ocular discomfort using Ora Calibra™ Scale, preferably at visits 3 and 4 (during CAESM exposure), and (xiv) daily diary.

Other pre-specified outcome measures include in particular visual acuity (ETDRS), preferably at visits 1, 2, 3 and 4 (Days −7, 1, 15 and 29) (pre-CAESM), slit-lamp biomicroscopy, preferably at visits 1, 2, 3 and 4 (Days −7, 1, 15 and 29) (pre- and post-CAESM), adverse event query, dilated fundoscopy biomicroscopy, preferably at visits 1 and 4 (Days −7 and 29), and intraocular pressure, preferably at visits 1 and 4 (Days −7 and 29).

Example 23: Effects of XG-104 (the JNK Inhibitor According to SEQ ID No. 172) in a Rat Model of Kidney Bilateral Ischemia Reperfusion This study is based on the previous study of XG-104 in renal ischemia/reperfusion (Example 15). The aim of the study was to evaluate the effect of XG-104 on histological damages in a rat model of kidney bilateral ischemia reperfusion.

Ischemia reperfusion (IR) injury is a complex phenomenon, which is often encountered in vascular surgery, organ procurement and transplantation in humans. The experimental model of kidney bilateral ischemia reperfusion (IR) in rodents leads to an acute tubular injury characterized by impaired kidney function and tubular degeneration. The present model is frequently used for providing a rapid proof of concept for the use of drug candidates in preventing renal IR damages.

Male Sprague-Dawley rats weighing 200-250 g at delivery were used (Charles River Laboratories, L'Arbresle, France). Animals were delivered to the laboratory at least 5 days before the experiments during which time they were acclimatized to laboratory conditions. This study included 3 groups of 11-12 rats each, as follow:

| Group | IR surgery | Treatment (i.v.) | Number of animals/group |
|---|---|---|---|
| 1 | Sham-operated | vehicle | 12 |
| 2 | yes | vehicle | 11 |
| 3 | yes | XG-104 (2 mg/kg) | 11 |

Figure 46:
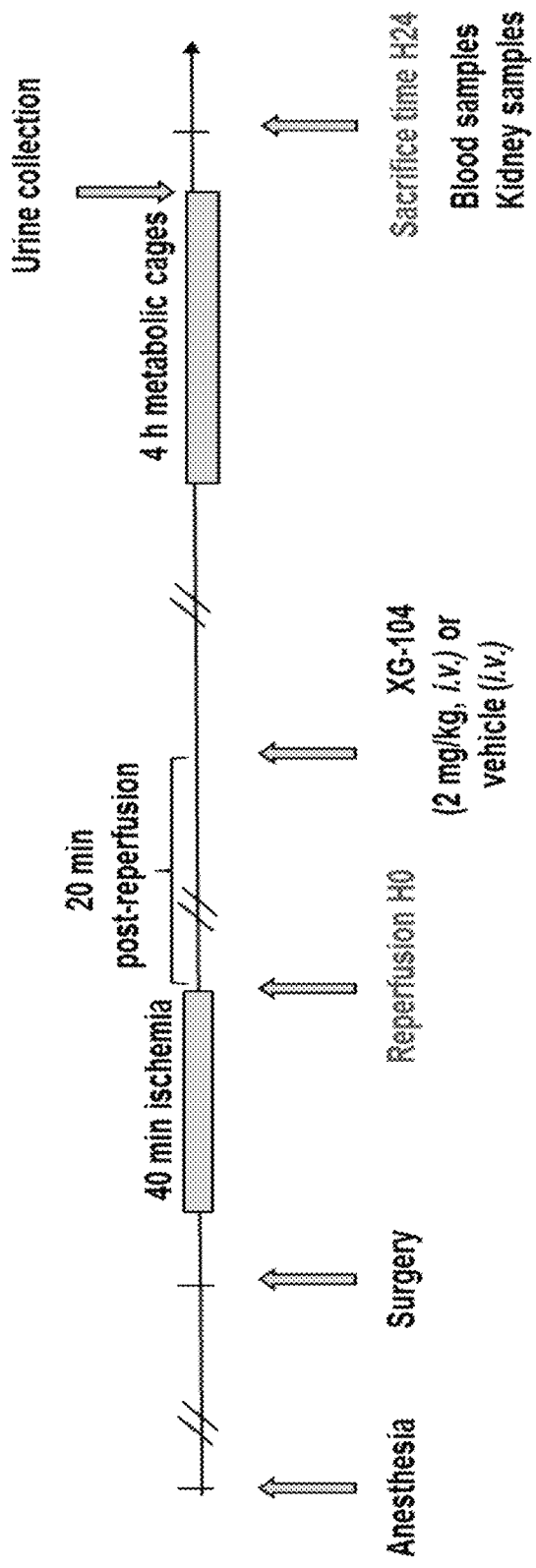
FIG. 46 shows for Example 23 the study design.

The study design is shown in FIG. 46.

The protocol of warm renal ischemia was similar to that previously described (Pechman K R et al., 2009). Briefly, under general anesthesia (pentobarbital; 60 mg/kg, i.p. and atropine; 1 mg/kg, i.p.), both renal pedicles were isolated and clamped for 40 minutes using atraumatic clamps. After this time, clamps were released to start reperfusion. Animals were maintained at 37° C. using a thermo-regulated system (TCAT-2LV Controller, Physitemp Instruments, Clifton, N.J., USA) during the surgery. All the animals were sacrificed 24 hours after the release of both vascular clamps (reperfusion). Sham-operated animals underwent the same surgical procedure without clamping of the kidney vessels.

XG-104 or vehicle (0.9% NaCl) were administered into the tail vein (i.v.) at the dose of 2 mg/kg twenty minutes after the release of the second vascular clamp. Intravenous administrations into the tail vein were performed using the volume of 1 mL/kg.

Figure 47:
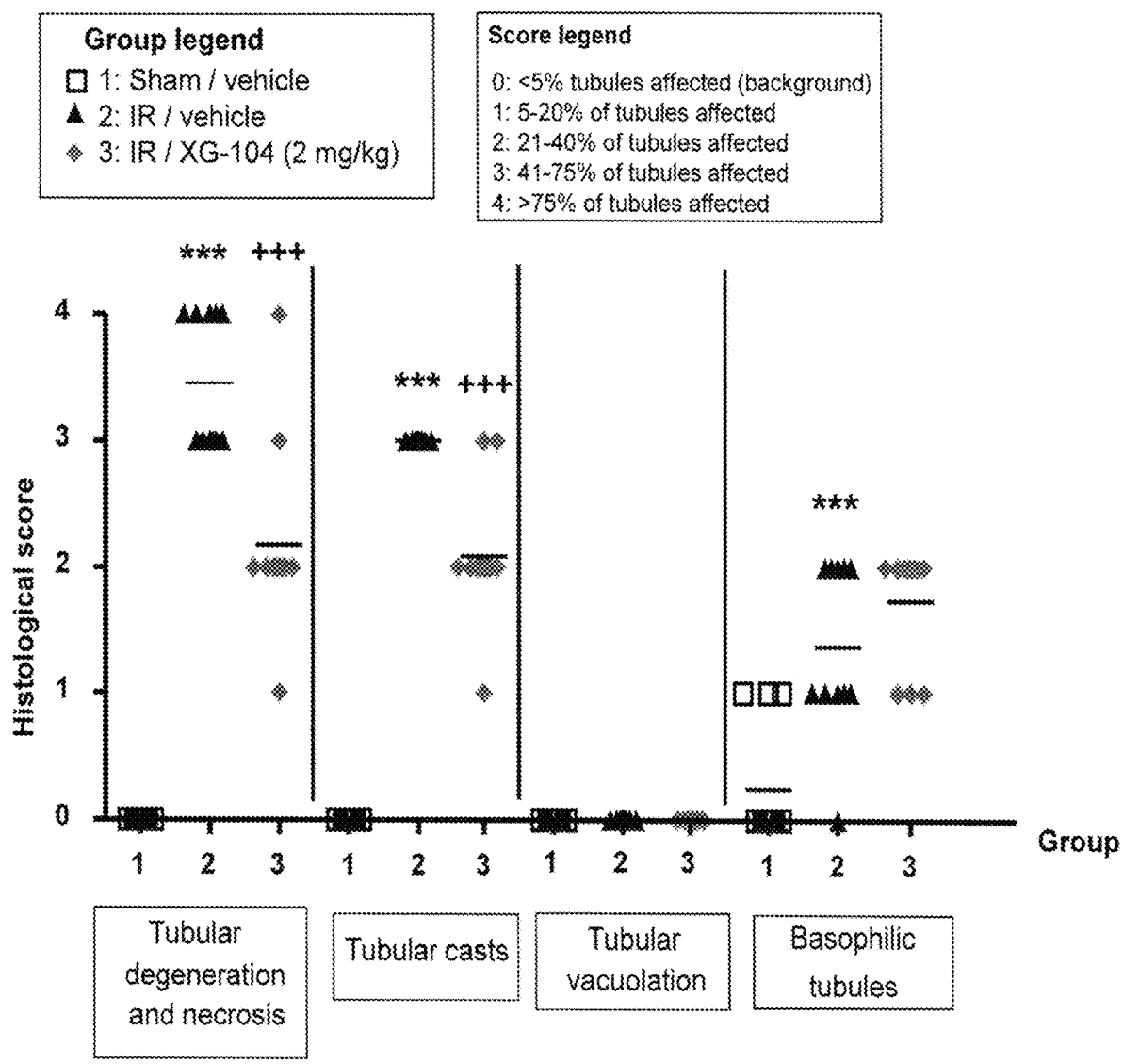
FIG. 47 shows for Example 23 the effects of vehicle and XG-104 (2 mg/kg, i.v.) on tubular damages in a rat model of bilateral IR. ***P<0.001 versus Group 1 (Sham/Vehicle) by a Student t-test ns; +P<0.05 versus Group 2 (IR/Vehicle) by a one way ANOVA followed by a Bonferroni's post test.

After sacrifice, kidneys were removed, cleaned from all connective tissue and capsule and weighted on an electronic balance (VWR, France). One kidney was transferred in formalin solution 10% (Sigma Aldrich, France) for at least 24 h and then transferred in ethanol 70% for further histological analysis performed by Histalim (Montpellier, France). Right and left kidneys were randomly chosen. Kidney samples were fixed in 10% formalin during 72 hours, transferred into 70% ethanol, then embedded in paraffin blocks by Histalim (Montpellier, France). One longitudinal section (3 to 5 □m) was made per block. Kidney sections of paraffin embedded tissue were stained by hematoxylin and eosin (H&E). All the slides were digitalized at ×20 magnitude using Nanozoomer 2.0 HT from Hamamatsu (Hamamatsu, Japan). Each tissue section was examined histologically in a blinded manner to determine if tubular changes were present. The severity of each finding was then graded as follows:

Tubular damage score consisted of either degeneration/necrosis, tubular epithelial vacuolation, regeneration (basophil tubules), and tubular cast:
 0: <5% tubules affected (background)
 1: 5-20% of tubules affected
 2: 21-40% of tubules affected
 3: 41-75% of tubules affected
 4: >75% of tubules affected As shown in FIG. 47, Group 2 (IR/Vehicle) animals showed a significant increase of tubular damages including tubular degeneration and necrosis, tubular cast formation, and basophilic tubules compared to Sham/Vehicle animals.

Figure 48:
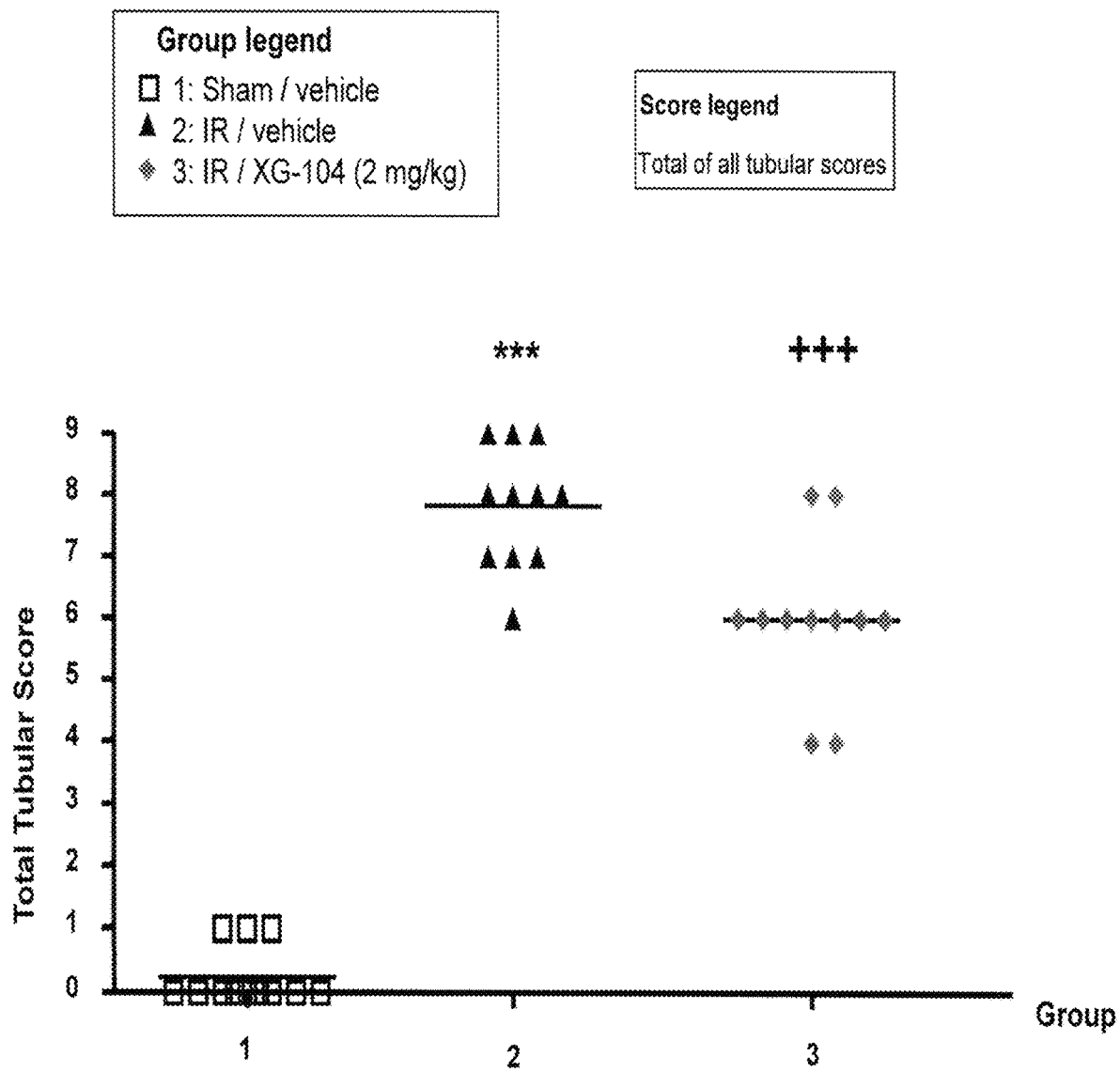
FIG. 48 shows for Example 23 the effects of of vehicle and XG-104 (2 mg/kg, i.v.) on total tubular histological scores in a rat model of bilateral IR. Total tubular score represents all tubular changes including degeneration and necrosis, tubular cast, tubular epithelial vacuolation and regeneration (basophil tubules). ***P<0.001 versus Group 1 (Sham/Vehicle) by a Student t-test; +P<0.05 versus Group 2 (IR/Vehicle) by a one way ANOVA followed by a Bonferroni's post test.
Figure 49:
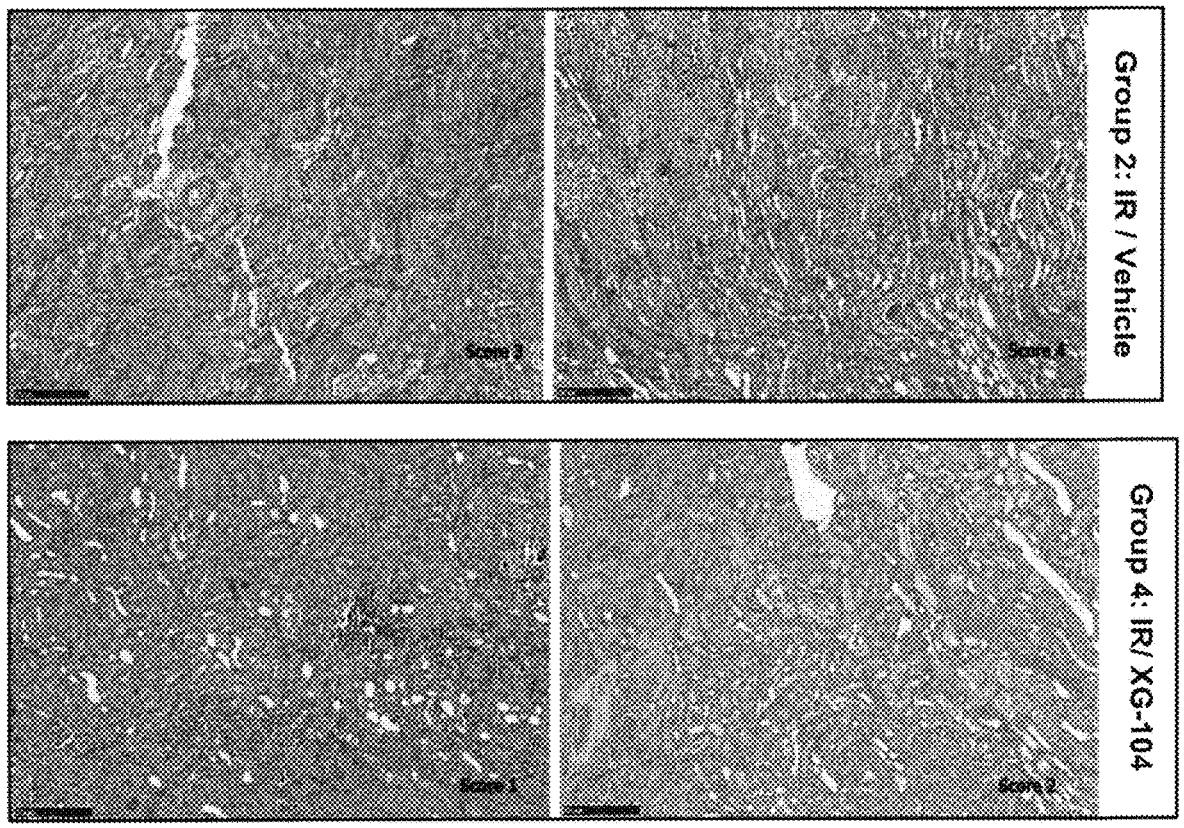
FIG. 49 shows for Example 23 representative images of hematoxylin/eosin stained kidney sections: comparison between Groups 2 (IR/Vehicle) and 3 (IR/XG-104). Animal 53 (Top Left), Animal 15 (Top Right), Animal 46 (Bottom left), and Animal 18 (Bottom right): 10×. Representative photomicrographs of tubular degeneration/necrosis and tubular casts in Group 2 (vehicle) and 3 (XG-104). Animals having scores from 1 to 4 are represented. The main difference between groups is that the severity of tubular necrosis and cast in Group 2 is generally higher than that observed in Group 3. In Group 2, lesions are extended partially or to the majority of the cortex. Comparatively, in Group 3, lesions are limited to the cortico-medullary junction. Lesions consist of a mixture of active necrosis, cellular tubular casts, hyaline casts, and occasional basophilic tubules.

XG-104 showed significant beneficial effects on tubular damages, specifically on tubular degeneration, necrosis and tubular cast formation (FIG. 47) and on the total tubular score (FIG. 48). The main difference in term of tubular degeneration and necrosis between animals from XG-104 treated rats (Group 3) and vehicle (Group 2) animals is that the number of tubules affected was lower, and the lesions were mostly limited to the cortico-medullary junction and not extended to the superficial cortex. Kidneys from Group 3 (IR/XG-104) presented also a less severe score for tubular casts when compared to Group 2 (IR/Vehicle). Representative images of these histologicals changes are included in FIG. 49.

In particular, tubular changes in Group 1 (Sham/Vehicle) were limited to the presence of single to a few basophilic tubules (Score 1) in 3/12 animals (FIG. 47). This incidence is within expected normal limits in naïve young adult control rats and was considered as incidental in origin. Comparatively, all animals in Group 2 (IR/Vehicle) presented moderate to marked (Score 3 and 4) tubular epithelial degeneration and necrosis (3.45±0.52). The most affected tubules were concentrated at the cortico-medullary junction and were histologically characterized by tubules containing large clumps of sloughed and necrotic epithelial cells. Tubular degenerative lesions were also present in most of the cortex in animals with the most severe lesions (Score 4). In addition to tubular degeneration, all animals showed a large number of tubular casts in lumen (Score 3). The presence of small to moderate number of basophilic tubules (Score 1 and 2, mean=1.36±0.67) was also observed throughout the cortex in 10/11 animals of Group 2 (IR/Vehicle). The basophilic tubules were indicative of early epithelial regeneration in tubules. For Group 3 (IR/XG-104), tubular lesions were essentially of the same nature and appearance to that observed in Group 2 (IR/Vehicle), but were generally less severe in distribution.

More specifically, the mean tubular epithelial degeneration/necrosis score were 2.67±0.65 and 2.18±0.75 in Group 3 (IR/XG-104), respectively. The main difference between Group 2 (IR/Vehicle) and Group 3 (IR/XG-104) was that several animals in the latter group showed a score of 2 (5/12 in Group 3 and 0/11 in Group 2). Finally, only 1/12 animal in Group 3 had a score of 4 comparatively to 5/11 for Group 2. Histologically, the main difference in term of tubular degeneration and necrosis between animals from Group 3 (IR/XG-104) in comparison to Group 2 (IR/Vehicle) was that the number of tubules affected was lower, and the lesions were mostly limited to the cortico-medullary junction and were not extended to the superficial cortex. Group 3 (IR/XG-104) and kidneys presented also a less severe score for tubular casts when compared to Group 2 (IR/Vehicle). Actually, tubular cast scores were 2.50±0.52 in Group 3 (IR/XG-104). In comparison, Group 2 (IR/vehicle) tubular cast score was 3.00±0.00. The number of basophilic tubules in Group 3 (IR/XG-104) were very comparable to that observed in Group 2. The mean basophilic tubule score for Group 3 (IR/XG-104) were respectively, 1.33±0.65 and 1.73±0.47; the score for Group 2 was 1.36±0.67 (FIG. 97).

More specifically, the mean tubular epithelial degeneration/necrosis score was 2.18±0.75 in Group 3 (IR/XG-104), respectively. The main difference between Group 2 (IR/Vehicle) and Group 3 (IR/XG-104) was that several animals in the latter group showed a score of 2 (8/11 in Group 3 and 0/11 in Group 2). In addition, 1/11 had a score of 1 in Group 3. Finally, only 1/11 animal in Group 3 had a score of 4 comparatively to 5/11 for Group 2. Histologically, the main difference in term of tubular degeneration and necrosis between animals from Group 3 (IR/XG-104) in comparison to Group 2 (IR/Vehicle) was that the number of tubules affected was lower, and the lesions were mostly limited to the cortico-medullary junction and were not extended to the superficial cortex. Group 3 (IR/XG-104) kidneys presented also a less severe score for tubular casts when compared to Group 2 (IR/Vehicle). Actually, tubular cast scores was 2.09±0.54 in Group 3 (IR/XG-104), respectively. In comparison, Group 2 (IR/vehicle) tubular cast score was 3.00±0.00. The number of basophilic tubules in Group 3 (IR/XG-104) was very comparable to that observed in Group 2. The mean basophilic tubule score for Group 3 (IR/XG-104) was 1.73±0.47; the score for Group 2 was 1.36±0.67 (FIG. 97).

There was no tubular vacuolation observed in any of the four experimental groups. Accordingly, the total tubular score in Group 1 (Sham/Vehicle) was very low as expected (0.25±0.45) since only few animals presented basophilic tubules without any other tubular changes. In Group 2, the total tubular score was the highest among the four experimental groups, and ranged from 6 to 9 (7.82±0.98). Group 3 total tubular score was relatively lower to that observed in Group 2 (IR/vehicle) with scores ranging from 4 to 8 (6.00±1.26). The differences observed between Group 2 (IR/vehicle) and Group 3 (IR/XG-104) were considered to be biologically significant.

Taken together, XG-104 showed significant beneficial effects on tubular damages and specifically on tubular degeneration, necrosis and tubular cast formation. The main difference in term of tubular degeneration and necrosis between animals from XG-104 treated rats (Group 3) and vehicle (Group 2) IR animals is that the number of tubules affected was lower, and the lesions were mostly limited to the cortico-medullary junction and not extended to the superficial cortex. Kidneys from Group 3 (IR/XG-104) presented also a less severe score for tubular casts when compared to Group 2 (IR/Vehicle).

Example 24: Effects of XG-104 (the JNK Inhibitor According to SEQ ID No. 172) Administered Intravesically on Acute Cystitis Model Induced by Cyclophosphamide in Conscious Rats: Evaluation of Visceral Pain and Urinary Bladder Inflammation The aim of the present study was to evaluate the effects of intravesical treatment with XG-104 (50 mg/mL) on urinary bladder pain and inflammation in acute CYP-induced cystitis in female Sprague-Dawley rats. This preclinical model is well-used to test therapeutic approaches for the treatment of interstitial cystitis/painful bladder syndrome (IC/PBS).

Adult female Sprague-Dawley rats (Janvier Labs, Le Genest Saint Isle, France), weighing 215±20 g at the beginning of the experiments, were used. Animals were acclimatized to the laboratory conditions for at least 3 days before the start of any experiments. The animals were allocated to the following four experimental groups (n=10 animals per group):

| Group | Injection (i.p.) | Treatment (i.ves.) | n |
|---|---|---|---|
| 1 | Saline | Vehicle (500 µL, i.ves.) | 10 |
| 2 | CYP | Vehicle (500 µL, i.ves.) | 10 |
| 3 | CYP | XG-104 (50 mg/mL, i.ves.) | 10 |
| 4 | CYP | Ibuprofen (50 mg/mL, i.ves.) | 10 |

To induce acute cystitis, a single i.p. injection of CYP at a dose of 150 mg/kg in a final volume of 5 mL/kg was performed. Control rats received physiological saline under the same experimental conditions as CYP (final volume of 5 mL/kg, i.p.).

On the day of each experiment, weight of rats was recorded. Then, in a randomized manner, 500 μL of XG-104 (50 mg/mL), ibuprofen (50 mg/mL) or vehicle were intravesically infused during 30 min under isoflurane anesthesia (2%-3%).

Assessment of Referred Visceral Pain Using Von Frey Filaments:

Standardized conditions including fixed time-of-day (a.m. to minimize the potential circadian variations in the behaviours responses) and single-experimenter testing of all animals were applied to minimize variability behavior-based pain testing. Visceral pain including allodynia and hyperalgesia was evaluated by applying to the lower abdomen, close to the urinary bladder, a set of 8 calibrated von Frey filaments of increasing forces (1, 2, 4, 6, 8, 10, 26 and 60 g) with an interstimulus interval of 5 seconds. Prior testing, the abdominal area designed for mechanical stimulation of each animal was shaved. Animals were then placed on a raised wire mesh floor under individual transparent Plexiglas box and acclimatized for at least 30 minutes before starting the von Frey test. Filaments were then applied 1-2 seconds through the mesh floor with enough strength to cause the filament to slightly bend. Each filament was tested 3 times. Care was taken to stimulate different areas within the lower abdominal region in the vicinity of the urinary bladder to avoid desensitization.

Nociceptive behaviors were scored for each animal and each filament as follows:

| Score | Behavior |
| --- | --- |
| 0 | no response |
| 1 | reaction of the animal (e.g. retraction of the abdomen) |
| 2 | reaction of the animal and change of position |
| 3 | reaction of the animal, change of position and licking of the site stimulated with von Frey filaments and/or vocalization |

Figure 50A:
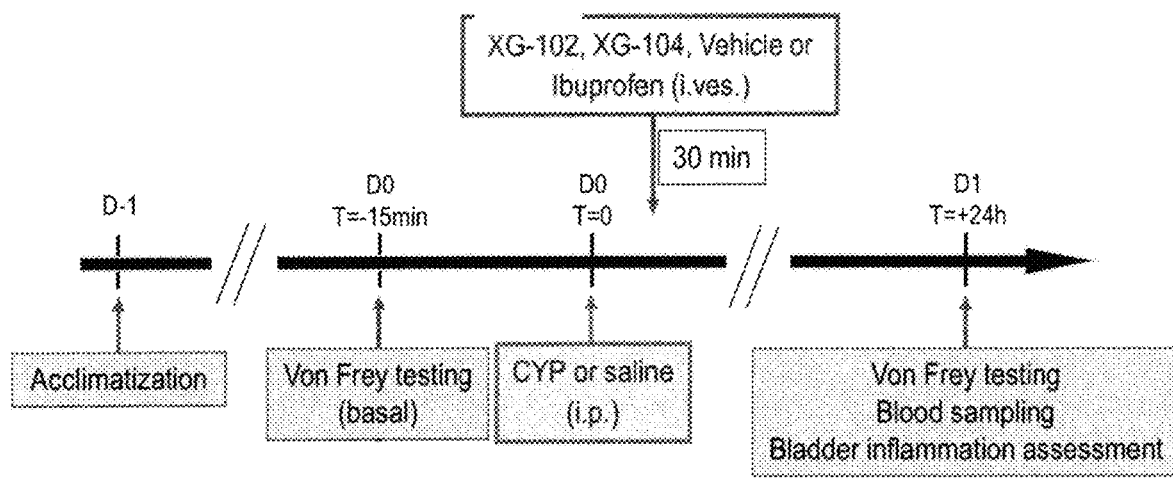
FIG. 50A and FIG. 50B show for Example 24 the study design (FIG. 50A) and the AUCs method to assess allodynia and hyperalgesia (FIG. 50B).
Figure 50B:
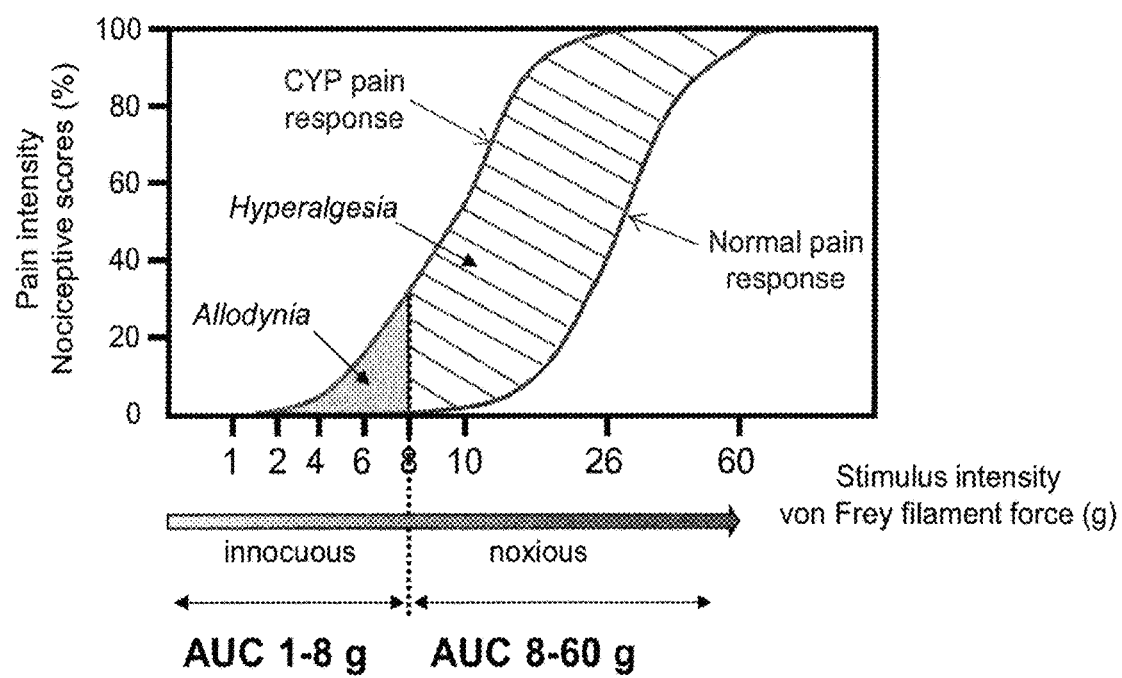
Figure 51A:
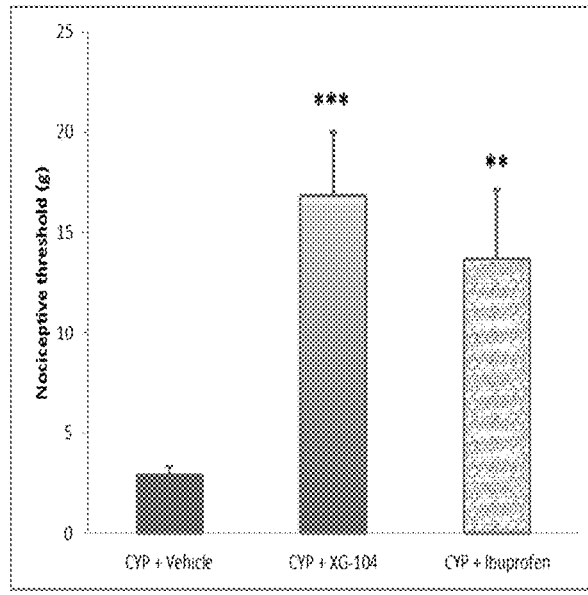
FIG. 51A-FIG. 51D show for Example 24 the effect of XG-104 (50 mg/mL, i.ves.) and ibuprofen (50 mg/mL, i.ves.) treatments on nociceptive parameters 24 h post-CYP injection. Nociceptive threshold (FIG. 51A), nociceptive scores (FIG. 51B), AUC 1-8 g (FIG. 51C) or AUC 8-60 g (FIG. 51D) 24 h after CYP injection. Results are expressed as mean±s.e.m. (n=10). * p<0.05,  p<0.01, *p<0.001 vs Vehicle-treated group, Mann Whitney test (FIG. 51A and FIG. 51C), Two-way RM ANOVA FIG. 51(B), and Unpaired t test and Mann Whitney test (FIG. 51D).
Figure 51B:
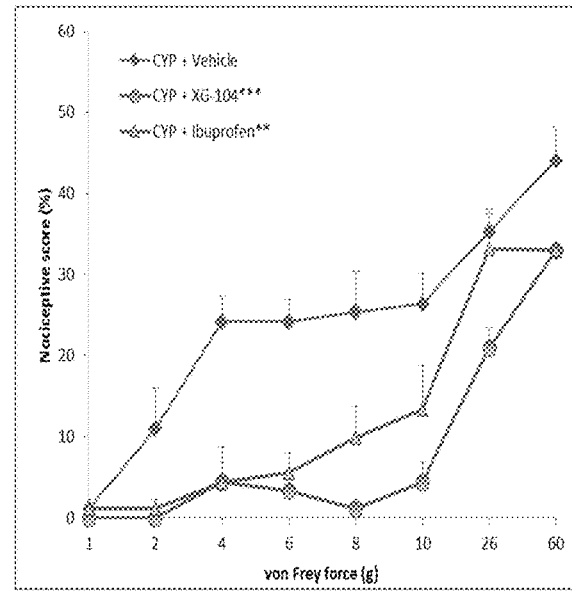
Figure 51C:
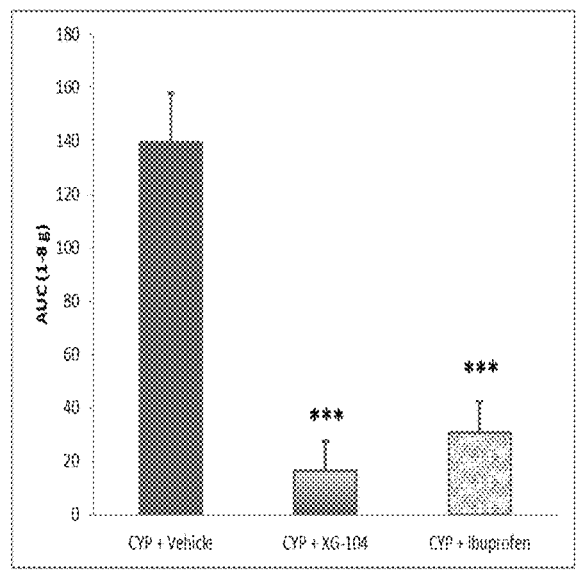
Figure 51D:
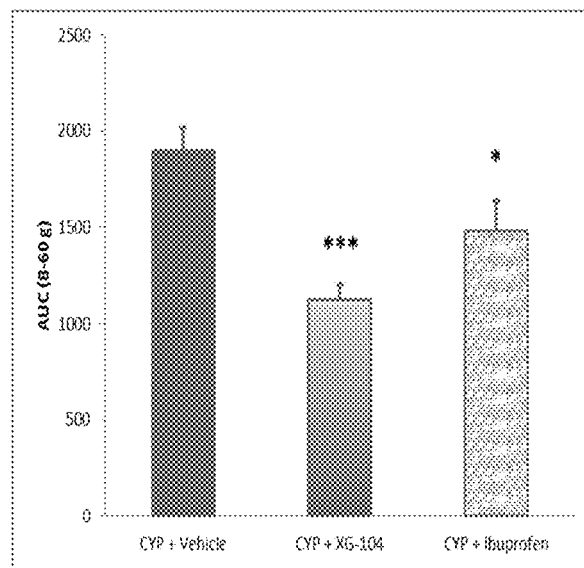

The study design is schematically shown in FIG. 50 A. Birefly, acute cystitis was induced by CYP injection (i.p.) at Do (as described above). XG-104, ibuprofen or vehicle was intravesically administrated once just after CYP injection (as described above). Von Frey testing was performed in a non-blinded manner as follow:
- At D−1, rats were acclimatized to the individual Plexiglas box for a minimum of 30 min and to the von Frey filaments application, in order to decrease the level of stress due to the new environment.
- At D0, von Frey testing was performed 15 min before CYP or saline injection in order to obtain basal values (D0, T=−15 min).
- At D1, von Frey testing was performed 24 hours after CYP or saline injection in order to analyze test compounds effect on CYP-induced visceral pain (D1, T=+24 h).
- Just after von Frey testing (+24 h), rats were anesthetized for blood samples collection, then sacrificed and urinary bladders were collected as described below.

At the end of the experiment, rats were sacrificed by injection of pentobarbital (54.7 mg/mL, 0.5 mL/rat, i.p.) followed by cervical dislocation. Urinary bladders were rapidly collected and cleaned from lipoid tissue. Urinary bladders were weighed, cut at the bladder neck as well as oedema and haemorrhage scoring was performed (see table below). Finally, wall thickness was measured using a digital caliper by placing the bladder wall between the two outside jaws. Urinary bladder oedema and haemorrhage scores were adapted from Gray's criteria (Gray et al., 1986) as follows:

| Scores | Oedema | Haemorrhage |
| --- | --- | --- |
| 0 | absent - normal aspect | absent - normal aspect |
| 1 | mild - between normal and moderate | telangiectasia - dilatation of the mucosal blood vessels |
| 2 | moderate - fluid confined to the internal mucosa | petechial haemorrhages - mucosal pinpoint red dots (glomerulation) |
| 3 | severe - fluid seen inside and outside bladder walls | Hemorrhagic spots with blood clots |

Nociceptive parameters are expressed as follows:

| Parameters | Expression | Description |
| --- | --- | --- |
| nociceptive threshold | g | von Frey filament for which a first score of at least 1 (for 3 applications) is obtained |
| nociceptive scores | % | % of the maximal response (maximum score = 9) for 3 pooled applications |
| area under the curve (AUC) 1-8 g (allodynia) area under the curve (AUC) 8-60 g (hyperalgesia) | % scores x g | plot of individual percentage of nociceptive scores against von Frey forces from: 1 to 8 g or 8 to 60 g |

AUCs were calculated using GraphPad Prism® (GraphPad Software Inc., La Jolla, Calif., USA). The AUCs method to assess allodynia and hyperalgesia is schematically shown in FIG. 50 B.

Macroscopic parameters are expressed as follows:

| Parameters | Expression |
| --- | --- |
| whole urinary bladder weight | mg and % of body weight |
| oedema | scores |
| haemorrhage | scores |
| urinary wall thickness | mm |

Results:

Before CYP injection, no significant difference in the nociceptive parameters were observed between the 3 different CYP-injected groups. In order to analyse effect of XG-104 on CYP-induced visceral pain, nociceptive parameters were compared between the Vehicle- and the XG-104-treated groups. Twenty-four hours after CYP injection, nociceptive threshold was significantly increased by XG-104 treatment as compared to vehicle ($p<0.01$, FIG. 51 A). XG-104 treatment also significantly decreased nociceptive scores in CYP-injected rats as compared to vehicle ($p<0.001$, FIG. 51 B). In addition, AUC 1-8 g was significantly decreased by XG-104 treatment as compared to vehicle ($p<0.001$, FIG. 51 C). Similarly, AUC 8-60 g was reduced by XG-104 treatment as compared to vehicle ($p<0.01$, FIG. 51 D). In order to analyse the effects of ibuprofen on CYP-induced visceral pain, nociceptive parameters were compared between the Vehicle- and the Ibuprofen-treated groups. Nociceptive threshold was significantly increased by ibuprofen treatment as compared to vehicle in CYPinjected rats ($p<0.01$, FIG. 51 A). Similarly in the Ibuprofen group significant decrease of nociceptive scores was observed as compared to vehicle ($p<0.01$, FIG.

51 B). In addition, AUC 1-8 g and AUC 8-60 g were significantly decreased by ibuprofen treatment as compared to vehicle (p<0.001 and p<0.05, FIGS. 51 C and 51 D, respectively).

Figure 52A:
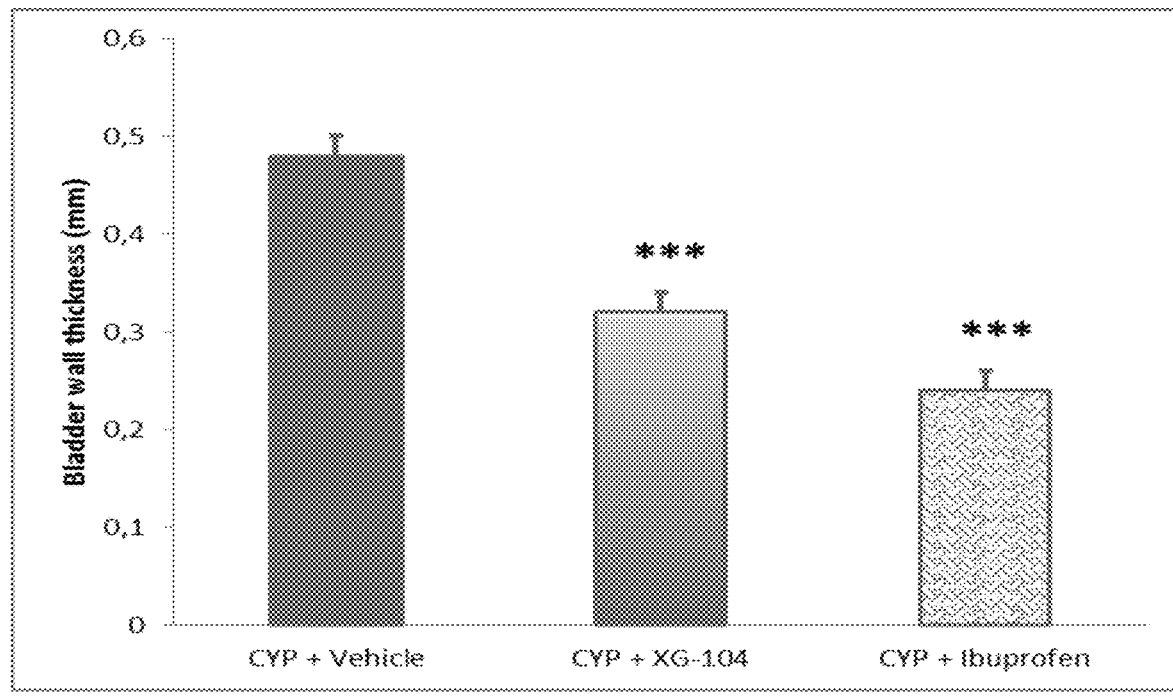
FIG. 52A-FIG. 52C show for Example 24 the effect of XG-104 (50 mg/mL, i.ves.) and ibuprofen (50 mg/mL, i.ves.) treatments on urinary bladder wall thickness as well as on oedema and haemorrhage scores 24 h post-CYP injection. Urinary bladder wall thickness (FIG. 52A), oedema scores (FIG. 52B), or haemorrhage scores (FIG. 52C) 24 h after CYP injection. Results are expressed as mean±s.e.m. (n=10). ns=p>0.05,  p<0.01, * p<0.001 vs Vehicle-treated group, Mann Whitney test and Unpaired t test (FIG. 52A) or Mann Whitney test (FIG. 52B and FIG. 52C).
Figures 52B, 52C:
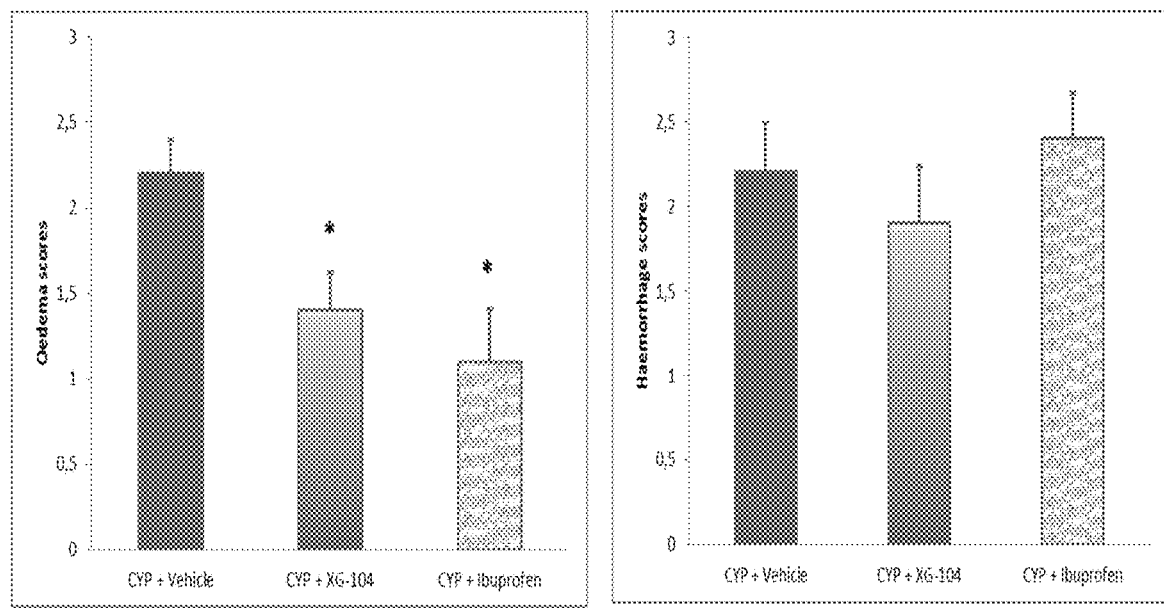
Figure 53A:
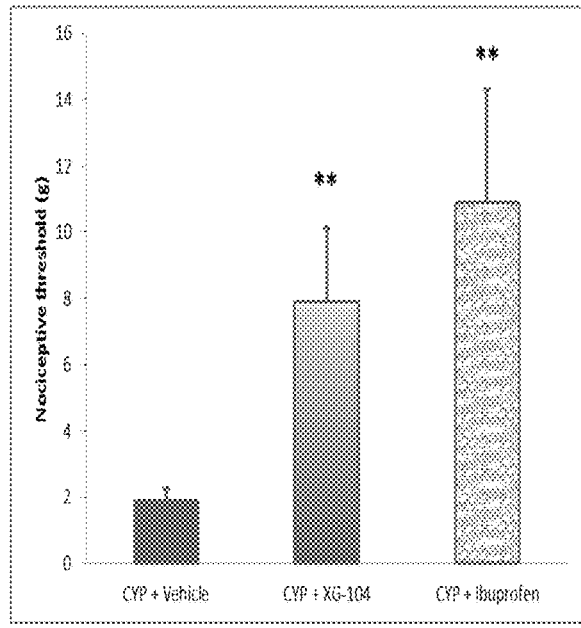
FIG. 53A-FIG. 53D show for Example 25 the effect of XG-104 (2 mg/kg, i.v.) and ibuprofen (10 mg/kg, i.v.) treatments on nociceptive parameters 24 h post-CYP injection. Nociceptive threshold (FIG. 53A), nociceptive scores (FIG. 53B), AUC 1-8 g (FIG. 53C) or AUC 8-60 g (FIG. 53D) 24 h after CYP injection. Results are expressed as mean±s.e.m. (n=10).  p<0.01, * p<0.001 vs Vehicle-treated group, Mann Whitney test (FIG. 53A), Two-way RM ANOVA (FIG. 53B), Mann Whitney test and Unpaired t test (FIG. 53C) and Unpaired t test (FIG. 53D).
Figure 53B:
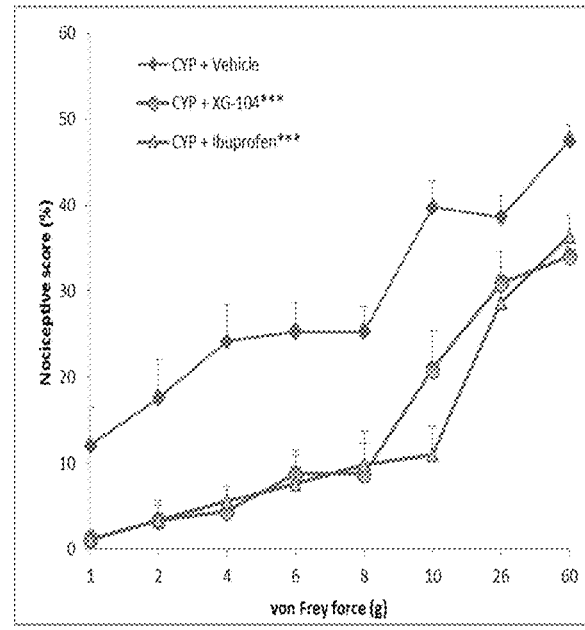
Figure 53C:
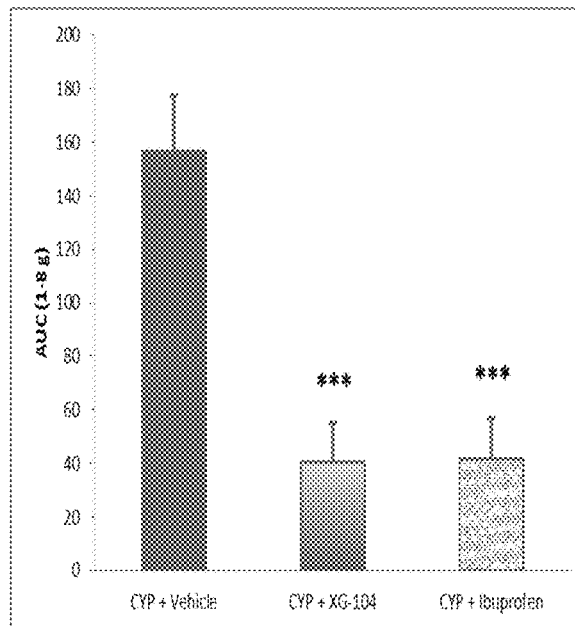
Figure 53D:
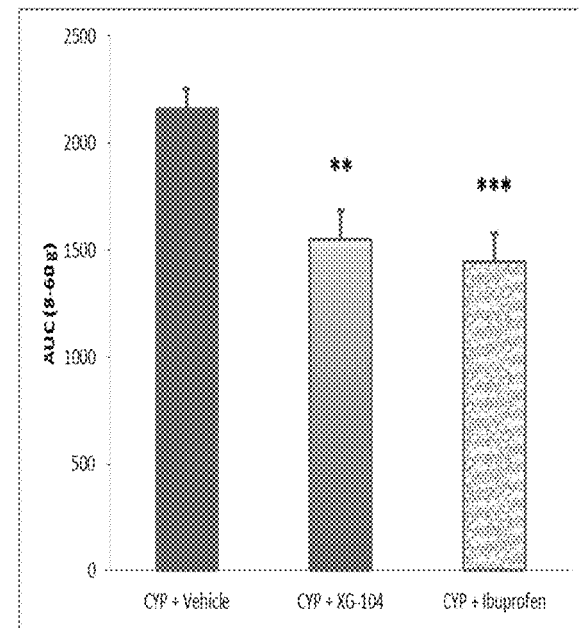

Moreover, urinary wall thickness was significantly decreased in XG-104-treated rats (p<0.01, FIG. 52 A). XG-104-treatment induced urinary wall thickness decrease was associated with a significant decrease in oedema scores whereas no significant change in haemorrhage scores was observed as compared to vehicle (p<0.05 and p>0.05 for oedema and haemorrhage scores respectively, FIGS. 52 B and 52 C). For ibuprofen, also a significant decrease was observed in urinary bladder wall thickness and in oedema scores (p<0.001 and p<0.05, FIG. 52 A, B). However, no significant change was observed regarding haemorrhage scores (p>0.05, FIG. 52 C) in the Ibuprofen-treated group. It is noteworthy that reddish urine was noticed for some animal in the Ibuprofen-treated group.

Taken together, intravesical treatment of XG-104 (50 mg/mL) significantly reversed visceral pain induced by CYP, 24 h after its injection. XG-104 efficiently inhibited both allodynia and hyperalgesia. On analyzed inflammatory parameters, XG-104 decreased urinary bladder inflammation (wall thickness) and oedema scores. In conclusion, administered intravesically, XG-104 displayed strong antinociceptive effects and significant anti-inflammatory properties in an experimental model of IC/PBS.

Example 25: Effects of XG-104 (the JNK Inhibitor According to SEQ ID No. 172) Administered Intravenously on Acute Cystitis Model Induced by Cyclophosphamide in Conscious Rats: Evaluation of Visceral Pain The aim of the present study was to evaluate the effects of intravenous treatment with XG-104 (2 mg/kg) on urinary bladder pain in acute CYP-induced cystitis in female Sprague-Dawley rats. This preclinical model is well-used to test therapeutic approaches for the treatment of interstitial cystitis/painful bladder syndrome (IC/PBS).

Adult female Sprague-Dawley rats (Janvier Labs, Le Genest Saint Isle, France), weighing 215±20 g at the beginning of the experiments, were used. Animals were acclimatized to the laboratory conditions for at least 3 days before the start of any experiments. The animals were allocated to the following four experimental groups (n=10 animals per group):

| Group | Injection (i.p.) | Treatment (i.ves.) | n |
|---|---|---|---|
| 1 | Saline | Vehicle (1 mL/kg, i.v.) | 10 |
| 2 | CYP | Vehicle (1 mL/kg, i.v.) | 10 |
| 3 | CYP | XG-104 (2 mg/kg, i.v.) | 10 |
| 4 | CYP | Ibuprofen (10 mg/kg, i.v.) | 10 |

To induce acute cystitis, a single i.p. injection of CYP at a dose of 150 mg/kg in a final volume of 5 mL/kg was performed. Control rats received physiological saline under the same experimental conditions as CYP (final volume of 5 mL/kg, i.p.).

On the day of each experiment, weight of rats was recorded. Then, in a randomized manner, XG-104 (2 mg/kg), ibuprofen (10 mg/kg) or vehicle were intravenously administered at a volume of 1 mL/kg.

Assessment of referred visceral pain using von Frey filaments: Standardized conditions including fixed time-of-day (a.m. to minimize the potential circadian variations in the behaviours responses) and single-experimenter testing of all animals were applied to minimize variability behavior-based pain testing. Visceral pain including allodynia and hyperalgesia was evaluated by applying to the lower abdomen, close to the urinary bladder, a set of 8 calibrated von Frey filaments of increasing forces (1, 2, 4, 6, 8, 10, 26 and 60 g) with an interstimulus interval of 5 seconds. Prior testing, the abdominal area designed for mechanical stimulation of each animal was shaved. Animals were then placed on a raised wire mesh floor under individual transparent Plexiglas box and acclimatized for at least 30 minutes before starting the von Frey test. Filaments were then applied 1-2 seconds through the mesh floor with enough strength to cause the filament to slightly bend. Each filament was tested 3 times. Care was taken to stimulate different areas within the lower abdominal region in the vicinity of the urinary bladder to avoid desensitization.

Nociceptive behaviors were scored for each animal and each filament as follows:

| Score | Behavior |
|---|---|
| 0 | no response |
| 1 | reaction of the animal (e.g. retraction of the abdomen) |
| 2 | reaction of the animal and change of position |
| 3 | reaction of the animal, change of position and licking of the site stimulated with von Frey filaments and/or vocalization |

The study design differs from that of Example 24 (cf. FIG. 50 A) only in the route of administration (intravenously instead of intravesically) and the doses as specified above. Birefly, acute cystitis was induced by CYP injection (i.p.) at Do (as described above). XG-104, ibuprofen or vehicle was intravenously administered once just after CYP injection (as described above). Von Frey testing was performed in a non-blinded manner as follow:

At D−1, rats were acclimatized to the individual Plexiglas box for a minimum of 30 min and to the von Frey filaments application, in order to decrease the level of stress due to the new environment.

At D0, von Frey testing was performed 15 min before CYP or saline injection in order to obtain basal values (D0, T=−15 min).

At D1, von Frey testing was performed 24 hours after CYP or saline injection in order to analyze test compounds effect on CYP-induced visceral pain (D1, T=+24 h).

Just after von Frey testing (+24 h), rats were anesthetized for blood samples collection, then sacrificed and urinary bladders were collected as described below.

Nociceptive parameters are expressed as follows:

| Parameters | Expression | Description |
|---|---|---|
| nociceptive threshold | g | von Frey filament for which a first score of at least 1 (for 3 applications) is obtained |
| nociceptive scores | % | % of the maximal response (maximum score = 9) for 3 pooled applications |
| area under the curve (AUC) 1-8 g (allodynia) | % scores x g | plot of individual percentage of nociceptive scores against von Frey forces from: 1 to 8 g or 8 to 60 g |
| area under the curve (AUC) 8-60 g (hyperalgesia) | | |

AUCs were calculated using GraphPad Prism® (GraphPad Software Inc., La Jolla, Calif., USA). The AUCs method to assess allodynia and hyperalgesia is schematically shown in FIG. 50 B.

Results:

Before CYP injection, no significant difference in the nociceptive parameters was observed between the 3 different CYP-injected groups ($p>0.05$). In order to analyse the effects of XG-104 on CYP-induced visceral pain, nociceptive parameters were compared between the Vehicle- and the XG-104-treated groups independently. Twenty-four hours after CYP injection, nociceptive threshold was significantly increased by XG-104 treatment as compared to vehicle ($p<0.01$, FIG. 53 A). XG-104 treatment significantly decreased nociceptive scores in CYP-injected rats as compared to vehicle ($p<0.001$, FIG. 53 B). In addition, AUC 1-8 g was significantly decreased by XG-104 treatment as compared to vehicle ($p<0.001$, FIG. 53 C). Similarly, AUC 8-60 g was significantly reduced by XG-104 treatment as compared to vehicle ($p<0.01$, FIG. 53 D).

Taken together, intravenous treatment of XG-104 (2 mg/kg) thus significantly reversed visceral pain induced by CYP, 24 h after its injection. XG-104 efficiently inhibited both allodynia and hyperalgesia. Similar effects were observed with intravenous administration of ibuprofen (10 mg/kg). In conclusion, in the experimental cystitis preclinical model, XG-104 displayed significant anti-nociceptive properties.

Example 26: Effects of XG-104 (the JNK Inhibitor According to SEQ ID No. 172) on β-Amyloid-Induced Neuronal Apoptosis (Alzheimer's Disease Model)

In this study, the effects of the JNK inhibitor XG-104 on JNK activation and on neuronal apoptosis after $A\beta_{42}$ cell stress was determined.

To this end, primary mouse cortical neuron cultures were exposed to either 2 μM or 25 μM of β-amyloid 1-42 ($A\beta_{42}$) for 5 hours to induce $A\beta_{42}$ cell stress. Neurons were pre-treated with or without 10 μM of the specific inhibitor of JNK, XG-104 (SEQ ID No. 172). Levels of phosphorylated JNK (pJNK), total JNK (JNK), cleaved PARP and Tubulin (control) were determined. The ratio of pJNK/JNK served as a measure of JNK activity. The level of cleaved protein PARP, which is known to increase during apoptosis, served as a measure of neuronal apoptosis.

Figure 54A:
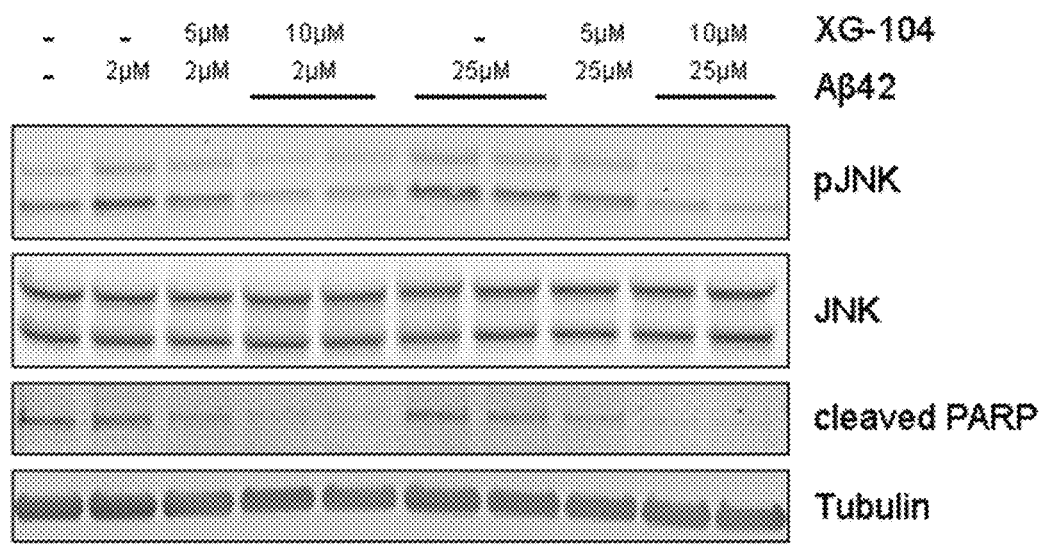
FIG. 54A-FIG. 54C show for Example 26 the effect of XG-104 on neuronal apoptosis.
Figure 54B:
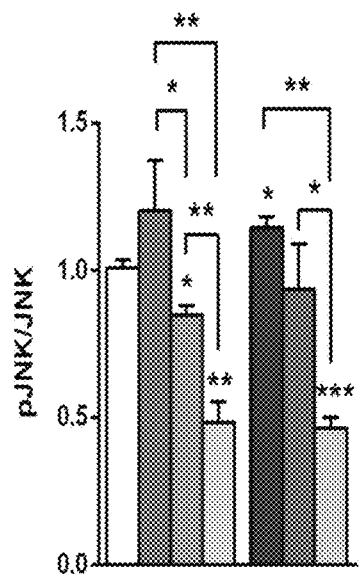
Figure 54C:
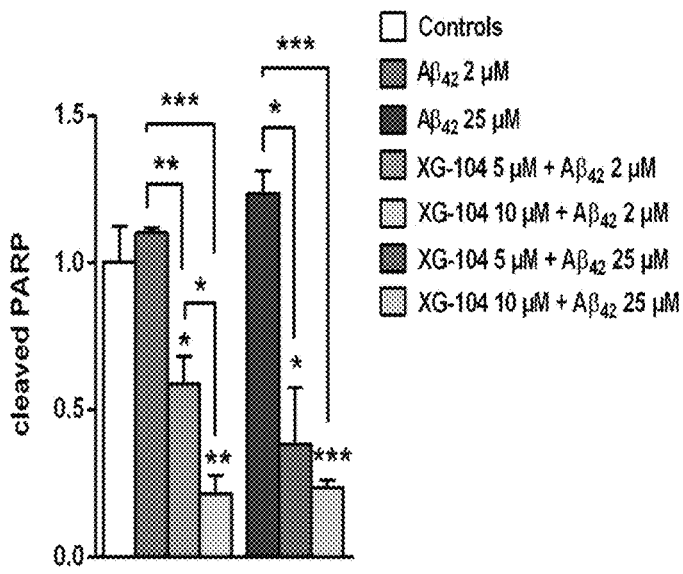

Results of the immunoblot analysis of the primary mouse cortical neuron cultures pre-treated with or without 10 μM of XG-104 and exposed to either 2 μM or 25 μM of β-amyloid 1-42 ($A\beta_{42}$) during 5 hours are shown in FIG. 54 (A). In FIG. 54 (B and C), the corresponding histograms are depicted showing the ratio of phosphorylated JNK on total JNK (pJNK/JNK) for the different experimental groups (B) and the level of cleaved protein PARP (C). Interestingly, in the condition of 2 μM of $A\beta_{42}$ no modification of JNK activity was observed. Pre-treatment with 5 μM and 10 μM of XG-104 decreased JNK activity by respectively 29.2% and 60% (FIG. 54 B). 25 μM $A\beta_{42}$ treatment of the neurons increased JNK activity by 14% (FIG. 54 B). Thus, pre-treatment with 5 μM and 10 μM XG-104 decreased JNK activity by, 17.5% and 59.6%, respectively. In both $A\beta_{42}$ cell stress conditions, 10 μM XG-104 concentration was more effective to decrease JNK activity (FIG. 54 B).

Neuronal apoptosis was measured by the level of cleaved protein PARP, which is increased during apoptosis (FIG. 54 C). Pre-treatment with 5 μM and 10 μM XG-104 decreased PARP cleavage by 46.8% and 80.2%, respectively, with 2 μM $A\beta_{42}$ and decreased by 69% and 80.6%, respectively, with 25 μM $A\beta_{42}$. Taken together, XG-104 thus decreased neuronal apoptosis induced by $A\beta_{42}$. XG-104 10 μM concentration was 1.7 more efficient than XG-104 5 μM concentration to reduce apoptosis.

Example 27: Effects of XG-104 (the JNK Inhibitor According to SEQ ID No. 172) Alone or in Combination with PKR Down-Regulation on β-Amyloid-Induced Neuronal Apoptosis (Alzheimer's Disease Model)

To obtain primary cortical neuronal cultures, E15.5 mice embryos were dissected in PBS (Phosphate Buffered Saline) 6% glucose, on ice. Embryos cortices were minced into small pieces and treated with PBS glucose trypsin (Sigma Aldrich, Saint-Louis, USA) for 20 min at 37° C. Dissociated cortical cells were cultured in Neurobasal media complemented with B27, Glutamax and penicillin-streptomycin (Gibco). Neurons were cultured at 37° C., 5% $CO_2$ on pre-coated with poly-L-lysin (Sigma Aldrich) petri dishes. Neurons were cultured to maturity (7 days) before use.

To induce $A\beta_4f$ stress 2 μM of Aβ1-42 (Thermo Fisher Scientific, Mass., USA) were used during 5 h on cortical neurons. Aβ42-1 inversed peptide (Thermo Fisher Scientific) was used as negative control. AP 1-42 and Aβ42-1 were dissolved in pure water and incubated at 37° C. for 48 h before use.

To inhibit JNK, cortical neurons were pre-treated with 10 μM of XG-104 1 h before cell-stress treatment.

For immunoblot analysis cells were lysed on ice in a lysis buffer containing 10 nM NaPi pH 7.8, 59 nM NaCl, 1% Triton, 0.5% DOC, 0.1% SDS, 10% glycerol, 0.1 μM calyculin A, 1 mM Na3VO4 and 1× of a protease inhibitor cocktail (Sigma Aldrich). Lysates were sonicated and centrifugated 10 min at 15000 g at 4° C. The supernatant protein concentration was determined with the Micro BCA protein assay kit (Thermo Scientific). Thirty micrograms of proteins were resolved on SDS-PAGE and transferred onto nitrocellulose membrane. After blocking with TBS 5% skim milk, the membranes were probed with primary antibodies to JNK full, c-Jun, PKR, eIF2α (Santa Cruz, Danvers, USA), pJNK (Millipore, Billerica, USA), phosphor eIF2a (Thermo Fisher Scientific), PARP and tubulin (Cell Signaling, Danvers, USA). IR Dyes 800 and 700 (Rockland Immunochemical Inc, Gilbertsville, USA) antibodies were used as secondary antibodies. Blots were reveled with Odyssey imaging system (LI-COR Biosciences, Lincoln, USA).

For caspase 3 activity analysis culture cell supernatants containing degenerating and dead neurons, and cell medium were collected in parallel of adhesive neurons lysis. Culture cell supernatants were centrifugated 10 min at 15000 g at 4° C. Pellets were then resuspended in lysis buffer and caspase 3 activity was measured by using the Caspase 3 Assay kit reagents and protocol (Abcam, Cambridge, UK).

Results:

Decrease of JNK and c-JNK Activations with XG-104 in $A\beta_{42}$-Stressed WT and PKR$^{-/-}$ Neurons In the neuronal cultures stressed by $A\beta_{42}$ peptides, the efficacy of XG-104 was investigated. XG-104 was used at 10 μM, and added to cell medium 1 hour before the induction of $A\beta_{42}$ stress. In WT neurons, JNK activation is reduced after XG-104 exposure (−60%, FIG. 55 A) in $A\beta_{42}$ stressed cultures. XG-104 showed −29% efficacy in order to decrease c-Jun phosphorylation (FIG. 55 C) and −62% efficacy in order to decrease c-Jun expression (FIG. 55 D), compared to stressed WT neurons without peptides. In PKR$^{-/-}$ neurons, JNK activation is reduced by XG-104 (−60%, FIG. 55 A) in Aβ$_{42}$ stressed cultures. In PKR$^{-/-}$ cultures, the use of XG-104 does not modify c-Jun activation (FIG. 55 C), but the use of XG-104 showed a decrease by 62% of c-Jun protein expression after Aβ$_{42}$ stress induction (FIG. 55 D).

Decrease of Neuronal Apoptosis after JNK Inhibition in Aβ$_{42}$-Stressed WT Neurons In WT neuronal cultures treated by Aβ$_{42}$ peptides, the use of XG-104 decreased apoptosis. With XG-104 it was noted a 61% reduction of cleaved caspase 3 expression level (FIG. 55 E), a 78% decrease of caspase 3 activity (FIG. 55 F), and a 77% decrease of cleaved PARP expression level (FIG. 55 G) compared to Aβ$_{42}$ treated WT neurons.

Neuronal Death Due to Aβ$_{42}$ Drastically Reduced after Dual Inhibition of PKR and JNK in Neurons In PKR$^{-/-}$ neurons treated by Aβ$_{42}$ and XG-104, the efficacy of the dual inhibition of PKR and JNK was assessed for neuronal apoptosis. The use of XG-104 on Aβ$_{42}$-stressed PKR$^{-/-}$ neurons showed a 42% decrease of cleaved caspase 3 expression level (FIG. 55 E), a 61% decrease of caspase 3 activity (FIG. 55 F), and a 86% decrease of cleaved PARP expression level (FIG. 55 G) compared to Aβ$_{42}$ treated PKR$^{-/-}$ neurons. In neurons dually inhibited for PKR and JNK, cleaved caspase 3, caspase 3 activity and PARP expression levels decreased respectively by 83%, 87% and 93% compared to treated WT neurons.

The invention claimed is:

1. A method for prophylaxis or treatment of interstitial cystitis/painful bladder syndrome (IC/PBS), for reducing symptoms associated with IC/PBS or for delaying progression of IC/PBS in a subject in need thereof comprising administering to the subject a JNK inhibitor, which comprises an inhibitory (poly-)peptide sequence according to the following general formula:

X1-X2-X3-R-X4-X5-X6-L-X7-L-X8, (SEQ ID NO: 1)

wherein X1 is an amino acid selected from amino acids R, P, Q and r, wherein X2 is an amino acid selected from amino acids R, P, G and r, wherein X3 is an amino acid selected from amino acids K, R, k and r, wherein X4 is an amino acid selected from amino acids P and K, wherein X5 is an amino acid selected from amino acids T, a, s, q, k or is absent, wherein X6 is an amino acid selected from amino acids T, D and A, wherein X7 is an amino acid selected from amino acids N, n, r and K; and
wherein X8 is an amino acid selected from F, f and w, and
wherein an amino acid residue given in capital letters indicates an L-amino acid,
while an amino acid residue given in small letters indicates a D amino acid residue, with the proviso that at least one of the amino acids selected from the group consisting of X1, X2, X3, X5, X7 and X8 is/are a D-amino acid(s),
wherein the JNK inhibitor comprises a transporter sequence and wherein the JNK inhibitor comprises
  a) the sequence of SEQ ID NO: 172 or
  b) a sequence sharing at least 80% sequence identity with SEQ ID NO: 172, with the proviso that said sequence sharing at least 80% sequence identity with SEQ ID NO: 172
    i) maintains the L-arginine (R) residue on position 4 in its sequence stretch corresponding to SEQ ID NO: 1,
    ii) maintains the two L-leucine (L) residues in its sequence stretch corresponding to SEQ ID NO: 1, and
    iii) exhibits at least one D-amino acid at positions X1, X2, X3, X5, X7 or X8 in its sequence stretch corresponding to SEQ ID NO: 1; and
wherein the JNK inhibitor is administered intravesically.

2. The method of claim 1, wherein at least one of the amino acids selected from the group consisting of X3, X5, X7 and X8 is/are a D-amino acid(s).

3. The method of claim 1, wherein the JNK inhibitor comprises SEQ ID NO: 8 or an inhibitory (poly-)peptide sequence sharing at least 80% sequence identity with SEQ ID NO: 8.

4. The method of claim 1, wherein said transporter sequence is according to SEQ ID NO: 46.

5. The method of claim 1, wherein said transporter sequence is positioned directly N-terminal or directly C-terminal of the inhibitory (poly-)peptide sequence.

6. The method of claim 1, wherein the JNK inhibitor is applied repeatedly.

7. The method of claim 6, wherein the JNK inhibitor is applied daily, every 2 or 3 days or weekly.

8. The method of claim 1, wherein the JNK inhibitor comprises or consists of the sequence of SEQ ID NO: 172.

9. The method of claim 1, wherein the JNK inhibitor is applied by intravesical infusion.

10. The method of claim 1, wherein the JNK inhibitor is administered in a single dose.

11. The method of claim 1, wherein the method reduces visceral pain and urinary bladder inflammation in the subject.

12. The method of claim 11, wherein the method reduces bladder wall thickness of the subject.

13. A method for prophylaxis or treatment of interstitial cystitis/painful bladder syndrome (IC/PBS), for reducing symptoms associated with IC/PBS or for delaying progression of IC/PBS in a subject in need thereof comprising administering to the subject a pharmaceutical composition comprising a JNK inhibitor, which comprises an inhibitory (poly-)peptide sequence according to the following general formula:

(SEQ ID NO: 1)
X1-X2-X3-R-X4-X5-X6-L-X7-L-X8, wherein X1 is an amino acid selected from amino acids R, P, Q and r,
wherein X2 is an amino acid selected from amino acids R, P, G and r,
wherein X3 is an amino acid selected from amino acids K, R, k and r,
wherein X4 is an amino acid selected from amino acids P and K,
wherein X5 is an amino acid selected from amino acids T, a, s, q, k or is absent,
wherein X6 is an amino acid selected from amino acids T, D and A,
wherein X7 is an amino acid selected from amino acids N, n, r and K; and
wherein X8 is an amino acid selected from F, f and w, and
wherein an amino acid residue given in capital letters indicates an L-amino acid,
while an amino acid residue given in small letters indicates a D amino acid residue, with the proviso that at least one of the amino acids selected from the group consisting of X1, X2, X3, X5, X7 and X8 is/are a D-amino acid(s),
wherein the JNK inhibitor comprises a transporter sequence and wherein the JNK inhibitor comprises
  a) the sequence of SEQ ID NO: 172 or
  b) a sequence sharing at least 80% sequence identity with SEQ ID NO: 172, with the proviso that said sequence sharing at least 80% sequence identity with SEQ ID NO: 172
    i) maintains the L-arginine (R) residue on position 4 in its sequence stretch corresponding to SEQ ID NO: 1,
    ii) maintains the two L-leucine (L) residues in its sequence stretch corresponding to SEQ ID NO: 1, and
    iii) exhibits at least one D-amino acid at positions X1, X2, X3, X5, X7 or X8 in its sequence stretch corresponding to SEQ ID NO: 1;
and a pharmaceutically acceptable carrier,
wherein the pharmaceutical composition is administered intravesically.

14. A method for prophylaxis or treatment of cystitis, for reducing symptoms associated with cystitis or for delaying progression of cystitis in a subject in need thereof comprising administering to the subject a JNK inhibitor, which comprises an inhibitory (poly-)peptide sequence according to the following general formula:

(SEQ ID NO: 1)
X1-X2-X3-R-X4-X5-X6-L-X7-L-X8, wherein X1 is an amino acid selected from amino acids R, P, Q and r,
wherein X2 is an amino acid selected from amino acids R, P, G and r,
wherein X3 is an amino acid selected from amino acids K, R, k and r,
wherein X4 is an amino acid selected from amino acids P and K,
wherein X5 is an amino acid selected from amino acids T, a, s, q, k or is absent,
wherein X6 is an amino acid selected from amino acids T, D and A,
wherein X7 is an amino acid selected from amino acids N, n, r and K; and
wherein X8 is an amino acid selected from F, f and w, and wherein an amino acid residue given in capital letters indicates an L-amino acid, while an amino acid residue given in small letters indicates a D amino acid residue, with the proviso that at least one of the amino acids selected from the group consisting of X1, X2, X3, X5, X7 and X8 is/are a D-amino acid(s), wherein the JNK inhibitor comprises a transporter sequence and wherein the JNK inhibitor comprises a) the sequence of SEQ ID NO: 172 or b) a sequence sharing at least 80% sequence identity with SEQ ID NO: 172, with the proviso that said sequence sharing at least 80% sequence identity with SEQ ID NO: 172 i) maintains the L-arginine (R) residue on position 4 in its sequence stretch corresponding to SEQ ID NO: 1, ii) maintains the two L-leucine (L) residues in its sequence stretch corresponding to SEQ ID NO: 1, and iii) exhibits at least one D-amino acid at positions X1, X2, X3, X5, X7 or X8 in its sequence stretch corresponding to SEQ ID NO: 1; and wherein the JNK inhibitor is administered intravesically.

15. The method of claim 14, wherein the method is for prophylaxis or treatment of acute cystitis, for reducing symptoms associated with acute cystitis or for delaying progression of acute cystitis in a subject in need thereof.

16. The method of claim 14, wherein the method is for prophylaxis or treatment of hemorrhagic cystitis, for reducing symptoms associated with hemorrhagic cystitis or for delaying progression of hemorrhagic cystitis in a subject in need thereof.

17. A method for prophylaxis or treatment of bladder infection, for reducing symptoms associated with bladder infection or for delaying progression of bladder infection in a subject in need thereof comprising administering to the subject a JNK inhibitor, which comprises an inhibitory (poly-)peptide sequence according to the following general formula:

(SEQ ID NO: 1)
X1-X2-X3-R-X4-X5-X6-L-X7-L-X8, wherein X1 is an amino acid selected from amino acids R, P, Q and r, wherein X2 is an amino acid selected from amino acids R, P, G and r, wherein X3 is an amino acid selected from amino acids K, R, k and r, wherein X4 is an amino acid selected from amino acids P and K, wherein X5 is an amino acid selected from amino acids T, a, s, q, k or is absent, wherein X6 is an amino acid selected from amino acids T, D and A, wherein X7 is an amino acid selected from amino acids N, n, r and K; and wherein X8 is an amino acid selected from F, f and w, and wherein an amino acid residue given in capital letters indicates an L-amino acid, while an amino acid residue given in small letters indicates a D amino acid residue, with the proviso that at least one of the amino acids selected from the group consisting of X1, X2, X3, X5, X7 and X8 is/are a D-amino acid(s), wherein the JNK inhibitor comprises a transporter sequence and wherein the JNK inhibitor comprises a) the sequence of SEQ ID NO: 172 or b) a sequence sharing at least 80% sequence identity with SEQ ID NO: 172, with the proviso that said sequence sharing at least 80% sequence identity with SEQ ID NO: 172 i) maintains the L-arginine (R) residue on position 4 in its sequence stretch corresponding to SEQ ID NO: 1, ii) maintains the two L-leucine (L) residues in its sequence stretch corresponding to SEQ ID NO: 1, and iii) exhibits at least one D-amino acid at positions X1, X2, X3, X5, X7 or X8 in its sequence stretch corresponding to SEQ ID NO: 1; and wherein the JNK inhibitor is administered intravesically.

* * * * *

SEQUENCE LISTING

```
<160> NUMBER OF SEQ ID NOS: 200

<210> SEQ ID NO 1
<211> LENGTH: 11
<212> TYPE: PRT
<213> ORGANISM: Artificial
<220> FEATURE:
<223> OTHER INFORMATION: Consensus new JNK inhibitors
<220> FEATURE:
<221> NAME/KEY: Variant
<222> LOCATION: (1)..(1)
<223> OTHER INFORMATION: X1 may  be R, P, Q or D-enantiomeric r
<220> FEATURE:
<221> NAME/KEY: Variant
<222> LOCATION: (2)..(2)
<223> OTHER INFORMATION: X2 may  be R, P, G or D-enantiomeric r
<220> FEATURE:
<221> NAME/KEY: Variant
<222> LOCATION: (3)..(3)
<223> OTHER INFORMATION: X3 may  be K, R or D-enantionmeric k or r
<220> FEATURE:
<221> NAME/KEY: Variant
<222> LOCATION: (5)..(5)
<223> OTHER INFORMATION: X4 may  be P or K
<220> FEATURE:
<221> NAME/KEY: Variant
<222> LOCATION: (6)..(6)
<223> OTHER INFORMATION: X5 may  be T, or D-enantiomeric a, s, q, k or
      absent
<220> FEATURE:
<221> NAME/KEY: Variant
<222> LOCATION: (7)..(7)
<223> OTHER INFORMATION: X6 may  be T, D or A
<220> FEATURE:
<221> NAME/KEY: Variant
<222> LOCATION: (9)..(9)
<223> OTHER INFORMATION: X7 may  be N, K or D-enantiomeric n or r
<220> FEATURE:
<221> NAME/KEY: Variant
<222> LOCATION: (11)..(11)
<223> OTHER INFORMATION: X8 may  be F or D-enantiomeric f or w

<400> SEQUENCE: 1

Xaa Xaa Xaa Arg Xaa Xaa Xaa Leu Xaa Leu Xaa
1               5                   10

<210> SEQ ID NO 2
<211> LENGTH: 11
<212> TYPE: PRT
<213> ORGANISM: Artificial
<220> FEATURE:
<223> OTHER INFORMATION: rPKRPTTLNLF JNK inhibitor
<220> FEATURE:
<221> NAME/KEY: Variant
<222> LOCATION: (1)..(1)
<223> OTHER INFORMATION: Arg is D-enantiomeric Arg
```

```
<400> SEQUENCE: 2

Arg Pro Lys Arg Pro Thr Thr Leu Asn Leu Phe
1               5                   10

<210> SEQ ID NO 3
<211> LENGTH: 11
<212> TYPE: PRT
<213> ORGANISM: Artificial
<220> FEATURE:
<223> OTHER INFORMATION: RPkRPTTLNLF JNK inhibitor
<220> FEATURE:
<221> NAME/KEY: Variant
<222> LOCATION: (3)..(3)
<223> OTHER INFORMATION: Lys is D-enantiomeric Lys

<400> SEQUENCE: 3

Arg Pro Lys Arg Pro Thr Thr Leu Asn Leu Phe
1               5                   10

<210> SEQ ID NO 4
<211> LENGTH: 11
<212> TYPE: PRT
<213> ORGANISM: Artificial
<220> FEATURE:
<223> OTHER INFORMATION: RPKRPaTLNLF JNK inhibitor
<220> FEATURE:
<221> NAME/KEY: Variant
<222> LOCATION: (6)..(6)
<223> OTHER INFORMATION: Ala is D-enantiomeric Ala

<400> SEQUENCE: 4

Arg Pro Lys Arg Pro Ala Thr Leu Asn Leu Phe
1               5                   10

<210> SEQ ID NO 5
<211> LENGTH: 11
<212> TYPE: PRT
<213> ORGANISM: Artificial
<220> FEATURE:
<223> OTHER INFORMATION: RPKRPTTLnLF JNK inhibitor
<220> FEATURE:
<221> NAME/KEY: Variant
<222> LOCATION: (9)..(9)
<223> OTHER INFORMATION: Asn is D-enantiomeric Asn

<400> SEQUENCE: 5

Arg Pro Lys Arg Pro Thr Thr Leu Asn Leu Phe
1               5                   10

<210> SEQ ID NO 6
<211> LENGTH: 11
<212> TYPE: PRT
<213> ORGANISM: Artificial
<220> FEATURE:
<223> OTHER INFORMATION: RPKRPTTLrLF JNK inhibitor
<220> FEATURE:
<221> NAME/KEY: Variant
<222> LOCATION: (9)..(9)
<223> OTHER INFORMATION: Arg is D-enantiomeric Arg

<400> SEQUENCE: 6

Arg Pro Lys Arg Pro Thr Thr Leu Arg Leu Phe
1               5                   10

<210> SEQ ID NO 7
<211> LENGTH: 11
<212> TYPE: PRT
<213> ORGANISM: Artificial
<220> FEATURE:
```

```
<223> OTHER INFORMATION: RPKRPTTLNLf JNK inhibitor
<220> FEATURE:
<221> NAME/KEY: Variant
<222> LOCATION: (11)..(11)
<223> OTHER INFORMATION: Phe is D-enantiomeric Phe

<400> SEQUENCE: 7

Arg Pro Lys Arg Pro Thr Thr Leu Asn Leu Phe
1               5                   10

<210> SEQ ID NO 8
<211> LENGTH: 11
<212> TYPE: PRT
<213> ORGANISM: Artificial
<220> FEATURE:
<223> OTHER INFORMATION: RPkRPaTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 8

Arg Pro Lys Arg Pro Ala Thr Leu Asn Leu Phe
1               5                   10

<210> SEQ ID NO 9
<211> LENGTH: 11
<212> TYPE: PRT
<213> ORGANISM: Artificial
<220> FEATURE:
<223> OTHER INFORMATION: RPkRPTTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 9

Arg Pro Lys Arg Pro Thr Thr Leu Asn Leu Phe
1               5                   10

<210> SEQ ID NO 10
<211> LENGTH: 11
<212> TYPE: PRT
<213> ORGANISM: Artificial
<220> FEATURE:
<223> OTHER INFORMATION: RPkRPTTLrLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 10
```

```
Arg Pro Lys Arg Pro Thr Thr Leu Arg Leu Phe
1               5                   10

<210> SEQ ID NO 11
<211> LENGTH: 11
<212> TYPE: PRT
<213> ORGANISM: Artificial
<220> FEATURE:
<223> OTHER INFORMATION: RRrRPTTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 11

Arg Arg Arg Arg Pro Thr Thr Leu Asn Leu Phe
1               5                   10

<210> SEQ ID NO 12
<211> LENGTH: 11
<212> TYPE: PRT
<213> ORGANISM: Artificial
<220> FEATURE:
<223> OTHER INFORMATION: QRrRPTTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (11)..(11)
<223> OTHER INFORMATION: Phe is D-enantiomeric Phe

<400> SEQUENCE: 12

Gln Arg Arg Arg Pro Thr Thr Leu Asn Leu Phe
1               5                   10

<210> SEQ ID NO 13
<211> LENGTH: 11
<212> TYPE: PRT
<213> ORGANISM: Artificial
<220> FEATURE:
<223> OTHER INFORMATION: RPkRPTTLNLw JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (11)..(11)
<223> OTHER INFORMATION: Trp is D-enantiomeric Trp

<400> SEQUENCE: 13

Arg Pro Lys Arg Pro Thr Thr Leu Asn Leu Trp
1               5                   10

<210> SEQ ID NO 14
<211> LENGTH: 11
<212> TYPE: PRT
<213> ORGANISM: Artificial
<220> FEATURE:
<223> OTHER INFORMATION: RPkRPTDLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
```

<222> LOCATION: (11)..(11)
<223> OTHER INFORMATION: Phe is D-enantiomeric Phe

<400> SEQUENCE: 14

Arg Pro Lys Arg Pro Thr Asp Leu Asn Leu Phe
1               5                   10

<210> SEQ ID NO 15
<211> LENGTH: 11
<212> TYPE: PRT
<213> ORGANISM: Artificial
<220> FEATURE:
<223> OTHER INFORMATION: RRrRPTTLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 15

Arg Arg Arg Arg Pro Thr Thr Leu Arg Leu Trp
1               5                   10

<210> SEQ ID NO 16
<211> LENGTH: 11
<212> TYPE: PRT
<213> ORGANISM: Artificial
<220> FEATURE:
<223> OTHER INFORMATION: QRrRPTTLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 16

Gln Arg Arg Arg Pro Thr Thr Leu Arg Leu Trp
1               5                   10

<210> SEQ ID NO 17
<211> LENGTH: 11
<212> TYPE: PRT
<213> ORGANISM: Artificial
<220> FEATURE:
<223> OTHER INFORMATION: RRrRPTDLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 17

Arg Arg Arg Arg Pro Thr Asp Leu Arg Leu Trp
1               5                   10

<210> SEQ ID NO 18
<211> LENGTH: 11
<212> TYPE: PRT
<213> ORGANISM: Artificial
<220> FEATURE:
<223> OTHER INFORMATION: QRrRPTDLrLw JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (11)..(11)
<223> OTHER INFORMATION: Trp is D-enantiomeric Trp

<400> SEQUENCE: 18

Gln Arg Arg Arg Pro Thr Asp Leu Arg Leu Trp
1               5                   10

<210> SEQ ID NO 19
<211> LENGTH: 11
<212> TYPE: PRT
<213> ORGANISM: Artificial
<220> FEATURE:
<223> OTHER INFORMATION: RRrRPaTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 19

Arg Arg Arg Arg Pro Ala Thr Leu Asn Leu Phe
1               5                   10

<210> SEQ ID NO 20
<211> LENGTH: 11
<212> TYPE: PRT
<213> ORGANISM: Artificial
<220> FEATURE:
<223> OTHER INFORMATION: QRrRPaTLNLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 20

Gln Arg Arg Arg Pro Ala Thr Leu Asn Leu Phe
1               5                   10

```
<210> SEQ ID NO 21
<211> LENGTH: 11
<212> TYPE: PRT
<213> ORGANISM: Artificial
<220> FEATURE:
<223> OTHER INFORMATION: RrKRPaTLNLf JNK inhibitor
<220> FEATURE:
<221> NAME/KEY: Variant
<222> LOCATION: (2)..(2)
<223> OTHER INFORMATION: Arg is D-enantiomeric Arg
<220> FEATURE:
<221> NAME/KEY: Variant
<222> LOCATION: (6)..(6)
<223> OTHER INFORMATION: Ala is D-enantiomeric Ala
<220> FEATURE:
<221> NAME/KEY: Variant
<222> LOCATION: (11)..(11)
<223> OTHER INFORMATION: Phe is D-enantiomeric Phe

<400> SEQUENCE: 21

Arg Arg Lys Arg Pro Ala Thr Leu Asn Leu Phe
1               5                   10

<210> SEQ ID NO 22
<211> LENGTH: 11
<212> TYPE: PRT
<213> ORGANISM: Artificial
<220> FEATURE:
<223> OTHER INFORMATION: RPkRPsTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Ser is D-enantiomeric Ser
<220> FEATURE:
<221> NAME/KEY: Variant
<222> LOCATION: (11)..(11)
<223> OTHER INFORMATION: Phe is D-enantiomeric Phe

<400> SEQUENCE: 22

Arg Pro Lys Arg Pro Ser Thr Leu Asn Leu Phe
1               5                   10

<210> SEQ ID NO 23
<211> LENGTH: 11
<212> TYPE: PRT
<213> ORGANISM: Artificial
<220> FEATURE:
<223> OTHER INFORMATION: RPkRPqTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Gln is D-enantiomeric Gln
<220> FEATURE:
<221> NAME/KEY: Variant
<222> LOCATION: (11)..(11)
<223> OTHER INFORMATION: Phe is D-enantiomeric Phe

<400> SEQUENCE: 23

Arg Pro Lys Arg Pro Gln Thr Leu Asn Leu Phe
1               5                   10

<210> SEQ ID NO 24
<211> LENGTH: 11
<212> TYPE: PRT
```

```
<213> ORGANISM: Artificial
<220> FEATURE:
<223> OTHER INFORMATION: RPkRPkTLNLf JNK inhibitor
<220> FEATURE:
<221> NAME/KEY: Variant
<222> LOCATION: (3)..(3)
<223> OTHER INFORMATION: Lys is D-enantiomeric Lys
<220> FEATURE:
<221> NAME/KEY: Variant
<222> LOCATION: (6)..(6)
<223> OTHER INFORMATION: Lys is D-enantiomeric Lys
<220> FEATURE:
<221> NAME/KEY: Variant
<222> LOCATION: (11)..(11)
<223> OTHER INFORMATION: Phe is D-enantiomeric Phe

<400> SEQUENCE: 24

Arg Pro Lys Arg Pro Lys Thr Leu Asn Leu Phe
1               5                   10

<210> SEQ ID NO 25
<211> LENGTH: 10
<212> TYPE: PRT
<213> ORGANISM: Artificial
<220> FEATURE:
<223> OTHER INFORMATION: rGKRKALKLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe  is D-enantiomeric Phe

<400> SEQUENCE: 25

Arg Gly Lys Arg Lys Ala Leu Lys Leu Phe
1               5                   10

<210> SEQ ID NO 26
<211> LENGTH: 10
<212> TYPE: PRT
<213> ORGANISM: Artificial
<220> FEATURE:
<223> OTHER INFORMATION: rGKRKALrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe is D-enantiomeric Phe

<400> SEQUENCE: 26

Arg Gly Lys Arg Lys Ala Leu Arg Leu Phe
1               5                   10

<210> SEQ ID NO 27
<211> LENGTH: 10
<212> TYPE: PRT
<213> ORGANISM: Artificial
<220> FEATURE:
<223> OTHER INFORMATION: RRrRKALrLf JNK inhibitor
<220> FEATURE:
<221> NAME/KEY: Variant
<222> LOCATION: (3)..(3)
<223> OTHER INFORMATION: Arg is D-enantiomeric Arg
<220> FEATURE:
```

```
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (10)..(10)
<223> OTHER INFORMATION: Phe is D-enantiomeric Phe

<400> SEQUENCE: 27

Arg Arg Arg Arg Lys Ala Leu Arg Leu Phe
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Description of artificial sequence: generic
      subformula (Ib) DlLLLxDmLLLyDn
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid""
<220> FEATURE:
<221> NAME/KEY: REPEAT
<222> LOCATION: (1)..(1)
<223> OTHER INFORMATION: number of repeats is 1 or 2
<220> FEATURE:
<221> NAME/KEY: REPEAT
<222> LOCATION: (4)..(4)
<223> OTHER INFORMATION: number of repeats is 0, 1 or 2
<220> FEATURE:
<221> NAME/KEY: VARIANT
<222> LOCATION: (5)..(5)
<223> OTHER INFORMATION: /replace="D-amino acid""
<220> FEATURE:
<221> NAME/KEY: REPEAT
<222> LOCATION: (5)..(5)
<223> OTHER INFORMATION: number of repeats is 1 or 2
<220> FEATURE:
<221> NAME/KEY: REPEAT
<222> LOCATION: (8)..(8)
<223> OTHER INFORMATION: number of repeats is 0, 1 or 2
<220> FEATURE:
<221> NAME/KEY: VARIANT
<222> LOCATION: (9)..(9)
<223> OTHER INFORMATION: /replace="D-amino acid""
<220> FEATURE:
<221> NAME/KEY: REPEAT
<222> LOCATION: (9)..(9)
<223> OTHER INFORMATION: number of repeats is 1 or 2

<400> SEQUENCE: 28

Xaa Xaa Xaa Xaa Xaa Xaa Xaa Xaa Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Description of artificial sequence: generic
      subformula (Ie) DLLLD(LLLD)a
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid"
```

```
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: REPEAT
<222> LOCATION: (6)..(9)
<223> OTHER INFORMATION: number of repeats is 0, 1, 2 or 3
<220> FEATURE:
<221> NAME/KEY: VARIANT
<222> LOCATION: (9)..(9)
<223> OTHER INFORMATION: /replace="D-amino acid"

<400> SEQUENCE: 29

Xaa Xaa Xaa Xaa Xaa Xaa Xaa Xaa Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Description of artificial sequence: generic
      subformula (If) DLLLDLLLD
<220> FEATURE:
<221> NAME/KEY: VARIANT
<222> LOCATION: (1)..(9)
<223> OTHER INFORMATION: /replace="any amino acid"
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 30

Xaa Xaa Xaa Xaa Xaa Xaa Xaa Xaa Xaa
1               5

<210> SEQ ID NO 31
<211> LENGTH: 9
<212> TYPE: PRT
<213> ORGANISM: Artificial
<220> FEATURE:
<223> OTHER INFORMATION: Description of sequence: consensus sequence
      rXXXrXXXr
<220> FEATURE:
<221> NAME/KEY: misc_feature
<222> LOCATION: (1)..(1)
<223> OTHER INFORMATION: Arg is D-enantiomeric Arg
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Arg is D-enantiomeric Arg
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Arg is D-enantiomeric Arg

<400> SEQUENCE: 31
```

```
Arg Xaa Xaa Xaa Arg Xaa Xaa Xaa Arg
1               5
```

<210> SEQ ID NO 32
<211> LENGTH: 9
<212> TYPE: PRT
<213> ORGANISM: Artificial
<220> FEATURE:
<223> OTHER INFORMATION: r3 (generic; right half)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (6)..(8)
<223> OTHER INFORMATION: Xaa can be any naturally occurring amino acid
<220> FEATURE:
<221> NAME/KEY: Variant
<222> LOCATION: (9)..(9)
<223> OTHER INFORMATION: Arg is D-enantiomeric Arg

<400> SEQUENCE: 32

```
Arg Lys Lys Arg Arg Xaa Xaa Xaa Arg
1               5
```

<210> SEQ ID NO 33
<211> LENGTH: 9
<212> TYPE: PRT
<213> ORGANISM: Artificial
<220> FEATURE:
<223> OTHER INFORMATION: r3 (generic; left half)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (2)..(4)
<223> OTHER INFORMATION: Xaa can be any naturally occurring amino acid
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 33

```
Arg Xaa Xaa Xaa Arg Gln Arg Arg Arg
1               5
```

<210> SEQ ID NO 34
<211> LENGTH: 9
<212> TYPE: PRT
<213> ORGANISM: Artificial
<220> FEATURE:
<223> OTHER INFORMATION: r3 (generic; individual)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (2)..(2)
<223> OTHER INFORMATION: Xaa is K or any other naturally occuring amino
      acid
<220> FEATURE:
<221> NAME/KEY: Variant

```
<222> LOCATION: (3)..(3)
<223> OTHER INFORMATION: Xaa is K or any other naturally occuring amino
      acid
<220> FEATURE:
<221> NAME/KEY: Variant
<222> LOCATION: (4)..(4)
<223> OTHER INFORMATION: Xaa is R or any other naturally occuring amino
      acid
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (6)..(6)
<223> OTHER INFORMATION: Xaa is Q or any other naturally occuring amino
      acid
<220> FEATURE:
<221> NAME/KEY: Variant
<222> LOCATION: (7)..(7)
<223> OTHER INFORMATION: Xaa is R or any other naturally occuring amino
      acid
<220> FEATURE:
<221> NAME/KEY: Variant
<222> LOCATION: (8)..(8)
<223> OTHER INFORMATION: Xaa is R or any other naturally occuring amino
      acid
<220> FEATURE:
<221> NAME/KEY: Variant
<222> LOCATION: (9)..(9)
<223> OTHER INFORMATION: Arg is D-enantiomeric Arg

<400> SEQUENCE: 34

Arg Xaa Xaa Xaa Arg Xaa Xaa Xaa Arg
1               5

<210> SEQ ID NO 35
<211> LENGTH: 86
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 1-86)

<400> SEQUENCE: 35

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 36
<211> LENGTH: 36
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence
      (aa 37-72)

<400> SEQUENCE: 36
```

```
Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35

<210> SEQ ID NO 37
<211> LENGTH: 22
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 37-58)

<400> SEQUENCE: 37

Cys Phe Ile Thr Lys Ala Leu Gly Ile Ser Tyr Gly Arg Lys Lys Arg
1               5                   10                  15

Arg Gln Arg Arg Arg Pro
            20

<210> SEQ ID NO 38
<211> LENGTH: 24
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 38-58) including an additional N-terminal GCC

<400> SEQUENCE: 38

Phe Ile Thr Lys Ala Leu Gly Ile Ser Tyr Gly Arg Lys Lys Arg Arg
1               5                   10                  15

Gln Arg Arg Arg Pro Gly Gly Cys
            20

<210> SEQ ID NO 39
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 47-58) including an additional C-terminal GCC

<400> SEQUENCE: 39

Cys Gly Gly Tyr Gly Arg Lys Lys Arg Arg Gln Arg Arg Arg Pro
1               5                   10                  15

<210> SEQ ID NO 40
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 47-58) including an additional N-terminal GCC

<400> SEQUENCE: 40

Tyr Gly Arg Lys Lys Arg Arg Gln Arg Arg Arg Pro Gly Gly Cys
1               5                   10                  15

<210> SEQ ID NO 41
<211> LENGTH: 56
<212> TYPE: PRT
```

```
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 1-72) including a mutated Cys to Ala residue at position 37

<400> SEQUENCE: 41

Met Glu Pro Val Asp Pro Arg Leu Glu Pro Trp Lys His Pro Gly Ser
1               5                   10                  15

Gln Pro Lys Thr Ala Phe Ile Thr Lys Ala Leu Gly Ile Ser Tyr Gly
            20                  25                  30

Arg Lys Lys Arg Arg Gln Arg Arg Pro Pro Gln Gly Ser Gln Thr
        35                  40                  45

His Gln Val Ser Leu Ser Lys Gln
    50                  55

<210> SEQ ID NO 42
<211> LENGTH: 10
<212> TYPE: PRT
<213> ORGANISM: Artificial
<220> FEATURE:
<223> OTHER INFORMATION: Description of sequence:  trafficking sequence
      L-TAT (s1a)

<400> SEQUENCE: 42

Gly Arg Lys Lys Arg Arg Gln Arg Arg Arg
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of sequence:  trafficking sequence
      L-TAT (s1b)

<400> SEQUENCE: 43

Arg Lys Lys Arg Arg Gln Arg Arg Arg
1               5

<210> SEQ ID NO 44
<211> LENGTH: 11
<212> TYPE: PRT
<213> ORGANISM: Artificial Sequence
<220> FEATURE:
<223> OTHER INFORMATION: Description of sequence:  trafficking sequence
      L-TAT (s1c)

<400> SEQUENCE: 44

Tyr Asp Arg Lys Lys Arg Arg Gln Arg Arg
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Description of artificial sequence: D-TAT
<220> FEATURE:
<221> NAME/KEY: VARIANT
<222> LOCATION: (1)..(9)
<223> OTHER INFORMATION: all amino acids are D-enantiomeric amino acids

<400> SEQUENCE: 45

Arg Arg Arg Gln Arg Arg Lys Lys Arg
1               5
```

```
<210> SEQ ID NO 46
<211> LENGTH: 9
<212> TYPE: PRT
<213> ORGANISM: Artificial Sequence
<220> FEATURE:
<223> OTHER INFORMATION: trafficking sequence r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 46

Arg Lys Lys Arg Arg Gln Arg Arg Arg
1               5

<210> SEQ ID NO 47
<211> LENGTH: 9
<212> TYPE: PRT
<213> ORGANISM: Artificial Sequence
<220> FEATURE:
<223> OTHER INFORMATION: trafficking sequence r3-L-TATi
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 47

Arg Arg Arg Gln Arg Arg Lys Lys Arg
1               5

<210> SEQ ID NO 48
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 48

Arg Lys Lys Arg Arg Gln Arg Arg Arg
1               5
```

<210> SEQ ID NO 49
<211> LENGTH: 9
<212> TYPE: PRT
<213> ORGANISM: Artificial Sequence
<220> FEATURE:
<223> OTHER INFORMATION: Description of sequence: trafficking sequence
      betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: b-Alanine modified
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 49

Arg Arg Arg Gln Arg Arg Lys Lys Arg
1               5

<210> SEQ ID NO 50
<211> LENGTH: 9
<212> TYPE: PRT
<213> ORGANISM: Artificial Sequence
<220> FEATURE:
<223> OTHER INFORMATION: Description of sequence: trafficking sequence
      FITC-betaA-r3-L-TAT
<220> FEATURE:
<221> NAME/KEY: MOD_RES
<222> LOCATION: (1)..(1)
<223> OTHER INFORMATION: FITC-b-Alanine modified
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 50

Arg Lys Lys Arg Arg Gln Arg Arg Arg
1               5

<210> SEQ ID NO 51
<211> LENGTH: 9
<212> TYPE: PRT
<213> ORGANISM: Artificial Sequence
<220> FEATURE:
<223> OTHER INFORMATION: Description of sequence: trafficking sequence
      FITC-betaA-r3-L-TAT
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: MOD_RES
<222> LOCATION: (1)..(1)
<223> OTHER INFORMATION: FITC-b-Alanine modified
<220> FEATURE:
<221> NAME/KEY: Variant

```
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 51

Arg Arg Arg Gln Arg Arg Lys Lys Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-1)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 52

Arg Ala Lys Arg Arg Gln Arg Arg Arg
1               5

<210> SEQ ID NO 53
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-2)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 53

Arg Lys Ala Arg Arg Gln Arg Arg Arg
1               5

<210> SEQ ID NO 54
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-3)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
```

```
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 54

Arg Lys Lys Ala Arg Gln Arg Arg Arg
1               5

<210> SEQ ID NO 55
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-4)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 55

Arg Lys Lys Arg Arg Ala Arg Arg Arg
1               5

<210> SEQ ID NO 56
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-5)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 56

Arg Lys Lys Arg Arg Gln Ala Arg Arg
1               5

<210> SEQ ID NO 57
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-6))
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
```

```
<220> FEATURE:
<221> NAME/KEY: Variant
<222> LOCATION: (9)..(9)
<223> OTHER INFORMATION: Arg is D-enantiomeric Arg

<400> SEQUENCE: 57

Arg Lys Lys Arg Arg Gln Arg Ala Arg
1               5

<210> SEQ ID NO 58
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-7)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 58

Arg Asp Lys Arg Arg Gln Arg Arg Arg
1               5

<210> SEQ ID NO 59
<211> LENGTH: 9
<212> TYPE: PRT
<213> ORGANISM: Artificial Sequence
<220> FEATURE:
<223> OTHER INFORMATION: trafficking sequence TAT(s2-8)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 59

Arg Lys Asp Arg Arg Gln Arg Arg Arg
1               5

<210> SEQ ID NO 60
<211> LENGTH: 9
<212> TYPE: PRT
<213> ORGANISM: Artificial Sequence
<220> FEATURE:
<223> OTHER INFORMATION: trafficking sequence TAT(s2-9)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
```

<223> OTHER INFORMATION: Arg is D-enantiomeric Arg

<400> SEQUENCE: 60

Arg Lys Lys Asp Arg Gln Arg Arg Arg
1               5

<210> SEQ ID NO 61
<211> LENGTH: 9
<212> TYPE: PRT
<213> ORGANISM: Artificial Sequence
<220> FEATURE:
<223> OTHER INFORMATION: trafficking sequence TAT(s2-10)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 61

Arg Lys Lys Arg Arg Asp Arg Arg Arg
1               5

<210> SEQ ID NO 62
<211> LENGTH: 9
<212> TYPE: PRT
<213> ORGANISM: Artificial Sequence
<220> FEATURE:
<223> OTHER INFORMATION: trafficking sequence TAT(s2-11)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 62

Arg Lys Lys Arg Arg Gln Asp Arg Arg
1               5

<210> SEQ ID NO 63
<211> LENGTH: 9
<212> TYPE: PRT
<213> ORGANISM: Artificial Sequence
<220> FEATURE:
<223> OTHER INFORMATION: trafficking sequence TAT(s2-12)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 63

Arg Lys Lys Arg Arg Gln Arg Asp Arg
1               5

<210> SEQ ID NO 64
<211> LENGTH: 9
<212> TYPE: PRT
<213> ORGANISM: Artificial Sequence
<220> FEATURE:
<223> OTHER INFORMATION: trafficking sequence TAT(s2-13)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 64

Arg Glu Lys Arg Arg Gln Arg Arg Arg
1               5

<210> SEQ ID NO 65
<211> LENGTH: 9
<212> TYPE: PRT
<213> ORGANISM: Artificial Sequence
<220> FEATURE:
<223> OTHER INFORMATION: trafficking sequence TAT(s2-14)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 65

Arg Lys Glu Arg Arg Gln Arg Arg Arg
1               5

<210> SEQ ID NO 66
<211> LENGTH: 9
<212> TYPE: PRT
<213> ORGANISM: Artificial Sequence
<220> FEATURE:
<223> OTHER INFORMATION: trafficking sequence TAT(s2-15)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 66

Arg Lys Lys Glu Arg Gln Arg Arg Arg
1               5

```
<210> SEQ ID NO 67
<211> LENGTH: 9
<212> TYPE: PRT
<213> ORGANISM: Artificial Sequence
<220> FEATURE:
<223> OTHER INFORMATION: trafficking sequence TAT(s2-16)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 67

Arg Lys Lys Arg Arg Glu Arg Arg Arg
1               5

<210> SEQ ID NO 68
<211> LENGTH: 9
<212> TYPE: PRT
<213> ORGANISM: Artificial Sequence
<220> FEATURE:
<223> OTHER INFORMATION: trafficking sequence TAT(s2-17)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 68

Arg Lys Lys Arg Arg Gln Glu Arg Arg
1               5

<210> SEQ ID NO 69
<211> LENGTH: 9
<212> TYPE: PRT
<213> ORGANISM: Artificial Sequence
<220> FEATURE:
<223> OTHER INFORMATION: trafficking sequence TAT(s2-18)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 69

Arg Lys Lys Arg Arg Gln Arg Glu Arg
1               5

<210> SEQ ID NO 70
<211> LENGTH: 9
<212> TYPE: PRT
<213> ORGANISM: Artificial Sequence
```

```
<220> FEATURE:
<223> OTHER INFORMATION: trafficking sequence TAT(s2-19)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 70

Arg Phe Lys Arg Arg Gln Arg Arg Arg
1               5

<210> SEQ ID NO 71
<211> LENGTH: 9
<212> TYPE: PRT
<213> ORGANISM: Artificial Sequence
<220> FEATURE:
<223> OTHER INFORMATION: trafficking sequence TAT(s2-20)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 71

Arg Lys Phe Arg Arg Gln Arg Arg Arg
1               5

<210> SEQ ID NO 72
<211> LENGTH: 9
<212> TYPE: PRT
<213> ORGANISM: Artificial Sequence
<220> FEATURE:
<223> OTHER INFORMATION: trafficking sequence TAT(s2-21)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 72

Arg Lys Lys Phe Arg Gln Arg Arg Arg
1               5

<210> SEQ ID NO 73
<211> LENGTH: 9
<212> TYPE: PRT
<213> ORGANISM: Artificial Sequence
<220> FEATURE:
<223> OTHER INFORMATION: trafficking sequence TAT(s2-22)
<220> FEATURE:
<221> NAME/KEY: Variant
```

```
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 73

Arg Lys Lys Arg Arg Phe Arg Arg Arg
1               5

<210> SEQ ID NO 74
<211> LENGTH: 9
<212> TYPE: PRT
<213> ORGANISM: Artificial Sequence
<220> FEATURE:
<223> OTHER INFORMATION: trafficking sequence TAT(s2-23)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 74

Arg Lys Lys Arg Arg Gln Phe Arg Arg
1               5

<210> SEQ ID NO 75
<211> LENGTH: 9
<212> TYPE: PRT
<213> ORGANISM: Artificial Sequence
<220> FEATURE:
<223> OTHER INFORMATION: trafficking sequence TAT(s2-24)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 75

Arg Lys Lys Arg Arg Gln Arg Phe Arg
1               5

<210> SEQ ID NO 76
<211> LENGTH: 9
<212> TYPE: PRT
<213> ORGANISM: Artificial Sequence
<220> FEATURE:
<223> OTHER INFORMATION: trafficking sequence TAT(s2-25)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
```

```
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 76

Arg Arg Lys Arg Arg Gln Arg Arg Arg
1               5

<210> SEQ ID NO 77
<211> LENGTH: 9
<212> TYPE: PRT
<213> ORGANISM: Artificial Sequence
<220> FEATURE:
<223> OTHER INFORMATION: trafficking sequence TAT(s2-26)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 77

Arg Lys Arg Arg Arg Gln Arg Arg Arg
1               5

<210> SEQ ID NO 78
<211> LENGTH: 9
<212> TYPE: PRT
<213> ORGANISM: Artificial Sequence
<220> FEATURE:
<223> OTHER INFORMATION: trafficking sequence TAT(s2-27)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 78

Arg Lys Lys Lys Arg Gln Arg Arg Arg
1               5

<210> SEQ ID NO 79
<211> LENGTH: 9
<212> TYPE: PRT
<213> ORGANISM: Artificial Sequence
<220> FEATURE:
<223> OTHER INFORMATION: trafficking sequence TAT(s2-28)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
```

```
<222> LOCATION: (9)..(9)
<223> OTHER INFORMATION: Arg is D-enantiomeric Arg

<400> SEQUENCE: 79

Arg Lys Lys Arg Arg Arg Arg Arg Arg
1               5

<210> SEQ ID NO 80
<211> LENGTH: 9
<212> TYPE: PRT
<213> ORGANISM: Artificial Sequence
<220> FEATURE:
<223> OTHER INFORMATION: trafficking sequence TAT(s2-29)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 80

Arg Lys Lys Arg Arg Gln Lys Arg Arg
1               5

<210> SEQ ID NO 81
<211> LENGTH: 9
<212> TYPE: PRT
<213> ORGANISM: Artificial Sequence
<220> FEATURE:
<223> OTHER INFORMATION: trafficking sequence TAT(s2-30)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 81

Arg Lys Lys Arg Arg Gln Arg Lys Arg
1               5

<210> SEQ ID NO 82
<211> LENGTH: 9
<212> TYPE: PRT
<213> ORGANISM: Artificial Sequence
<220> FEATURE:
<223> OTHER INFORMATION: trafficking sequence TAT(s2-31)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 82
```

```
Arg His Lys Arg Arg Gln Arg Arg Arg
1               5
```

<210> SEQ ID NO 83
<211> LENGTH: 9
<212> TYPE: PRT
<213> ORGANISM: Artificial Sequence
<220> FEATURE:
<223> OTHER INFORMATION: trafficking sequence TAT(s2-32)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 83

```
Arg Lys His Arg Arg Gln Arg Arg Arg
1               5
```

<210> SEQ ID NO 84
<211> LENGTH: 9
<212> TYPE: PRT
<213> ORGANISM: Artificial Sequence
<220> FEATURE:
<223> OTHER INFORMATION: trafficking sequence TAT(s2-33)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 84

```
Arg Lys Lys His Arg Gln Arg Arg Arg
1               5
```

<210> SEQ ID NO 85
<211> LENGTH: 9
<212> TYPE: PRT
<213> ORGANISM: Artificial Sequence
<220> FEATURE:
<223> OTHER INFORMATION: trafficking sequence TAT(s2-34)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 85

```
Arg Lys Lys Arg Arg His Arg Arg Arg
1               5
```

```
<210> SEQ ID NO 86
<211> LENGTH: 9
<212> TYPE: PRT
<213> ORGANISM: Artificial Sequence
<220> FEATURE:
<223> OTHER INFORMATION: trafficking sequence TAT(s2-35)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 86

Arg Lys Lys Arg Arg Gln His Arg Arg
1               5

<210> SEQ ID NO 87
<211> LENGTH: 9
<212> TYPE: PRT
<213> ORGANISM: Artificial Sequence
<220> FEATURE:
<223> OTHER INFORMATION: trafficking sequence TAT(s2-36)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 87

Arg Lys Lys Arg Arg Gln Arg His Arg
1               5

<210> SEQ ID NO 88
<211> LENGTH: 9
<212> TYPE: PRT
<213> ORGANISM: Artificial Sequence
<220> FEATURE:
<223> OTHER INFORMATION: trafficking sequence TAT(s2-37)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 88

Arg Ile Lys Arg Arg Gln Arg Arg Arg
1               5

<210> SEQ ID NO 89
<211> LENGTH: 9
<212> TYPE: PRT
```

```
<213> ORGANISM: Artificial Sequence
<220> FEATURE:
<223> OTHER INFORMATION: trafficking sequence TAT(s2-38)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 89

Arg Lys Ile Arg Arg Gln Arg Arg Arg
1               5

<210> SEQ ID NO 90
<211> LENGTH: 9
<212> TYPE: PRT
<213> ORGANISM: Artificial Sequence
<220> FEATURE:
<223> OTHER INFORMATION: trafficking sequence TAT(s2-39)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 90

Arg Lys Lys Ile Arg Gln Arg Arg Arg
1               5

<210> SEQ ID NO 91
<211> LENGTH: 9
<212> TYPE: PRT
<213> ORGANISM: Artificial Sequence
<220> FEATURE:
<223> OTHER INFORMATION: trafficking sequence TAT(s2-40)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 91

Arg Lys Lys Arg Arg Ile Arg Arg Arg
1               5

<210> SEQ ID NO 92
<211> LENGTH: 9
<212> TYPE: PRT
<213> ORGANISM: Artificial Sequence
<220> FEATURE:
<223> OTHER INFORMATION: trafficking sequence TAT(s2-41)
<220> FEATURE:
```

```
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 92

Arg Lys Lys Arg Arg Gln Ile Arg Arg
1               5

<210> SEQ ID NO 93
<211> LENGTH: 9
<212> TYPE: PRT
<213> ORGANISM: Artificial Sequence
<220> FEATURE:
<223> OTHER INFORMATION: trafficking sequence TAT(s2-42)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 93

Arg Lys Lys Arg Arg Gln Arg Ile Arg
1               5

<210> SEQ ID NO 94
<211> LENGTH: 9
<212> TYPE: PRT
<213> ORGANISM: Artificial Sequence
<220> FEATURE:
<223> OTHER INFORMATION: trafficking sequence TAT(s2-43)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 94

Arg Leu Lys Arg Arg Gln Arg Arg Arg
1               5

<210> SEQ ID NO 95
<211> LENGTH: 9
<212> TYPE: PRT
<213> ORGANISM: Artificial Sequence
<220> FEATURE:
<223> OTHER INFORMATION: trafficking sequence TAT(s2-44)
<220> FEATURE:
<221> NAME/KEY: Variant
<222> LOCATION: (1)..(1)
<223> OTHER INFORMATION: Arg is D-enantiomeric Arg
<220> FEATURE:
```

-continued

```
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 95

Arg Lys Leu Arg Arg Gln Arg Arg Arg
1               5

<210> SEQ ID NO 96
<211> LENGTH: 9
<212> TYPE: PRT
<213> ORGANISM: Artificial Sequence
<220> FEATURE:
<223> OTHER INFORMATION: trafficking sequence TAT(s2-45)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 96

Arg Lys Lys Leu Arg Gln Arg Arg Arg
1               5

<210> SEQ ID NO 97
<211> LENGTH: 9
<212> TYPE: PRT
<213> ORGANISM: Artificial Sequence
<220> FEATURE:
<223> OTHER INFORMATION: trafficking sequence TAT(s2-46)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 97

Arg Lys Lys Arg Arg Leu Arg Arg Arg
1               5

<210> SEQ ID NO 98
<211> LENGTH: 9
<212> TYPE: PRT
<213> ORGANISM: Artificial Sequence
<220> FEATURE:
<223> OTHER INFORMATION: trafficking sequence TAT(s2-47)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
```

```
<221> NAME/KEY: Variant
<222> LOCATION: (9)..(9)
<223> OTHER INFORMATION: Arg is D-enantiomeric Arg

<400> SEQUENCE: 98

Arg Lys Lys Arg Arg Gln Leu Arg Arg
1               5

<210> SEQ ID NO 99
<211> LENGTH: 9
<212> TYPE: PRT
<213> ORGANISM: Artificial Sequence
<220> FEATURE:
<223> OTHER INFORMATION: trafficking sequence TAT(s2-48)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 99

Arg Lys Lys Arg Arg Gln Arg Leu Arg
1               5

<210> SEQ ID NO 100
<211> LENGTH: 9
<212> TYPE: PRT
<213> ORGANISM: Artificial Sequence
<220> FEATURE:
<223> OTHER INFORMATION: trafficking sequence TAT(s2-49)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 100

Arg Met Lys Arg Arg Gln Arg Arg Arg
1               5

<210> SEQ ID NO 101
<211> LENGTH: 9
<212> TYPE: PRT
<213> ORGANISM: Artificial Sequence
<220> FEATURE:
<223> OTHER INFORMATION: trafficking sequence TAT(s2-50)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
```

```
<400> SEQUENCE: 101

Arg Lys Met Arg Arg Gln Arg Arg Arg
1               5

<210> SEQ ID NO 102
<211> LENGTH: 9
<212> TYPE: PRT
<213> ORGANISM: Artificial Sequence
<220> FEATURE:
<223> OTHER INFORMATION: trafficking sequence TAT(s2-51)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 102

Arg Lys Lys Met Arg Gln Arg Arg Arg
1               5

<210> SEQ ID NO 103
<211> LENGTH: 9
<212> TYPE: PRT
<213> ORGANISM: Artificial Sequence
<220> FEATURE:
<223> OTHER INFORMATION: trafficking sequence TAT(s2-52)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 103

Arg Lys Lys Arg Arg Met Arg Arg Arg
1               5

<210> SEQ ID NO 104
<211> LENGTH: 9
<212> TYPE: PRT
<213> ORGANISM: Artificial Sequence
<220> FEATURE:
<223> OTHER INFORMATION: trafficking sequence TAT(s2-53)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 104

Arg Lys Lys Arg Arg Gln Met Arg Arg
1               5
```

<210> SEQ ID NO 105
<211> LENGTH: 9
<212> TYPE: PRT
<213> ORGANISM: Artificial Sequence
<220> FEATURE:
<223> OTHER INFORMATION: trafficking sequence TAT(s2-54)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 105

Arg Lys Lys Arg Arg Gln Arg Met Arg
1               5

<210> SEQ ID NO 106
<211> LENGTH: 9
<212> TYPE: PRT
<213> ORGANISM: Artificial Sequence
<220> FEATURE:
<223> OTHER INFORMATION: trafficking sequence TAT(s2-55)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 106

Arg Asn Lys Arg Arg Gln Arg Arg Arg
1               5

<210> SEQ ID NO 107
<211> LENGTH: 9
<212> TYPE: PRT
<213> ORGANISM: Artificial Sequence
<220> FEATURE:
<223> OTHER INFORMATION: trafficking sequence TAT(s2-56)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 107

Arg Lys Asn Arg Arg Gln Arg Arg Arg
1               5

<210> SEQ ID NO 108
<211> LENGTH: 9

```
<212> TYPE: PRT
<213> ORGANISM: Artificial Sequence
<220> FEATURE:
<223> OTHER INFORMATION: trafficking sequence TAT(s2-57)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 108

Arg Lys Lys Asn Arg Gln Arg Arg Arg
1               5

<210> SEQ ID NO 109
<211> LENGTH: 9
<212> TYPE: PRT
<213> ORGANISM: Artificial Sequence
<220> FEATURE:
<223> OTHER INFORMATION: trafficking sequence TAT(s2-58)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 109

Arg Lys Lys Arg Arg Asn Arg Arg Arg
1               5

<210> SEQ ID NO 110
<211> LENGTH: 9
<212> TYPE: PRT
<213> ORGANISM: Artificial Sequence
<220> FEATURE:
<223> OTHER INFORMATION: trafficking sequence TAT(s2-59)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 110

Arg Lys Lys Arg Arg Gln Asn Arg Arg
1               5

<210> SEQ ID NO 111
<211> LENGTH: 9
<212> TYPE: PRT
<213> ORGANISM: Artificial Sequence
<220> FEATURE:
<223> OTHER INFORMATION: trafficking sequence TAT(s2-60)
```

```
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 111

Arg Lys Lys Arg Arg Gln Arg Asn Arg
1               5

<210> SEQ ID NO 112
<211> LENGTH: 9
<212> TYPE: PRT
<213> ORGANISM: Artificial Sequence
<220> FEATURE:
<223> OTHER INFORMATION: trafficking sequence TAT(s2-61)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 112

Arg Gln Lys Arg Arg Gln Arg Arg Arg
1               5

<210> SEQ ID NO 113
<211> LENGTH: 9
<212> TYPE: PRT
<213> ORGANISM: Artificial Sequence
<220> FEATURE:
<223> OTHER INFORMATION: trafficking sequence TAT(s2-62)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 113

Arg Lys Gln Arg Arg Gln Arg Arg Arg
1               5

<210> SEQ ID NO 114
<211> LENGTH: 9
<212> TYPE: PRT
<213> ORGANISM: Artificial Sequence
<220> FEATURE:
<223> OTHER INFORMATION: trafficking sequence TAT(s2-63)
<220> FEATURE:
<221> NAME/KEY: Variant
<222> LOCATION: (1)..(1)
<223> OTHER INFORMATION: Arg is D-enantiomeric Arg
```

```
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 114

Arg Lys Lys Gln Arg Gln Arg Arg Arg
1               5

<210> SEQ ID NO 115
<211> LENGTH: 9
<212> TYPE: PRT
<213> ORGANISM: Artificial Sequence
<220> FEATURE:
<223> OTHER INFORMATION: trafficking sequence TAT(s2-64)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 115

Arg Lys Lys Arg Arg Lys Arg Arg Arg
1               5

<210> SEQ ID NO 116
<211> LENGTH: 9
<212> TYPE: PRT
<213> ORGANISM: Artificial Sequence
<220> FEATURE:
<223> OTHER INFORMATION: trafficking sequence TAT(s2-65)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 116

Arg Lys Lys Arg Arg Gln Gln Arg Arg
1               5

<210> SEQ ID NO 117
<211> LENGTH: 9
<212> TYPE: PRT
<213> ORGANISM: Artificial Sequence
<220> FEATURE:
<223> OTHER INFORMATION: trafficking sequence TAT(s2-66)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
```

```
<220> FEATURE:
<221> NAME/KEY: Variant
<222> LOCATION: (9)..(9)
<223> OTHER INFORMATION: Arg is D-enantiomeric Arg

<400> SEQUENCE: 117

Arg Lys Lys Arg Arg Gln Arg Gln Arg
1               5

<210> SEQ ID NO 118
<211> LENGTH: 9
<212> TYPE: PRT
<213> ORGANISM: Artificial Sequence
<220> FEATURE:
<223> OTHER INFORMATION: trafficking sequence TAT(s2-67)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 118

Arg Ser Lys Arg Arg Gln Arg Arg Arg
1               5

<210> SEQ ID NO 119
<211> LENGTH: 9
<212> TYPE: PRT
<213> ORGANISM: Artificial Sequence
<220> FEATURE:
<223> OTHER INFORMATION: trafficking sequence TAT(s2-68)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 119

Arg Lys Ser Arg Arg Gln Arg Arg Arg
1               5

<210> SEQ ID NO 120
<211> LENGTH: 9
<212> TYPE: PRT
<213> ORGANISM: Artificial Sequence
<220> FEATURE:
<223> OTHER INFORMATION: trafficking sequence TAT(s2-69)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
```

<400> SEQUENCE: 120

Arg Lys Lys Ser Arg Gln Arg Arg Arg
1               5

<210> SEQ ID NO 121
<211> LENGTH: 9
<212> TYPE: PRT
<213> ORGANISM: Artificial Sequence
<220> FEATURE:
<223> OTHER INFORMATION: trafficking sequence TAT(s2-70)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 121

Arg Lys Lys Arg Arg Ser Arg Arg Arg
1               5

<210> SEQ ID NO 122
<211> LENGTH: 9
<212> TYPE: PRT
<213> ORGANISM: Artificial Sequence
<220> FEATURE:
<223> OTHER INFORMATION: trafficking sequence TAT(s2-71)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 122

Arg Lys Lys Arg Arg Gln Ser Arg Arg
1               5

<210> SEQ ID NO 123
<211> LENGTH: 9
<212> TYPE: PRT
<213> ORGANISM: Artificial Sequence
<220> FEATURE:
<223> OTHER INFORMATION: trafficking sequence TAT(s2-72)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 123

Arg Lys Lys Arg Arg Gln Arg Ser Arg

```
<210> SEQ ID NO 124
<211> LENGTH: 9
<212> TYPE: PRT
<213> ORGANISM: Artificial Sequence
<220> FEATURE:
<223> OTHER INFORMATION: trafficking sequence TAT(s2-73)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 124

Arg Thr Lys Arg Arg Gln Arg Arg Arg
1               5

<210> SEQ ID NO 125
<211> LENGTH: 9
<212> TYPE: PRT
<213> ORGANISM: Artificial Sequence
<220> FEATURE:
<223> OTHER INFORMATION: trafficking sequence TAT(s2-74)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 125

Arg Lys Thr Arg Arg Gln Arg Arg Arg
1               5

<210> SEQ ID NO 126
<211> LENGTH: 9
<212> TYPE: PRT
<213> ORGANISM: Artificial Sequence
<220> FEATURE:
<223> OTHER INFORMATION: trafficking sequence TAT(s2-75)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 126

Arg Lys Lys Thr Arg Gln Arg Arg Arg
1               5

<210> SEQ ID NO 127
```

```
<211> LENGTH: 9
<212> TYPE: PRT
<213> ORGANISM: Artificial Sequence
<220> FEATURE:
<223> OTHER INFORMATION: trafficking sequence TAT(s2-76)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 127

Arg Lys Lys Arg Arg Thr Arg Arg Arg
1               5

<210> SEQ ID NO 128
<211> LENGTH: 9
<212> TYPE: PRT
<213> ORGANISM: Artificial Sequence
<220> FEATURE:
<223> OTHER INFORMATION: trafficking sequence TAT(s2-77)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 128

Arg Lys Lys Arg Arg Gln Thr Arg Arg
1               5

<210> SEQ ID NO 129
<211> LENGTH: 9
<212> TYPE: PRT
<213> ORGANISM: Artificial Sequence
<220> FEATURE:
<223> OTHER INFORMATION: trafficking sequence TAT(s2-78)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 129

Arg Lys Lys Arg Arg Gln Arg Thr Arg
1               5

<210> SEQ ID NO 130
<211> LENGTH: 9
<212> TYPE: PRT
<213> ORGANISM: Artificial Sequence
<220> FEATURE:
```

```
<223> OTHER INFORMATION: trafficking sequence TAT(s2-79)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 130

Arg Val Lys Arg Arg Gln Arg Arg Arg
1               5

<210> SEQ ID NO 131
<211> LENGTH: 9
<212> TYPE: PRT
<213> ORGANISM: Artificial Sequence
<220> FEATURE:
<223> OTHER INFORMATION: trafficking sequence TAT(s2-80)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 131

Arg Lys Val Arg Arg Gln Arg Arg Arg
1               5

<210> SEQ ID NO 132
<211> LENGTH: 9
<212> TYPE: PRT
<213> ORGANISM: Artificial Sequence
<220> FEATURE:
<223> OTHER INFORMATION: trafficking sequence TAT(s2-81)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 132

Arg Lys Lys Val Arg Gln Arg Arg Arg
1               5

<210> SEQ ID NO 133
<211> LENGTH: 9
<212> TYPE: PRT
<213> ORGANISM: Artificial Sequence
<220> FEATURE:
<223> OTHER INFORMATION: trafficking sequence TAT(s2-82)
<220> FEATURE:
<221> NAME/KEY: Variant
<222> LOCATION: (1)..(1)
```

```
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 133

Arg Lys Lys Arg Arg Val Arg Arg Arg
1               5

<210> SEQ ID NO 134
<211> LENGTH: 9
<212> TYPE: PRT
<213> ORGANISM: Artificial Sequence
<220> FEATURE:
<223> OTHER INFORMATION: trafficking sequence TAT(s2-83)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 134

Arg Lys Lys Arg Arg Gln Val Arg Arg
1               5

<210> SEQ ID NO 135
<211> LENGTH: 9
<212> TYPE: PRT
<213> ORGANISM: Artificial Sequence
<220> FEATURE:
<223> OTHER INFORMATION: trafficking sequence TAT(s2-84)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 135

Arg Lys Lys Arg Arg Gln Arg Val Arg
1               5

<210> SEQ ID NO 136
<211> LENGTH: 9
<212> TYPE: PRT
<213> ORGANISM: Artificial Sequence
<220> FEATURE:
<223> OTHER INFORMATION: trafficking sequence TAT(s2-85)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
```

```
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 136

Arg Trp Lys Arg Arg Gln Arg Arg Arg
1               5

<210> SEQ ID NO 137
<211> LENGTH: 9
<212> TYPE: PRT
<213> ORGANISM: Artificial Sequence
<220> FEATURE:
<223> OTHER INFORMATION: trafficking sequence TAT(s2-86)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 137

Arg Lys Trp Arg Arg Gln Arg Arg Arg
1               5

<210> SEQ ID NO 138
<211> LENGTH: 9
<212> TYPE: PRT
<213> ORGANISM: Artificial Sequence
<220> FEATURE:
<223> OTHER INFORMATION: trafficking sequence TAT(s2-87)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 138

Arg Lys Lys Trp Arg Gln Arg Arg Arg
1               5

<210> SEQ ID NO 139
<211> LENGTH: 9
<212> TYPE: PRT
<213> ORGANISM: Artificial Sequence
<220> FEATURE:
<223> OTHER INFORMATION: trafficking sequence TAT(s2-88)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
```

```
<223> OTHER INFORMATION: Arg is D-enantiomeric Arg

<400> SEQUENCE: 139

Arg Lys Lys Arg Arg Trp Arg Arg Arg
1               5

<210> SEQ ID NO 140
<211> LENGTH: 9
<212> TYPE: PRT
<213> ORGANISM: Artificial Sequence
<220> FEATURE:
<223> OTHER INFORMATION: trafficking sequence TAT(s2-89)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 140

Arg Lys Lys Arg Arg Gln Trp Arg Arg
1               5

<210> SEQ ID NO 141
<211> LENGTH: 9
<212> TYPE: PRT
<213> ORGANISM: Artificial Sequence
<220> FEATURE:
<223> OTHER INFORMATION: trafficking sequence TAT(s2-90)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 141

Arg Lys Lys Arg Arg Gln Arg Trp Arg
1               5

<210> SEQ ID NO 142
<211> LENGTH: 9
<212> TYPE: PRT
<213> ORGANISM: Artificial Sequence
<220> FEATURE:
<223> OTHER INFORMATION: trafficking sequence TAT(s2-91)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 142
```

```
Arg Tyr Lys Arg Arg Gln Arg Arg Arg
1               5
```

<210> SEQ ID NO 143
<211> LENGTH: 9
<212> TYPE: PRT
<213> ORGANISM: Artificial Sequence
<220> FEATURE:
<223> OTHER INFORMATION: trafficking sequence TAT(s2-92)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 143

```
Arg Lys Tyr Arg Arg Gln Arg Arg Arg
1               5
```

<210> SEQ ID NO 144
<211> LENGTH: 9
<212> TYPE: PRT
<213> ORGANISM: Artificial Sequence
<220> FEATURE:
<223> OTHER INFORMATION: trafficking sequence TAT(s2-93)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 144

```
Arg Lys Lys Tyr Arg Gln Arg Arg Arg
1               5
```

<210> SEQ ID NO 145
<211> LENGTH: 9
<212> TYPE: PRT
<213> ORGANISM: Artificial Sequence
<220> FEATURE:
<223> OTHER INFORMATION: trafficking sequence TAT(s2-94)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 145

```
Arg Lys Lys Arg Arg Tyr Arg Arg Arg
1               5
```

```
<210> SEQ ID NO 146
<211> LENGTH: 9
<212> TYPE: PRT
<213> ORGANISM: Artificial Sequence
<220> FEATURE:
<223> OTHER INFORMATION: trafficking sequence TAT(s2-95)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 146

Arg Lys Lys Arg Arg Gln Tyr Arg Arg
1               5

<210> SEQ ID NO 147
<211> LENGTH: 9
<212> TYPE: PRT
<213> ORGANISM: Artificial Sequence
<220> FEATURE:
<223> OTHER INFORMATION: Trafficking sequence TAT(s2-96)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 147

Arg Lys Lys Arg Arg Gln Arg Tyr Arg
1               5

<210> SEQ ID NO 148
<211> LENGTH: 8
<212> TYPE: PRT
<213> ORGANISM: Artificial
<220> FEATURE:
<223> OTHER INFORMATION: Trafficking sequence TAT(s2-97)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 148

Arg Lys Lys Arg Arg Gln Arg Arg
1               5

<210> SEQ ID NO 149
<211> LENGTH: 9
<212> TYPE: PRT
<213> ORGANISM: Artificial
```

```
<220> FEATURE:
<223> OTHER INFORMATION: Trafficking sequence TAT(s2-98)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 149

Arg Lys Lys Arg Arg Gln Arg Arg Lys
1               5

<210> SEQ ID NO 150
<211> LENGTH: 9
<212> TYPE: PRT
<213> ORGANISM: Artificial
<220> FEATURE:
<223> OTHER INFORMATION: Trafficking sequence TAT(s2-99)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg

<400> SEQUENCE: 150

Arg Lys Lys Arg Arg Gln Arg Arg Arg
1               5

<210> SEQ ID NO 151
<211> LENGTH: 9
<212> TYPE: PRT
<213> ORGANISM: Artificial Sequence
<220> FEATURE:
<223> OTHER INFORMATION: trafficking sequence r3R6
<220> FEATURE:
<221> NAME/KEY: VARIANT
<222> LOCATION: (1)..(1)
<223> OTHER INFORMATION: /replace="D-enatiomeric amino acid arginine"
<220> FEATURE:
<221> NAME/KEY: VARIANT
<222> LOCATION: (5)..(5)
<223> OTHER INFORMATION: /replace="D-enatiomeric amino acid arginine"
<220> FEATURE:
<221> NAME/KEY: VARIANT
<222> LOCATION: (9)..(9)
<223> OTHER INFORMATION: /replace="D-enatiomeric amino acid arginine"

<400> SEQUENCE: 151

Arg Arg Arg Arg Arg Arg Arg Arg Arg
1               5

<210> SEQ ID NO 152
<211> LENGTH: 9
<212> TYPE: PRT
<213> ORGANISM: Artificial Sequence
<220> FEATURE:
<223> OTHER INFORMATION: trafficking sequence L-R9

<400> SEQUENCE: 152
```

```
Arg Arg Arg Arg Arg Arg Arg Arg Arg
1               5

<210> SEQ ID NO 153
<211> LENGTH: 8
<212> TYPE: PRT
<213> ORGANISM: Artificial Sequence
<220> FEATURE:
<223> OTHER INFORMATION: trafficking sequence L-R8

<400> SEQUENCE: 153

Arg Arg Arg Arg Arg Arg Arg Arg
1               5

<210> SEQ ID NO 154
<211> LENGTH: 7
<212> TYPE: PRT
<213> ORGANISM: Artificial Sequence
<220> FEATURE:
<223> OTHER INFORMATION: trafficking sequence L-R7

<400> SEQUENCE: 154

Arg Arg Arg Arg Arg Arg Arg
1               5

<210> SEQ ID NO 155
<211> LENGTH: 6
<212> TYPE: PRT
<213> ORGANISM: Artificial Sequence
<220> FEATURE:
<223> OTHER INFORMATION: trafficking sequence L-R6

<400> SEQUENCE: 155

Arg Arg Arg Arg Arg Arg
1               5

<210> SEQ ID NO 156
<211> LENGTH: 5
<212> TYPE: PRT
<213> ORGANISM: Artificial Sequence
<220> FEATURE:
<223> OTHER INFORMATION: trafficking sequence L-R5

<400> SEQUENCE: 156

Arg Arg Arg Arg Arg
1               5

<210> SEQ ID NO 157
<211> LENGTH: 9
<212> TYPE: PRT
<213> ORGANISM: Artificial
<220> FEATURE:
<223> OTHER INFORMATION: all D transporter construct (all amino acid
      residues are D-amino acids)
<220> FEATURE:
<221> NAME/KEY: Variant
<222> LOCATION: (1)..(9)
<223> OTHER INFORMATION: Arg is D-enantiomeric Arg

<400> SEQUENCE: 157

Arg Arg Arg Arg Arg Arg Arg Arg Arg
1               5

<210> SEQ ID NO 158
<211> LENGTH: 9
<212> TYPE: PRT
<213> ORGANISM: Artificial
```

```
<220> FEATURE:
<223> OTHER INFORMATION: Description of sequence: D/L transporter
      construct (D and L amino acid residues alternate, beginning wit D
      amino acids)
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (3)..(3)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (7)..(7)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 158

Arg Arg Arg Arg Arg Arg Arg Arg Arg
1               5

<210> SEQ ID NO 159
<211> LENGTH: 9
<212> TYPE: PRT
<213> ORGANISM: Artificial
<220> FEATURE:
<223> OTHER INFORMATION: Description of sequence: DD/LL transporter
      construct
<220> FEATURE:
<221> NAME/KEY: Variant
<222> LOCATION: (1)..(2)
<223> OTHER INFORMATION: Arg is D-enantiomeric Arg
<220> FEATURE:
<221> NAME/KEY: Variant
<222> LOCATION: (5)..(6)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg

<400> SEQUENCE: 159

Arg Arg Arg Arg Arg Arg Arg Arg Arg
1               5

<210> SEQ ID NO 160
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 160

Tyr Ala Arg Ala Ala Ala Arg Gln Ala Arg Ala
1               5                   10

<210> SEQ ID NO 161
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 161
```

```
Trp Ala Arg Ala Ala Ala Arg Gln Ala Arg Ala
1               5                   10
```

<210> SEQ ID NO 162
<211> LENGTH: 11
<212> TYPE: PRT
<213> ORGANISM: Artificial Sequence
<220> FEATURE:
<223> OTHER INFORMATION: trafficking sequence PTD-4

<400> SEQUENCE: 162

```
Trp Ala Arg Ala Gln Arg Ala Ala Ala Arg Ala
1               5                   10
```

<210> SEQ ID NO 163
<211> LENGTH: 16
<212> TYPE: PRT
<213> ORGANISM: Artificial Sequence
<220> FEATURE:
<223> OTHER INFORMATION: trafficking sequence L-P1 (Penetratin)

<400> SEQUENCE: 163

```
Arg Gln Val Lys Val Trp Phe Gln Asn Arg Arg Met Lys Trp Lys Lys
1               5                   10                  15
```

<210> SEQ ID NO 164
<211> LENGTH: 16
<212> TYPE: PRT
<213> ORGANISM: Artificial Sequence
<220> FEATURE:
<223> OTHER INFORMATION: trafficking sequence D-P1 (Penetratin)

<400> SEQUENCE: 164

```
Lys Lys Trp Lys Met Arg Arg Asn Gln Phe Trp Val Lys Val Gln Arg
1               5                   10                  15
```

<210> SEQ ID NO 165
<211> LENGTH: 17
<212> TYPE: PRT
<213> ORGANISM: Artificial Sequence
<220> FEATURE:
<223> OTHER INFORMATION: trafficking sequence JNK1, bestfit

<400> SEQUENCE: 165

```
Trp Lys Arg Ala Ala Ala Arg Lys Ala Arg Ala Met Ser Leu Asn Leu
1               5                   10                  15

Phe
```

<210> SEQ ID NO 166
<211> LENGTH: 17
<212> TYPE: PRT
<213> ORGANISM: Artificial Sequence
<220> FEATURE:
<223> OTHER INFORMATION: trafficking sequence JNK1, bestfit (variant 1)

<400> SEQUENCE: 166

```
Trp Lys Arg Ala Ala Ala Arg Ala Ala Arg Ala Met Ser Leu Asn Leu
1               5                   10                  15

Phe
```

<210> SEQ ID NO 167
<211> LENGTH: 9
<212> TYPE: PRT
<213> ORGANISM: Artificial Sequence
<220> FEATURE:
<223> OTHER INFORMATION: trafficking sequence MDCK transcytose sequence

```
<400> SEQUENCE: 167

Arg Tyr Arg Gly Asp Leu Gly Arg Arg
1               5

<210> SEQ ID NO 168
<211> LENGTH: 4
<212> TYPE: PRT
<213> ORGANISM: Artificial Sequence
<220> FEATURE:
<223> OTHER INFORMATION: trafficking sequence YKGL

<400> SEQUENCE: 168

Tyr Lys Gly Leu
1

<210> SEQ ID NO 169
<211> LENGTH: 4
<212> TYPE: PRT
<213> ORGANISM: Artificial
<220> FEATURE:
<223> OTHER INFORMATION: trafficking sequence RRTK

<400> SEQUENCE: 169

Arg Arg Thr Lys
1

<210> SEQ ID NO 170
<211> LENGTH: 4
<212> TYPE: PRT
<213> ORGANISM: Artificial
<220> FEATURE:
<223> OTHER INFORMATION: trafficking sequence RRPK

<400> SEQUENCE: 170

Arg Arg Pro Lys
1

<210> SEQ ID NO 171
<211> LENGTH: 20
<212> TYPE: PRT
<213> ORGANISM: Artificial
<220> FEATURE:
<223> OTHER INFORMATION: rKKrQRRrRPkRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 171

Arg Lys Lys Arg Arg Gln Arg Arg Arg Pro Lys Arg Pro Thr Thr
1               5                   10                  15

Leu Asn Leu Phe
```

```
<210> SEQ ID NO 172
<211> LENGTH: 20
<212> TYPE: PRT
<213> ORGANISM: Artificial
<220> FEATURE:
<223> OTHER INFORMATION: rKKRrQRRrRPkRPaTLNLf  JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ala is D-enantiomeric Ala
<220> FEATURE:
<221> NAME/KEY: Variant
<222> LOCATION: (20)..(20)
<223> OTHER INFORMATION: Phe is D-enantiomeric Phe

<400> SEQUENCE: 172

Arg Lys Lys Arg Arg Gln Arg Arg Arg Pro Lys Arg Pro Ala Thr
1               5                   10                  15

Leu Asn Leu Phe
            20

<210> SEQ ID NO 173
<211> LENGTH: 20
<212> TYPE: PRT
<213> ORGANISM: Artificial
<220> FEATURE:
<223> OTHER INFORMATION: rKKRrQRRrRPkRPTTLrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (18)..(18)
<223> OTHER INFORMATION: Arg is D-enantiomeric Arg
<220> FEATURE:
<221> NAME/KEY: Variant
<222> LOCATION: (20)..(20)
<223> OTHER INFORMATION: Phe is D-enantiomeric Phe

<400> SEQUENCE: 173

Arg Lys Lys Arg Arg Gln Arg Arg Arg Pro Lys Arg Pro Thr Thr
1               5                   10                  15
```

Leu Arg Leu Phe
            20

<210> SEQ ID NO 174
<211> LENGTH: 17
<212> TYPE: PRT
<213> ORGANISM: Artificial
<220> FEATURE:
<223> OTHER INFORMATION: rKKrQRRrRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (17)..(17)
<223> OTHER INFORMATION: Phe is D-enantiomeric Phe

<400> SEQUENCE: 174

Arg Lys Lys Arg Arg Gln Arg Arg Arg Pro Thr Thr Leu Asn Leu
1               5                   10                  15

Phe

<210> SEQ ID NO 175
<211> LENGTH: 16
<212> TYPE: PRT
<213> ORGANISM: Artificial
<220> FEATURE:
<223> OTHER INFORMATION: rKKrQRrRPTTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (16)..(16)
<223> OTHER INFORMATION: Phe is D-enantiomeric Phe

<400> SEQUENCE: 175

Arg Lys Lys Arg Arg Gln Arg Arg Arg Pro Thr Thr Leu Asn Leu Phe
1               5                   10                  15

<210> SEQ ID NO 176
<211> LENGTH: 20
<212> TYPE: PRT
<213> ORGANISM: Artificial
<220> FEATURE:
<223> OTHER INFORMATION: rKKrQRRrRPkRPTTLNLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:

```
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Trp is D-enantiomeric Trp

<400> SEQUENCE: 176

Arg Lys Lys Arg Arg Gln Arg Arg Arg Pro Lys Arg Pro Thr Thr
1               5                   10                  15

Leu Asn Leu Trp
            20

<210> SEQ ID NO 177
<211> LENGTH: 20
<212> TYPE: PRT
<213> ORGANISM: Artificial
<220> FEATURE:
<223> OTHER INFORMATION: rKKrQRRrRPkRPTDLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 177

Arg Lys Lys Arg Arg Gln Arg Arg Arg Pro Lys Arg Pro Thr Asp
1               5                   10                  15

Leu Asn Leu Phe
            20

<210> SEQ ID NO 178
<211> LENGTH: 17
<212> TYPE: PRT
<213> ORGANISM: Artificial
<220> FEATURE:
<223> OTHER INFORMATION: rKKrQRRrRPTTLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (15)..(15)
<223> OTHER INFORMATION: Arg is D-enantiomeric Arg
```

```
<220> FEATURE:
<221> NAME/KEY: Variant
<222> LOCATION: (17)..(17)
<223> OTHER INFORMATION: Trp is D-enantiomeric Trp

<400> SEQUENCE: 178

Arg Lys Lys Arg Arg Gln Arg Arg Arg Pro Thr Thr Leu Arg Leu
1               5                   10                  15

Trp

<210> SEQ ID NO 179
<211> LENGTH: 16
<212> TYPE: PRT
<213> ORGANISM: Artificial
<220> FEATURE:
<223> OTHER INFORMATION: rKKRrQRrRPTTLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Trp is D-enantiomeric Trp

<400> SEQUENCE: 179

Arg Lys Lys Arg Arg Gln Arg Arg Pro Thr Thr Leu Arg Leu Trp
1               5                   10                  15

<210> SEQ ID NO 180
<211> LENGTH: 17
<212> TYPE: PRT
<213> ORGANISM: Artificial
<220> FEATURE:
<223> OTHER INFORMATION: rKKRrQRRrRPTDLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (15)..(15)
<223> OTHER INFORMATION: Arg is D-enantiomeric Arg
<220> FEATURE:
<221> NAME/KEY: Variant
<222> LOCATION: (17)..(17)
<223> OTHER INFORMATION: Trp is D-enantiomeric Trp

<400> SEQUENCE: 180

Arg Lys Lys Arg Arg Gln Arg Arg Arg Pro Thr Asp Leu Arg Leu
1               5                   10                  15

Trp
```

```
<210> SEQ ID NO 181
<211> LENGTH: 16
<212> TYPE: PRT
<213> ORGANISM: Artificial
<220> FEATURE:
<223> OTHER INFORMATION: rKKRrQRrRPTDLrLw JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Trp is D-enantiomeric Trp

<400> SEQUENCE: 181

Arg Lys Lys Arg Arg Gln Arg Arg Pro Thr Asp Leu Arg Leu Trp
1               5                   10                  15

<210> SEQ ID NO 182
<211> LENGTH: 17
<212> TYPE: PRT
<213> ORGANISM: Artificial
<220> FEATURE:
<223> OTHER INFORMATION: rKKRrQRRrRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Ala is D-enantiomeric Ala
<220> FEATURE:
<221> NAME/KEY: Variant
<222> LOCATION: (17)..(17)
<223> OTHER INFORMATION: Phe is D-enantiomeric Phe

<400> SEQUENCE: 182

Arg Lys Lys Arg Arg Gln Arg Arg Arg Pro Ala Thr Leu Asn Leu
1               5                   10                  15

Phe

<210> SEQ ID NO 183
<211> LENGTH: 16
<212> TYPE: PRT
<213> ORGANISM: Artificial
<220> FEATURE:
<223> OTHER INFORMATION: rKKRrQRrRPaTLNLf JNK inhibitor
<220> FEATURE:
<221> NAME/KEY: Variant
<222> LOCATION: (1)..(1)
```

<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (11)..(11)
<223> OTHER INFORMATION: Ala is D-enantiomeric Ala
<220> FEATURE:
<221> NAME/KEY: Variant
<222> LOCATION: (16)..(16)
<223> OTHER INFORMATION: Phe is D-enantiomeric Phe

<400> SEQUENCE: 183

Arg Lys Lys Arg Arg Gln Arg Arg Arg Pro Ala Thr Leu Asn Leu Phe
1               5                   10                  15

<210> SEQ ID NO 184
<211> LENGTH: 17
<212> TYPE: PRT
<213> ORGANISM: Artificial
<220> FEATURE:
<223> OTHER INFORMATION: rKKRrQRrKRPaTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (8)..(8)
<223> OTHER INFORMATION: Arg is D-enantiomeric Arg
<220> FEATURE:
<221> NAME/KEY: Variant
<222> LOCATION: (12)..(12)
<223> OTHER INFORMATION: Ala is D-enantiomeric Ala
<220> FEATURE:
<221> NAME/KEY: Variant
<222> LOCATION: (17)..(17)
<223> OTHER INFORMATION: Phe is D-enantiomeric Phe

<400> SEQUENCE: 184

Arg Lys Lys Arg Arg Gln Arg Arg Lys Arg Pro Ala Thr Leu Asn Leu
1               5                   10                  15

Phe

<210> SEQ ID NO 185
<211> LENGTH: 20
<212> TYPE: PRT
<213> ORGANISM: Artificial
<220> FEATURE:
<223> OTHER INFORMATION: rKKRrQRRrRPkRPsTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant -continued

```
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ser is D-enantiomeric Ser
<220> FEATURE:
<221> NAME/KEY: Variant
<222> LOCATION: (20)..(20)
<223> OTHER INFORMATION: Phe is D-enantiomeric Phe

<400> SEQUENCE: 185

Arg Lys Lys Arg Arg Gln Arg Arg Arg Pro Lys Arg Pro Ser Thr
1               5                   10                  15

Leu Asn Leu Phe
            20

<210> SEQ ID NO 186
<211> LENGTH: 20
<212> TYPE: PRT
<213> ORGANISM: Artificial
<220> FEATURE:
<223> OTHER INFORMATION: rKKRrQRRrRPkRPqTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Gln is D-enantiomeric Gln
<220> FEATURE:
<221> NAME/KEY: Variant
<222> LOCATION: (20)..(20)
<223> OTHER INFORMATION: Phe is D-enantiomeric Phe

<400> SEQUENCE: 186

Arg Lys Lys Arg Arg Gln Arg Arg Arg Pro Lys Arg Pro Gln Thr
1               5                   10                  15

Leu Asn Leu Phe
            20

<210> SEQ ID NO 187
<211> LENGTH: 20
<212> TYPE: PRT
<213> ORGANISM: Artificial
<220> FEATURE:
<223> OTHER INFORMATION: rKKRrQRRrRPkRPkTLNLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
```

```
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Lys is D-enantiomeric Lys
<220> FEATURE:
<221> NAME/KEY: Variant
<222> LOCATION: (20)..(20)
<223> OTHER INFORMATION: Phe is D-enantiomeric Phe

<400> SEQUENCE: 187

Arg Lys Lys Arg Arg Gln Arg Arg Arg Pro Lys Arg Pro Lys Thr
1               5                   10                  15

Leu Asn Leu Phe
            20

<210> SEQ ID NO 188
<211> LENGTH: 18
<212> TYPE: PRT
<213> ORGANISM: Artificial
<220> FEATURE:
<223> OTHER INFORMATION: rKKRrQRRrGKRKALKLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (18)..(18)
<223> OTHER INFORMATION: Phe is D-enantiomeric Phe

<400> SEQUENCE: 188

Arg Lys Lys Arg Arg Gln Arg Arg Gly Lys Arg Lys Ala Leu Lys
1               5                   10                  15

Leu Phe

<210> SEQ ID NO 189
<211> LENGTH: 18
<212> TYPE: PRT
<213> ORGANISM: Artificial
<220> FEATURE:
<223> OTHER INFORMATION: rKKRrQRRrGKRKALrLf JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (16)..(16)
<223> OTHER INFORMATION: Arg is D-enantiomeric Arg
<220> FEATURE:
<221> NAME/KEY: Variant
<222> LOCATION: (18)..(18)
<223> OTHER INFORMATION: Phe is D-enantiomeric Phe
```

```
<400> SEQUENCE: 189

Arg Lys Lys Arg Arg Gln Arg Arg Gly Lys Arg Lys Ala Leu Arg
1               5                   10                  15

Leu Phe

<210> SEQ ID NO 190
<211> LENGTH: 16
<212> TYPE: PRT
<213> ORGANISM: Artificial
<220> FEATURE:
<223> OTHER INFORMATION: rKKrQRRrRKALrLf  JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (14)..(14)
<223> OTHER INFORMATION: Arg is D-enantiomeric Arg
<220> FEATURE:
<221> NAME/KEY: Variant
<222> LOCATION: (16)..(16)
<223> OTHER INFORMATION: Phe is D-enantiomeric Phe

<400> SEQUENCE: 190

Arg Lys Lys Arg Arg Gln Arg Arg Arg Lys Ala Leu Arg Leu Phe
1               5                   10                  15

<210> SEQ ID NO 191
<211> LENGTH: 8
<212> TYPE: PRT
<213> ORGANISM: Artificial
<220> FEATURE:
<223> OTHER INFORMATION: RPTTLNLF JNK inhibitor

<400> SEQUENCE: 191

Arg Pro Thr Thr Leu Asn Leu Phe
1               5

<210> SEQ ID NO 192
<211> LENGTH: 9
<212> TYPE: PRT
<213> ORGANISM: Artificial
<220> FEATURE:
<223> OTHER INFORMATION: KRPTTLNLF JNK inhibitor

<400> SEQUENCE: 192

Lys Arg Pro Thr Thr Leu Asn Leu Phe
1               5

<210> SEQ ID NO 193
<211> LENGTH: 11
<212> TYPE: PRT
<213> ORGANISM: Artificial
<220> FEATURE:
<223> OTHER INFORMATION: L-IB1(s24)

<400> SEQUENCE: 193

Arg Pro Lys Arg Pro Thr Thr Leu Asn Leu Phe
1               5                   10
```

<210> SEQ ID NO 194
<211> LENGTH: 29
<212> TYPE: PRT
<213> ORGANISM: Artificial
<220> FEATURE:
<223> OTHER INFORMATION: GRKKRRQRRRPPKRPTTLNLFPQVPRSQD JNK inhibitor

<400> SEQUENCE: 194

Gly Arg Lys Lys Arg Arg Gln Arg Arg Pro Pro Lys Arg Pro Thr
1               5                   10                  15

Thr Leu Asn Leu Phe Pro Gln Val Pro Arg Ser Gln Asp
            20                  25

<210> SEQ ID NO 195
<211> LENGTH: 25
<212> TYPE: PRT
<213> ORGANISM: Artificial
<220> FEATURE:
<223> OTHER INFORMATION: GRKKRRQRRRPTTLNLFPQVPRSQD JNK inhibitor

<400> SEQUENCE: 195

Gly Arg Lys Lys Arg Arg Gln Arg Arg Pro Thr Thr Leu Asn Leu
1               5                   10                  15

Phe Pro Gln Val Pro Arg Ser Gln Asp
            20                  25

<210> SEQ ID NO 196
<211> LENGTH: 31
<212> TYPE: PRT
<213> ORGANISM: Artificial
<220> FEATURE:
<223> OTHER INFORMATION: L-TAT-IB1

<400> SEQUENCE: 196

Gly Arg Lys Lys Arg Arg Gln Arg Arg Arg Pro Pro Arg Pro Lys Arg
1               5                   10                  15

Pro Thr Thr Leu Asn Leu Phe Pro Gln Val Pro Arg Ser Gln Asp
            20                  25                  30

<210> SEQ ID NO 197
<211> LENGTH: 31
<212> TYPE: PRT
<213> ORGANISM: Artificial
<220> FEATURE:
<223> OTHER INFORMATION: D-TAT-IB1
<220> FEATURE:
<221> NAME/KEY: Variant
<222> LOCATION: (1)..(31)
<223> OTHER INFORMATION: All amino acids are D-enantiomeric amino acids

<400> SEQUENCE: 197

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
            20                  25                  30

<210> SEQ ID NO 198
<211> LENGTH: 39
<212> TYPE: PRT
<213> ORGANISM: Artificial
<220> FEATURE:
<223> OTHER INFORMATION: cJun (29-67)

<400> SEQUENCE: 198

Ser Asn Pro Lys Ile Leu Lys Gln Ser Met Thr Leu Asn Leu Ala Asp

```
1               5                   10                  15
Pro Val Gly Ser Leu Lys Pro His Leu Arg Ala Lys Asn Ser Asp Leu
                20                  25                  30

Leu Thr Ser Pro Asp Val Gly
        35

<210> SEQ ID NO 199
<211> LENGTH: 20
<212> TYPE: PRT
<213> ORGANISM: Artificial
<220> FEATURE:
<223> OTHER INFORMATION: RKKRRQRRRRPKRPATLNLF antibody negative control

<400> SEQUENCE: 199

Arg Lys Lys Arg Arg Gln Arg Arg Arg Pro Lys Arg Pro Ala Thr
1               5                   10                  15

Leu Asn Leu Phe
            20

<210> SEQ ID NO 200
<211> LENGTH: 20
<212> TYPE: PRT
<213> ORGANISM: Artificial
<220> FEATURE:
<223> OTHER INFORMATION: rKKRrQRRrR PkAAaAANAf    JNK inhibitor
<220> FEATURE:
<221> NAME/KEY: Variant
<222> LOCATION: (1)..(1)
<223> OTHER INFORMATION: Arg is D-enantiomeric Arg
<220> FEATURE:
<221> NAME/KEY: Variant
<222> LOCATION: (5)..(5)
<223> OTHER INFORMATION: Arg is D-enantiomeric Arg
<220> FEATURE:
<221> NAME/KEY: Variant
<222> LOCATION: (9)..(9)
<223> OTHER INFORMATION: Arg is D-enantiomeric Arg
<220> FEATURE:
<221> NAME/KEY: Variant
<222> LOCATION: (12)..(12)
<223> OTHER INFORMATION: Lys is D-enantiomeric Lys
<220> FEATURE:
<221> NAME/KEY: Variant
<222> LOCATION: (15)..(15)
<223> OTHER INFORMATION: Ala is D-enantiomeric Ala
<220> FEATURE:
<221> NAME/KEY: Variant
<222> LOCATION: (20)..(20)
<223> OTHER INFORMATION: Phe is D-enantiomeric Phe

<400> SEQUENCE: 200

Arg Lys Lys Arg Arg Gln Arg Arg Arg Pro Lys Ala Ala Ala Ala
1               5                   10                  15

Ala Asn Ala Phe
            20
```